US008883445B2

(12) United States Patent
Contreras et al.

(10) Patent No.: US 8,883,445 B2

(45) **Date of Patent: *Nov. 11, 2014**

(54) PROTEIN GLYCOSYLATION MODIFICATION IN METHYLOTROPHIC YEAST

(75) Inventors: Roland Contreras, Merelbeke (BE); Nico L. M. Callewaert, Lichtervelde (BE); Steven C. J. Geysens, Kruishoutem (BE); Vladimir Kaigorodov, Ghent (BE); Vervecken Wouter, Gent-Ledeberg (BE)

(73) Assignees: Research Corporation Technologies, Inc., Tucson, AZ (US); Universiteit Gent, Ghent (BE); Vib, VZW, Zwijnaarde (BE)

( * ) Notice: Subject to any disclaimer, the term of this patent is extended or adjusted under 35 U.S.C. 154(b) by 0 days.

This patent is subject to a terminal disclaimer.

(21) Appl. No.: 11/827,998

(22) Filed: Jul. 13, 2007

(65) Prior Publication Data

US 2008/0009037 A1 Jan. 10, 2008

Related U.S. Application Data

(62) Division of application No. 10/185,475, filed on Jun. 26, 2002, now Pat. No. 7,252,933.

(51) Int. Cl.

| | |
|---|---|
| ***C12P 21/00*** | (2006.01) |
| ***C12Q 1/48*** | (2006.01) |
| ***C12Q 1/34*** | (2006.01) |
| ***C12N 9/12*** | (2006.01) |
| ***C12N 15/81*** | (2006.01) |
| ***C12N 9/24*** | (2006.01) |
| *C07H 21/00* | (2006.01) |
| *C07K 14/00* | (2006.01) |
| *C12N 1/19* | (2006.01) |
| *C12N 15/00* | (2006.01) |

(52) U.S. Cl.

CPC ....... *C12Y 302/01114* (2013.01); *C12N 9/1288* (2013.01); *C12N 15/815* (2013.01); *C12Y 302/01024* (2013.01); *C12N 9/2488* (2013.01)

USPC .................. 435/69.1; 435/254.23; 435/254.2; 435/320.1; 435/193; 435/200; 435/15; 435/18; 536/23.2; 530/395

(58) Field of Classification Search

USPC ............. 435/320.1, 254.23, 254.2, 193, 200, 435/440, 15, 18; 530/395, 350; 536/23.2

See application file for complete search history.

(56) References Cited

U.S. PATENT DOCUMENTS

| | | | | |
|---|---|---|---|---|
| 5,834,251 | A | 11/1998 | Maras et al. ................. | 435/71.1 |
| 7,029,872 | B2 * | 4/2006 | Gerngross .................... | 435/69.1 |
| 2002/0137134 | A1 | 9/2002 | Gerngross .................... | 435/69.1 |

FOREIGN PATENT DOCUMENTS

| | | |
|---|---|---|
| EP | 1 211 310 A1 | 6/2002 |
| WO | WO 92/09694 | 6/1992 |
| WO | WO 96/21038 | 7/1996 |
| WO | WO 02/00856 A2 | 1/2002 |
| WO | WO 02/00879 A2 | 1/2002 |

OTHER PUBLICATIONS

Branden et al., Introduction to Protein Structure, Garland Publishing Inc., New York, p. 247, 1991.*

Witkowski et al., Biochemistry 38:11643-11650, 1999.*

Seffernick et al., J. Bacteriol. 183(8):2405-2410, 2001.*

Kumar et al., PNAS 87:9948-9952, 1990.*

Maras et al., Journal of Biotechnology 77:255-263, 2000.*

Yoshida et al., Bioscience Biotechnology and Biochemistry 62(2):309-315, 1998.*

Mucha et al., Glycobiology 11(9):769-778, 2001.*

Lal et al., J. Biol. Chem. 269(13):9872-9881, 1994.* van Petegem et al., J. Mol. Biol. 312:157-165, 2001.*

Nilsson et al., Journal of Cell Science 109:1975-1989, 1996.*

Yoshida et al., Glycobiology 9(1):53-58, 1999.*

Schwientek et al., Journal of Biological Chemistry 271(7):3398-3405, 1996.*

Kornfeld et al., Annu. Rev. Biochem. 54:631-664, 1985.*

B.K. Choi, et al., "Use of Combinatorial Genetic Libraries to Humanize N-Linked Glycosylation in the Yeast *Pichia pastoris", PNAS*, vol. 100, No. 9, pp. 5022-5027, (2003).

S.R. Hamilton, et al., "Production of Complex Human Glycoproteins in Yeast", *Science*, vol. 301, pp. 1244-1246, (2003).

Maras, M., et al., "In vitro Conversion of the Carbohydrate Moiety of Fungal Glycoproteins to Mammalian-Type Oligosaccharides", *Eur. J. Biochem.* vol. 249, pp. 701-707 (1997).

Martinet, W., et al., "Modification of the Protein Glycosylation Pathway in the Methylotrophic Yeast *Pichia pastoris", Biotechnology Letters*, vol. 20, No. 12, pp. 1171-1177 (1998).

Martinet, W., et al., "Protection of Mice Against a Lethal Influenza Challenge by Immunization with Yeast-Derived Recombinant Influenza Neuraminidase", vol. 247, pp. 332-338 (1997), Eur. J. Biochem.

Cereghino, G., et al., "New Selectable Marker/Auxotrophic Host Strain Combinations for Molecular Genetic Manipulation of *Pichia pastoris*", vol. 263, pp. 159-169 (2001).

Callewaert, N. et al., "Use of HDEL-tagged *Trichoderma reesei* Mannosyl Oligosaccharide 1,2-α-D-mannosidase for N-glycan Engineering in *Pichia pastoris*" FEBS Letters (Aug. 17, 2001) pp. 173-178, vol. 503, No. 2-3.

(Continued)

*Primary Examiner* — Delia Ramirez

(74) *Attorney, Agent, or Firm* — Scully, Scott, Murphy & Presser, P.C.

(57) ABSTRACT

The present invention provides genetically engineered strains of methylotrophic yeast including *Pichia* and especially *Pichia pastoris* capable of producing proteins with reduced or modified glycosylation. Methods of producing glycoproteins with reduced and/or modified glycosylation using such genetically engineered strains of *Pichia* are also provided. Vectors, which comprise coding sequences for α-1,2-mannosidase I, glucosidase II, GlcNAc-tranferase I and mannosidase II or comprising OCH1 disrupting sequence, for transforming methylotrophic yeasts are contemplated by the present invention. Kit for providing the comtemplated vectors are also included in this invention.

16 Claims, 35 Drawing Sheets

(56) References Cited

OTHER PUBLICATIONS

Chiba, Y. et al., "Production of Human Compatible High Mannose-type (Man5GlcNAc2) Sugar Chains in *Saccharomyces cerevisiae*" The Journal of Biological Chemistry (Oct. 9, 1998) pp. 26298-26304, vol. 273, No. 41.

Bretthauer, R.K., "Genetic Engineering of *Pichia pastoris* to Humanize N-glycosylation of Proteins" Trends in Biotechnology (Nov. 1, 2003) pp. 459-462, vol. 21, No. 11.

European Search Report dated Feb. 4, 2011 issued in European Application No. EP 10 01 1710.

* cited by examiner

Glucose units
5
6
7
8
9
10
11
12
13
Relative fluorescence units
A
B
C
D
E
F
90
60
30
0
270
180
150
100
50

Scan
1100 1200 1300 1400 1500 1600 1700 1800 1900 2000 2100 2200 2300 2400 2500 2600
Glc8 Glc9 Glc10
RFU
1
2
3
4
5
6

GAP
Amp R
pGAPADEIglsII
7236 bp
GLS2
ADE 1
myc-tag/his6
AOX1 TT

Glucosidase II assay on commercially available alpha-glucosidase

Glucosidase II assay on heterologously expressed Pichia protein

Construct for single homologous recombination in the Pichia OCH1 locus.

Structure of *OCH1* locus after recombination with pZ5'PpOCH1Trunc.

Kai 10 - Kai7 =. ~ 1050 bp

Kai 11 - Kai5 = ~ 2100 bp

PROTEIN GLYCOSYLATION MODIFICATION IN METHYLOTROPHIC YEAST

CROSS REFERENCE TO RELATED APPLICATIONS

This application is a divisional of U.S. patent application Ser. No. 10/185,475, filed Jun. 26, 2002, now U.S. Pat. No. 7,252,933 B1.

FIELD OF THE INVENTION

The present invention relates to methods and vectors useful for genetically modifying the glycosylation process in methylotrophic yeast strains, including *Pichia* and especially *Pichia pastoris*, for the purpose of producing glycoproteins with reduced or modified glycosylation. The present invention further relates to methylotrophic yeast strains generated using the present methods and vectors, as well as glycoproteins produced from such genetically modified strains.

BACKGROUND OF THE INVENTION

The methylotrophic yeasts including *Pichia pastoris* have been widely used for production of recombinant proteins of commercial or medical importance. Many pharmaceutical compositions consist glycoproteins produced in methylotrophic yeasts including *Pichia pastoris*. However, production and medical applications of some therapeutic glycoproteins can be hampered by the differences in the protein-linked carbohydrate biosynthesis between these yeasts and the target organisms such as a mammalian subject.

Protein N-glycosylation originates in the endoplasmic reticulum (ER), where the precursor N-linked oligosaccharide of 14 sugars ($Glc_3Man_9GlcNAc_2$) is assembled on a dolichol (a lipid carrier intermediate), and it is transferred to the appropriate Asn of growing nascent polypeptides. This is an event common to all eukaryotic N-linked glycoproteins. These glycans are then subjected to extensive modification as the glycoproteins mature and move through the ER via the Golgi complex to their final destinations inside and outside the cell. Three terminal glucose residues are trimmed away by glucosidase I and II, and one terminal α-1,2-linked mannose residue is removed by one or more different mannosidase in the ER, such as ER-mannosidase, resulting in the oligosaccharide $Man_8GlcNAc_2$. This glycoprotein is then transported to the Golgi apparatus where the sugar moiety undergoes various modifications. There are significant differences in the modifications of the sugar branches in the Golgi apparatus between yeasts and higher eukaryotes.

In mammalian cells, the modification of the sugar branches in the Golgi apparatus proceeds via three different pathways depending on the protein moieties to which the sugars are added. They are, (1) where the glycoprotein does not change; (2) where the glycoprotein is modified by adding the N-acetylglucosamine-1-phosphate moiety (GlcNAc-1-P) in UDP-N-acetyl glucosamine (UDP-GlcNAc) to the 6-position of mannose in the sugar branch, followed by removing the GlcNAc moiety to form an acidic sugar branch in the glycoprotein; or (3) where the N-linked glycan is first converted into $Man_5GlcNAc_2$ by removing three mannose residues by Golgi mannosidase I; $Man_5GlcNAc_2$ is further modified by adding one GlcNAc by N-acetylglucosamine transferase I (GlcNAc-Transferase I or GnTI) and removing two more mannose residues by mannosidase II. During subsequent terminal glycosylation there is addition of new terminal sugars including GlcNAc, galactose (Gal), fucose, and N-acetylneuraminic acid (also called sialic acid (NeuNAc)) to produce various hybrid or complex glycans (R. Kornfeld and S. Kornfeld, *Ann. Rev. Biochem.* 54: 631-664, 1985; Chiba et al *J. Biol. Chem.* 273: 26298-26304, 1998; Helenius A and Aebi M, *Science* 291:2364-2369, 2001).

In yeasts, the modification of the sugar branches in the Golgi apparatus involves a series of additions of mannose residues by different mannosyltransferases ("outer chain" glycosylation). The structure of the outer chain glycosylation is specific to the organisms, typically with more than 50 mannose residues in *S. cerevisiae*, and most commonly with structures smaller than $Man_{14}GlcNAc_2$ in *Pichia pastoris*. This yeast-specific outer chain glycosylation of the high mannose type is also denoted hyperglycosylation.

Hyperglycosylation is often undesired since it leads to heterogeneity of a recombinant protein product in both carbohydrate composition and molecular weight, which may complicate the protein purification. The specific activity (units/weight) of the hyperglycosylated proteins may be lowered by the increased portion of carbohydrate. In addition, the outer chain glycosylation is strongly immunogenic which is undesirable in a therapeutic application. Moreover, the large outer chain sugar can mask the immunogenic determinants of a therapeutic protein. For example, the influenza neuraminidase (NA) expressed in *P. pastoris* is glycosylated with N-glycans containing up to 30-40 mannose residues. The hyperglycosylated NA has a reduced immunogenicity in mice, as the variable and immunodominant surface loops on top of the NA molecule are masked by the N-glycans (Martinet et al. *Eur J. Biochem.* 247: 332-338, 1997).

Therefore, it is desirable to genetically engineer methylotrophic yeast strains in which glycosylation of proteins can be manipulated and from which recombinant glycoproteins can be produced having a mammalian-like glycosylation pattern.

SUMMARY OF THE INVENTION

The present invention is directed to methods and vectors useful for genetically modifying the glycosylation process in methylotrophic yeast strains to produce glycoproteins with reduced or modified glycosylation. Methylotrophic yeast strains generated using present methods and vectors, as well as glycoproteins produced from such genetically modified strains, are also provided.

In one embodiment, the present invention provides vectors useful for making genetically engineered methylotrophic yeast strains which are capable of producing glycoproteins with reduced or modified glycosylation.

In one aspect, the present invention provides "knock-in" vectors which are capable of expressing in a methylotrophic yeast strain one or more proteins whose enzymatic activities lead to a reduction or modification of glycosylation in glycoproteins produced by the methylotrophic yeast strain.

In a preferred embodiment, the knock-in vectors of the present invention include a nucleotide sequence coding for an α-1,2-mannosidase or a functional part thereof and are capable of expressing the α-1,2-mannosidase or the functional part in a methylotrophic yeast strain. A preferred nucleotide sequence is a nucleotide sequence encoding the α-1,2-mannosidase of a fungal species, and more preferably, *Trichoderma reesei*. Preferably, the α-1,2-mannosidase expression vector is engineered such that the α-1,2-mannosidase or a functional part thereof expressed from the vector includes an ER-retention signal. A preferred ER-retention signal is HDEL. The α-1,2-mannosidase coding sequence can be operably linked to a constitutive or an inducible promoter, and a 3' termination sequence. The vectors can be integrative vectors or replicative vectors. Particularly preferred α-1,2-mannosidase expression vectors include pGAPZMFManHDEL, pGAPZMFManMycHDEL, pPICZBMFManMycHDEL, pGAPZmManHDEL, pGAPZmMycManHDEL, pPIC9 mMycManHDEL and pGAPZmMycManHDEL.

In another preferred embodiment, the knock-in vectors of the present invention include a sequence coding for a glucosidase II or a functional part thereof and are capable of expressing the glucosidase II or the functional part in a methylotrophic yeast strain. A preferred nucleotide sequence is a nucleotide sequence encoding the glucosidase II of a fungal species, and more preferably, *Saccharomyces cerevisiae*. Preferably, the glucosidase II expression vector is engineered such that the glucosidase II or a functional part thereof expressed from the vector includes an ER-retention signal. A preferred ER-retention signal is HDEL. The glucosidase II coding sequence can be operably linked to a constitutive or an inducible promoter, and a 3' termination sequence. The vectors can be integrative vectors or replicative vectors. Particularly preferred glucosidase II expression vectors include pGAPZAGLSII, pPICZAGLSII, pAOX2ZAGLSII, pYPTIZAGLSII, pGAPADEglsII, pPICADEglsII, pAOX2ADEglsII, pYPTIADEglsII, pGAPZAglsIIHDEL and pGAPADEglsIIHDEL.

Expression vectors which include both of an α-1,2-mannosidase expression unit and a glucosidase II expression unit are also provided by the present invention.

By "expression unit" is meant that a nucleotide sequence capable of expressing a gene of interest. In general, an express unit includes the gene to be expressed, which is operably linked to a promoter, a termination sequence and any other sequence that may be appropriate.

In a preferred embodiment, the knock-in vectors of the present invention include a nucleotide sequence encoding a N-acetylglucosamine transferase I (GlcNAc-transferase I or GnTI) or a functional part thereof and are capable of expressing the GlcNAc-transferase I or the functional part in a methylotrophic yeast strain. A preferred nucleotide sequence is a nucleotide sequence encoding the GlcNAc-transferase I of a mammalian species, e.g., human. Preferably, the GlcNAc-transferase I expression vector is engineered such that the GlcNAc-transferase I or a functional part thereof expressed from the vector includes a yeast Golgi localization signal. A preferred yeast Golgi localization signal is a peptide derived from the N-terminal part of *S. cerevisiae* Kre2 (ScKre2). The GlcNAc-transferase I coding sequence can be operably linked to a constitutive or an inducible promoter, and a 3' termination sequence. The vectors can be integrative vectors or replicative vectors. Particularly preferred GlcNAc-transferase I expression vectors include pPIC6AKreconGnTI.

In another preferred embodiment, the knock-in vectors of the present invention include a sequence encoding a mannosidase II or a functional part thereof and are capable of expressing the mannosidase II or the functional part thereof in a methylotrophic yeast strain. A preferred nucleotide sequence is a nucleotide sequence encoding the mannosidase II of a mammalian species, e.g., human. Preferably, the mannosidase II expression vector is engineered such that the mannosidase II or a functional part thereof expressed from the vector includes a yeast Golgi localization signal. A preferred Golgi localization signal is a peptide derived from the N-terminal part of ScKre2. The mannosidase II coding sequence can be operably linked to a constitutive or an inducible promoter, and a 3' termination sequence. The vectors can be integrative vectors or replicative vectors. Particularly preferred mannosidase II expression vectors include pGAPKreManII.

Expression vectors which include both of a GlcNAc-transferase I expression unit and a mannosidase II expression unit are also provided by the present invention.

Expression vectors which include two or more of an α-1,2-mannosidase expression unit, a glucosidase II expression unit, a GlcNAc-transferase I expression unit and a mannosidase II expression unit, are also provided by the present invention.

In another aspect, the present invention provides inactivation vectors which, when introduced into a methylotrophic yeast strain, inactivate or disrupt a gene thereby facilitating the reduction in the glycosylation of glycoproteins produced in the methylotrophic yeast strain.

In one embodiment, the present invention provides an inactivation vector which, when introduced into a methylotrophic yeast strain, inactivates or disrupts the OCH1 gene. A preferred OCH1 inactivation vector is pBLURA5'PpOCH1 and pZMFManHDEL5'PpOch1Mut.

Still another embodiment of the present invention provides "knock-in-inactivation" vectors which include at least a "knock-in unit" and at least a "inactivation unit". By "knock-in unit" is meant an expression unit which is capable of expressing in a methylotrophic yeast strain one or more proteins whose enzymatic activities lead to a reduction or modification of glycosylation in glycoproteins produced by the methylotrophic yeast strain. By "inactivation unit" is meant an expression unit which, when introduced into a methylotrophic yeast strain, inactivates or disrupts the endogenous OCH1 gene or other mannosyltransferase genes. When a "knock-in-and inactivation" vector is introduced to a methylotrophic yeast strain, potent exdogenous enzyme expression and endogenous mannosyltransferase disruption can be achieved simultaneously. A preferred knock-in-and-inactivation vector is pZMFManHDEL5'PpOCH1Mut.

Another embodiment of the present invention provides methods of modifying the glycosylation in a methylotrophic yeast strain by transforming the yeast with one or more vectors of the present invention.

Strains of a methylotrophic yeast which can be modified using the present invention include, but are not limited to, yeast strains capable of growing on methanol, such as yeasts of the genera *Candida, Hansenula, Torulopsis*, and *Pichia*. Preferred methylotrophic yeasts are of the genus *Pichia*. Especially preferred are *Pichia pastoris* strains GS115 (NRRL Y-15851), GS190 (NRRL Y-18014), PPF1 (NRRL Y-18017), PPY120H, YGC4, and strains derived therefrom. Methylotrophic yeast strains which can be modified using the present methods also include those methylotrophic yeast strains which have been engineered to express one or more heterologous proteins of interest. The glycosylation on the heterologous proteins expressed from these previously genetically engineered strains can be reduced by transforming such strains with one or more of the vectors of the present invention.

Methylotrophic yeast strains which are modified by practicing the present methods are provided in another embodiment of the present invention.

A further aspect of the present invention is directed to methods of producing glycoproteins with reduced or modified glycosylations.

In accordance with such methods, a nucleotide sequence capable of expressing a glycoprotein can be introduced into a methylotrophic yeast strain which has previously been transformed with one or more of the vectors of the present invention. Alternatively, a methylotrophic yeast strain which has been genetically engineered to express a glycoprotein can be transformed with one or more of the vectors of the present invention. Moreover, if a methylotrophic yeast strain is not transformed with a nucleotide sequence encoding a glycoprotein of interest or any of the vectors of the present invention, such yeast strain can be transformed, either consecutively or simultaneously, with both a nucleotide sequence capable of expressing a glycoprotein and one or more vectors of the present invention. Additionally, a methylotrophic yeast strain can be transformed with one or more of the present knock-in and/or inactivation vectors which also include a nucleotide sequence capable of expressing a glycoprotein in the methylotrophic yeast strain.

Glycoprotein products produced by using the methods of the present invention, i.e., glycoproteins with reduced or modified N-glycosylation, are also part of the present invention.

Kits which include one or more of the vectors of the present invention, or one or more strains modified to produce glycoproteins with reduced or modified glycosylation, are also provided.

DETAILED DESCRIPTION OF THE INVENTION

Figure 1:
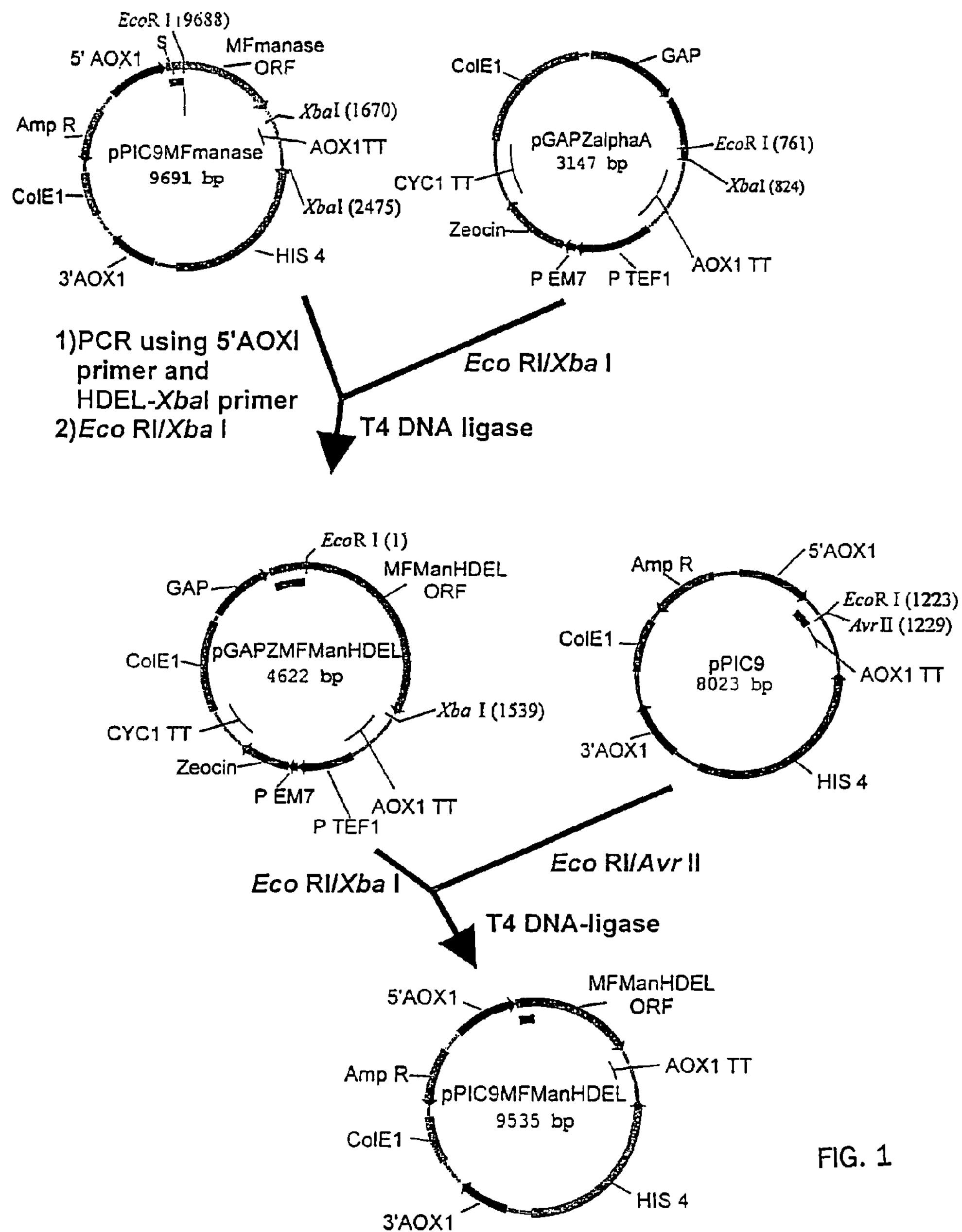
FIG. 1 depicts vectors carrying an HDEL-tagged *Trichoderma reesei* α-1,2-mannosidase expression cassette and describes the way in which these vectors were constructed according to methods known in the art. Abbreviations used throughout construction schemes: 5' AOX1 or AOX1 P: *Pichia pastoris* AOX1 promoter sequence; Amp R: ampicillin resistance gene; ColE1: ColE1 origin of replication; 3'AOX1: 3' sequences of the *Pichia pastoris* AOX1 gene; HIS4: HIS4 gene of *Pichia pastoris*. AOX TT: transcription terminator sequence of the *Pichia pastoris* AOX1 gene; ORF: open reading frame; S: secretion signal; P TEF1: the promoter sequence of the *Saccharomyces cerevisiae* transcription elongation factor 1 gene; P EM7: synthetic constitutive prokaryotic promotor EM7; Zeocin: Zeocin resistance gene; CYC1 TT: 3' end of the *S. cerevisiae* CYC1 gene; GAP: promoter sequence of the *Pichia pastoris* glyceraldehyde-3-phosphate dehydrogenase gene; PpURA3: *Pichia pastoris* URA3 gene. As can be seen in this figure, the *Trichoderma reesei* α-1,2-mannosidase was operably linked to the coding sequence for the *S. cerevisiae* α-mating factor secretion signal sequence and further operably linked at the 3' terminus of the coding sequence to the coding sequence for an HDEL peptide. The whole fusion construct was operably linked to either the *P. pastoris* AOX1 promoter (in pPIC9MFManHDEL) or to the *P. pastoris* GAP promotor (in pGAPZMFManHDEL).
Figure 2:
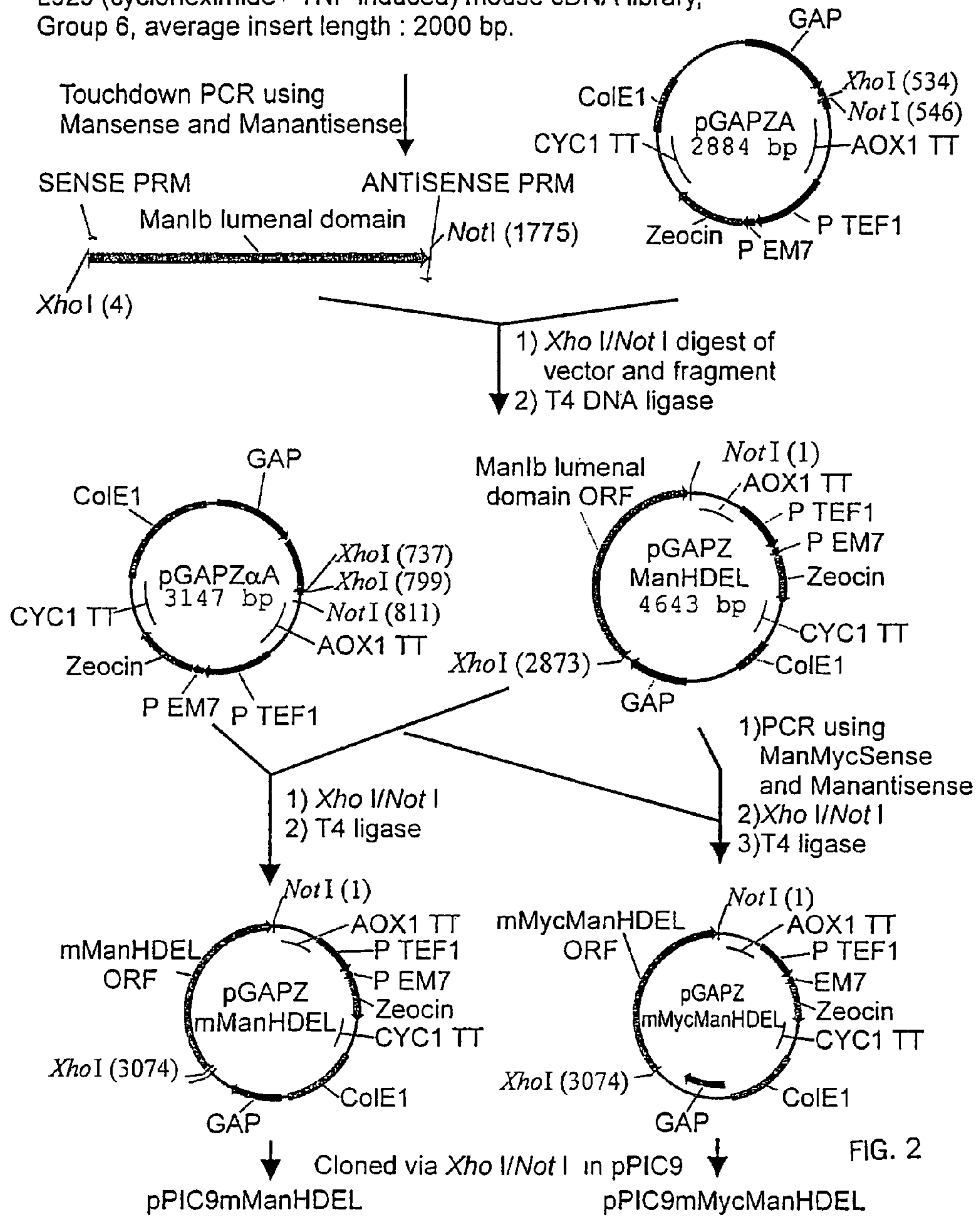
FIG. 2 depicts vectors carrying an HDEL-tagged *Mus musculus* α-1,2-mannosidase IB expression cassette and describes the way in which these vectors were constructed according to methods known in the art. As can be seen in this figure, the catalytic domain of the *Mus musculus* α-1,2-mannosidase IB was operably linked to the coding sequence for the *S. cerevisiae* α-mating factor secretion signal sequence and further operably linked at the 3' terminus of the coding sequence to the coding sequence for an HDEL peptide. The whole fusion construct was operably linked to either the *P. pastoris* AOX1 promoter (in pPIC9 mManHDEL) or to the *P. pastoris* GAP promotor (in pGAPZmManHDEL). Furthermore, variants of the expression cassette were made in which the coding sequence for a cMyc epitope tag was inserted between the coding sequence for the *S. cerevisiae* α-mating factor secretion signal sequence and the coding sequence for the catalytic domain of the *Mus musculus* α-1,2-mannosidase IB. This expression cassette was also operably linked to either the *P. pastoris* AOX1 promoter (in pPIC9 mMycManHDEL) or to the *P. pastoris* GAP promotor (in pGAPZmMycManHDEL).
Figure 3:
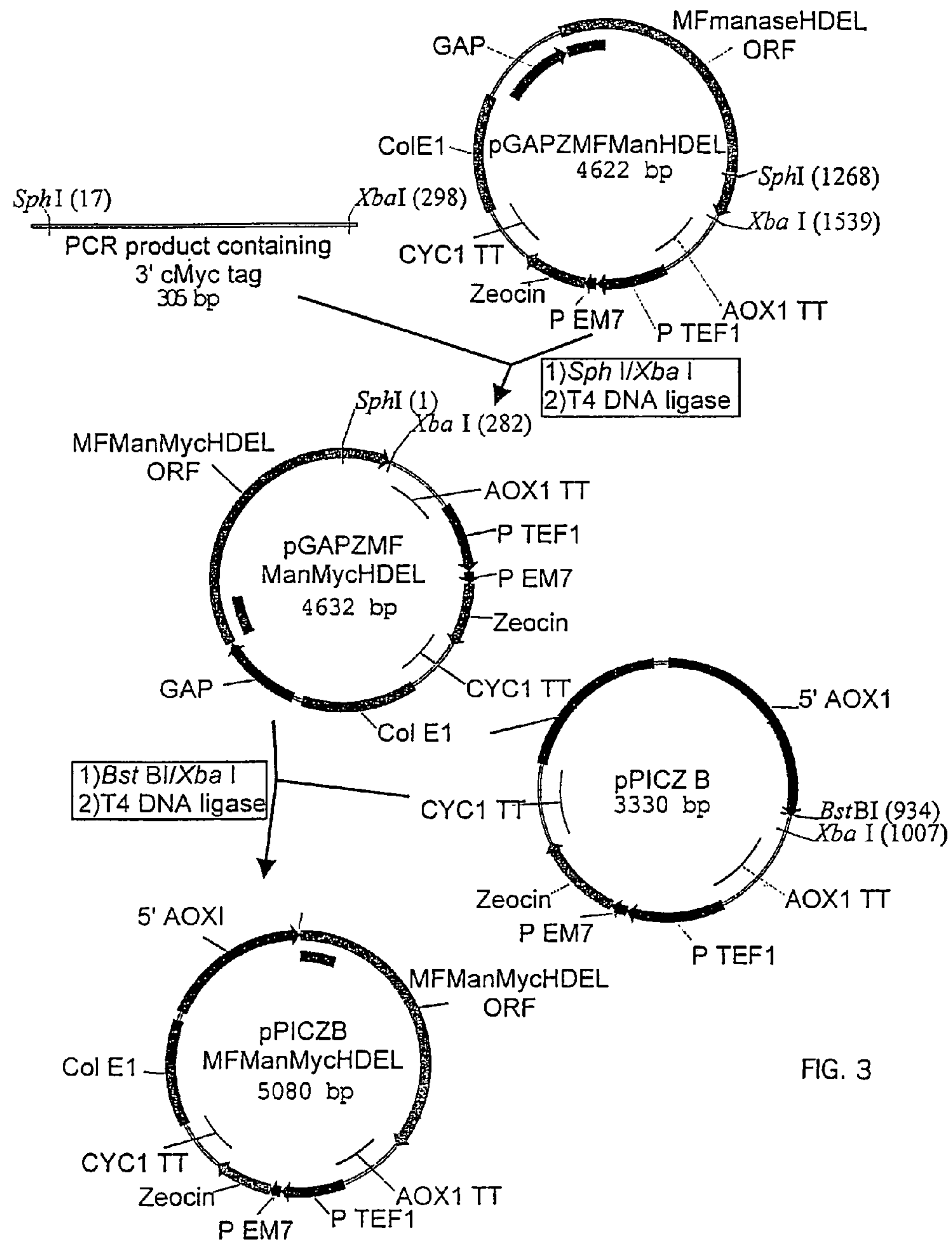
FIG. 3 depicts vectors carrying a MycHDEL tagged *Trichoderma reesei* α-1,2-mannosidase and the way in which these vectors were obtained. The resulting fusion construction was again operably linked to either the *P. pastoris* AOX1 promoter (in pPICZBMFManMycHDEL) or to the *P. pastoris* GAP promotor (in pGAPZMFManMycHDEL).

It has been established that the majority of N-glycans on glycoproteins leaving the endoplasmic reticulum (ER) of methylotrophic yeasts, including *Pichia* and especially *Pichia pastoris*, have the $Man_8GlcNAc_2$ oligosaccharide structure. After the proteins are transported from the ER to the Golgi apparatus, additional mannose residues are added to this core sugar moiety by different mannosyltransferases, resulting in glycoproteins with oligosaccharide structures consisting of a high manose core, or extended branched mannan outer chains. Such hyperglycosylation of recombinant glycoproteins is undesirable in many instances. Accordingly, the present invention provides methods and vectors for genetically modifying methylotrophic yeast strains to produce glycoproteins with reduced or modified glycosylation. Methylotrophic yeast strains generated using the present methods and vectors, as well as glycoproteins produced from such genetically modified strains are also provided.

By the term "reduced or modified glycosylation", it is meant that a host yeast strain used for the production of a protein of interest has been genetically modified, such that the protein expressed from the genetically modified strain bears oligosaccharide side branches with fewer mannose residues, as compared to a protein from unmodified yeast strains.

Yeast strains genetically engineered in accordance with the present invention are also capable of producing proteins with oligosaccharide side branches that are "mammalian-like". By the term "mammalian-like", it is meant that the oligosaccharide is of a structure ordinarily seen on a mammalian glycoprotein, e.g., glycoproteins comprising glycans with fewer terminal mannose residues or glycans with a hybrid- or a complex-type glycosylation pattern, as compared to glycans with high terminal mannose residues on yeast glycoproteins. Typical mammalian-like oligosaccharide structures start from $Man_5GlcNAc_2$, $GlcNAcMan_5GlcNAc_2$ and $GlcNAcMan_3GlcNAc_2$. Branched structures, e.g., bi-, tri, and tetra-antennary, are synthesized by the GlcNAc-transferase-catalyzed addition of GlcNAc to regions of the oligosaccharide residue. Subsequent to their formation, the antennary structures are terminated with different sugars including Gal, GalNAc, GlcNAc, Fuc and sialic acid residues.

In one embodiment, the present invention provides vectors useful for genetically modifying methylotrophic yeast strains to produce glycoproteins with reduced or modified glycosylation.

In one aspect, the present invention provides "knock-in" vectors which are capable of expressing in a methylotrophic yeast strain one or more proteins whose enzymatic activities lead to a reduction or modification of glycosylation in glycoproteins produced by the methylotrophic yeast strain. According to the present invention, such proteins include, e.g., an α-1,2-mannosidase, a glucosidase II, a GlcNAc-transferase I (GnTI), a mannosidase II, or functional parts thereof.

In a preferred embodiment, the vectors of the present invention include a sequence coding for an α-1,2-mannosidase or a functional part thereof and are capable of expressing the α-1,2-mannosidase or the functional part thereof in methylotrophic yeast.

An α-1,2-mannosidase cleaves the α-1,2-linked mannose residues at the non-reducing ends of $Man_8GlcNAc_2$, and converts this core oligosaccharide on glycoproteins to $Man_5GlcNAc_2$. In vitro, $Man_5GlcNAc_2$ is a very poor substrate for any *Pichia* Golgi mannosyltransferase, i.e., mannose residues can not be added to this sugar structure. On the other hand, $MansGlcNAc_2$ is the acceptor substrate for the mammalian N-acetylglucosaminyl-transferase I and is an intermediate for the hybrid- and complex-type sugar chains characteristic of mammalian glycoproteins. Thus, by way of introducing an α-1,2-mannosidase into methylotrophic yeasts such as *Pichia*, glycoproteins with reduced mannose content glycans, such as $Man_5GlcNAc_2$, can be produced. The branching of mammalian-like oligosaccharide structures will then occur after trimming of the oligosaccharide to the $Man_5GlcNAc_2$.

According to the present invention, the nucleotide sequence encoding an α-1,2-mannosidase for use in the expression vector of the present invention can derive from any species. A number of α-1,2-mannosidase genes have been cloned and are available to those skilled in the art, including mammalian genes encoding, e.g., a murine α-1,2-mannosidase (Herscovics et al. *J. Biol. Chem.* 269: 9864-9871, 1994), a rabbit α-1,2-mannosidase (Lal et al. *J. Biol. Chem.* 269: 9872-9881, 1994) or a human α-1,2-mannosidase (Tremblay et al. *Glycobiology* 8: 585-595, 1998), as well as fungal genes encoding, e.g., an *Aspergillus* α-1,2-mannosidase (msdS gene), a *Trichoderma reesei* α-1,2-mannosidase (Maras et al. *J. Biotechnol.* 77: 255-263, 2000), or a *Saccharomyces cerevisiae* α-1,2-mannosidase. Protein sequence analysis has revealed a high degree of conservation among the eukaryotic α-1,2-mannosidases identified so far.

Preferably, the nucleotide sequence for use in the present vectors encodes a fungal α-1,2-mannosidase, more preferably, a *Trichoderma reesei* α-1,2-mannosidase, and more particularly, the *Trichoderma reesei* α-1,2-mannosidase described by Maras et al. *J. Biotechnol.* 77: 255-63 (2000).

According to the present invention, the nucleotide sequence can also code for only a functional part of an α-1,2-mannosidase.

By "functional part" is meant a polypeptide fragment of an α-1,2-mannosidase which substantially retains the enzymatic activity of the full-length protein. By "substantially" is meant that at least about 40%, or preferably, at least 50% or more of the enzymatic activity of the full-length α-1,2-mannosidase is retained. For example, as illustrated by the present invention, the catalytic domain of the murine α-1,2-mannosidase IB constitutes a "functional part" of the murine α-1,2-mannosidase IB. Those skilled in the art can readily identify and make functional parts of an α-1,2-mannosidase using a combination of techniques known in the art. Predictions of the portions of an α-1,2-mannosidase essential to or sufficient to confer the enzymatic activity can be made based on analysis of the protein sequence. The activity of a portion of an α-1,2-mannosidase of interest, expressed and purified from an appropriate expression system, can be verified using in vitro or in vivo assays described hereinbelow.

In accordance with the present invention, an α-1,2-mannosidase or a functional part thereof expressed in a methylotrophic yeast strain preferably is targeted to a site in the secretory pathway where $Man_8GlcNAc_2$ (the substrate of α-1,2-mannosidase) is already formed on a glycoprotein, but has not reached a Golgi glycosyltransferase which elongates the sugar chain with additional mannose residues.

Accordingly, in a preferred embodiment of the present invention, the α-1,2-mannosidase expression vector is engineered as such that the α-1,2-mannosidase or a functional part thereof expressed from the vector includes an ER-retention signal.

An "ER retention signal" refers to a peptide sequence which directs a protein having such peptide sequence to be transported to and retained in the ER. Such ER retention sequences are often found in proteins that reside and function in the ER.

Multiple choices of ER retention signals are available to those skilled in the art, e.g., the first 21 amino acid residues of the *S. cerevisiae* ER protein MNS1 (Martinet et al. *Biotechnology Letters* 20: 1171-1177, 1998). A preferred ER retention signal for use in the present invention is peptide HDEL (SEQ ID NO: 1). The HDEL peptide sequence, found in the C-terminus of a number of yeast proteins, acts as a retention/retrieval signal for the ER (Pelham *EMBO J.* 7: 913-918, 1988). Proteins with an HDEL sequence are bound by a membrane-bound receptor (Erd2p) and then enter a retrograde transport pathway for return to the ER from the Golgi apparatus.

According to the present invention, an ER retention signal can be placed anywhere in the protein sequence of an α-1,2-mannosidase, but preferably at the C-terminus of the α-1,2-mannosidase.

The α-1,2-mannosidase for use in the present invention can be further modified, e.g., by insertion of an epitope tag to which antibodies are available, such as Myc, HA, FLAG and His6 tags, which are well-known in the art. An epitope-tagged α-1,2-mannosidase can be conveniently purified, or monitored for both expression and intracellular localization.

An ER retention signal and an epitope tag can be readily introduced into a protein of interest by inserting nucleotide sequences coding for such signal or tag into the nucleotide sequence encoding the protein of interest, using any of the molecular biology techniques known in the art.

In another preferred embodiment, the vectors of the present invention include a sequence coding for a glucosidase II or a functional part thereof and are capable of expressing the glucosidase II or the functional part in the methylotrophic yeast strain.

It has been established that the initial N-linked oligosaccharide ($Glc_3Man_9GlcNAc_2$), transferred in the ER onto a protein, is cleaved in the ER by specific glucosidases to remove 3 glucose residues, and by a mannosidase to remove 1 specific α-1,2-linked mannose. It has been observed by the present inventors that some recombinant proteins expressed in *Pichia* have residual glucose residues on the sugar moiety when such proteins leave the ER for the Golgi apparatus. The residual glucose molecules present on the sugar structure prevent the complete digestion of the sugar moiety by an α-1,2-mannosidase, and the introduction of an exogenous glucosidase can facilitate the removal of these glucose residues.

According to the present invention, the nucleotide sequence encoding a glucosidase II can derive from any species. The Glucosidase II genes have been cloned from a number of mammalian species including rat, mouse, pig and human. The glucosidase II protein from these mammalian species consists of an alpha and a beta subunit. The alpha subunit is about 110 kDa and contains the catalytic activity of the enzyme, while the beta subunit has a C-terminal HDEL ER-retention sequence and is believed to be important for the ER localization of the enzyme. The glucosidase II gene from *S. cerevisiae* has also been cloned (ORF YBR229c, located on chromosome II). This gene encodes a protein of about 110 kDa, which shows a high degree of homology to the mammalian alpha subunits.

A preferred glucosidase II gene for use in the present vectors is from a fungal species such as *Pichia pastoris* and *S. cerevisiae*. An example of a fungal glucosidase II gene is the *S. cerevisiae* glucosidase II gene.

According to the present invention, the nucleotide sequence can also encode only a functional part of a glucosidase II. By "functional part" is meant a polypeptide fragment of a glucosidase II which substantially retains the enzymatic activity of the full-length protein. By "substantially" is meant that at least about 40%, or preferably, at least 50% or more of the enzymatic activity of the full-length glucosidase II is retained. Functional parts of a glucosidase II can be identified and made by those skilled in the art using a variety of techniques known in the art.

In a preferred embodiment of the present invention, the glucosidase II protein is engineered to include an ER retention signal such that the protein expressed in a methylotrophic yeast strain is targeted to the ER and retains therein for function. ER retention signals are as described hereinabove, e.g., the HDEL peptide sequence.

The glucosidase II for use in the present invention can be further modified, e.g., by insertion of an epitope tag to which antibodies are available, such as Myc, HA, FLAG, and His6 tag, which are well-known in the art.

According to the present invention, the "knock-in" vectors can include either or both of an α-1,2-mannosidase coding sequence and a glucosidase II coding sequence.

In another preferred embodiment, the vectors of the present invention include a sequence coding for a GlcNAc-Transferase I or a functional part thereof and are capable of expressing the GlcNAc-Transferase I or the functional part thereof in a methylotrophic yeast strain.

A GlcNAc-Transferase I is responsible for the addition of β-1,2-GlcNAc to a $Man_5GlcNAc_2$, and converts this core oligosaccharide on glycoproteins to $GlcNAcMan_5GlcNAc_2$. The mannose residues of $GlcNAcMan_5GlcNAc_2$ can be further trimmed by a mammalian Golgi mannosidase II. New sugars are added to form hybrid- or complex-type sugar branches characteristic of mammalian glycoproteins. Thus, by way of introducing a GlcNAc-transferase I into methylotrophic yeasts such as *Pichia*, glycoproteins with a mammalian-like glycosylation pattern, such as glycoproteins with glycans $GlcNAcMan_5GlcNAc_2$, can be produced.

According to the present invention, the nucleotide sequence encoding a GlcNAc-transferase I (GnTI) for use in the expression vector of the present invention can derive from any species, e.g., rabbit, rat, human, plants, insects, nematodes and protozoa such as *Leishmania tarentolae*, or can be obtained through protein engineering experiments. Preferably, the nucleotide sequence for use in the present vectors encodes a human GnTI, and more preferably, the GnTI having a sequence as set forth in SEQ ID NO: 34.

According to the present invention, the nucleotide sequence can also encode only a functional part of a GlcNAc-Transferase I.

By "functional part" is meant a polypeptide fragment of a GlcNAc-1-Transferase I which substantially retains the enzymatic activity of the full-length protein. By "substantially" is meant that at least about 40%, or preferably, at least 50% or more of the enzymatic activity of the full-length GlcNAc-Transferase I is retained. For example, as illustrated by the present invention, the catalytic domain of the human GnTI constitutes a "functional part" of the human GnTI. Those skilled in the art can readily identify and make functional parts of a GlcNAc-Transferase I using a combination of techniques known in the art. Predictions of the portions of a GlcNAc-Transferase I essential to, or sufficient to confer, the enzymatic activity can be made based on analysis of the protein sequence. The activity of a portion of a GlcNAc-Transferase I of interest, expressed and purified from an appropriate expression system, can be verified using in vitro or in vivo assays described hereinbelow.

In accordance with the present invention, a GnTI or a functional part thereof expressed in a methylotrophic yeast strain preferably is targeted to a site in the secretory pathway where $Man_5GlcNAc_2$ (the substrate of GnTI) is already formed on a glycoprotein. Preferably, the GnTI or a functional part thereof is targeted to the Golgi apparatus; and more preferably, to the Golgi apparatus of a yeast strain which is also transformed with α-1,2-mannosidase.

Accordingly, in a preferred embodiment of the present invention, the GnTI is engineered such that the GnTI or a functional part thereof expressed from the vector includes a yeast Golgi localization signal.

A yeast "Golgi localization signal" refers to a peptide sequence which directs a protein having such peptide sequence to be retained in the Golgi apparatus. Such Golgi localization sequences are often found in proteins that reside and function in the Golgi apparatus.

Choices of Golgi localization signals are available to those skilled in the art. A preferred Golgi localization signal for use in the present invention is a peptide derived from the N-terminal part of a *Saccharomyces cerevisiae* Kre2 protein (ScKre2). More preferably, the Kre2 gene has a sequence as set forth in SEQ ID NO: 30. A particularly preferred Golgi localization signal is a peptide having amino acid 1-100 (SEQ ID NO: 35) of the ScKre2 protein having SWISS-PROT Accession No. P27809 (SEQ ID NO: 38).

According to the present invention, a Golgi localization signal can be placed anywhere within the GnTI, but preferably at the terminus of the GnTI, and more preferably at the N-terminus of the GnTI.

The GnTI for use in the present invention can be further modified, e.g., by insertion of an epitope tag to which antibodies are available, such as Myc, HA, FLAG and His6 tags well-known in the art. An epitope-tagged GnTI can be conveniently purified, or monitored for both expression and intracellular localization.

A Golgi localization signal and an epitope tag can be readily introduced into a protein of interest by inserting nucleotide sequences coding for such signal or tag into the nucleotide sequence encoding the protein of interest, using any of the molecular biology techniques known in the art.

In another preferred embodiment, the vectors of the present invention include a sequence coding for a mannosidase II or a functional part thereof and are capable of expressing the mannosidase II or the functional part in a methylotrophic yeast strain.

It has been established that a GlcNAc-Transferase I adds a β-1,2-GlcNAc to a $Man_5GlcNAc_2$, and converts the core oligosaccharide $Man_5GlcNAc_2$ on glycoproteins to $GlcNAcMan_5GlcNAc_2$. $GlcNAcMan_5GlcNAc_2$ is the substrate of, and can be further processed by, a mammalian Golgi mannosidase II, to remove more mannose residues. The resulting oligosaccharide group can be further modified to produce hybrid or complex type sugar branches characteristic of mammalian glycoproteins. Thus, by way of introducing a mannosidase II into methylotrophic yeasts such as *Pichia*, and especially *Pichia pastoris*, glycoproteins with a reduced mannose content can be produced. The glycosylation pattern on the proteins so produced is also characteristic of mammalian glycoproteins.

According to the present invention, the nucleotide sequence encoding a Golgi mannosidase II can derive from any species. The Mannosidase II genes have been cloned from a number of mammalian species.

A preferred mannosidase II gene for use in the present vectors is from a mammalian species. An example of a mammalian mannosidase II gene is the human mannosidase II cDNA, as published in EMBL with Accession NO 31520 (SEQ ID NO: 34).

According to the present invention, the nucleotide sequence can also encode only a functional part of a mannosidase II. By "functional part" is meant a polypeptide fragment of a mannosidase II which substantially retains the enzymatic activity of the full-length protein. By "substantially" is meant that at least about 40%, or preferably, at least 50% or more of the enzymatic activity of the full-length mannosidase II is retained. Functional parts of a mannosidase II can be identified and made by those skilled in the art using a variety of techniques known in the art.

In a preferred embodiment of the present invention, the mannosidase II protein is engineered to include a Golgi localization signal such that the protein expressed in a methylotrophic yeast strain is targeted to the Golgi compartment and retains therein for function. The Golgi localization signals which can be used in connection with a mannosidase II are as described hereinabove in connection with GnTI, e.g., a peptide derived from the N-terminal part of the ScKre2.

The mannosidase II for use in the present invention can be further modified, e.g., by insertion of an epitope tag to which antibodies are available, such as Myc, HA, FLAG, and His6 tag, which are well-known in the art.

According to the present invention, the "knock-in" vectors can include either or both of a GnTI coding sequence and a mannosidase II coding sequence.

Vectors including two or more of α-1,2-mannosidase coding sequence, glucosidase II coding sequence, GnTI coding sequence and mannosidase II coding sequence are also provided by present invention.

Further according to the present invention, the nucleotide sequence encoding the enzyme to be expressed (e.g., an α-1,2-mannosidase or a functional part thereof, or a glucosidase II or a functional part thereof, a GnTI or a functional part thereof, or a mannosidase II or a functional part thereof) can be placed in an operable linkage to a promoter and a 3' termination sequence.

Promoters appropriate for expression of a protein in a methylotrophic yeast can include both constitutive promoters and inducible promoters. Constitutive promoters include, e.g., the *Pichia pastoris* glyceraldehyde-3-phosphate dehydrogenase promoter ("the GAP promoter") and the *Pichia pastoris* YPT1 promoter (Sears et al, Yeast 14: 783-790, 1998). Examples of inducible promoters include, e.g., the *Pichia pastoris* alcohol oxidase I promoter ("the AOXI promoter") (U.S. Pat. No. 4,855,231), the *Pichia pastoris* alcohol oxidase II ("the AOX2 promoter") (Ohi et al., Mol. Gen. Genet. 243: 489-499, 1994), or the *Pichia pastoris* formaldehyde dehydrogenase promoter ("the FLD promoter") (Shen et al. Gene 216: 93-102, 1998).

3' termination sequences are sequences 3' to the stop codon of a structural gene which function to stabilize the mRNA transcription product of the gene to which the sequence is operably linked, such as sequences which elicit polyadenylation. 3' termination sequences can be obtained from *Pichia* or other methylotrophic yeast. Examples of *Pichia pastoris* 3' termination sequences useful for the practice of the present invention include termination sequences from the AOX1 gene, p40 gene, HIS4 gene and FLD1 gene.

The vectors of the present invention preferably contain a selectable marker gene. The selectable marker may be any gene which confers a selectable phenotype upon a methylotrophic yeast strain and allows transformed cells to be identified and selected from untransformed cells. The selectable marker system may include an auxotrophic mutant methylotrophic yeast strain and a wild type gene which complements the host's defect. Examples of such systems include the *Saccharomyces cerevisiae* or *Pichia pastoris* HIS4 gene which may be used to complement his4 *Pichia* strains, or the *S. cerevisiae* or *Pichia pastoris* ARG4 gene which may be used to complement *Pichia pastoris* arg mutants, or the *Pichia pastoris* URA3 and ADE1 genes, which may be used to complement *Pichia pastoris* ura3 resp. ade1 mutants. Other selectable marker genes which function in *Pichia pastoris* include the $Zeo^R$ gene, the $G418^R$ gene, blastisidin resistance gene, and the like.

The vectors of the present invention can also include an autonomous replication sequence (ARS). For example, U.S. Pat. No. 4,837,148 describes autonomous replication sequences which provide a suitable means for maintaining plasmids in *Pichia pastoris*. The disclosure of U.S. Pat. No. 4,837,148 is incorporated herein by reference.

The vectors can also contain selectable marker genes which function in bacteria, as well as sequences responsible for replication and extrachromosomal maintenance in bacteria. Examples of bacterial selectable marker genes include ampicillin resistance ($Amp^r$, tetracycline resistance ($Tet^r$), neomycin resistance, hygromycin resistance and zeocin resistance ($Zeo^R$) genes.

According to the present invention, the nucleotide sequence encoding the protein to be expressed in a methylotrophic yeast can be placed in an integrative vector or a replicative vector (such as a replicating circular plasmid).

Integrative vectors are disclosed, e.g., in U.S. Pat. No. 4,882,279 which is incorporated herein by reference. Integrative vectors generally include serially arranged sequences of at least a first insertable DNA fragment, a selectable marker gene, and a second insertable DNA fragment. The first and second insertable DNA fragments are each about 200 nucleotides in length and have nucleotide sequences which are homologous to portions of the genomic DNA of the species to be transformed. A nucleotide sequence containing a structural gene of interest for expression is inserted in this vector between the first and second insertable DNA fragments whether before or after the marker gene. Integrative vectors can be linearized prior to yeast transformation to facilitate the integration of the nucleotide sequence of interest into the host cell genome.

Replicative and integrative vectors carrying one or more of an α-1,2-mannosidase coding sequence, a glucosidase II coding sequence, a GnTI coding sequence, and a mannosidase II coding sequence can be constructed by standard techniques known to one of ordinary skill in the art and found, for example, in Sambrook et al. (1989) Molecular Cloning: A Laboratory Manual, or any of a myriad of laboratory manuals on recombinant DNA technology that are widely available.

Preferred vectors of the present invention carrying an α-1,2-mannosidase expression sequence include pGAPZMF-ManHDEL, pGAPZMFManMycHDEL, pPICZBMFManMycHDEL, pGAPZmManHDEL, pGAPZmMycManHDEL, pPIC9 mMycManHDEL and pGAPZmMycManHDEL, which are further described in the Examples hereinbelow.

Preferred vectors of the present invention carrying a glucosidase II expression sequence include pGAPZAGLSII, pPICZAGLSII, pAOX2ZAGLSII, pYPTIZAGLSII, pGAPADE1glsII, pPICADE1glsII, pAOX2ADE1glsII, pYPTIADE1glsII, pGAPZAglsIIHDEL and pGAPADE1glsIIHDEL, which are further described in the Examples hereinbelow.

Preferred vectors of the present invention carrying a GlcNAc-transferase I expression sequence include pPIC6AKrecoGnTI, which are further described in the Examples hereinbelow.

Preferred vectors of the present invention carrying a mannosidase II expression sequence include pGAPKreManII, which are further described in the Examples hereinbelow.

In another aspect, the present invention provides inactivation vectors which, when introduced into a methylotrophic yeast strain, inactivate or disrupt a gene thereby facilitating the reduction in the glycosylation of glycoproteins produced in the methylotrophic yeast strain.

In one embodiment, the present invention provides a inactivation vector which, when introduced into a methylotrophic yeast strain, inactivates or disrupts the OCH1 gene.

The *S. cerevisiae* OCH1 gene has been cloned (Nakayama et al. *EMBO J.* 11: 2511-2519, 1992). It encodes a membrane bound α-1,6-mannosyltransferase, localized in the early Golgi complex, that is functional in the initiation of α-1,6-polymannose outer chain addition to the N-linked core oligosaccharide ($Man_5GlcNAc_2$ and $Man_8GlcNAc_2$) (Nakanishi-Shindo et al. *J. Biol. Chem.* 268: 26338-26345, 1993).

A *Pichia* sequence has been described in Japanese Patent Application No. 07145005 that encodes a protein highly homologous to the *S. cerevisiae* OCH1. For purpose of the present invention, this sequence is denoted herein as "the *Pichia* OCH1 gene". Those skilled in the art can isolate the OCH1 genes from other methylotrophic yeasts using techniques well known in the art.

According to the present invention, a disruption in the OCH1 gene of a methylotrophic yeast can result in either the production of an inactive protein product or no product. The disruption may take the form of an insertion of a heterologous DNA sequence into the coding sequence and/or the deletion of some or all of the coding sequence. Gene disruptions can be generated by homologous recombination essentially as described by Rothstein (in *Methods in Enzymology*, Wu et al., eds., vol 101:202-211, 1983).

To disrupt the OCH1 gene by homologous recombination, an OCH1 inactivation vector can be constructed in such a way to include a selectable marker gene. The selectable marker gene is operably linked, at both 5' and 3'end', to portions of the OCH1 gene of sufficient length to mediate homologous recombination. The selectable marker can be one of any number of genes which either complement host cell auxotrophy or provide antibiotic resistance, including URA3, ARG4, HIS4, ADE1, LEU2 and HIS3 genes. Other suitable selectable markers include the CAT gene, which confers chloramphenicol resistance on yeast cells, or the lacZ gene, which results in blue colonies due to the expression of active β-galactosidase. Linearized DNA fragments of an OCH1 inactivation vector are then introduced into host methylotrophic yeast cells using methods well known in the art. Integration of the linear fragments into the genome and the disruption of the OCH1 gene can be determined based on the selection marker and can be verified by, for example, Southern Blot analysis.

Alternatively, an OCH1 inactivation vector can be constructed in such a way to include a portion of the OCH1 gene to be disrupted, which portion is devoid of any OCH1 promoter sequence and encodes none or an inactive fragment of the OCH1 protein. By "an inactive fragment", it is meant a fragment of the OCH1 protein which has, preferably, less than about 10% and most preferably, about 0% of the activity of the full-length OCH1 protein. Such portion of the OCH1 gene is inserted in a vector in such a way that no known promoter sequence is operably linked to the OCH1 sequence, but that preferably a stop codon and a transcription termination sequence are operably linked to the portion of the OCH1 gene. This vector can be subsequently linearized in the portion of the OCH1 sequence and transformed into a methylotrophic yeast strain using any of the methods known in the art. By way of single homologous recombination, this linearized vector is then integrated in the OCH1 gene. Two OCH1 sequences are produced in the chromosome as a result of the single homologous recombination. The first OCH1 sequence is the portion of the OCH1 gene from the vector, which is now under control of the OCH1 promoter of the host methylotrophic yeast, yet cannot produce an active OCH1 protein as such OCH1 sequence codes for no or an inactive fragment of the OCH1 protein, as described hereinabove. The second OCH1 sequence is a full or mutated OCH1 coding sequence, which is not operably linked to any known promoter sequence and thus, no active messenger is expected to be formed for synthesis of an active OCH1 protein. Preferably, an inactivating mutation is introduced in the OCH1 sequence, to the 5' end of the site of linearization of the vector and to the 3' end of the translation initiation codon of OCH1. By "inactivating mutation" it is meant a mutation introducing a stop codon, a frameshift mutation or any other mutation causing a disruption of the reading frame, or a 5' truncation of the OCH1 reading frame. A preferred inactivating mutation is a point mutation. Preferably, by introduction of a stop codon at the amino acid 12 at the very 5' end of OCH1 as described in Example 8. Such mutation can be introduced into an OCH1 sequence using any of the site directed mutagenesis methods known in the art. Another inactivating mutation is 5' truncation of the open reading frame. Inactivating mutations as described above ensure that no functional OCH1 protein can be formed even if there exist some promoter sequences 5' to the OCH1 sequence in the inactivation vector.

Preferred OCH1 inactivation vectors of the present invention include pBLURA5'PpOCH1, pZ5'PpOCH1 Trunc and pZMFManHDEL5'PpOCH1 Mut, which are further described in the Examples hereinbelow.

If desired, one or more of an α-1,2-mannosidase expression sequence, a glucosidase expression sequence, a GnTI expression sequence, or a mannosidase II expression sequence can be carried on the same plasmid used to disrupt the OCH1 gene to create a "knock-in-and-inactivation" vector.

In a preferred embodiment, the vectors of the present invention include a sequence coding for an α-1,2-mannosidase or a functional part thereof, and a sequence which is capable of disrupting or inactivating the endogenous OCH1 gene or a functional part thereof. Such vector(s) is/are capable of expressing the α-1,2-mannosidase or the functional part, and is/are capable of disrupting the OCH1 gene in methylotrophic yeast, including *Pichia*, especially *Pichia pastoris*.

Preferred knock-in-and-inactivation vectors of the present invention include pZMFManHDEL5'PpOCH1Mut, which are further described in the Examples hereinbelow.

Additionally, any of the above-described vectors can further include a nucleotide sequence capable of expressing a glycoprotein of interest in a methylotrophic yeast strain, including *Pichia*, especially *Pichia pastoris*.

Another aspect of the present invention is directed to methods of modifying methylotrophic yeast strains to reduce or modify glycosylations, to a mammalian-like pattern, on proteins produced by the methylotrophic yeast strains. In accordance with the present methods, methylotrophic yeast strains are modified by transforming these yeast strains with one or more, i.e., at least one, knock-in and/or inactivation vectors of the present invention as described herein above.

Methylotrophic yeast strains which can be modified using the present methods include but are not limited to yeasts capable of growing on methanol, such as yeasts of the genera *Candida, Hansenula, Torulopsis*, and *Pichia*. A list of species which are exemplary of this class of yeasts can be found in C. Anthony (1982), *The Biochemistry of Methylotrophs,* 269. *Pichia pastoris, Pichia methanolica, Pichia anomola, Hansenula polymorpha* and *Candida boidinii* are examples of methylotrophic yeasts useful in the practice of the present invention. Preferred methylotrophic yeasts are of the genus *Pichia*. Especially preferred are *Pichia pastoris* strains GS115 (NRRL Y-15851); GS190 (NRRL Y-18014) disclosed in U.S. Pat. No. 4,818,700; PPF1 (NRRL Y-18017) disclosed in U.S. Pat. No. 4,812,405; PPY120H and YGC4; as well as strains derived therefrom.

Methylotrophic yeast strains which can be modified using the present methods also include those methylotrophic yeast strains which have been genetically engineered to express one or more heterologous glycoproteins of interest. The glycosylation on the heterologous glycoproteins expressed from these previously engineered strains can be reduced or modified to mammalian-like pattern by transforming such strains with one or more of the vectors of the present invention.

The vectors of the present invention can be introduced into the cells of a methylotrophic yeast strain using known methods such as the spheroplast technique, described by Cregg et al. 1985, or the whole-cell lithium chloride yeast transformation system, Ito et al. *Agric. Biol. Chem.* 48:341, modified for use in *Pichia* as described in EP 312,934. Other published methods useful for transformation of the plasmids or linear vectors include U.S. Pat. No. 4,929,555; Hinnen et al. *Proc. Nat. Acad. Sci. USA* 75:1929 (1978); Ito et al. *J. Bacteriol.* 153:163 (1983); U.S. Pat. No. 4,879,231; Sreekrishna et al. *Gene* 59:115 (1987). Electroporation and PEG1000 whole cell transformation procedures may also be used, as described by Cregg and Russel, *Methods in Molecular Biology: Pichia Protocols*, Chapter 3, Humana Press, Totowa, N.J., pp. 27-39 (1998).

Transformed yeast cells can be selected by using appropriate techniques including, but not limited, to culturing auxotrophic cells after transformation in the absence of the biochemical product required (due to the cell's auxotrophy), selection for and detection of a new phenotype, or culturing in the presence of an antibiotic which is toxic to the yeast in the absence of a resistance gene contained in the transformants. Transformants can also be selected and/or verified by integration of the expression cassette into the genome, which can be assessed by, e.g., Southern Blot or PCR analysis.

In one embodiment, a methylotrophic yeast strain is transformed with a vector which includes a nucleotide sequence coding for an α-1,2-mannosidase or a functional part thereof. The nucleotide sequence is capable of expressing the α-1,2-mannosidase or the functional part in the methylotrophic yeast strain, and is, preferably, integrated into the genome of the methylotrophic yeast strain.

The expression of an α-1,2-mannosidase introduced in a methylotrophic yeast strain can be verified both at the mRNA level, e.g., by Northern Blot analysis, and at the protein level, e.g., by Western Blot analysis. The intracellular localization of the protein can be analyzed by using a variety of techniques, including subcellular fractionation and immunofluorescence experiments. An ER localization of an α-1,2-mannosidase can be determined by co-sedimentation of this enzyme with a known ER resident protein (e.g., Protein Disulfide Isomerase) in a subcellular fractionation experiment. An ER localization can also be determined by an immunofluorescence staining pattern characteristic of ER resident proteins, typically a perinuclear staining pattern.

To confirm that an α-1,2-mannosidase or a functional part thereof expressed in a methylotrophic yeast strain has the expected mannose-trimming activity, both in vitro and in vivo assays can be employed. Typically, an in vitro assay involves digestion of an in vitro synthesized substrate, e.g., $Man_8GlcNAc_2$, with the enzyme expressed and purified from a methylotrophic yeast strain, and assessing the ability of such enzyme to trim $Man_8GlcNAc_2$ to, e.g., $Man_5GlcNAc_2$. Alternatively, the mannosidase activity in *Pichia* cell lysates can be assayed using a chromogenic substrate for the enzyme, such as DNP-α-D-mannopyranoside (T. Desmedt, N. Callewaert, R. Contreras and M. Claeyssens, Anal. Biochem., in press). In in vivo assays, the α-1,2-mannosidase or a functional part thereof is co-expressed in a methylotrophic yeast with a glycoprotein known to be glycosylated with N-glycans bearing terminal α-1,2-linked mannose residues in such yeast. The enzymatic activity of such an α-1,2-mannosidase or a functional part thereof can be measured based on the reduction of the number of α-1,2-linked mannose residues in the structures of the N-glycans of the glycoprotein. In both in vitro and in vivo assays, the composition of a carbohydrate group can be determined using techniques that are well known in the art and are illustrated in the Examples hereinbelow.

In another embodiment, a methylotrophic yeast strain is transformed with a vector which includes a nucleotide sequence coding for a glucosidase II or a functional part thereof. The nucleotide sequence is capable of expressing the glucosidase II or the functional part in the methylotrophic yeast strain, and is, preferably, integrated into the genome of the methylotrophic yeast strain.

The expression of Glucosidase II introduced in a methylotrophic yeast strain can be verified both at the mRNA level, e.g., by Northern Blot analysis, and at the protein level, e.g., by Western Blot analysis. The intracellular localization of the protein can be analyzed by using a variety of techniques, including subcellular fractionation and immunofluorescence experiments.

The enzymatic activity of a glucosidase II or a functional part thereof expressed in a transformed methylotrophic yeast strain can be assessed using a variety of assays. For example, methylotrophic yeast cells transformed with a sequence encoding a glucosidase II or a functional part thereof can be set to grow on solid medium containing a substrate of the glucosidase, e.g., 5-bromo-4-chloro-3-indolyl-α-D-glucopyranoside or 4-MU-α-D-Glc. When the enzyme is expressed by the *Pichia* and secreted extracellularly, the substrate is acted upon by the enzyme, giving rise to detectable signals around the colonies such as blue color or fluorescent glow. Alternatively, liquid culture medium containing the expressed protein molecules can be collected and incubated in test tubes with a substrate, e.g., p-nitrophenyl-α-D-glucopyranoside or 4-MU-α-D-Glc. The enzymatic activity can be determined by measuring the specific product released. Moreover, in vivo assays can be employed, where a glucosidase II is co-expressed in yeast with a glycoprotein known to be N-glycosylated with glucose residues, e.g., influenza neuraminidase. The enzymatic activity of the glucosidase II can be measured based on the reduction of the glucose content in the sugar chain(s) of the glycoprotein.

In one embodiment, a methylotrophic yeast strain, such as *Pichia* and particularly *Pichia pastoris*, is transformed with a vector which includes a nucleotide sequence coding for GlcNAc-transferase I or a functional part thereof. The nucleotide sequence is capable of expressing the GlcNAc-transferase I or the functional part in the methylotrophic yeast strain, and is, preferably, integrated into the genome of the methylotrophic yeast strain.

The expression of GlcNAc-transferase I introduced in a methylotrophic yeast strain can be verified both at the mRNA level, e.g., by Northern Blot analysis, and at the protein level, e.g., by Western Blot analysis. The intracellular localization of the protein can be analyzed by using a variety of techniques, including subcellular fractionation and immunofluorescence experiments.

To confirm that GlcNAc-transferase I or a functional part thereof expressed in a methylotrophic yeast strain has the expected $GlcNAcMan_5GlcNAc_2$, both in vitro and in vivo assays can be employed. In both in vitro and in vivo assays, the composition of a carbohydrate group can be determined using techniques that are well known in the art and are illustrated in Example 6 hereinbelow.

In another embodiment, a methylotrophic yeast strain, such as *Pichia* and particularly *Pichia pastoris*, is transformed with a vector which includes a nucleotide sequence coding for a mannosidase II or a functional part thereof. The nucleotide sequence is capable of expressing the mannosidase II or the functional part in the methylotrophic yeast strain, and is, preferably, integrated into the genome of the methylotrophic yeast strain.

The expression and enzymatic activity of a mannosidase II or a functional part thereof expressed in a transformed methylotrophic yeast strain can be assessed using a variety of techniques and assays, such as gemomic analysis and glycan assay.

In still another embodiment of the present invention, a methylotrophic yeast strain is transformed with an OCH1 inactivation vector. As a result of the transformation and integration of the vector, the endogenous genomic OCH1 gene in the yeast strains is disrupted.

In still another embodiment of the present invention, a methylotrophic yeast strain is transformed with a knock-in-and-inactivation vector, such as an α-1,2-mannosidase-disrupted OCH1 vector. As a result of the transformation and integration of the vector, the genomic OCH1 gene in the yeast strains is disrupted and a potent α-1,2-mannosidase is expressed in the yeast.

In a further embodiment of the present invention, a methylotrophic yeast strain, such as *Pichia* and particularly *Pichia pastoris*, is transformed with one or more of an α-1,2-mannosidase expression vector, a glucosidase II expression vector, a GnTI expression vector, a mannosidase II expression vector, an OCH1 inactivation vector or an α-1,2-mannosidase-disrupted OCH1 knock-in-and-inactivation vector. Such modification can be achieved by serial, consecutive transformations, i.e., introducing one vector at a time, or alternatively by co-transformation, i.e., introducing the vectors simultaneously.

Preferably, a strain transformed with a vector encoding GnTI is also transformed with a vector encoding α-1,2-mannosidase, either simultaneously or sequentially. Also preferably, a strain transformed with a vector encoding mannosidase II is also transformed with a vector encoding GnTI and α-1,2-mannosidase.

The modified methylotrophic yeast strains described hereinabove can be further modified if desired. For example, additional disruption of genes encoding any other yeast mannosyltransferases can be made. Genes encoding mammalian enzymes can also be introduced to produce glycoproteins having hybrid- or complex-type N-glycans, if desired.

Methylotrophic yeast strains which are modified by using the present methods, i.e., by transforming with one or more of the vectors of the present invention, form another embodiment of the present invention.

It should be understood that certain aspects of the present invention, especially the introduction of an intracellularly expressed α-1,2-mannosidase activity, are also useful to obtain a reduced or modified glycosylation of the O-linked glycans on glycoproteins produced in a methylotrophic yeast, as it is known in the art that these O-linked glycans consist mainly of α-1,2-linked mannose residues. O-linked glycans as used herein refer to carbohydrate structures linked to serine or threonine residues of glycoproteins.

A further aspect of the invention is directed to methods of producing a glycoprotein with reduced or modified glycosylation, preferably a mammalian-like pattern of glycosylation with hybrid or complex glycans, in a methylotrophic yeast, especially a glycoprotein heterologous to the methylotrophic yeast.

"A glycoprotein" as used herein refers to a protein which, in methylotrophic yeasts, is either glycosylated on one or more asparagines residues having the consensus sequence "Asn-Xaa-Thr" or "Asn-Xaa-Ser" (where Xaa is any amino acid except proline), or on one or more serine (or threonine) residues, or on both asparagines and serine (or threonine) residues.

The term "reduced or modified glycosylation" refers to a reduced size of the carbohydrate moiety on the glycoprotein, particularly with fewer mannose residues or modified to desired, such as mammalian-like, complex glycans on the glycoprotein, when the glycoprotein is expressed in a methylotrophic yeast strain which has been modified in accordance with the present invention, as compared to a wild type, unmodified strain of the methylotrophic yeast.

In accordance with the present invention, the production of a glycoprotein of interest with reduced or modified glycosylation can be achieved in a number of ways. A nucleotide sequence capable of expressing a glycoprotein can be introduced into a methylotrophic yeast strain which has been previously modified in accordance with the present invention, i.e., a strain transformed with one or more of the vectors of the present invention and capable of producing glycoproteins with reduced and/or modified glycosylation. Alternatively, a methylotrophic yeast strain which has already been genetically engineered to express a glycoprotein can be transformed with one or more of the vectors of the present invention. Otherwise, if a methylotrophic yeast strain does not express a glycoprotein of interest, nor is the strain transformed with any of the vectors of the present invention, such yeast strain can be transformed, either consecutively or simultaneously, with both a nucleotide sequence capable of expressing the glycoprotein and one or more vectors of the present invention. Additionally, a methylotrophic yeast strain can be transformed with one or more of the present knock-in and/or inactivation and/or knock-in-and-inactivation vectors which also include a nucleotide sequence capable of expressing a glycoprotein in the methylotrophic yeast strain.

The nucleotide sequence capable of expressing a glycoprotein in a methylotrophic yeast can be made to include from 5' to 3', a promoter, a sequence encoding the glycoprotein, and a 3' termination sequence. Promoters and 3' termination sequences which are suitable for expression of a glycoprotein can include any of those promoters and 3'-termination sequences described hereinabove.

The nucleotide sequence for expression of a glycoprotein can include additional sequences, e.g., signal sequences coding for transit peptides when secretion of a protein product is desired. Such sequences are widely known, readily available and include *Saccharomyces cerevisiae* alpha mating factor prepro (αmf), *Pichia pastoris* acid phosphatase (PHO1) signal sequence and the like.

The nucleotide sequence for expression of a glycoprotein can be placed on a replicative vector or an integrative vector. The choice and construction of such vectors are as described hereinabove.

The nucleotide sequence capable of expressing a glycoprotein can be carried on the same replicative plasmid as a plasmid carrying any number (at least one) of, an α-1,2-mannosidase, a glucosidase II, a GnTI, a mannosidase II, an inactived OCH1 and an α-1,2-mannosidase-inactivated OCH1 expression unit. Alternatively, the nucleotide sequence containing the glycoprotein coding sequence is carried on a separate plasmid or integrated into the host genome.

Glycoproteins produced can be purified by conventional methods. Purification protocols can be determined by the nature of the specific protein to be purified. Such determination is within the ordinary level of skill in the art. For example, the cell culture medium is separated from the cells and the protein secreted from the cells can be isolated from the medium by routine isolation techniques such as precipitation, immunoabsorption, fractionation or a variety of chromatographic methods.

Glycoproteins which can be produced by the methods of the present invention include, e.g., *Bacillus amyloliquefaciens* α-amylase, *S. cerevisiae invertase, Trypanosoma cruzi* trans-sialidase, HIV envelope protein, influenza virus A haemagglutinin, influenza neuraminidase, Bovine herpes virus type-1 glycoprotein D, human angiostatin, human B7-1, B7-2 and B-7 receptor CTLA-4, human tissue factor, growth factors (e.g., platelet-derived growth factor), tissue plasminogen activator, plasminogen activator inhibitor-I, urokinase, human lysosomal proteins such as α-galactosidase, plasminogen, thrombin, factor XIII and immunoglobulins. For additional useful glycoproteins which can be expressed in the genetically engineered *Pichia* strains of the present invention, see Bretthauer and Castellino, *Biotechnol. Appl. Biochem.* 30: 193-200 (1999), and Kukuruzinska et al. *Ann Rev. Biochem.* 56: 915-44 (1987).

Glycoproteins produced by using the methods of the present invention, i.e., glycoproteins with reduced or modified glycosylation, are also part of the present invention.

Still another aspect of the present invention provides kits which contain at least one of the knock-in vectors, inactivation vectors, or knock-in-and-inactivation vectors of the present invention described above. More particularly, a kit of the present invention contains at least one of the following vectors: a vector capable of expressing an α-mannosidase I in a methylotrophic yeast, a vector capable of expressing a glucosidase II in a methylotrophic yeast, a vector capable of expressing a GnTI in a methylotrophic yeast, a vector capable of expressing a mannosidase II in a methylotrophic yeast and a vector capable of inactivating the OCH1 gene in a methylotrophic yeast.

The kit can also include a nucleotide sequence which encodes and is capable of expressing a heterologous glycoprotein of interest. Such nucleotide sequence can be provided in a separate vector or in the same vector which contains sequences for knocking-in or inactivating as described hereinabove.

In addition, the kit can include a plasmid vector in which a nucleotide sequence encoding a heterologous protein of interest can be subsequently inserted for transformation into and expression in a methylotrophic yeast. Alternatively, the knock-in, inactivation or knock-in-and-inactivation vectors in the kits have convenient cloning sites for insertion of a nucleotide sequence encoding a heterologous protein of interest.

The kit can also include a methylotrophic yeast strain which can be subsequently transformed with any of the knock-in, inactivation or knock-in-and-inactivation vectors described hereinabove. The kit can also include a methylotrophic yeast strain which has been transformed with one or more of the knock-in, inactivation or knock-in-inactivation vectors. Furthermore, the kit can include a methylotrophic yeast strain which has been transformed with a nucleotide sequence encoding and capable of expressing a heterologous glycoprotein of interest.

The present invention is further illustrated by the following examples.

Example 1

Introduction of α-1,2-Mannosidase to the ER-Golgi Border 1.1 Plasmids

| Plasmid | Promoter | Enzyme | Tag |
|---|---|---|---|
| pGAPZMFManHDEL | GAP | *T. reesei* α-1,2-mannosidase | — |
| pGAPZMFManMycHDEL | GAP | *T. reesei* α-1,2-mannosidase | Myc |
| pPICZBMFManMycHDEL | AOX1 | *T. reesei* α-1,2-mannosidase | Myc |
| pGAPZMFmManHDEL | GAP | mouse mannosidase IB catalytic domain | — |
| pGAPZMFmMycManHDEL | GAP | mouse mannosidase IB catalytic domain | Myc |

The *Trichoderma reesei* α-1,2-mannosidase gene has been isolated and described by Maras et al. (*J. Biotechnol.* 77; 255-263, 2000). The sequence of this gene is available at NCBI Genbank under Accession No. AF212153. A construction fragment was generated by PCR using the pPIC9MFmanase plasmid (same as pPP1MFmds1 described by Maras et al. (2000)) as the template and using the following oligonucleotide primers: 5'-GACTGGTTCCAATTGACAAGC-3' (SEQ ID NO:2) and 5'-AGTCTAGATTACAACTCGTCGTGAGCAAGGTGGCCGCCCCG TCG-3' (SEQ ID NO:3). The resulting product contained the 3' end of the *Pichia pastoris* AOXI promoter, the prepro-signal sequence of the *S. cerevisiae* α-mating factor, the open reading frame of the *Trichoderma reesei* α-1,2-mannosidase cloned in frame with the signal sequence, the coding sequence for HDEL, a stop codon and an Xba I restriction site. This fragment was digested with Eco RI and Xba I, removing the 5' sequences up to the mannosidase ORF, and then cloned into the vector pGAPZαA (Invitrogen, Baarn, The Netherlands) which had been digested with Eco RI and Xba I, thus restoring the fusion with the *S. cerevisiae* α-mating factor signal sequence. The resulting plasmid was named pGAPZMFManHDEL and is graphically depicted in FIG. 1. The ORF sequence of the MFManHDEL fusion in pGAPZMFManHDEL is set forth in SEQ ID NO: 14.

In order to introduce the coding sequence for a c-Myc tag between the catalytic domain and the HDEL-signal, the 3' end of the ORF of *T. reesei* α-1,2-mannosidase was PCR-amplified using a sense primer 5'-CCATTGAGGACGCATGCCGCGCC-3' (SEQ ID NO: 4) (containing an Sph I restriction site) and an antisense primer GTATCTAGATTACAACTCGTCGTGCAGATCCTCTTCTGAGATGAGTTTTTGT TCAGCAAGGTGGCCGCCCCGTCGTGATGATGAA (SEQ ID NO: 5) (containing the coding sequences of the c-Myc tag and the HDEL signal, followed by a stop codon and an Xba I restriction site). The resulting PCR product was digested with Sph I and Xba I, purified by agarose gel electrophoresis and inserted into pGAPZMFManHDEL which had been cut with the same restriction enzymes, resulting in plasmid pGAPZMFManMycHDEL. To put the ORF of pGAPZMFManMycHDEL under the control of the inducible AOXI promoter, the entire ORF was liberated from pGAPZMFManMycHDEL with Bst BI and Xba I, and cloned in pPICZB (Invitrogen, Baarn, The Netherlands), resulting in pPICZBMFManMycHDEL.

Cloning of the mouse mannosidase IB catalytic domain with concomitant addition of the coding sequence for a C-terminal HDEL-tag was done by PCR on a mouse cDNA library (mRNA isolated from the L929 cell line induced with cycloheximide and mouse Tumor Necrosis Factor. Average insert length of the cDNA library was 2000 bp). The PCR oligonucleotide primers used were: 5'AACTCGAGATGGACTCTTCAAAACACAAACGC3' (SEQ ID NO: 6) and 5'TTGCGGCCGCTTACAACTCGTCGTGTCGGACAGCAGGATTACCTGA3' (SEQ ID NO: 7). The product contained a 5' Xho I site and the coding sequence for C-terminal HDEL-site, followed by a stop codon and a Not I site at the 3' end. The product was cloned in pGAPZαA via the Xho I/Not I sites in the PCR product and the vector, resulting in an in frame fusion of the mouse mannosidase catalytic domain with the *S. cerevisiae* α-mating factor signal sequence. The sequence of the entire open reading frame generated is set forth in SEQ ID NO: 15.

1.2 Yeast Transformation and Genomic Integration

TABLE 2

| Parental strain | DNA transformed |
|---|---|
| GS115 (his4) | pGAPZMFManHDEL<br>pPIC9MFManHDEL<br>pPIC9mManHDEL<br>pPIC9mMycManHDEL<br>pGAPZmManHDEL<br>pGAPZmMycManHDEL |
| GS115 (his4 complemented by pPIC9InfluenzaHA) | pGAPZMFManHDEL<br>pGAPZmManHDEL<br>pGAPZmMycManHDEL |
| PPY120H (his4 complemented by pPIC9sOCH1) | pGAPZMFManMycHDEL<br>pPICZBMFManMycHDEL |
| yGC4 (his4 arg1 ade2 ura3 complemented by pBLURA5'PpOCH1) | pPIC9InfluenzaNeuraminidase<br>pGAPZMFManHDEL<br>pPIC9Glucoseoxidase |

All transformations to *Pichia pastoris* were performed with electroporation according to the directions of Invitrogen. Transformants of vectors carrying the Zeocin resistance gene were selected on YPD containing 100 μg/ml Zeocine (Invitrogen, Baarn, the Netherlands) and 1M sorbitol. Selection of transformants of pPIC9 derivatives was done on minimal medium lacking histidine and containing 1M sorbitol. Genomic integration of the expression cassettes was verified using PCR on genomic DNA purified from the *Pichia* strains using the Yeast Miniprep method (Nucleon). In all cases concerning the *Trichoderma reesei* gene fusions, the primers used were the sense primer 5'-CCATTGAGGACGCATGCCGCGCC-3' (SEQ ID NO: 8), which annealed to the 3' half of the mannosidase ORF, and the aritisense primer 3' AOXI 5'-GCAAATGGCATTCTGACATCCT-3' (SEQ ID NO: 9), which annealed to the AOXI transcription terminator that was present in all our expression constructs. For the control of genomic integration of the mouse mannosidase transgenes, PCR was done using the sense primer 5'GAP 5'GTCCCTATTTCAATCAATTGAA3' (SEQ ID NO: 10, annealing to the GAP promoter or 5'AOXI 5'GACTGGTTCCAATTGACAAGC3' (SEQ ID NO:11), annealing to AOXI promoter), and the antisense primer 3'AOXI (above). For the expression constructs containing a Myc tagged *Trichoderma reesei* α-1,2-mannosidase expression unit, further evidence for genomic integration was obtained using Southern Blotting with the entire MFManMycHDEL ORF ($^{32}P$ labelled using HighPrime, Boehringer Mannheim) as a probe.

1.3 Expression of α-1,2-mannosidase

Measurement of Intracellular Class I Mannosidase Activity.

Lysate preparation: yeast cells (*P. pastoris* GS115 wild type and clones of the same strain transformed with pGAPZMFManHDEL (Callewaert et al., 2001)) were grown in YPD to an $OD_{600}$=2-2.5, in a volume of 10 ml. After pelleting of the cells by centrifugation at 3000×g for 5 min, the cells were washed twice in sterile water and subsequently resuspended in 500 μl of the lysis buffer: 100 mM NaAc, pH 5, containing EDTA-free Complete protease inhibitor cocktail (Boehringer) in the dilution specified by the supplier and 1% Triton X100. After transfer of the cell suspension to a 1.5 ml eppendorf tube, glass beads were added to the meniscus of the tube and the tubes were shaken in a Retsch cell disrupter for 5×1 min., with 1 min. pauses on ice in between the vortex steps, to avoid over-heating. Finally, the cell debris was precipitated by centrifugation at 5000 rpm in a microcentrifuge and the supernatant was used for protein concentration determination (Pierce BCA kit, the sample was diluted tenfold prior to measurement in order to lower the concentration of Triton, which may interfere with this protein concentration measurement procedure). The protein concentration in lysates obtained as described above should average about 3.5 mg/ml.

Figure 31:
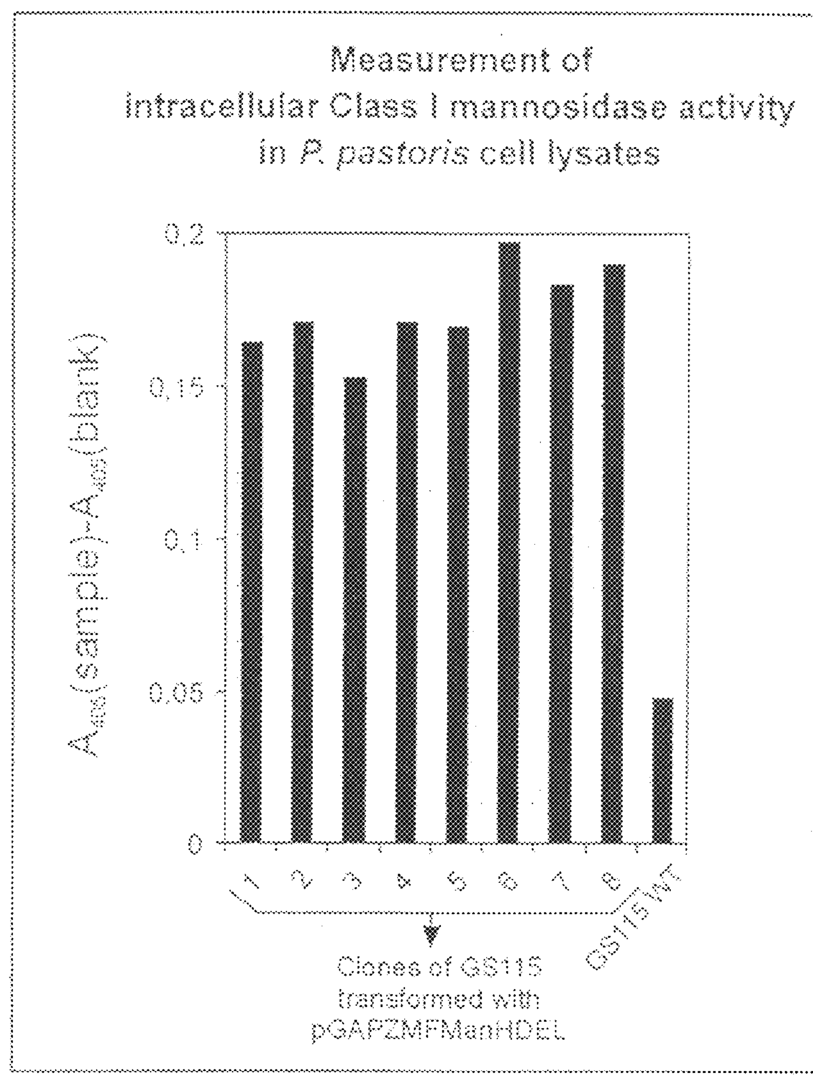
FIG. 31 depicts a measurement of intracellular class I mannosidase activity in *Pichia pastoris* cells transformed with pGAPZMFManHDEL. The hydrolysis of DNP-Man was measured by spectrophotometry at 405 nm. In all transformants, a three- to four fold increase in activity was measured as compared to the GS115 parent strain.

Activity measurement: samples containing 375 μg protein were volume-adjusted to 150 μl with 100 mM NaAc, pH 5 and incubated at 50° C. for 1 h. This denatured most of the proteins in the preparation, yielding a milky white appearance of the solution after incubation. The *Trichoderma reesei* α-1,2-mannosidase was heat-stable under these conditions. The denatured proteins were precipitated by centrifuging at full speed for 10 min in a microcentrifuge (20000×g). The supernatant was transferred to wells in a standard microtiter plate. Subsequently, 5011 of a working solution was added, containing 250 μM swainsonine (inhibitor for a specific class II mannosidases), 4 mM DNP-mannose and 2 mM $CaCl_2$. As blank control, 150 μl of the lysis buffer was used, supplemented with 50 microliter of the working solution. After incubation at 50° C. for 1 h, the absorbance was measured at 405 nm in a standard microtiter plate reader. The reported values in FIG. 31 are blank-subtracted.

Expression of an α-1,2-Mannosidase in GS115 strains expressing influenza virus haemagglutinin was verified by qualitative Northern blot. Expression of an α-1,2-Mannosidase in PPY120H strains was verified by anti-Myc Western blot.

Qualitative Northern Blot—

Total RNA was purified from *Pichia* strains and the yield was determined spectrophotometrically. Northern blotting was performed according to standard procedures and an estimate of the quantity of RNA loaded was made using methylene blue staining of the blot, visualizing the rRNA bands. The blot was probed with a ClaI/NarI fragment of the mannosidase, labelled with $^{32}P$ using HighPrime (Boehringer Mannheim).

SDS-PAGE and Western Blotting—

Total yeast cell lysates were prepared by washing the cells twice with PBS, followed by boiling in 1 volume of 2× concentrated Laemmli loading buffer for 5 min. The lysate was spun briefly in a microcentrifuge prior to gel loading and only the supernatant was loaded. For the analysis of proteins secreted into the growth media, the proteins were precipitated from 200 μl of these media using desoxycholate/trichloroacetic acid according to standard procedures. The pellet was redissolved in 2× concentrated Laemmli loading buffer and the solutions were pH-corrected using Tris. SDS-PAGE was performed and followed by semidry electroblotting to nitrocellulose membranes. For Western Blotting, the 9E10 anti-Myc and the anti-HA mouse monoclonals (Boehringer Mannheim) were used at a concentration of 1 μg/ml, and the rabbit anti-PDI antiserum (Stressgen) was used at a dilution of 1/500. The secondary antibodies were goat anti-mouse IgG conjugated to alkaline phosphatase for the monoclonals and goat anti-rabbit IgG conjugated to peroxidase for the polyclonal (secondary antibodies from Sigma). Detection was performed using the NBT/BCIP system for alkaline phosphatase and the Renaissance substrate (NENBiosciences) for peroxidase. Imaging of the latter blot result was done on a Lumilager imaging device (Boehringer Mannheim).

Figure 4:
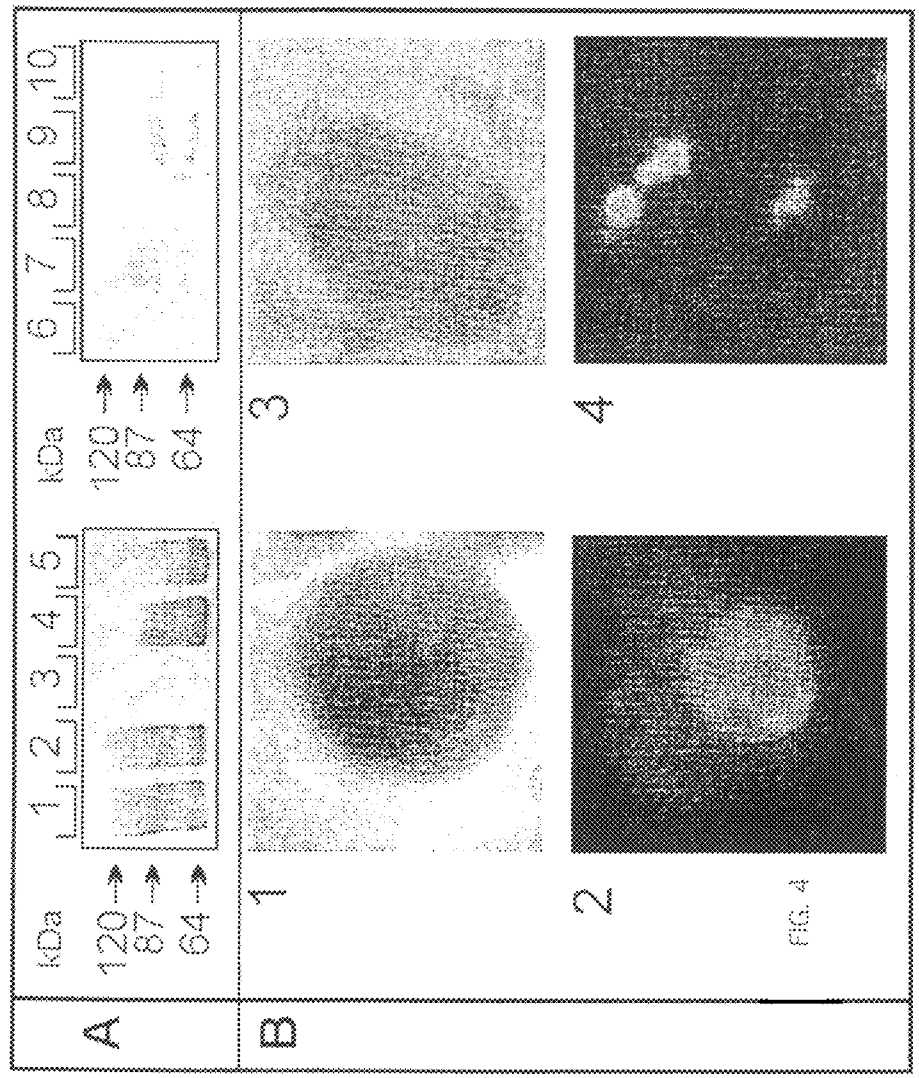
FIG. 4 demonstrates the intracellular localization of the MycHDEL-tagged *Trichoderma reesei* α-1,2-mannosidase and indicates ER-targeting by immunofluorescence analysis. Panel A Western blotting. Yeast strains were grown in 10 ml YPG cultures to an $OD_{600}$=10, diluted fivefold and grown in YPM for 48 h. 1/50th of the culture medium and 1/65th of the cells were analysed by SDS-PAGE and Western blotting with the mouse monoclonal 9E10 anti-Myc antibody. The position of molecular weight marker proteins are indicated with arrows. Lanes 1-5: cellular lysates. 1 and 2: pGAPZMFManMycHDEL transformants. 3: non-transformed PPY120H (negative control). 4 and 5: pPICZBMFManMycHDEL transformants. Lanes 6-10: culture media. 6: non transformed PPY120H (negative control). 7 and 8: pGAPZMFManMycHDEL transformants. 9 and 10: pPICZBMFManMycHDEL transformants. Panel B Immunofluorescence microscopy. 1: phase contrast image of a *P. pastoris* cell (strain PPY12OH transformed with pGAPZMFManHDEL) at 1000× magnification. The nucleus is visible as an ellipse in the lower right quadrant of the cell. 2: same cell as in 1, but in fluorescence microscopy mode to show localization of the *T. reesei* mannosidase-Myc-HDEL protein. The protein is mainly localized in a circular distribution around the nucleus (nuclear envelope), which is typical for an endoplasmic reticulum steady-state distribution. 3: phase contrast image of a *P. pastoris* cell (strain PPY120H transformed with pGAPZMFManHDEL) at 1000× magnification. 4: same cell in fluorescence microscopy to show localization of the Golgi marker protein OCH1-HA in *P. pastoris* strain PPY120H. The dot-like distribution throughout the cytoplasm, with 3-4 dots per cell is typical for cis-Golgi distribution in *P. pastoris.*

The results shown in FIG. 4 indicated that the great majority of the HDEL-tagged protein was retained intracellularly, both when expressed from the strong constitutive GAP promoter and when expressed from the strong inducible AOXI promoter.

1.4 Localization of α-1,2-Mannosidase

Isopycnic Sucrose Density Gradient Centrifugation—

To determine the localization of the HDEL-tagged mannosidase, subcellular fractionation was carried out using cells expressing the mannosidase-Myc-HDEL from the strong constitutive GAP promoter.

Briefly, 0.5 g of wet weight yeast cells were lysed using 4×1 min vortexing with 4.5 g glass beads in 1 ml lysis-buffer (50 mM Tris-HCL pH 7.5 containing 0.6 M sorbitol, 10 mM β-mercaptoethanol and 5 mM $MgCl_2$). Between vortexing periods, the mixture was placed on ice for 5 min. The supernatant was collected and the glass beads were washed once with lysis-buffer, and the supernatant of this washing step was added to the first supernatant. This lysate was subjected to a differential centrifugation procedure. The P10000 pellet was solubilized in 0.5 ml of a 60% sucrose solution in lysis buffer. This solution was placed at the bottom of an Ultraclear ultracentrifuge tube (Beckman) of 14×89 mm. Subsequently, 1.5 ml each of sucrose solutions of 55, 50, 45, 42.5, 40, and 37.5% were carefully layered over each other. The tube was filled to the edge with 35% sucrose. Isopycnic sucrose gradient centrifugation was performed for 14 h at 180,000 g in a Beckman SW 41 rotor in a Beckman Model L8-70 preparative ultracentrifuge. After completion, 1 ml fractions were collected from the top and partially dialysed from excess sucrose, evaporated to dryness in a vacuum centrifuge. After redissolving the pellet in Laemmli buffer, the samples were subjected to SDS-PAGE in triplicate and the Western blots were treated with anti-HA, anti-Myc or anti-PDI ("PDI" for Protein Disulfide Isomerase), respectively.

Figure 5:
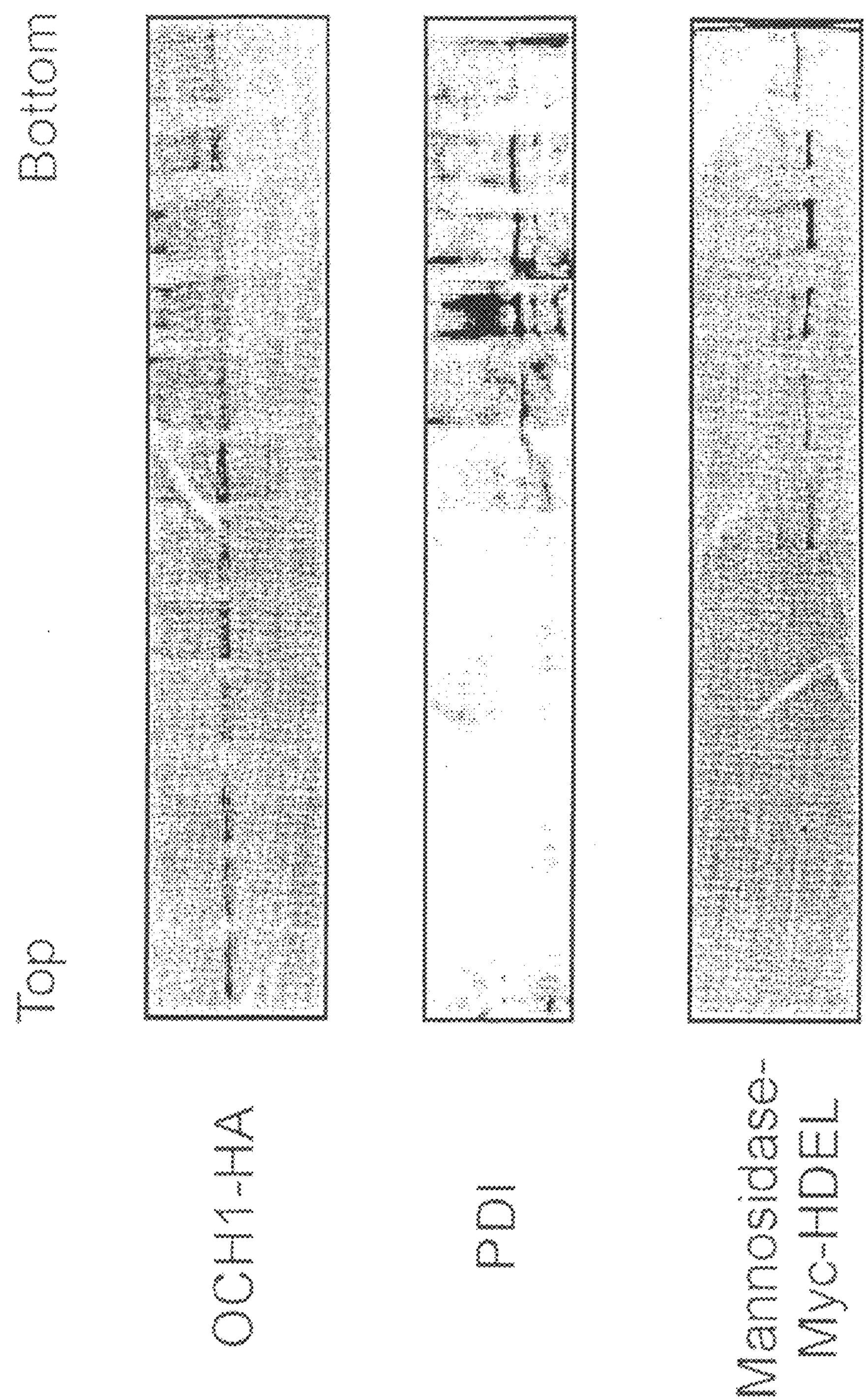
FIG. 5 depicts the co-sedimentation of mannosidase-MycHDEL with Protein Disulfide Isomerase in sucrose density gradient centrifugation. The top panel shows the distribution over the different fractions of the sucrose gradient of the OCH1-HA Golgi marker protein. The middle panel shows this distribution for the Protein Disulfide Isomerase endoplasmic reticulum marker protein. Finally, the bottom panel shows the distribution of the MycHDEL-tagged *Trichoderma reesei* α-1,2-mannosidase over the same fractions. It is concluded that the mannosidase-MycHDEL almost exactly matches the distribution of the ER marker PDI and thus mainly resides in the ER of the *Pichia pastoris* yeast cells.

The results illustrated almost exact cosedimentation of the MFManMycHDEL protein with the Protein Disulfide Isomerase marker protein (which is also targeted with a HDEL signal sequence) (FIG. 5). In the same assay, the HA-tagged OCH1 was distributed over the whole gradient, with the highest abundance in fractions having a density lower than that of the fractions containing the mannosidase and the PDI. This result indicated that the mannosidase was targeted to the expected location (the ER-Golgi boundary) by the addition of an HDEL signal. In contrast, the mannosidase without HDEL, expressed from inducible alcohol oxidase I promoter (which was of comparable strength as the GAP promoter), was secreted at a high level of about 20 mg/l.

Immunofluorescence Microscopy—

To confirm the correct targeting of the mannosidase-Myc-HDEL, an immunofluorescence microscopy experiment was performed.

Briefly, yeast cultures were grown to $OD_{600}$ in YPD (for pGAPZMFManMycHDEL) or in YMP following a YPGlycerol growth phase for pPICZBMFManMycHDEL. Formaldehyde was added to the yeast cultures to a final concentration of 4% and incubated for 10 min at room temperature. Cells were pelleted and resuspended in 50 mM potassium phosphate buffer pH 6.5 containing 1 mM $MgCl_2$ and 4% formaldehyde and incubated for 2 h at room temperature. After pelleting, the cells were resuspended to an $OD_{600}$=10 in 100 mM potassium phosphate buffer pH 7.5 containing 1 mM $MgCl_2$ and EDTA-free Complete™ protease inhibitor cocktail (Boehringer Mannheim). To 100 μl of cell suspension, 0.6 μl of β-mercaptoethanol and 20 μl of 20,000 U/ml Zymolyase 100T (ICN) were added, followed by a 25 minute incubation with gentle shaking. The cells were washed twice in the incubation buffer and added to poly-lysine coated cover slips (these are prepared using adhesive rings normally in use for reinforcing perforations in paper). Excess liquid was blotted with a cotton swab and the cells were allowed to dry at 20° C. All blocking, antibody incubation and washing steps are performed in PBS containing 0.05% bovine serum albumin. Primary antibodies are used at 2 μg/μl and secondary antibodies conjugated to fluorophores (Molecular probes) were used at 5 μg/μl. The nucleus was stained with the nucleic acid stain HOECHST 33258. After fixation and cell wall permeabilization, the integrity of the yeast cell morphology was checked in phase contrast microscopy and after immunostaining, the slides were examined under a Zeiss Axiophot fluororesensce microscope equipped with a Kodak digital camera. Images were processed using Macprobe 4.0 software and prepared with Corel Photopaint 9.0.

The Golgi marker protein OCH1-HA gave the typical Golgi staining pattern described in the literature (speckle-like staining). Staining with the 9E10 monoclonal anti-Myc antibody, recognizing mannosidase-Myc-HDEL, gave a perinuclear staining pattern with some disparate staining in the cytoplasm, highly indicative for an ER targeting (FIG. 4).

Based on the foregoing experiments, it is concluded that the *Trichoderma reesei* mannosidase-Myc-HDEL was targeted to the ER-Golgi boundary.

Example 2

Co-expression of Mannosidase-HDEL with Recombinant Glycoproteins

Co-Expression of Mannosidase-HDEL with the *Trypanosoma cruzi* Trans-Sialidase

The cloning of a *Trypanosoma cruzi* trans-sialidase gene coding for an active trans-sialidase member without the C-terminal repeat domain has been described by Laroy et al. (*Protein Expression and Purification* 20: 389, 2000) which is incorporated herein by reference. The sequence of this *Trypanosoma cruzi* trans-sialidase gene is available through NCBI Genbank under the Accession No. A3276679. For expression in *P. pastoris*, the entire gene was cloned in pHILD2 (Invitrogen, San Diego, Calif.), creating pHILD2-TS. To allow better secretion, pPIC9-TS was created in which trans-sialidase was linked to the prepro secretion signal of the yeast α-mating factor. Plasmids pPIC9-TSE and pCAGGS-prepro-TSE were created where the epitope E-tag was added to the C-terminal of the trans-sialidase to allow easy detection and purification. The construction of pHILD2-TS, pPIC9-TSE and pCAGGS-prepro-TSE has been described by Laroy et al. (2000), incorporated herein by reference. The vectors used in the construction were made available through *Belgian Co-Ordinated Collections of Micro-Organisms* for pCAGGS (No. LMBP 2453), Invitrogen, San Diego, Calif. for pHILD2 and pPIC9, and Pharmacia Biotech for pCANTAB-5E.

Plasmid pPIC9-TSE was linearized with SstI and was transformed into *P. pastoris* GS115 (his4) strain by electroporation according to the manufacturer's instructions (Invitrogen). One of the transformants was further transformed with plasmid pGAPZMFManHDEL, establishing a strain co-expressing Mannosidase-HDEL and the *Trypanosoma cruzi* trans-sialidase.

Fermentation and protein purification was according to the procedures described by Laroy et al. (2000).

Purified trans-sialidase was subject to carbohydrate analysis according to Callewaert et al., *Glycobiology* 11, 4, 275-281, 2001. Briefly, the glycoproteins were bound to the PVDF membrane in the wells of a 96-well plate, reduced, alkylated and submitted to peptide-N-glycosidase F deglycosylation. The glycans were derivatised with 8-amino-1,3,6-pyrenetrisulfonic acid by reductive amination. Subsequently, the excess free label was removed using Sephadex G10-packed spin columns and the glycans were analysed by electrophoresis on a 36 cm sequencing gel on an ABI 377A DNA-sequencer and detected using the built-in argon laser. Digests with 3 mU/ml purified *T. reesei* α-1,2-mannosidase (described by Maras et al., *J. Biotechnol.* 77, 255-63, 2000) were also performed in 20 mM sodium acetate pH=5.0. The glycans derived from 1 μg of the purified recombinant glycoproteins were used as the substrate. 1 U of the α-1,2-mannosidase is defined as the amount of enzyme that releases 1 μmol of mannose from baker's yeast mannan per minute at 37° C. and pH=5.0.

Figure 6:
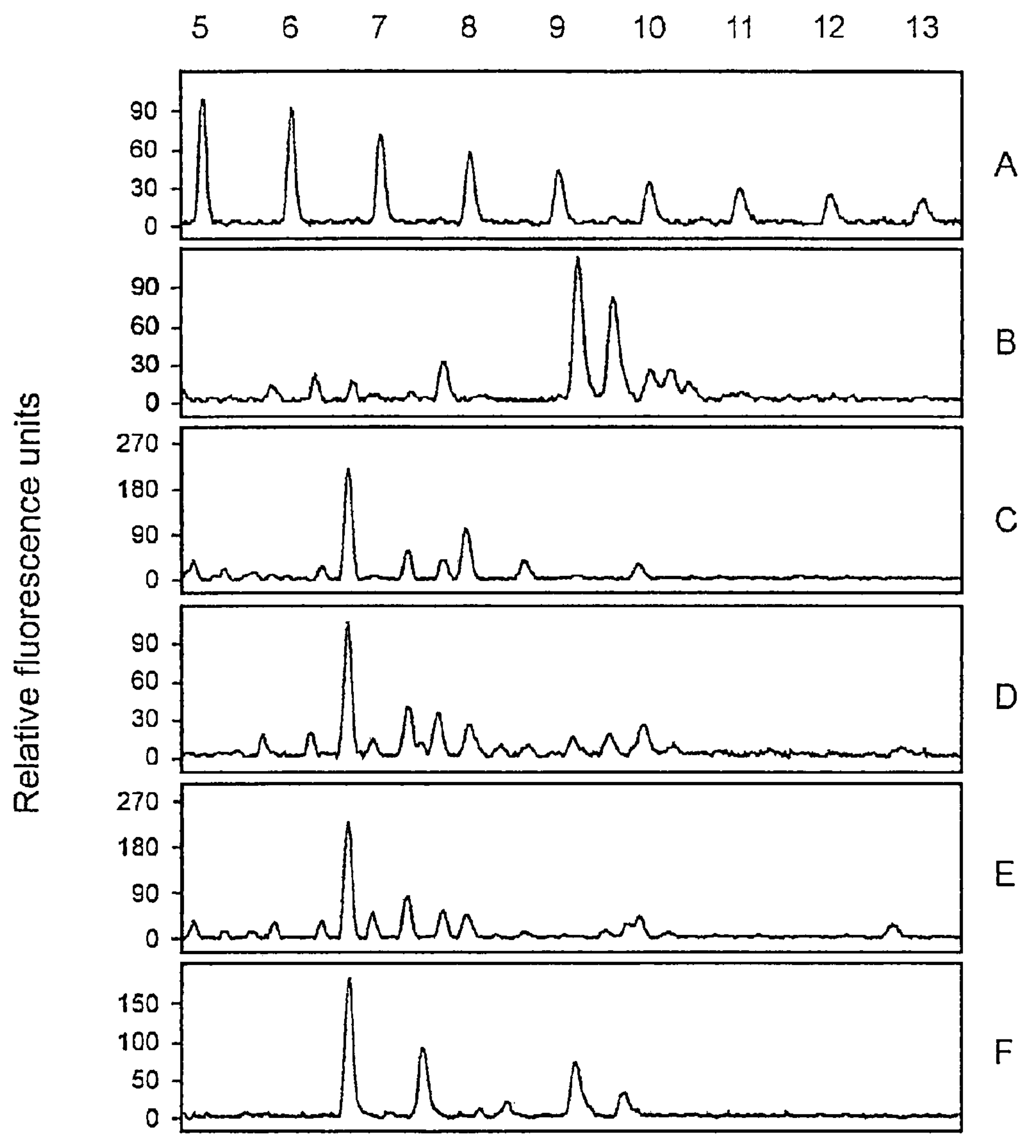
FIG. 6 depicts the N-glycan analysis of *Trypanosoma cruzi* trans-sialidase coexpressed with *Trichoderma reesei* mannosidase-HDEL. Panel A: malto-oligosaccharide size reference ladder. Sizes of the glycans are expressed in Glucose Units (GU) by comparison of their electrophoretic mobility to the mobility of these malto-oligosaccharides. Panel B: N-glycans derived from recombinant *Trypanosoma cruzi* trans-sialidase expressed in *Pichia pastoris*. The peak at GU=9,2 corresponds to $Man_8GlcNAc_2$. Panel C: same analytes as panel 2, but after overnight treatment with 3 U/ml purified recombinant *T. reesei* α-1,2-mannosidase. Panel D: N-glycans derived from recombinant trans-sialidase co-expressed in *Pichia pastoris* with *T. reesei* mannosidase-HDEL (under control of the GAP promotor). The peak at GU=7,6 corresponds to the $Man_5GlcNAc_2$ peak in the profile of RNase B (Panel F). Panel E: same analytes as panel D, but after overnight treatment with 3 mU/ml purified recombinant *T. reesei* α-1,2-mannosidase. Panel F: N-glycans derived from bovine RNase B. These glycans consist of $Man_5GlcNAc_2$ to $Man_8GlcNAc_2$. Different isomers are resolved, accounting for the number of peaks for $Man_7GlcNAc_2$.

As can be seen in FIG. 6, panel B, the major N-glycan on trans-sialidase was $Man_8GlcNAc_2$ (Compare with panel F, representing an analysis of the N-glycans of bovine RNAseB. The one but last peak in this profile is $Man_8GlcNAc_2$, the first peak is $Man_5GlcNAc_2$). In vitro, this glycan was digestible to $Man_5GlcNAc_2$ with α-1,2-mannosidase (FIG. 6, panel C). In the N-glycan profile of the trans-sialidase co-expressed with mannosidase-HDEL, the major peak corresponded to $Man_5GlcNAc_2$ (FIG. 6, panel D).

Co-Expression of Mannosidase-HDEL with the Influenza A Virus Haemagglutinin

The Influenza A virus haemagglutinin was known to be glycosylated in *Pichia pastoris* with high-mannose N-glycans containing 9-12 mannose residues (Saelens et al. *Eur. J. Biochem.* 260: 166-175, 1999). The effect of a co-expressed mannosidase on the N-glycans of the haemagglutinin was assessed in an N-glycan profiling method described below. In addition, to compare the efficiency of the *Trichoderma* enzyme (having a temperature optimum of 60° C.) with a mammalian mannosidase having a temperature optimum of 37° C., the catalytic domain of the mouse mannosidase IB from a mouse cDNA-library was cloned and tagged with a HDEL signal by PCR amplification. This ORF was cloned after the prepro-signal sequence of the *S. cerevisiae* α-mating factor under the control of the GAP promoter. Expression of the mannosidase-HDEL transgenes on the mRNA level was confirmed by qualitative Northern blotting.

The haemagglutinin was expressed and purified from a non-mannosidase expressing control strain and from a strains co-expressing the *Trichoderma reesei* mannosidase-HDEL or the mouse mannosidase IB-HDEL according to the procedure described by Kulakosky et al. *Glycobiology* 8: 741-745 (1998). The purified haemagglutin was subjected to PNGase F digestion as described by Saelens et al. *Eur. J. Biochem.* 260: 166-175, 1999. The proteins and glycans were precipitated with 3 volumes of ice-cold acetone and the glycans were extracted from the pellet with 60% methanol. Following vacuum evaporation, the glycans were labeled with 8-amino-1,3,6 pyrenetrisulfonic acid by adding 1 μl of a 1:1 mixture of 20 mM APTS in 1.2M citric acid and 1M $NaCNBH_3$ in DMSO and incubating for 16 h at 37° C. at the bottom of a 250 μl PCR-tube. The reaction was stopped by the addition of 10 μl deionized water and the mixture was loaded on a 1.2 cm Sephadex G10 bed packed to dryness in a microspin-column by centrifugation in a swinging bucket rotor, which provided for a flat resin surface. After loading, 50 μl deionised water was carefully added to the resin bed and the spin column was briefly centrifuged for 5 seconds at 750 g in a tabletop centrifuge. This elution process was repeated twice and all the eluates were pooled and evaporated to dryness in a Speedvac vacuum centrifuge (Savant). The labeled glycans were reconstituted in 1.5 μl gel loading buffer containing 50% formamide and 0.5 μl Genescan 500™, labeled with rhodamine (Perkin Elmer Bioscience), serving as an internal reference standard. This mixture was loaded on a DNA-sequencing gel containing 10% of a 19:1 mixture of acrylamide:bisacrylamide (Biorad, Hercules, Calif., USA) and made up in the standard DNA-sequencing buffer (89 mM Tris, 89 mM borate, 2.2 mM EDTA). Polymerization of the gel was catalyzed by the addition of 200 μl 10% ammononiumpersulfate solution in water and 20 μl TEMED. The gel was of the standard 36 cm well-to-read length and was run on an Applied Biosystems Model 373A DNA-sequencing apparatus. Prerunning of the gel was done at 1000 V for 15 min. and after loading, the gel was electrophoresed for 8 h at 1250 V without heating. This methodology gives a limit of detection of 10 fmol per peak. The data were analysed with Genescan 3.0 software.

Figure 7:
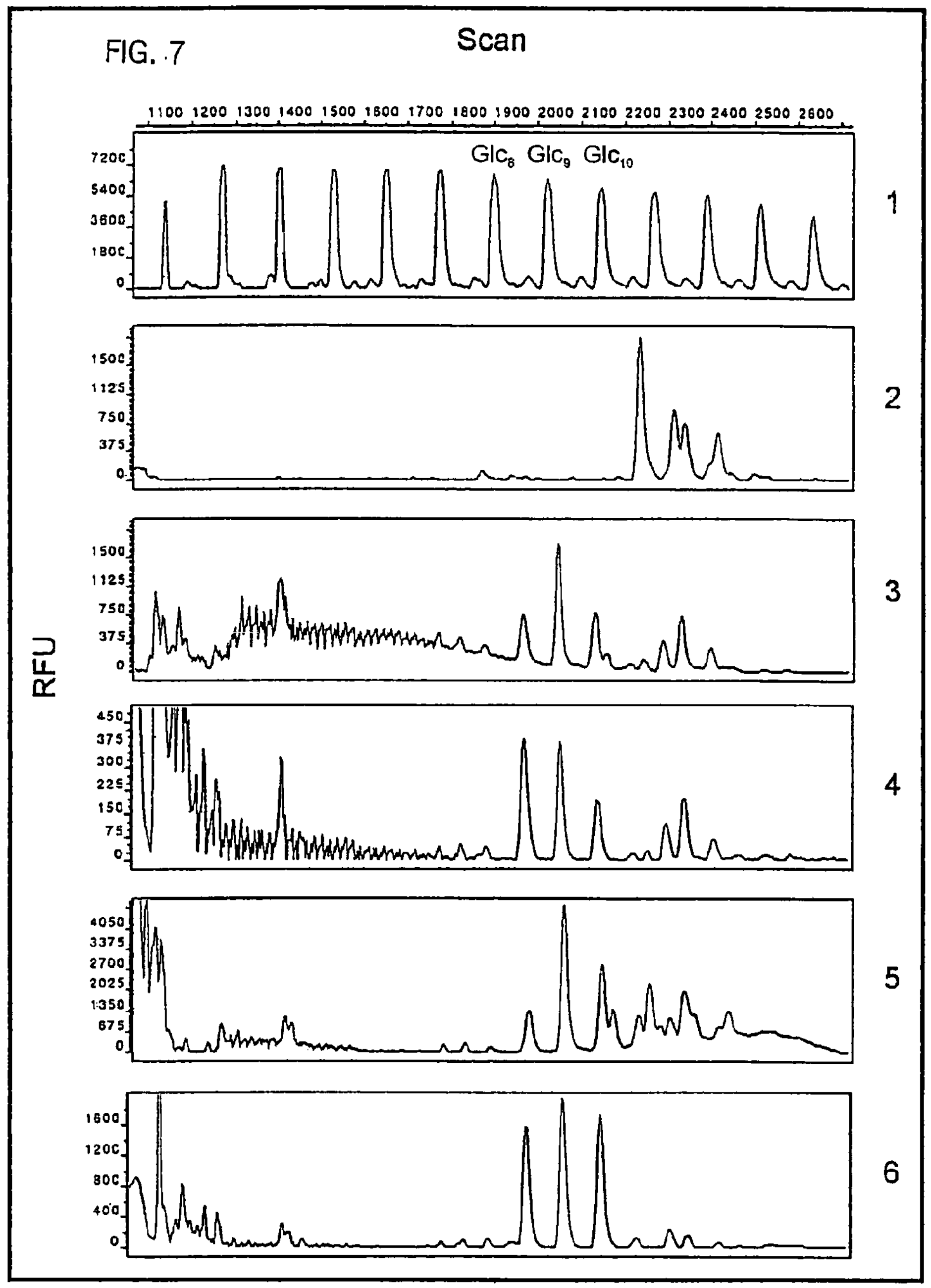
FIG. 7 depicts the processing of influenza haemagglutinin N-glycans by HDEL-tagged *Trichoderma reesei* α-1,2-mannosidase and the HDEL-tagged catalytic domain of murine α-1,2-mannosidase IB. The $Man_5GlcNAc_2$ reference oligosaccharide runs at scan 1850 in this analysis (not shown). Panel 1: malto-oligosaccharide size reference ladder. Panel 2: N-glycans derived from recombinant influenza haemagglutinin expressed in *Pichia pastoris*. The peak at scan 2250 corresponds to $Man_9GlcNAc_2$ Panel 3: N-glycans derived from recombinant haemagglutinin co-expressed in *Pichia pastoris* with *T. reesei* mannosidase-HDEL (under control of the GAP promotor). The peak at scan 1950 corresponds to $Man_6GlcNAc_2$. Panel 4: Same analytes as for panel 3, but after overnight treatment with 30 mU purified recombinant *T. reesei* α-1,2-mannosidase. Panel 5: N-glycans derived from recombinant haemagglutinin co-expressed in *Pichia pastoris* with mouse mannosidase IB-HDEL (under control of the GAP promotor). Panel 6: same analytes as for panel 5, but after overnight treatment with 30 mU purified recombinant *T. reesei* α-1,2-mannosidase.

As shown in FIG. 7, the *Trichoderma reesei* α-1,2-mannosidase provided the most complete reduction in the number of α-1,2-mannoses present on the N-glycans. The N-glycan processing by mouse mannosidase IB-HDEL was less efficient than by the *Trichoderma reesei* α-1,2-mannosidase.

Despite the efficient removal of α-1,2-mannoses from the N-glycans of haemagglutinin, no $Man_5GlcNAc_2$ was obtained. Even after digestion of the N-glycans with 3 mU of purified *Trichoderma reesei* α-1,2-mannosidase, only $Man_6GlcNAc_2$ was obtained as the smallest sugar chain. These results indicated that the remaining residues were possibly α-1,6-linked mannoses, originating from the initiating OCH1 α-1,6-mannosyltransferase enzymatic activities. OCH1 was observed to be localized to very early part of the Golgi apparatus and could act on the N-glycans of haemagglutinin before complete digestion of the $Man_8GlcNAc_2$ precursor to $Man_5GlcNAc_2$ by the mannosidases-HDEL. Thus, for proteins whose glycans are efficiently modified by the α-1,6-mannosyltransferase, an inactivation of the OCH1 gene coding for the transferase would be desirable in order to obtain proteins with $Man_5GlcNAc_2$.

Example 3

Inactivation of the *Pichia* OCH1 Gene

A *Pichia pastoris* sequence was found in the GenBank under Accession No. E12456 and was described in Japanese Patent Application No. 07145005, incorporated herein by reference. This sequence shows all typical features of an α-1,6-mannosyltransferase and is most homologous to the *S. cerevisiae* OCH1, thus referred to herein as the *Pichia pastoris* OCH1 gene.

Figure 8:
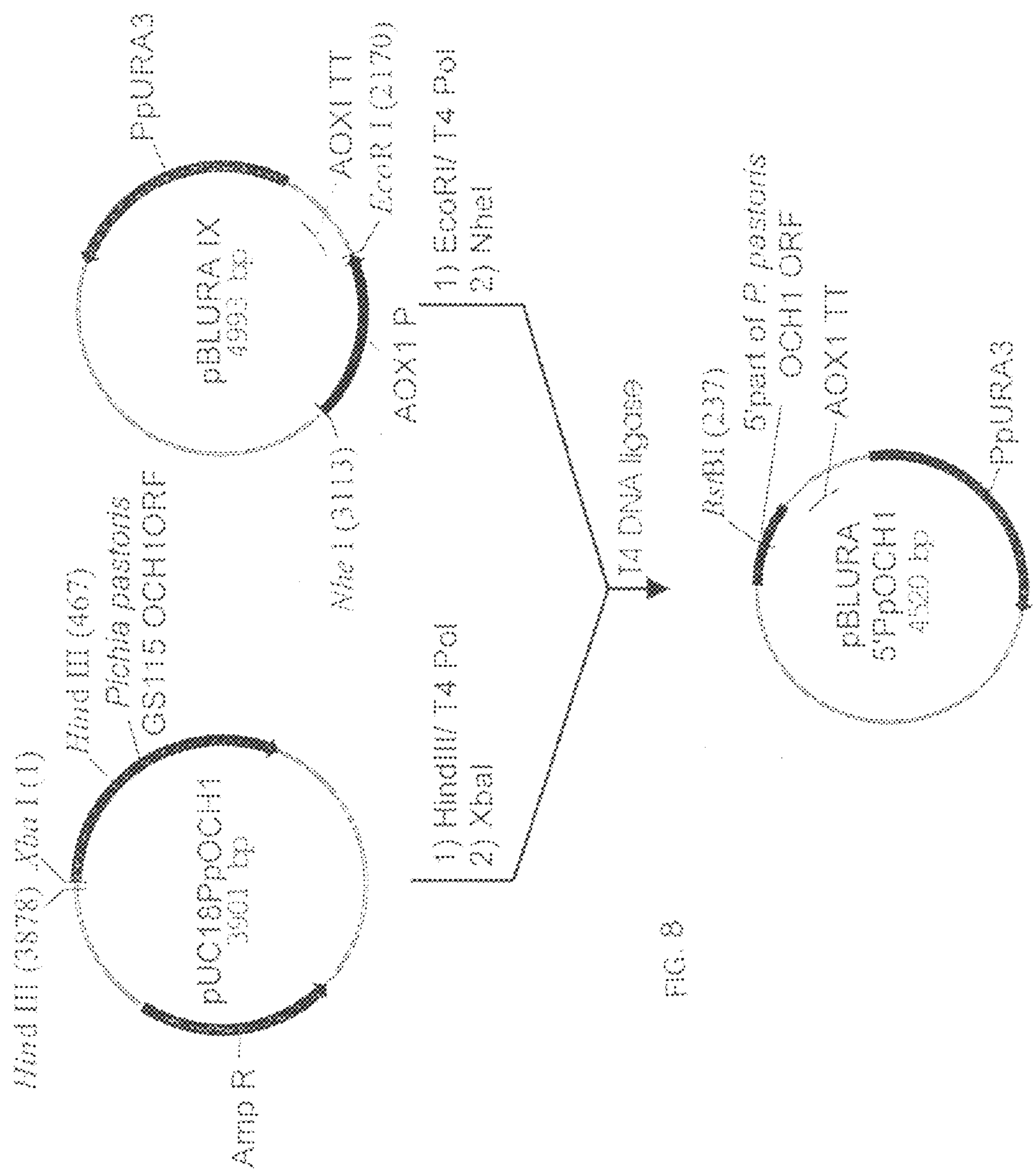
FIG. 8 graphically depicts vector pBLURA5'PpOCH1 and the way in which it was constructed.

First, the full ORF of the *Pichia pastoris* OCH1 gene was PCR cloned in pUC18 to obtain plasmid pUC18pOCH1. pUC18pOCH1 was cut with HindIII, blunt-ended with T4 polymerase, then cut with XbaI, releasing a fragment containing the 5' part of the *Pichia pastoris* OCH1 gene. This fragment was ligated into the vector pBLURA IX (available from the Keck Graduate Institute, Dr. James Cregg, which had been cut with Eco RI, blunt-ended with T4 polymerase, and then cut with Nhe I. This ligation generated pBLURA5'PpPCH1, as shown in FIG. 8.

Figure 9:
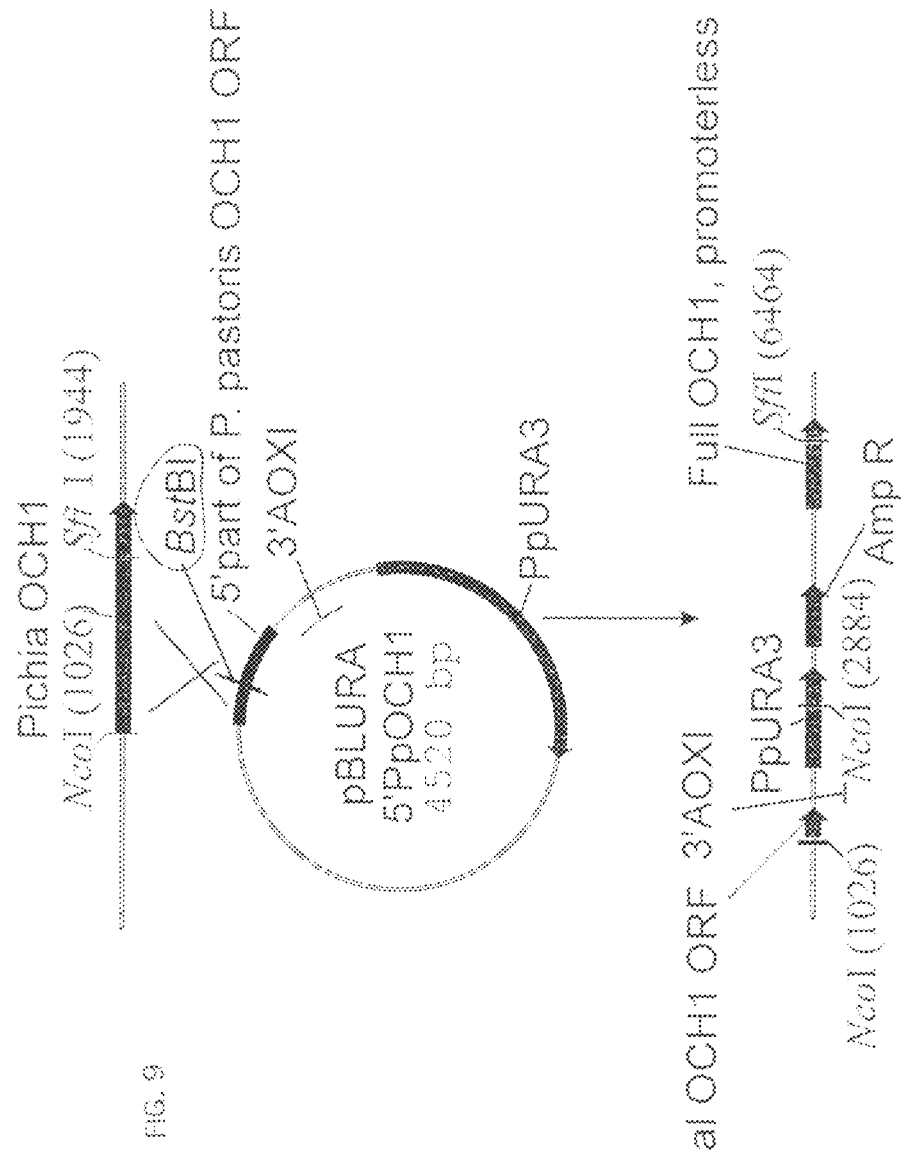
FIG. 9 depicts the scheme for disrupting the *Pichia pastoris* OCH1 gene by single homologous recombination using pBLURA5'PpOCH1.

Disruption of this *Pichia* OCH1 gene in the *Pichia* genome was achieved by single homologous recombination using pBLURA5'PpOCH1, as illustrated in FIG. 9. As a result of the single homologous recombination, the OCH1 gene on the *Pichia* chromosome was replaced with two OCH1 sequences: one consisted only about the first one third of the full OCH1 ORF, the other had a full OCH1 ORF without a OCH1 promoter. Single homologous recombination was achieved as follows. Cells of the *Pichia* strain yGC4 were transformed by electroporation with pBLURA5'PpOCH1 which had been linearized with the single cutter Bst BI. About 500 transformants were obtained on minimal medium containing 1M sorbitol, biotin, arginine, adenine and histidine and incubation at 27° C. Thirty-two of these transformants were picked and re-selected under the same conditions. Twelve clones were further analyzed for correct genomic integration of the cassette by PCR. Seven of the twelve URA prototrophic clones contained the cassette in the correct locus.

Figure 10:
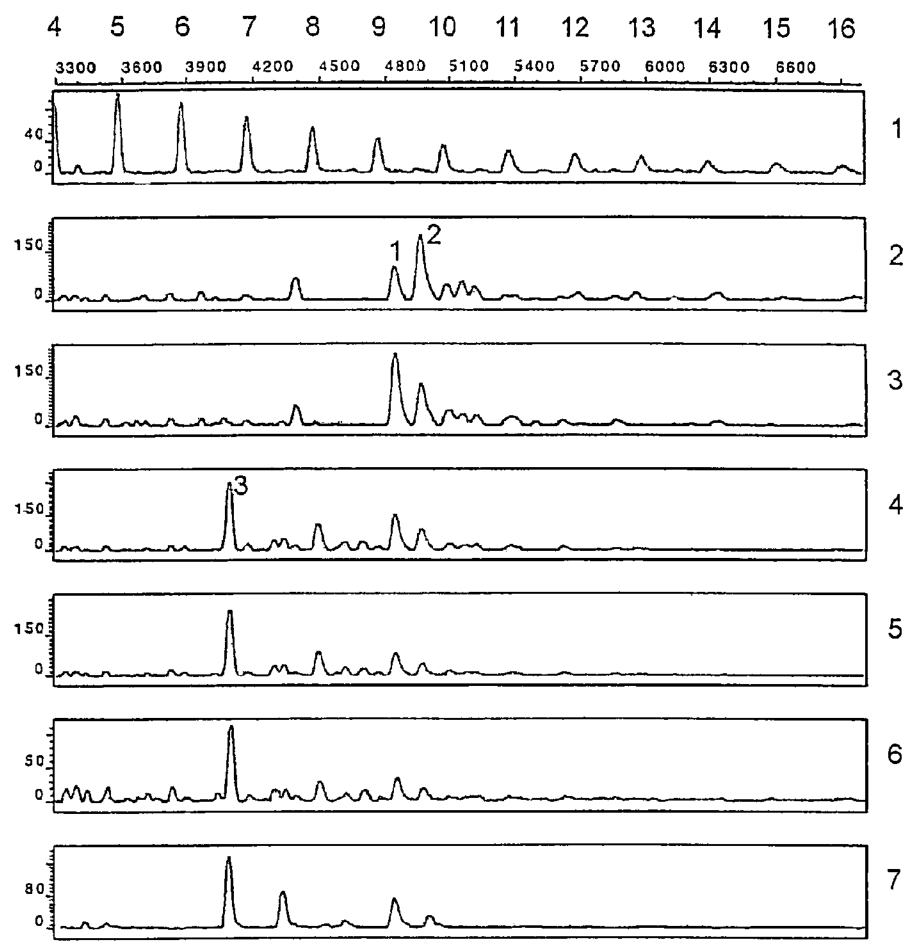
FIG. 10 depicts the cell wall glycoprotein N-glycan analysis of the OCH1-inactivated clone and three clones derived from this OCH1-inactivated clone by transformation with pGAPZMFManHDEL. Panel 1 shows the analysis of a mixture of malto-oligosaccharides, the degree of polymerisation of which is given by the numbers on the very top of the figure. This analysis serves as a size reference for the other panels. On the vertical axis of all panels, peak intensity in relative fluorescence units is given. Panel 2-6: analysis of the cell wall glycoprotein N-glycans of the following strains: Panel 2, non-engineered *P. pastoris* strain YGC4; Panel 3, YGC4 transformed with pBLURA5'PpOCH1; 4-6, three clones of the strain of Panel 3, supplementarily transformed with pGAPZMFManHDEL. Panel 7: the N-glycans derived from bovine RNaseB, consisting of a mixture of $Man_{5-9}GlcNAc_2$. As can be seen from comparison between panel 2 and 3 and reference to panel 7, transformation with pBLURA5'PpOCH1 leads to a strongly increased abundance of the $Man_8GlcNAc_2$ substrate N-glycan (named peak 1 in Panel 2) of OCH1p. Peak 2 represents the $Man_9GlcNAc_2$ product of OCH1p. Furthermore, upon supplementary transformation of pGAPZMFManHDEL, the major glycan on the cell wall glycoproteins of three independent clones is the $Man_5GlcNAc_2$ end product (peak 3 in panel 4) of *T. reesei* α-1,2-mannosidase digestion of the $Man_8GlcNAc_2$ substrate.
Figure 11:
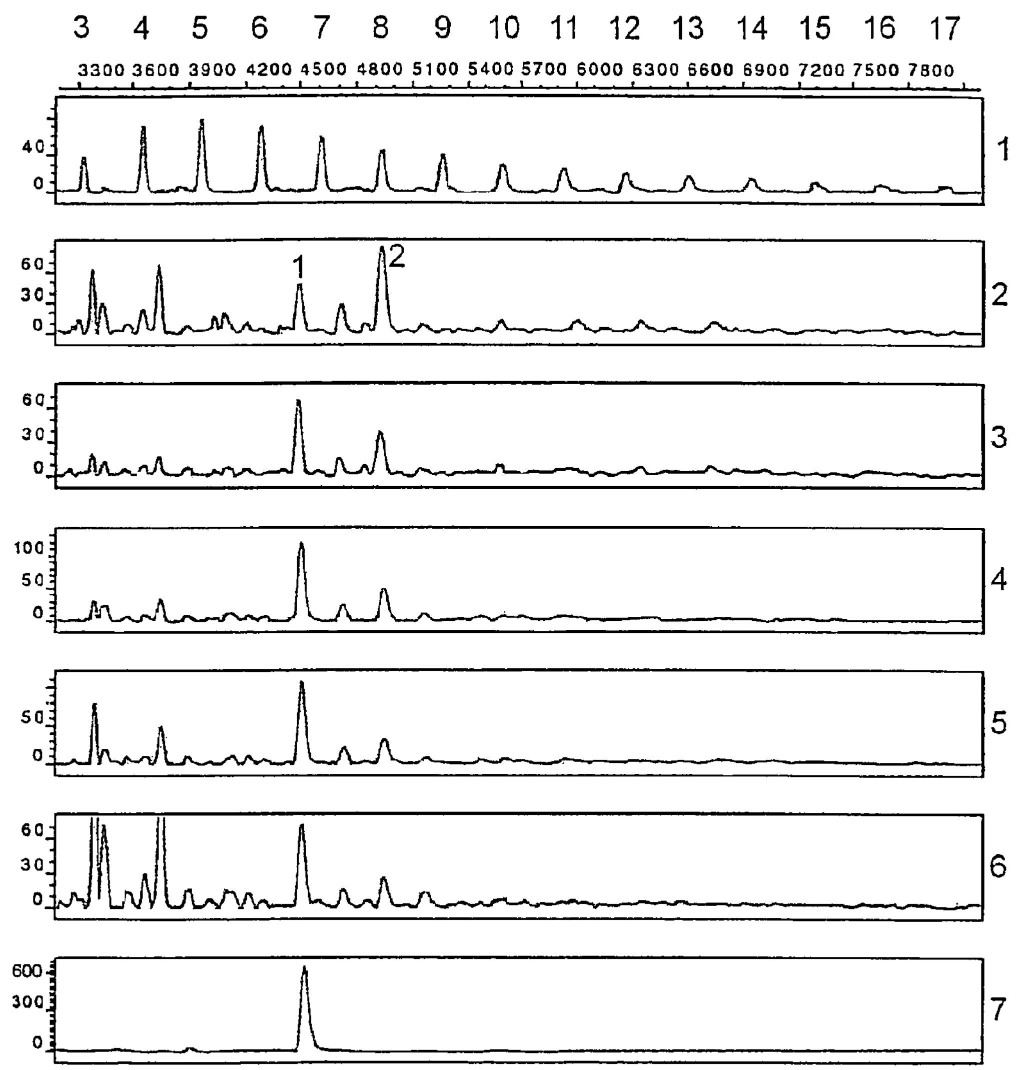
FIG. 11 depicts the analysis of exactly the same glycan mixtures as in FIG. 10, but after an in vitro digest with 3 mU/ml purified *Trichoderma reesei* α-1,2-mannosidase, overnight in 20 mM sodium acetate pH=5.0. Axis assignment is the same as in FIG. 10. More $Man_5GlcNAc_2$ is formed in the pBLURA5'PpOCH1 transformed strain (Panel 3) than in the parent strain (Panel 2). Peaks in all panels before scan 3900 come from contaminants and should be ignored in the analysis.
Figure 12:
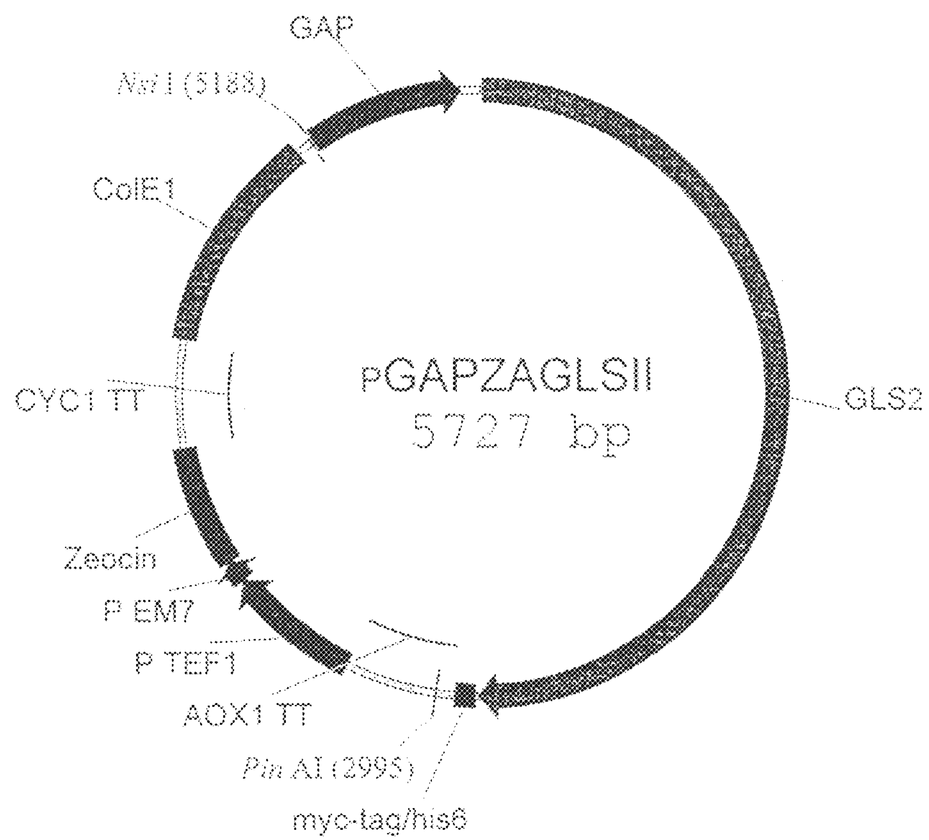
FIG. 12 depicts the expression vector pGAPZAGLSII (SEQ ID NO: 18). P TEF1: promotor of *S. cerevisiae* transcription elongation factor gene. P Em7: synthetic prokaryotic promotor. Zeocin: zeocine resistance marker gene. CYC1 TT: transcription terminator of *S. cerevisiae* cytochrome C1 gene. Col E1: bacterial origin of replication. GAP: promotor of the *P. pastoris* GAP gene. GLS2: *S. cerevisiae* glucosidase II gene. AOX1 TT: transcription terminator of the *P. pastoris* AOX1 gene.
Figure 13:
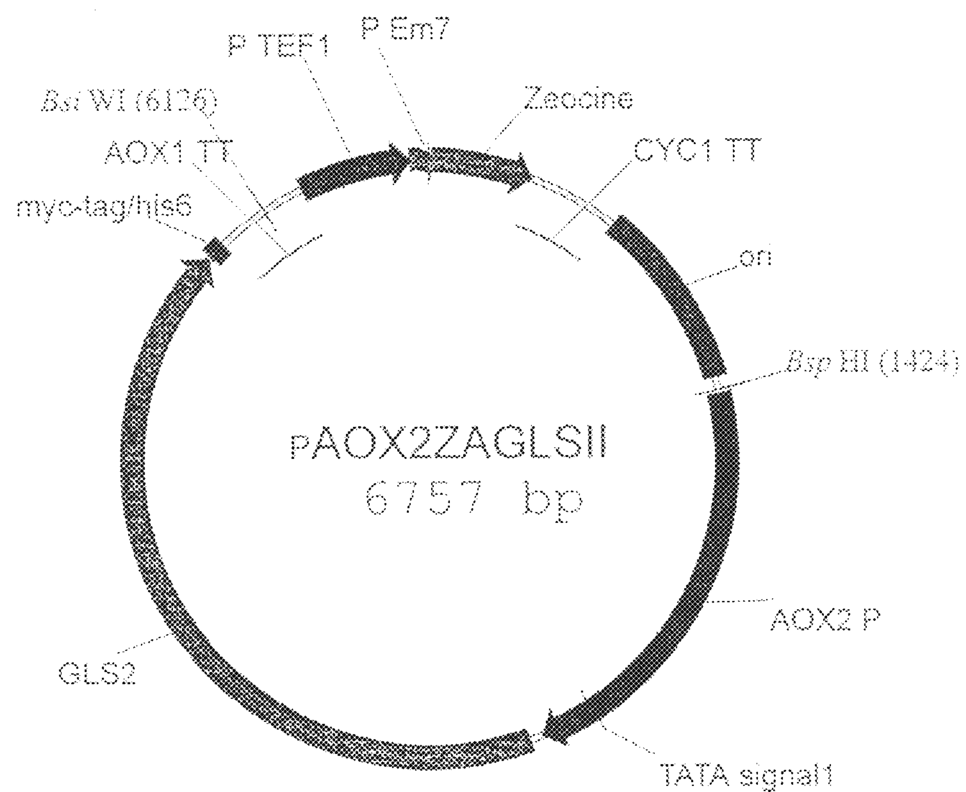
FIG. 13 depicts the expression vector pAOX2ZAGLSII (SEQ ID NO: 16). P TEF1: promotor of *S. cerevisiae* transcription elongation factor gene. P Em7: synthetic prokaryotic promotor. Zeocin: zeocine resistance marker gene. CYC1 TT: transcription terminator of *S. cerevisiae* cytochrome C1 gene. Col E1: bacterial origin of replication. AOX2 P: promotor of the *P. pastoris* AOX2 gene. GLS2: *S. cerevisiae* glucosidase II gene. AOX1 TT: transcription terminator of the *P. pastoris* AOX1 gene
Figure 14:
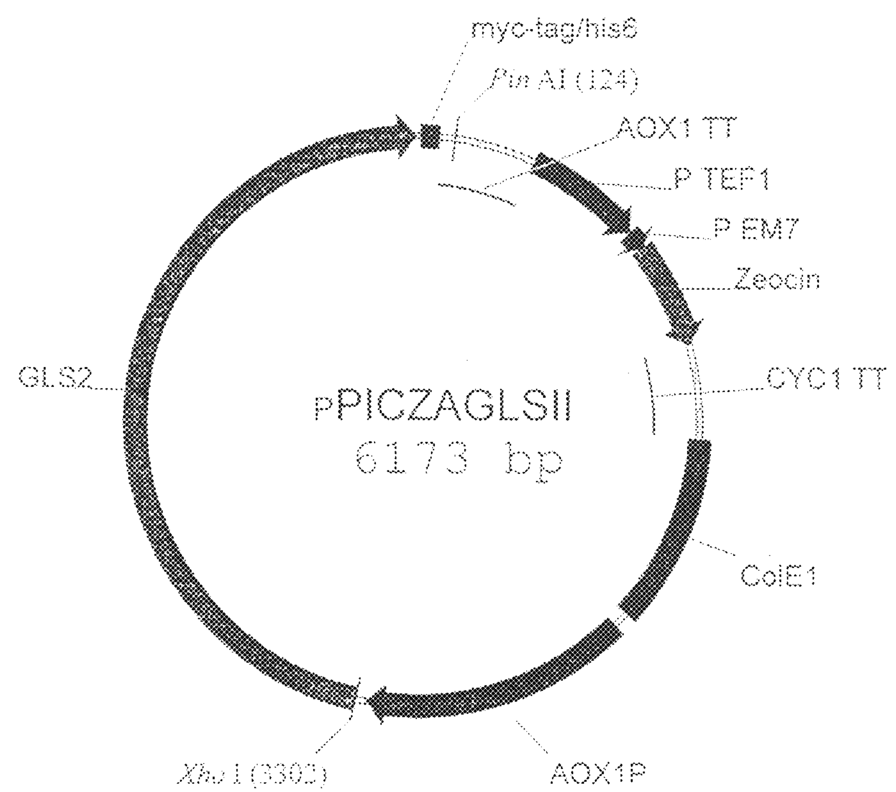
FIG. 14 depicts the expression vector pPICZAGLSII (SEQ ID NO: 20). P TEF1: promotor of *S. cerevisiae* transcription elongation factor gene. P Em7: synthetic prokaryotic promotor. Zeocin: zeocine resistance marker gene. CYC1 TT: transcription terminator of *S. cerevisiae* cytochrome C1 gene. Col E1: origin of replication. AOX1 P: promotor of the *P. pastoris* AOX1 gene. GLS2: *S. cerevisiae* glucosidase II gene. AOX1 TT: transcription terminator of the *P. pastoris* AOX1 gene
Figure 15:
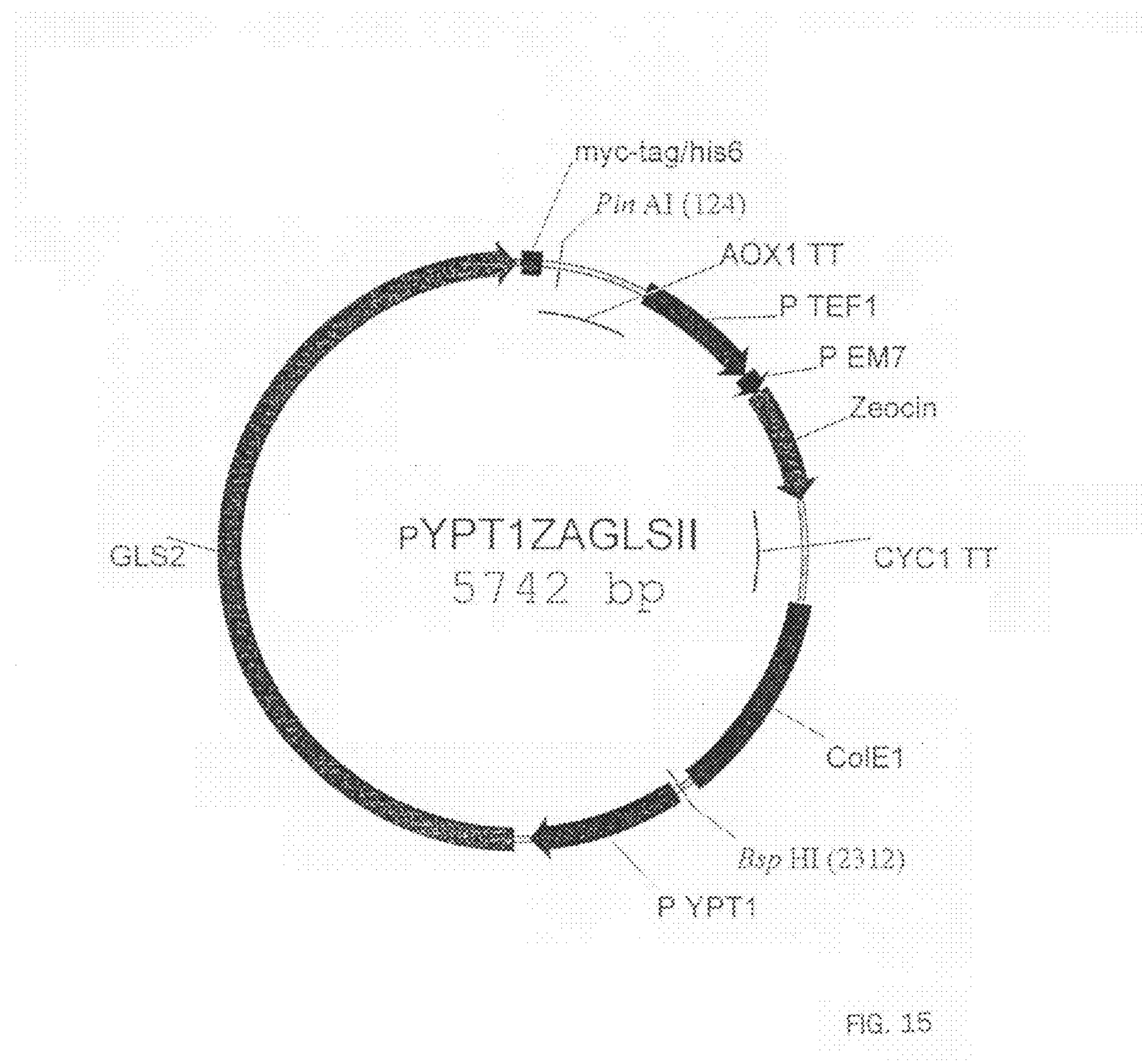
FIG. 15 depicts the expression vector pYPT1ZAGLSII ((SEQ ID NO: 22). P TEF1: promotor of *S. cerevisiae* transcription elongation factor gene. P Em7: synthetic prokaryotic promotor. Zeocin: zeocine resistance marker gene. CYC1 TT: transcription terminator of *S. cerevisiae* cytochrome C1 gene. Col E1: origin of replication. P YPT1: promotor of the *P. pastoris* YPT1 gene. GLS2: *S. cerevisiae* glucosidase II gene. AOX1 TT: transcription terminator of the *P. pastoris* AOX1 gene.
Figure 16:
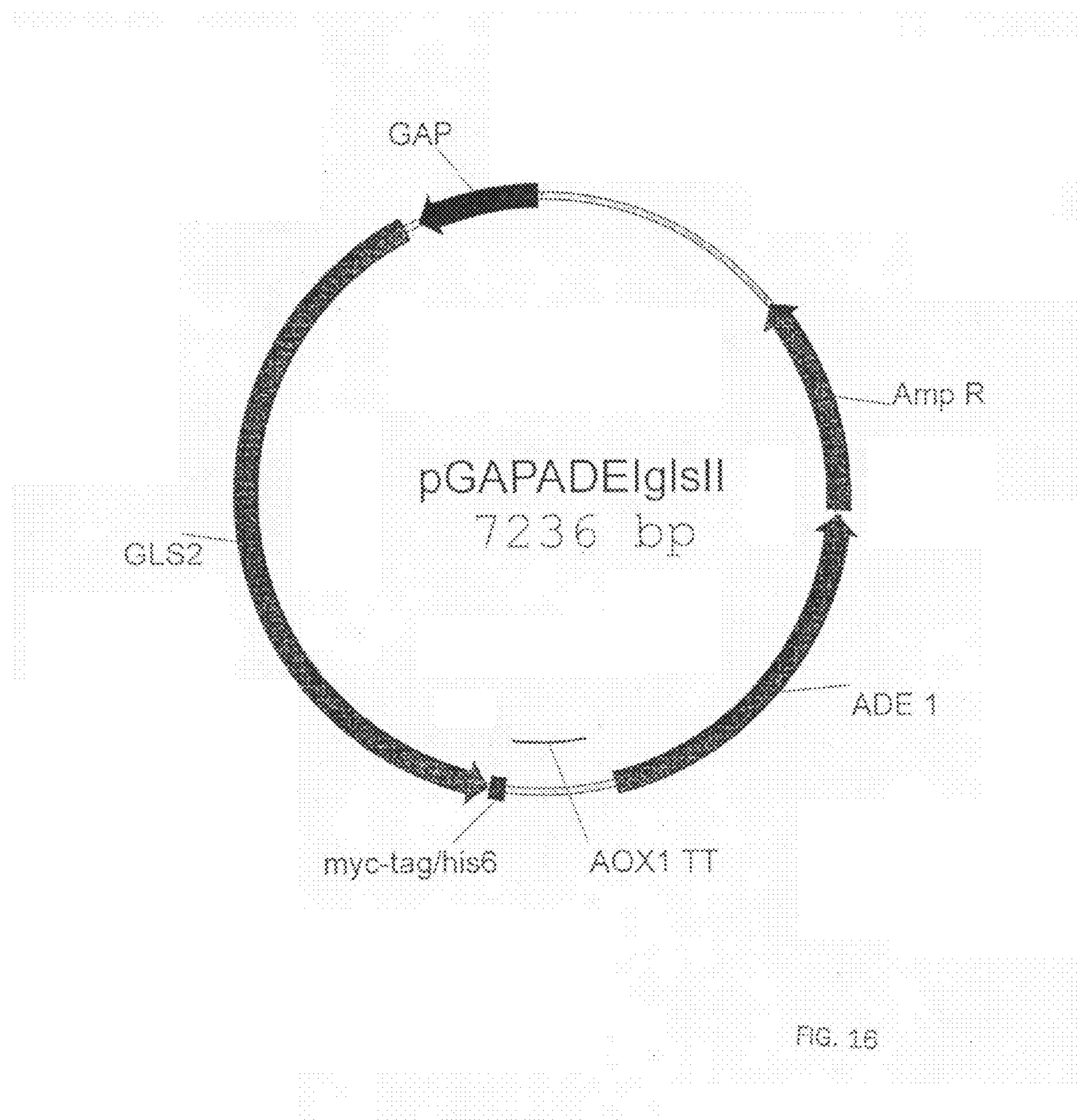
FIG. 16 depicts the expression vector pGAPADE1glsII (SEQ ID NO: 19). Amp R: Ampillicin resistance marker gene. ADE1: *P. pastoris* ADE1 selection marker gene. GAP: promotor of the *P. pastoris* GAP gene. GLS2: *S. cerevisiae* glucosidase II gene. AOX1 TT: transcription terminator of the *P. pastoris* AOX1 gene
Figure 17:
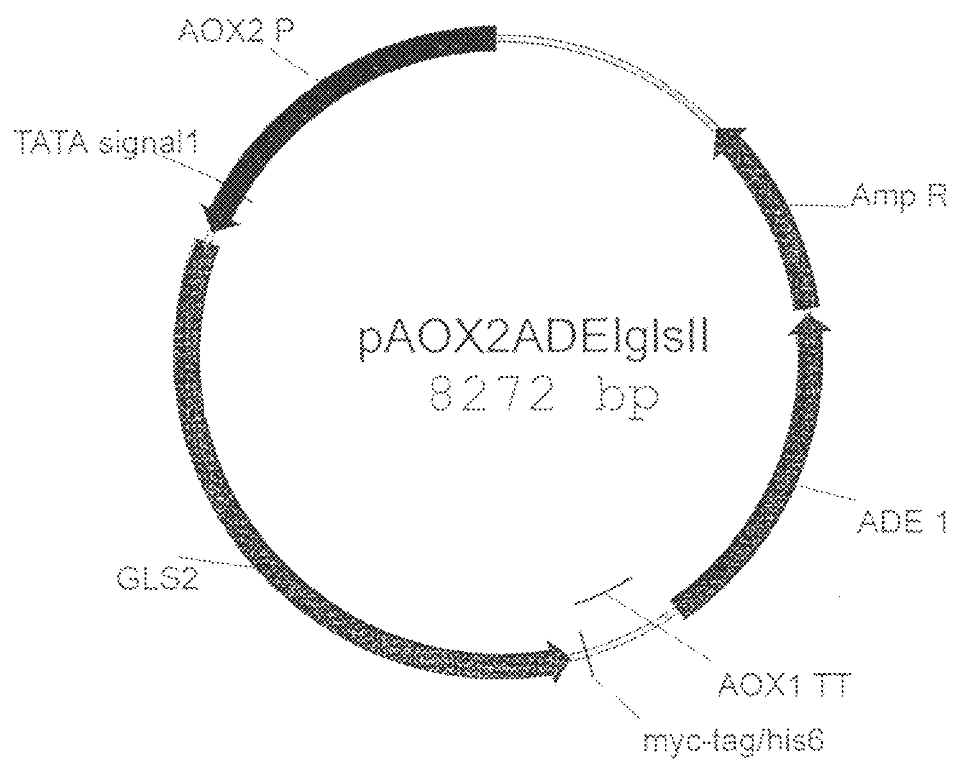
FIG. 17 depicts the expression vector pAOX2ADE1glsII (SEQ ID NO: 17). Amp R: Ampillicin resistance marker gene. ADE1: *P. pastoris* ADE1 selection marker gene. AOX2 P: promotor of the *P. pastoris* AOX2 gene. GLS2: *S. cerevisiae* glucosidase II gene. AOX1 TT: transcription terminator of the *P. pastoris* AOX1 gene.
Figure 18:
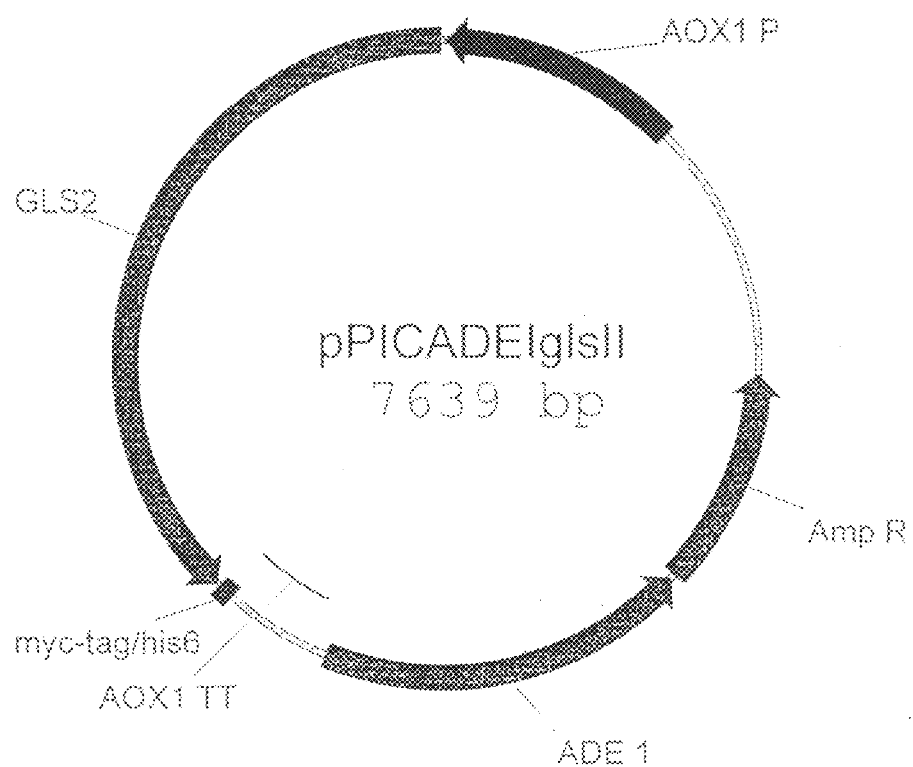
FIG. 18 depicts the expression vector pPICADE1glsII (SEQ ID NO: 21). Amp R: Ampillicin resistance marker gene. ADE1: *P. pastoris* ADE1 selection marker gene. AOX1 P: promotor of the *P. pastoris* AOX1 gene. GLS2: *S. cerevisiae* glucosidase II gene. AOX1 TT: transcription terminator of the *P. pastoris* AOX1 gene.
Figure 19:
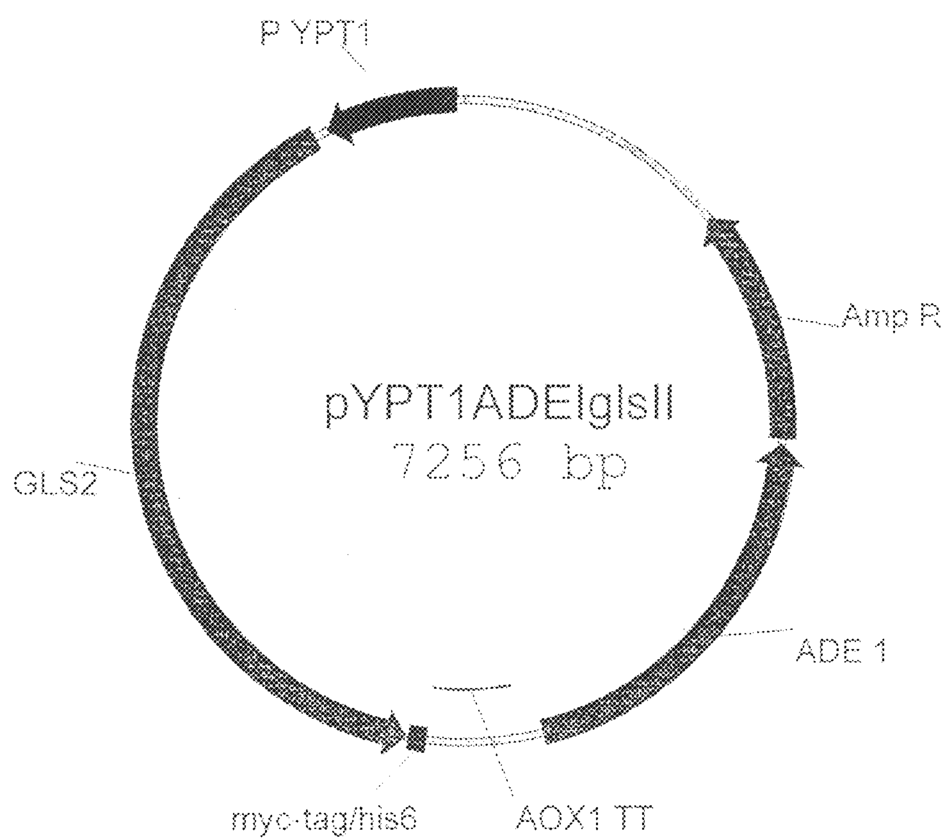
FIG. 19 depicts the expression vector pYPT1ADE1glsII (SEQ ID NO: 23). Amp R: Ampillicin resistance marker gene. ADE1: *P. pastoris* ADE1 selection marker gene. P YPT1: promotor of the *P. pastoris* YPT1 gene. GLS2: *S. cerevisiae* glucosidase II gene. AOX1 TT: transcription terminator of the *P. pastoris* AOX1 gene.

One of the OCH1-inactivated clones was also further transformed with pGAPZMFManHDEL to produce "supertransformants". Both the OCH1-inactivated clone and three supertransformants also expressing the ManHDEL were evaluated in cell wall glycan analysis as follows. Yeast cells were grown in 10 ml YPD to an $OD_{600}$=2 and mannoproteins were prepared by autoclaving the yeast cells in 20 mM sodium citrate buffer pH7 for 90 min at 120° C. and recovery of the supernatant after centrifugation. Proteins were precipitated from this supernatant with 3 volumes of cold methanol. The protein preparation obtained in this way was used for N-glycan analysis using DSA-FACE as described by Callewaert et al. (2001) *Glycobiology* 11, 275-281. As shown in FIG. 10, there was an increased amount of $Man_8GlcNAc_2$ glycan in the OCH1-inactivanted clone as compared to parent strain yGC4, indicative of a reduced activity of the OCH1 enzyme. In all three supertransformants which also expressed the HDEL-tagged α-1,2 mannosidase, the production of $Man_5GlcNAc_2$ was observed. Furthermore, upon digestion of the same glycan mixtures with 3 mU/ml purified recombinant *Trichoderma reesei* α-1,2-mannosidase, more $Man_5GlcNAc_2$ was formed in the strain transformed with pBLURA5'PpOCH1 than in the parent strain (FIG. 11, compare panel 2 and 3).

These results indicated that the production of glycoproteins with $Man_5$ glycans could be facilitated by the inactivation of the OCH1 gene.

Mutagenesis PCR was performed on plasmid pPICZB5'PpOCH1Mut (plasmid construction described in Example 8) using the forward primer Kai 13: 5'-ATCTAAgCTATATTCgCCgTTTCTgTCATT-3' (SEQ ID NO: 43) and the reverse primer Kai 14: 5'-CgATTATggATgTTAgATCTgATCTCATgA-3' (SEQ ID NO: 44). This PCR resulted in a product that lacked the entire AOX1 promoter and the coding sequence for the first 24 amino acids of the OCH1 fragment in pPICZB5'PpOCH1Mut. This product was self-ligated and the resulting plasmid was named pZ5'PpOCH1Trunc (SEQ ID NO: 45).

Figure 32:
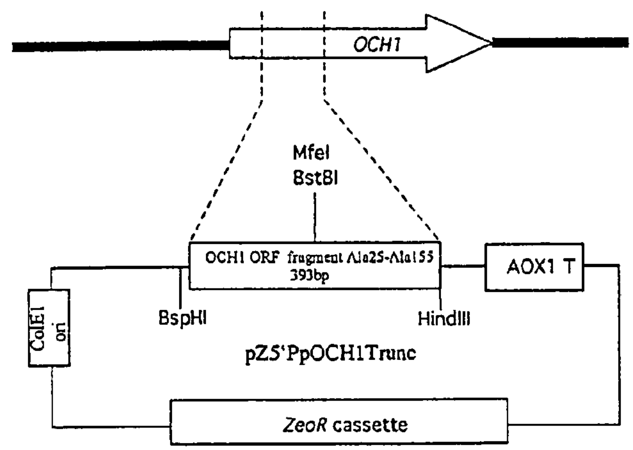
FIG. 32 depicts the scheme of the genomic rearrangement upon transformation with pZ5'PpOCH1Trunc. pZ5'PpOCH1Trunc contains the promoterless coding sequence for amino acid 25-155 of *Pichia* OCH1, followed by the 3' AOXI transcription terminator. This vector is linearized with BstBI in the OCH1-homologous part, inducing specific homologous recombination into the OCH1 locus. After integration, two OCH1 sequence parts are generated: the first OCH1 sequence consists of the genomic OCH1 sequence up to the site of recombination with the vector, followed by the portion of OCH1 sequence that is present on the vector. This first OCH1 sequence is now under control of the OCH1 promoter of the host methylotrophic yeast, yet cannot produce an active OCH1 protein as such OCH1 sequence codes for no or an inactive fragment of the OCH1 protein, as described hereinabove. The second OCH1 sequence is a truncated OCH1 coding sequence (lacks the first 24 amino acids). Moreover this truncated OCH1 coding sequence is not operably linked to any known promoter sequence and thus, no messenger is expected to be formed for synthesis of an active OCH1 protein.
Figure 32:
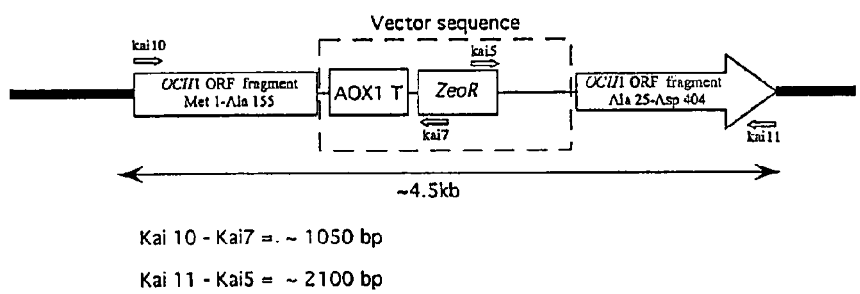

This plasmid was linearized with BstBI and the product was transformed to *Pichia pastoris* GS115 and yGC4. Transformants were selected on YPDS-Zeo and the genomic integration was tested using 2 PCR reactions: one with the primer couple Kai10 (SEQ ID NO: 41)/Kai7 (SEQ ID NO: 40) and one with the couple Kai5 (SEQ ID NO: 39)/Kai 11 (SEQ ID NO: 42). The primer hybridisation sites can be seen on FIG. 32. In FIG. 32, the desirable genomic situation at the OCH1 locus after transformation is shown.

Figure 34:
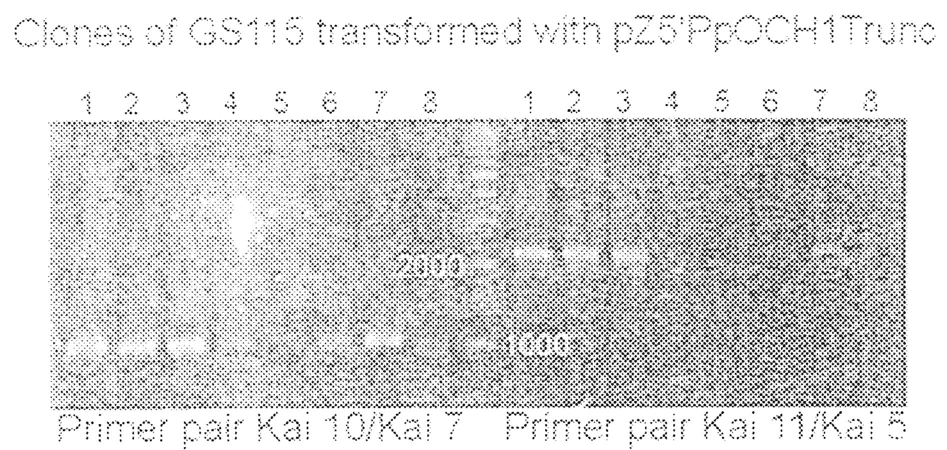
FIG. 34 depicts genomic analysis of GS 115 clones transformed with pZ5'PpOCH1Trunc. For clones that have correctly integrated the plasmid in the OCH1 locus, the expected product length for the primer couple Kai10/Kai 7 is 1050 bp, whereas for the primer couple Kai11/Kai 5, it is 2100 bp. It is clear that clones 1, 2, 3 and 8 fulfill this requirement. We conclude that the OCH1 locus has been disrupted in these clones.

24 clones were analysed using these PCR reactions and the result for 8 clones is shown in FIG. 34. We found that at least 8/24 clones had the plasmid correctly integrated in the OCH1 locus.

All clones with a correct integration were vanadate resistant (YPD plates containing 5 mM sodium vanadate, growth at 30° C.), a typical hallmark for N-glycosylation defective yeast cells (Proc Natl Acad Sci USA 1991 Apr. 15; 88(8): 3209-12).

Example 4

Expression of Glucosidase II in *Pichia pastoris*

4.1 Amplification of the GLSII Alpha Subunit ORF from *S. cerevisiae.*

Genomic DNA was prepared from the *S. cerevisiae* strain INVS (α, leu2-3, 112 his3є1, trp1-289, ura3-52), using the Nucleon kit (Amersham). A touch-down PCR reaction was performed using this genomic DNA as template and the LA TaKaRa polymerase (ImTec Diagnostics). The sequence of the PCR primers was based on the known sequence of the *S. cerevisiae* GLSII ORF:

```
Sense primer:
                                     (SEQ ID NO:12)
5' CCG CTC GAG ATG GTC CTT TTG AAA TGG CTC 3'
        XhoI

Antisense primer:
                                     (SEQ ID NO:13)
5' CCG GGC CCA AAA ATA ACT TCC CAA TCT TCA G 3'
      Apa I
```

4.2 Cloning of the *S. cerevisiae* Glucosidase II ORF into *Pichia pastoris* Expression Vectors.

Construction of the Glucosidase II Expression Vectors—

The PCR fragment was digested with Xho I/Apa I and ligated into the pGAPZA vector (Invitrogen), thereby placing the ORF under the transcriptional control of the GAP promoter. Using this strategy, the myc and the His6 tag were placed in frame to the C-terminus of Glucosidase II, creating pGAPZAGLSII. The complete ORF of pGAPZAGLSII was then sequenced to ensure that no mutations were generated in the PCR reaction. The sequence of the vector pGAPZAGLSII was set forth in SEQ ID NO: 18. The GLSII ORF from the pGAPZAGLSII vector was cloned into vector pPICZA (Invitrogen) to create pPICZAGLSII, thereby placing the ORF under the transcriptional control of the AOXI promoter. The GLSII ORF from the pGAPZAGLSII vector was cloned into vector pAOX2ZA, thereby placing the ORF under the transcriptional control of the AOX2 promoter. This vector was created by replacing the multi cloning site of vector pAOX2ZB with the multi cloning site of pPICZA. Vector pAOX2ZB was generated by replacing the AOX1 promotor of pPICZB by the AOX2 promoter region of the AOX2 gene (Martinet et al., Biotechnology Letters 21). The AOX2 promotor region was generated by PCR on *Pichia* genomic DNA with the sense primer 5'GACGAGATCTTTTTTTCAGACCATATGACCGG 3' (SEQ ID NO: 26) and the antisense primer 5'GCGGAATTCTTTTCTCAGTTGATTTGTTTGT 3' (SEQ ID NO: 27). The GLSII ORF from the pGAPZGLSII vector was cloned into vector pYPT1ZA to create pYPTIZA-GLSII, thereby placing the ORF under the transcriptional control of the YPT1 promoter. Vector pYPTZA was created by replacing the AOX1 promoter of pPICZA by the YPT1 promoter present on the plasmid pIB3 (GenBank accession number AF027960)(Sears et al., Yeast 14, pg 783-790, 1998). All constructs contain the phleomycin resistance gene. The resulting final expression vectors (pGAPZAGLSII, pAOX2ZAGLSII, pPICZAGLSII and pYPT1ZAGLSII) are depicted in FIGS. 12-15.

Similar expression vectors were constructed, carrying the Ampicillin resistance marker and the *Pichia* ADE1 selection marker. In principle, the Zeocin resistance expression cassette of the plasmids pAOX2ZAGLSII, pGAPZAGLSII and pYPT1ZAGLSII was replaced by the Ampicillin and *Pichia* ADE1 cassette of the vector pBLADE IX (Cregg, J. M.) to result in the vectors pAOX2ADE1glsII, pGAPADE1glsII and pYPT1ADE1glsII. Vector pPICADE1glsII was obtained by inserting the glucosidase II open reading frame into the multiple cloning site of the vector pBLADE IX (Cregg, J. M.). The resulting final expression vectors (pGAPADE1glsII, pAOX2ADE1 glsII, pPICADE1 glsII and pYPT1ADE1glsII) are depicted in FIGS. 16-20.

Adding the ER Retention Tag HDEL to Glucosidase II Expression Vectors—

The following primers were used to generate an HDEL-containing PCR fragment:

```
Primer 1:
                                             (SEQ ID NO:28)
5'GCG GGT CGA C/CA C/GA C/GA A/CT G/TG A/GT TTT
         SalI    H    D    E    L    stop

AGC CTT AGA CAT GAC 3'

Primer 2:
                                             (SEQ ID NO:29)
5'CAG GAG CAAA GCT CGT ACG AG 3'
                      SplI
```

Figure 20:
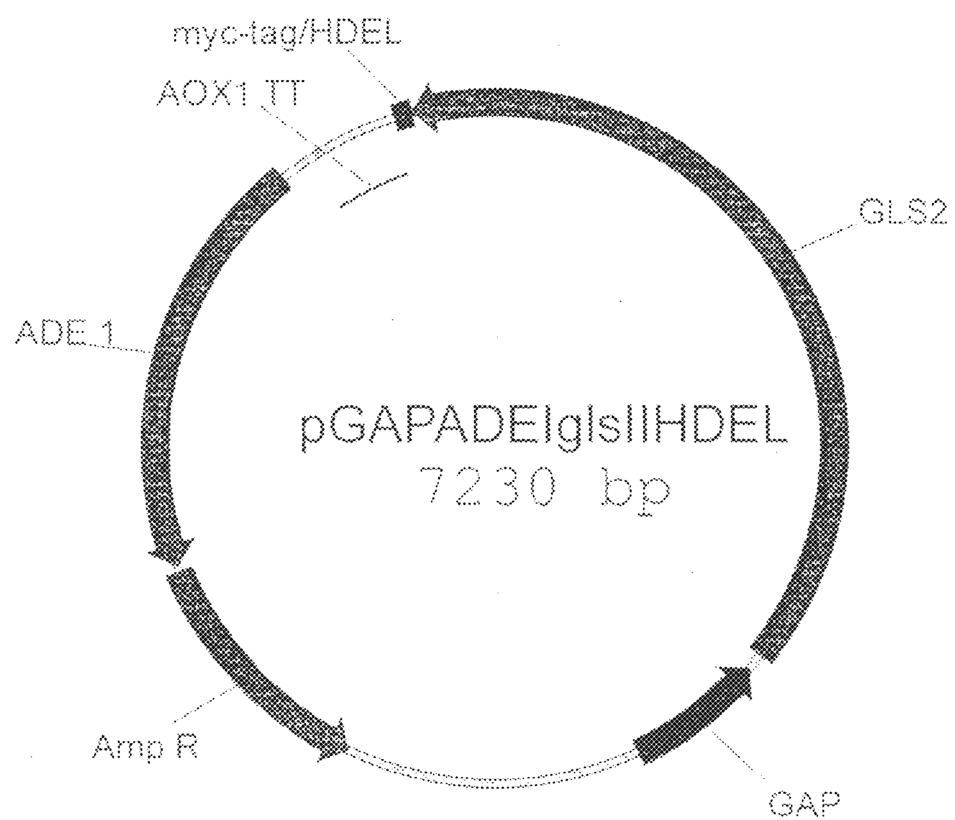
FIG. 20 depicts the expression vector pGAPADE1glsIIHDEL (SEQ ID NO: 25). Amp R: Ampillicin resistance marker gene. ADE1: *P. pastoris* ADE1 selection marker gene. GAP: promotor of the *P. pastoris* GAP gene. GLS2: *S. cerevisiae* glucosidase II gene. AOX1 TT: transcription terminator of the *P. pastoris* AOX1 gene.
Figure 21:
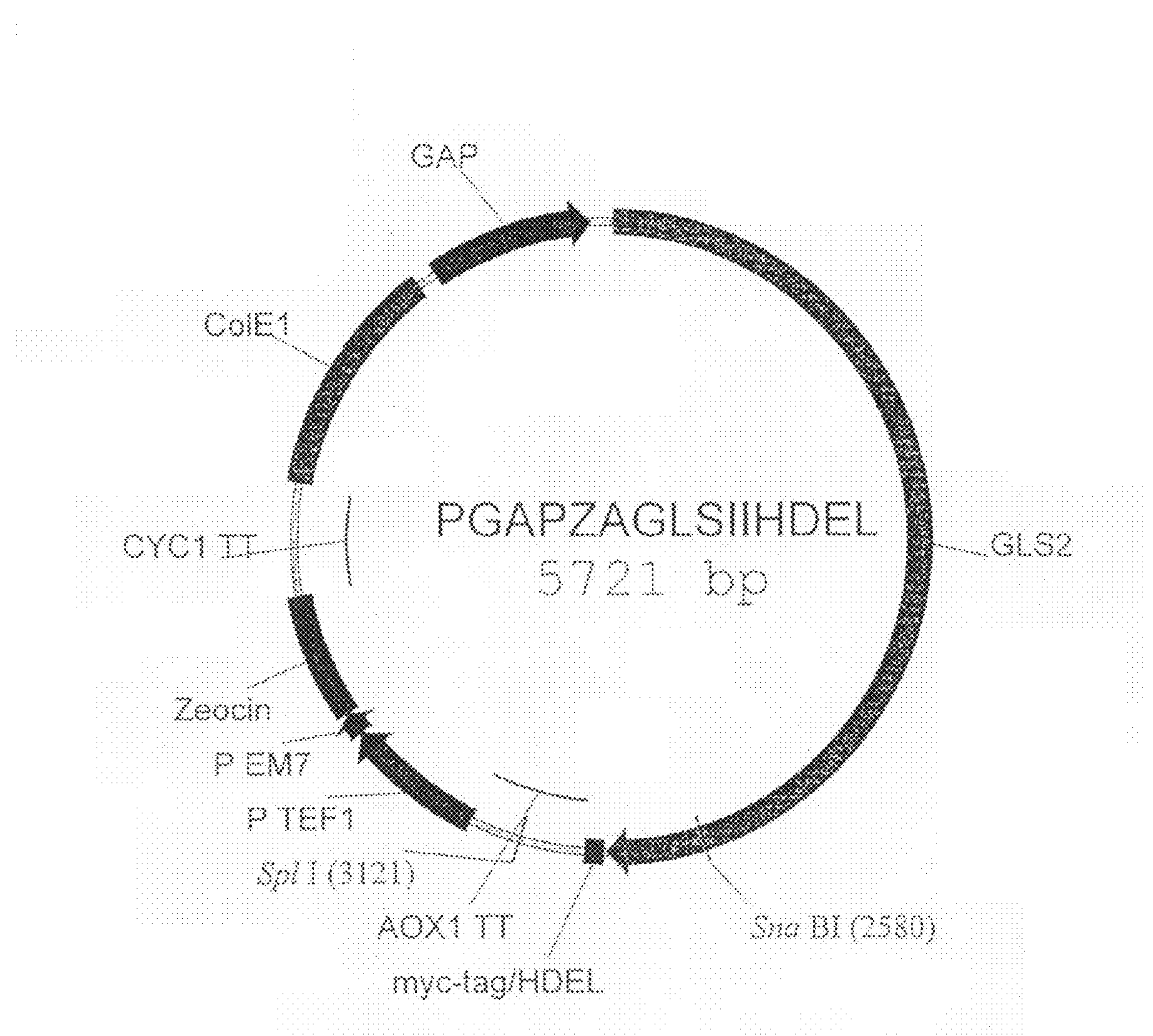
FIG. 21 depicts the expression vector pGAPZAglsIIHDEL (SEQ ID NO: 24). P TEF1: promotor of *S. cerevisiae* transcription elongation factor gene. P Em7: synthetic prokaryotic promotor. Zeocin: zeocine resistance marker gene. CYC1 TT: transcription terminator of *S. cerevisiae* cytochrome C1 gene. Col E1: bacterial origin of replication. GAP: promotor of the *P. pastoris* GAP gene. GLS2: *S. cerevisiae* glucosidase II gene. AOX1 TT: transcription terminator of the *P. pastoris* AOX1 gene.

PCR was performed on pGAPZAGLSII with Taq pol., at 60° C. The PCR fragment of 225 bp was cut with Sal I/Spl I and ligated into the Sal I/Spl I opened pGAPZAGLSII vector, creating plasmid pGAPZAglsIIHDEL. The sequence of plasmid pGAPZAglsIIHDEL is set forth in SEQ ID NO: 24. The construction strategy and the resulting final expression vectors (pGAPADE1glsIIHDEL and pGAPZAglsIIHDEL) are depicted in FIGS. 20-21.

4.3 Transformation of a *Pichia pastoris* Strain.

Transformation was performed using the conventional electroporation techniques, as described by Invitrogen. Cells of the *Pichia pastoris* strain PPY12-OH were transformed with pGAPZGLSII which had been cut with the single cutter Avr II. Transformants were selected based on their resistance to zeocin.

Genomic Analysis of the Transformants—

Genomic DNA was prepared from some zeocin resistant *Pichia* transformants. A PCR reaction was performed on the genomic DNA in order to determine whether or not the glucosidase II gene was integrated into the yeast genome. PCR was performed using Taq DNA polymerase (Boehinger) (2.5 mM $MgCl_2$, 55° C. for annealing). The primers were the same as the ones we used for the amplification of the ORF on *S. cerevisiae* genomic DNA. pGAPZAGLSII transformants were confirmed by the presence of a specific PCR product indicative of the glucosidase II ORF.

4.4 Expression and Secretion of the *S. cerevisiae* Glucosidase II Alpha Subunit in *Pichia pastoris*

Analysis at the Transcriptional Level—

RNA was prepared from the transformants which scored positive after the genomic analysis. RNA was prepared using acid phenol. From each sample, 15 μg of RNA was loaded on a formaldehyde agarose gel. After electrophoresis the RNA was blotted on a Hybond N membrane. The membrane was hybridized using a radioactive probe, which consists of a 344 bp glucosidase II specific fragment, corresponding to the 3' region of the glucosidase II ORF. No signals were detected with non-transformed control strains, whereas clear signals were observed with transformants.

Analysis at the Protein Level Using a Double Membrane Assay—

A nitrocellulose membrane was placed on a buffered dextrose medium (BMDY). On top of that nitrocellulose membrane, a cellulose acetate membrane Was placed. *Pichia* transformants of pGAPZAGLSII were streaked on the cellulose acetate and grown for a few days. The yeast cells remained on the cellulose acetate, while the secreted proteins crossed this membrane. As such the secreted protein was captured onto the nitrocellulose membrane. After a few days the cellulose acetate, containing the yeast colonies, was removed. The nitrocellulose membrane was analyzed for the presence of glucosidase II using anti-myc antibody. Most of the transformants gave a clear signal as compared to a faint, hardly visible signal with the WT, non-transformed strain.

Extracellular Expression—

PPY12-OH transformants of the construct pGAPZAGLSII (mychis6) (strains 12, 14 and 18) and transformants of the construct pGAPZAGLSII(myc)HDEL (strains H1, H2 and H3) were grown for 2 days on 2×10 ml BMDY medium. These 6 transformants earlier scored positive both on the genomic level (PCR on gDNA) and on the RNA level (Northern blot). The culture medium was collected by centrifugation and concentrated with Vivaspin columns to about 1 ml. Proteins from this concentrate were precipitated with TCA, resuspended in Laemmli buffer and loaded for SDS-PAGE analysis. Proteins were blotted to nitrocellulose membrane. The blot was incubated overnight with anti-myc Ab. The secondary Ab was linked to peroxidase. Using the Renaissance luminiscence detection kit (NEN) and a light sensitive film (Kodak), a strong band at about 110 kDa was observed for the transformants 12, 14 and 18, indicating that GLSII was expressed and secreted from these transformants. No signal was obtained for the transformants H1-3, which indicate that the HDEL tag, which was added C-terminally to the GLSII ORF, resulted in an ER localization of the protein, preventing GLSII to be secreted into the growth medium.

Intracellular Expression—

The 6 transformants and the WT strain were grown for 2 days in 500 ml BMDY. The cells were collected by centrifugation, washed, resuspended into a minimal volume (50 mM Tris.HCl pH 7.5, 5% glycerol) and broken using glass beads. The cell debris was removed through several centrifugation steps (low speed centrifugation (2000-3000 g)). Membranes were obtained from the supernatant through ultracentrifugation. The pellets were resuspended in Laemmli buffer and loaded for SDS-PAGE analysis. The proteins were blotted on a nitrocellulose membrane. The intracellular GLSII expression was checked using anti-myc Ab and peroxidase conjugated secondary Ab. Following the luminescence detection, a band of about 110 kDA was observed with the GLSIIHDEL transformants (H1 and H3 and faint signal for H2), but not with the WT and the GLSII expression strains. These results, together with the results obtained for the extracellular expression, clearly indicated that the heterologous glucosidase II was retained within the ER when HDEL tagged.

Since this way of preparing intracellular proteins resulted in a rather big background signal, a new method was used. The WT strain (PPY12-OH) and two transformed strains 18 (GLSII) and H3 (GLSIIHDEL) were grown in 200 ml BMGY for two days at 30 degrees celcius, until an OD600 of about 12 was reached. Cells were washed with 50 mM Tris.HCl pH 7.5 and resuspended in 10 ml of that same buffer. Cells lysis was performed through French press (3 times). Cell debris was precipitated at 3000 g for 10 minutes. The resulting supernatant was ultracentrifuged for 1 hr at 35,000 rpm in a Beckman SW41.1 rotor to precipitate the intracellular membranes. The membrane pellet was resuspended in membrane suspension buffer (50 mM Tris.HCl pH 7.4-150 mM NaCl-1 mM EDTA pH 8.0-25× complete protease inhibitor (Roche)). To this suspension Triton-X100 was added to 1% final volume. The suspension was incubated overnight at 4 degrees Celcius on a rotating wheel. Next, the membranes were precipitated through ultracentrifugation (1 hr at 40,000 rpm in a Beckman SW50.1 rotor). The supernatant contains the overnight extracted membrane and luminal proteins. Protein concentration was measured and equal amounts (500 ug) of the three strains were loaded for SDS-PAGE analysis. After electrophoresis, proteins were transferred to a nitrocellulose membrane. Membranes were screened with antibodies as described earlier. This time, the intracellular presence of glucosidase II could not only be established in transformant H3 (in which a HDEL tagged GLSII ORF was transformed), but also in transformant 18 (the one in which a non-HDEL tagged GLSII ORF was transformed). This could be the result from the interaction of the heterologous glucosidase alpha subunit with the endogenous *Pichia* beta subunit. It was believed to be the result of the slow trafficking of the heterologous glucosidase II within the secretion pathway, due to folding problems. Since only low amounts of the protein were discovered in the secretion medium of the GLSII expression strains (i.e. strain 18), this certainly was the case.

4.5 Purification and Activity Assays of the Recombinant Glucosidase II Alpha Submit Glucosidase II Assay on Extracellular Medium:

A GLSII assay was set up as follows and was tested using a commercially available yeast alpha-glucosidase (Sigma) as a positive control.

Figure 22:
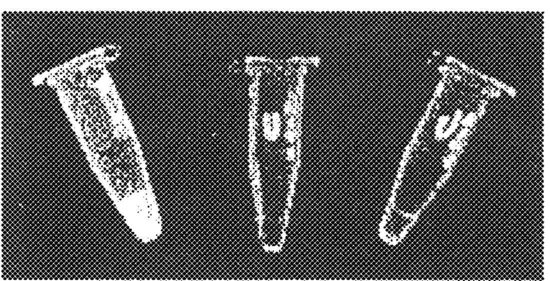
FIG. 22 depicts the test of the GLSII activity assay using a commercially available yeast alpha-glucosidase (Sigma: Cat. No. G-5003). The assay mixture contains phosphate-citrate buffer pH 6.8, mannose, 2-deoxy-D-glucose, the substrate 4-methylumbellyferyl-alpha-D-glucopyranoside and alpha-glucosidase from Sigma. 1: assay mixture illuminated with UV-light after-overnight incubation at 37° C.; 2: same as 1, but this time, the assay mixture lacks the alpha-glucosidase; 3: same as 1, but this time, the assay mixture lacks the substrate.

Composition: 70 μl 80 mM phosphate-citrate buffer pH 6.8, 7 μl 250 mM mannose, 3.5 μl 250 mM 2-deoxy-D-glucose, 0.8 μl 4-MeUmbelliferyl-alpha-D-glucopyranoside (1 μM). Three assays were performed: one with 1 unit commercial enzyme, one without the enzyme and one with the enzyme but without the substrate. The assay mixture was incubated overnight at 30° C. When illuminated with UV, only the reaction mixture with both the enzyme and the substrate showed fluorescence (FIG. 22). This indicates that the assay was very specific in detecting the activity of the alpha-glucosidase.

Figure 23:
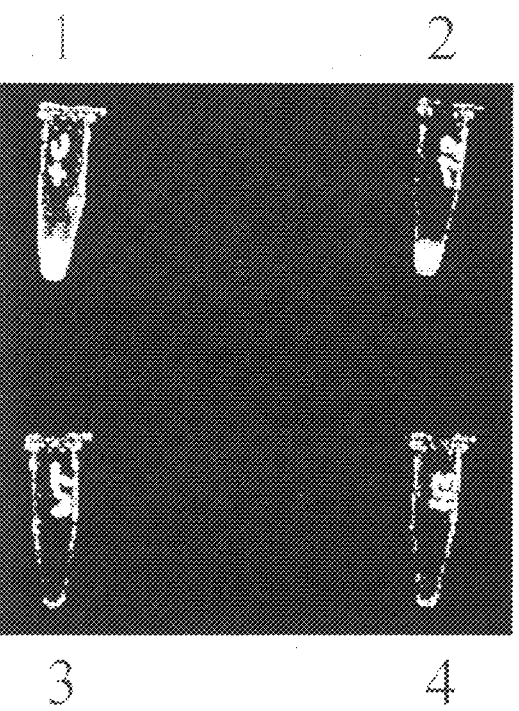
FIG. 23 depicts the results of the activity of recombinantly expressed GLSII from *Pichia pastoris*. All assay mixtures were incubated overnight at 37° C. and afterwards illuminated with UV-light. 1: assay with yeast alpha-glucosidase (Sigma: Cat. No. G-5003); 2: assay with the purified medium of strain 18 (PPY12-OH transformed with pGAPZAGLSII); 3: assay with purified medium of the WT PPY12-OH strain; 4: assay with the purified medium of strain H3 (PPY12-OH transformed with pGAPZAglsIIHDEL).

WT PPY12-OH, strain 18 and strain H3 were grown during 2 days in 2×10 ml growth medium. Cells were spun down and medium was adjusted to 300 mM NaCl and 10 mM imidazol and concentrated with Vivaspin columns to 0.5-1 ml. Medium was loaded onto a Ni-NTA spin column (Qiagen) and the purification was performed according to the manufactures recommendations. Protein was eluted from the column in 2×100 μl elution buffer (50 mM $NaH_2PO_4$, 300 mM NaCl, 250 mM imidazol pH 8.0). From each eluate, 20 μl was assayed for its glucosidase II activity. 0.33 units of the commercial enzyme diluted in 20 μl of the elution buffer was used as a positive control. Fluorescence was observed with the positive control and the elute of strain 18, the strain which secreted the enzyme into the growth medium. These results indicate that the recombinant *S. cerevisiae* GLSII alpha subunit, secreted by *Pichia pastoris*, was a functionally active enzyme. The activity was not seen in the WT (untransformed) strain, nor in strain H3 as the GLSII was expressed intracellularly (FIG. 23). These results also indicate that the beta subunit is not necessary for the functionality of the alpha part of the protein.

Glucosidase II Activity on Intracellular Total Protein:

Membrane and luminal proteins from the WT strain, transformant 18 and transformant H3, were prepared by breaking the cells through a French press, as described in section 4.4 (intracellular expression). Equal amounts of total intracellular protein were assayed through the GLSII assay as described above. Due to the substrate used, total intracellular alpha-glucosidase activity (glucosidase I and II, lysosomal alpha-glucosidases, etc.) was assayed, and not only the glucosidase II activity. However, when performing the assay on both WT and transformants 18 and H3, a twofold higher alpha-glucosidase activity was found in both transformed strains. Since these strains only differ from the WT strain in the expression of the *S. cerevisiae* glucosidase II protein (with or without HDEL), it is believed that this twofold increase in activity results from the activity of the recombinant protein. The whole procedure of protein preparation and glucosidase II assay was repeated a second time; again a twofold increase in total intracellular alpha-glucosidase activity was found for the two transformants, when compared to the WT untransformed strain.

Example 5

Creating *Pichia* Strains Expressing Both Glucosidase II and Mannosidase

Strain GS115 was transformed with pGAPZGLSII and pGAPZglsIIHDEL. Transformants were selected on YPDSzeo.

Strain YGC4 was transformed with the following constructs, respectively:

(1) pGAPADEglsII and pGAPADEglsIIHDEL, selection on synthetic sorbitol medium without adenine;

(2) pGAPZMFManHDEL: selection on YPDSzeo; and (3) pGAPZMFManHDEL/pGAPADEglsIIHDEL: selection on synthetic sorbitol medium without adenine and with zeocin.

Strain YGC4 with pBLURA5'PpOCH1 and expressing MFmannosidaseHDEL was transformed with pGAPADEglsII and pGAPADEglsIIHDEL. Selection of transformants was done on synthetic sorbitol medium without adenine and uracil.

For all transformations, colonies were obtained. Transformants with the expression vector(s) integrated into the genome, determined by PCR, were obtained. Expression of GLSII from some of these transformants was observed.

Example 6

Introduction of GlcNAc-Transferase I in *Pichia pastoris*

6.1 Vector Construction

Figure 24:
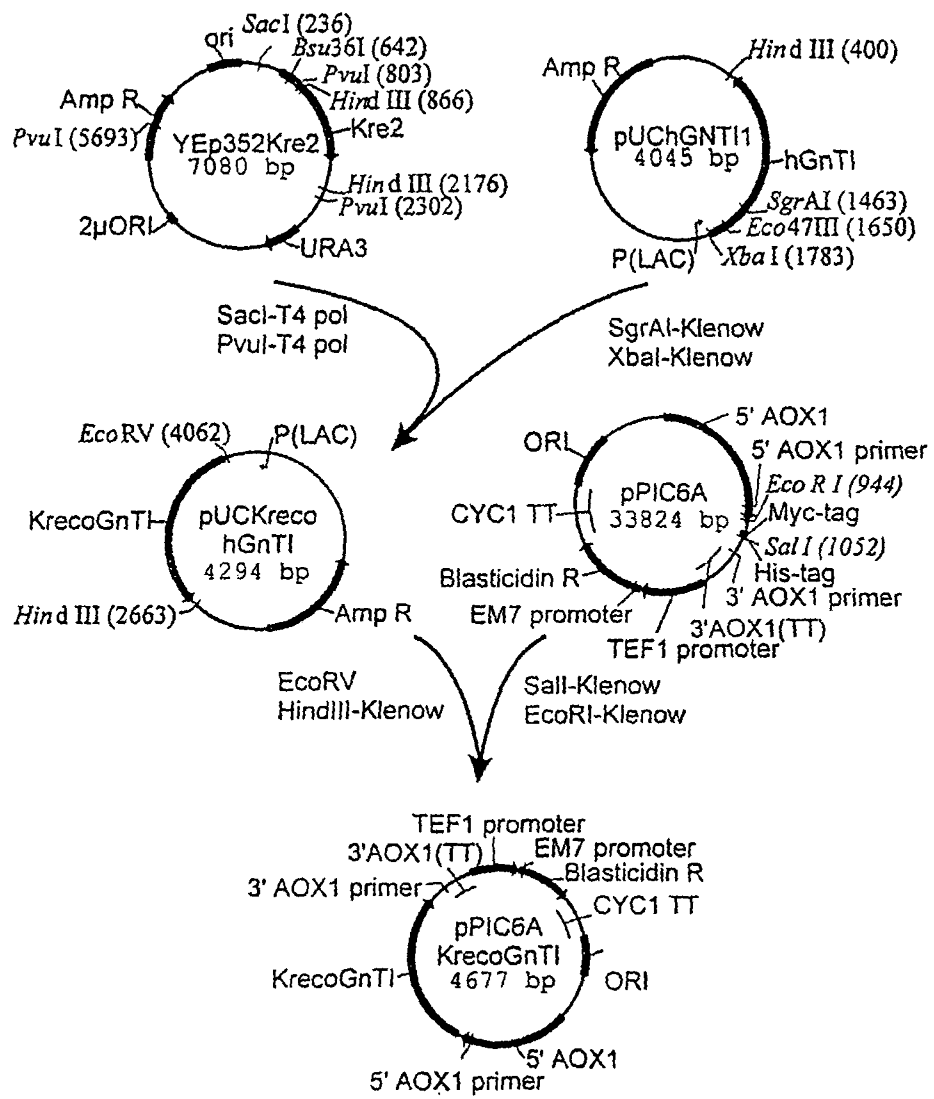
FIG. 24 depicts vectors carrying a ScKre2-tagged human GlcNAc-transferase I (GnTI) expression cassette and describes the way in which these vectors were constructed according to methods known in the art. Abbreviations used throughout the construction schemes: 5' AOX1 or AOX1 P: *Pichia pastoris* AOX1 promoter sequence; Amp R: ampicillin resistance gene; ColE1: ColE1 origin of replication; 3'AOX1: 3' sequences of the *Pichia pastoris* AOX1 gene; AOX TT: transcription terminator sequence of the *Pichia pastoris* AOX1 gene; ORF: open reading frame; Blastisidin R: blastisidin resistance gene; CYC1 TT: 3' end of the *S. cerevisiae* CYC1 gene. As can be seen in this figure, the human GnTI was operably linked at the 5' terminus of the coding sequence to the coding sequence for a peptide derived from the N-terminal part of ScKre2. The whole fusion construct was operably linked to the *P. pastoris* AOX1 promoter.

The human GnTI gene was isolated and described by Kumar et al (*Proc Natl Acad Sci USA*. 87(24):9948-52, 1990). The sequence of this gene is available at NCBI GenBank under Accession No. M61829, as set in forth by SEQ ID NO: 34. pUChGnTI (Maras et al. *Eur J. Biochem.* 249(3):701-7, 1997), which contains the full length human GnTI, was digested by SgrA I and Xba I and blunted by Klenow enzyme. The resulting vector contained the catalytic domain of GnTI. This fragment was then ligated with an insert fragment from plasmid Yep352Kre2 digested by Sac I and Pvu I, then made blunt by T4 DNA Polymerase. The insert fragment encodes a peptide derived from the N-terminal part of *S. cerevisiae* Kre2 which is responsible for the localization of expressed proteins in Golgi apparatus of *Pichia pastoris*. The resulting plasmid pUCKrecohGnTI was then cut by EcoR V and Hind III, blunted by Klenow enzyme. The fragment containing the Kre2 and hGnTI fusion was then inserted into vector pPIC6A which was digested by Sal I and EcoR I, blunted by Klenow enzyme. The final plasmid was named pPIC6AKrecoGnTI and the construction strategy is graphically depicted in FIG. 24. pPIC6AKrecoGnTI (SEQ ID NO: 36, Open Reading Frame: 2699 bp-4027 bp) contains the fusion construct KrecoGnTI under promoter AOX1 and blasticidin resistance marker.

6.2 Yeast Transformation and Genomic Integration

All transformations to *Pichia pastoris* were performed with electroporation according to the methods in Invitrogen. The strain used was GS115 containing $\alpha$-1,2-mannosidase-HDEL and Trans-sialidase (TS). Plasmid pPIC6AKrecoGntI was linearised by Nsi I digestion in the 5' AOX region. Transformants carrying blasticidin resistance gene were selected on YPD containing 500 ug/ml blasticidin and 1M sorbitol. Genomic intergration of expression cassettes was verified using PCR with genomic DNA purified from *Pichia* strains according the Yeast Miniprep method (Nucleon). The 5' (SEQ ID NO: 11) and 3' AOX1 (SEQ ID NO: 9) primers were used to verify the presence of the construct.

The results indicated that the correct insert of 1620 bp was obtained from all 4 blasticidin resistant colonies. The control colony (a wild type or an untransformed strain) did not have this PCR fragment.

6.3 Glycan Analyses

Figure 25:
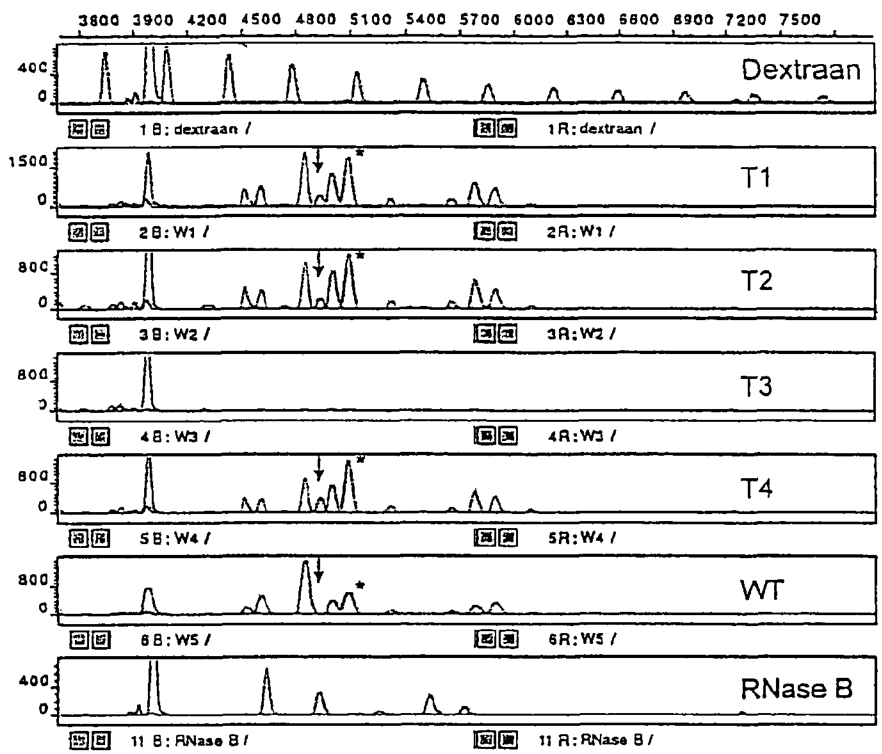
FIG. 25 depicts an analysis of native N-glycans from proteins secreted by *P. pastoris* transformants with GlcNAc-transferase I, separated by means of DSA-FACE. Panel 1 shows the analysis of Dextran. This analysis serves as a size reference for the other panels. On the vertical axis of all panels, peak intensity in relative fluorescence units is given. Panel 2-5 (T1-T4) shows the results from the analysis of the N-glycans from transformants 1-4. The analysis on a WT or untransformed organism is shown in Panel 6.
Figure 26:
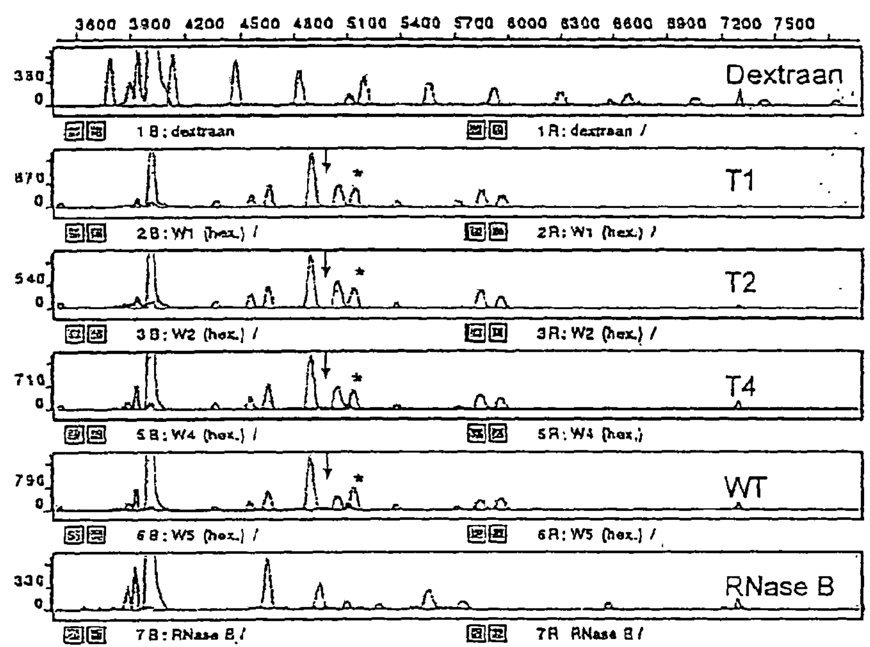
FIG. 26 depicts an analysis of N-glycans from secreted proteins of *P. pastoris* transformants with GlcNAc-transferase I digested with Jack Bean beta-N-acetylhexosaminidase.

The transformants and the untransformed organism (WT: GS115 containing TS and ManHDEL) were grown overnight in BMGY. The AOX1 promoter was induced during 24 h with 1% MetOH. Extra cellular medium was collected and dialysed against PBS. Oligosaccharides were isolated and separated by DSA-FACE. The results are shown in FIG. 25. A peak where $GlcNAcMan_5GlcNAc_2$ was observed (indicated by an arrow in FIG. 25). This peak was absent in the WT strain. Additionally an increase of the peak indicated with an asterix was also observed. Both, the additional peak and the increased peak returned to the WT situation after digestion with Jack Bean $\beta$-N-acetylhexosaminidase, a glycosidase lysing $\beta$-N-acetylhexosaminyl residues (presented in FIG. 26).

In order to evaluate the transfer of GlcNAc to glycans of a heterologous protein or the percentage of $Man_5GlcNAc_2$ that was converted to $GlcNAcMan_5GlcNAc_2$, Transsialidase (TS) was purified. Yeast strains were cultured in BMMY during 30 h. Medium was collected and loaded on an anti E-tag column. Glycans were then analysed.

Figure 27:
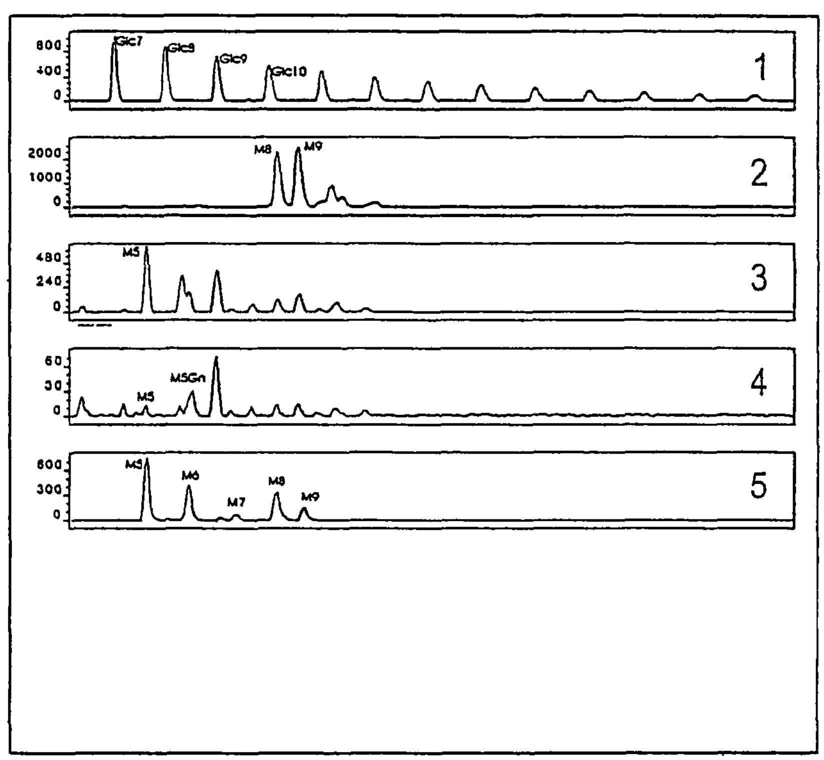
FIG. 27 depicts an analysis of N-glycans from Transsialidase (TS) produced in three different strains. Panel 1: oligomaltose reference. Panel 2: Glycans from TS produced in GS115. The two main peaks are from $Man_9GlcNAc_2$ and $Man_9GlcNAc_2$. While TS produced in GS115 which was transformed with MannosidaseHDEL presented mainly $Man_5GlcNAc_2$, there were still some $Man_6GlcNAc_2$ and $Man_7GlcNAc_2$ peaks, as shown in panel 3. But glycans from TS produced in GS115 strain which was transformed with both MannosidaseHDEL and Kre2-GlcNAc-transferase I showed that almost all $Man_5GlcNAc_2$ was converted to $GlcNAcMan_5GlcNAc_2$ (panel 4).

Transsialidase (TS) produced in three different strains (i.e. GS115, GS115 ManHDEL and GS115 ManHDEL Kre2GnTI) was purified by affinity chromatography (anti E-tag column). The N-glycans were isolated by digestion with PNGase F and analyzed by DSA-FACE. As shown in FIG. 27 shows that, in glycans from TS produced in GS115 containing MannosidaseHDEL and Kre2-GlcNAc-transferase, almost all $Man_5GlcNAc_2$ was converted to GlcNAcMan5GlcNAc2.

Figure 28:
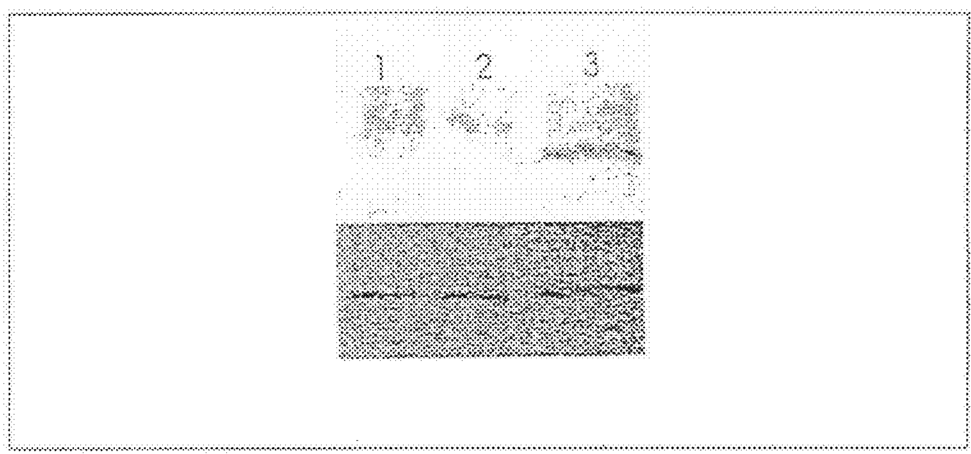
FIG. 28 depicts a lectin blot of Transsialidase (TS). Above: lectin blot of TS from 3 different strains. Lane 1: TS from GS115, lane 2: TS from GS115 ManHDEL, lane 3: GS115 ManHDEL Kre2GnTI. Below: Same blot stained with Ponceau red. Only the band in lane 3 is stained by the lectin, indicating that only there terminal GlcNAc is present.

Alternatively TS from the three different strains was separated by SDS-PAGE and blotted on a nitrocellulose membrane. First the proteins were visualized by Ponceau red staining to show that equal amounts of protein were loaded. Then they were screened by biotin conjugated lectin GSII, a lectin specific against terminal GlcNAc. The lectin was visualized by POD conjugated streptavidin and a luminescent substrate. The two blots are presented in FIG. 28, showing that only the band in lane 3 was stained by the lectin. Lane 3 represents TS produced from strain GS115 containing ManHDEL Kre2GnTI. These results indicate that terminal GlcNAc is present only in strains with ManHDEL Kre2GnTI.

An additional proof of the presence of $GlcNAcMan_5GlcNAc_2$ was obtained from digestions with exoglycosidases on the N-glycans of TS produced in the strain GS115 ManHDEL Kre2GnTI. TS was purified, and its N-glycans were isolated and analyzed by DSA-FACE. Digestions with Jack Bean β-N-acetylhexosaminidase were performed. The result is shown in FIG. 29.

Figure 29:
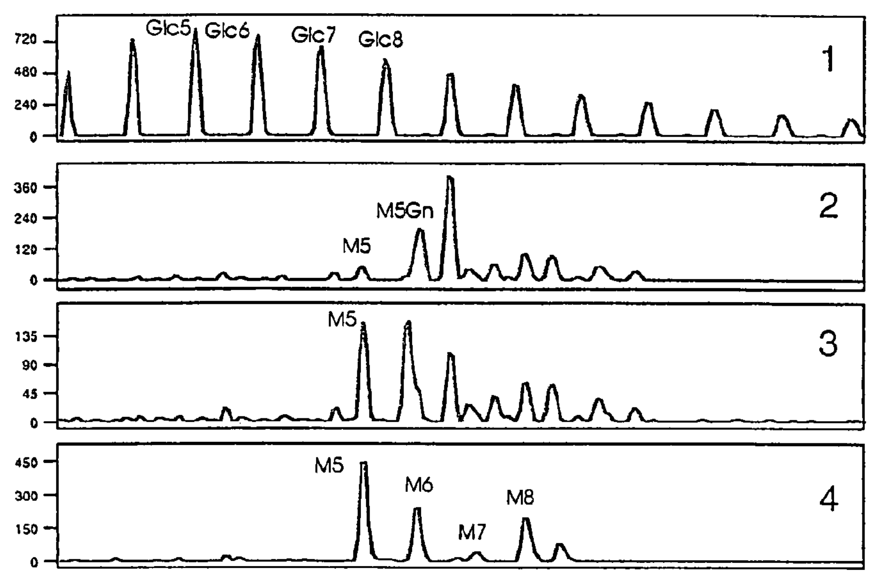
FIG. 29 depicts an N-glycan analysis of a GnTI-transformant treated with Jack Bean β-N-acetylhexosaminidase.

As can be seen in FIG. 29, panel 2, almost no $Man_5GlcNAc_2$ was present in undigested N-glycans from TS produced in strain GS115 ManHDEL Kre2GnTI. Both the $Man_5GlcNAc_2$ and the $Man_6GlcNAc_2$ peaks were increased if the same glycans as in panel 2 were digested with β-N-acetylhexosaminidase, as seen in panel 3. This indicates the presence of GlcNAc on both structures. Panel 1 is oligomaltose reference, while panel 4 is the result of N-glycans from RNaseB.

Example 7

Mannosidase II Expression in *Pichia*

7.1 Vector Construction

Mammalian mannosidase II is located in the same Golgi region as is GnTI. Therefore the N-terminal part of mannosidase II that is responsible for the localization of the protein in the Golgi was replaced by that of ScKre2, as was done to localize GnTI in the Golgi apparatus of *Pichia pastoris*. A construction strategy was set up that ultimately led to a plasmid containing Kre2ManII ORF under the control of the gap promoter with the ARG4 marker for selection in *Pichia pastoris*. The plasmid containing the human mannosidase II gene was pcDNA3ManII. The sequence of this gene is available at EMBL under Accession No. U31520 (SEQ ID NO: 31). Plasmid pBLARGIX was as published in Cereghino et al. Gene 263(1-2):159-69, 2001.

Figure 30A:
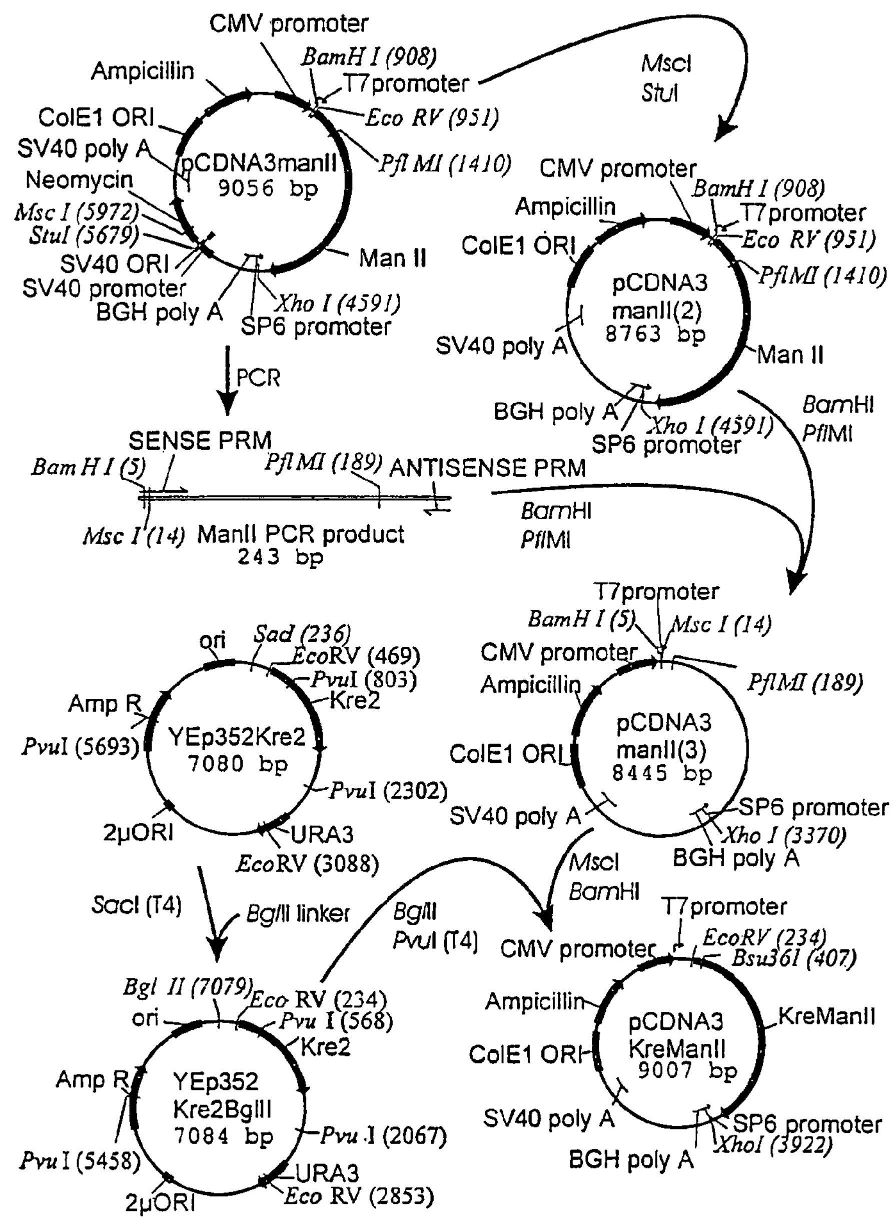
FIG. 30 depicts vectors carrying a SrKre2-tagged human mannosidase II expression cassette and describes the way in which these vectors were constructed. Abbreviations used throughout the construction schemes: 5' AOX1 or AOX1 P: *Pichia pastoris* AOX1 promoter sequence; Amp R: ampicillin resistance gene; ColE1: ColE1 origin of replication; 3'AOX1: 3' sequences of the *Pichia pastoris* AOX1 gene; ARG4: ARG4 gene of *Pichia pastoris*. AOX TT: transcription terminator sequence of the *Pichia pastoris* AOX1 gene; ORF: open reading frame; P EM7: synthetic constitutive prokaryotic promotor EM7; Zeocin: Zeocin resistance gene; CYC1 TT: 3' end of the *S. cerevisiae* CYC1 gene; GAP: promoter sequence of the *Pichia pastoris* glyceraldehyde-3-phosphate dehydrogenase gene; PpURA3: *Pichia pastoris* URA3 gene. As can be seen in this figure, the human mannosidase II is operably linked at the 5' terminus of the coding sequence to the coding sequence for a peptide derived from the N-terminal part of ScKre2. The whole fusion construct was operably linked to the *P. pastoris* GAP promoter.
Figure 30B:
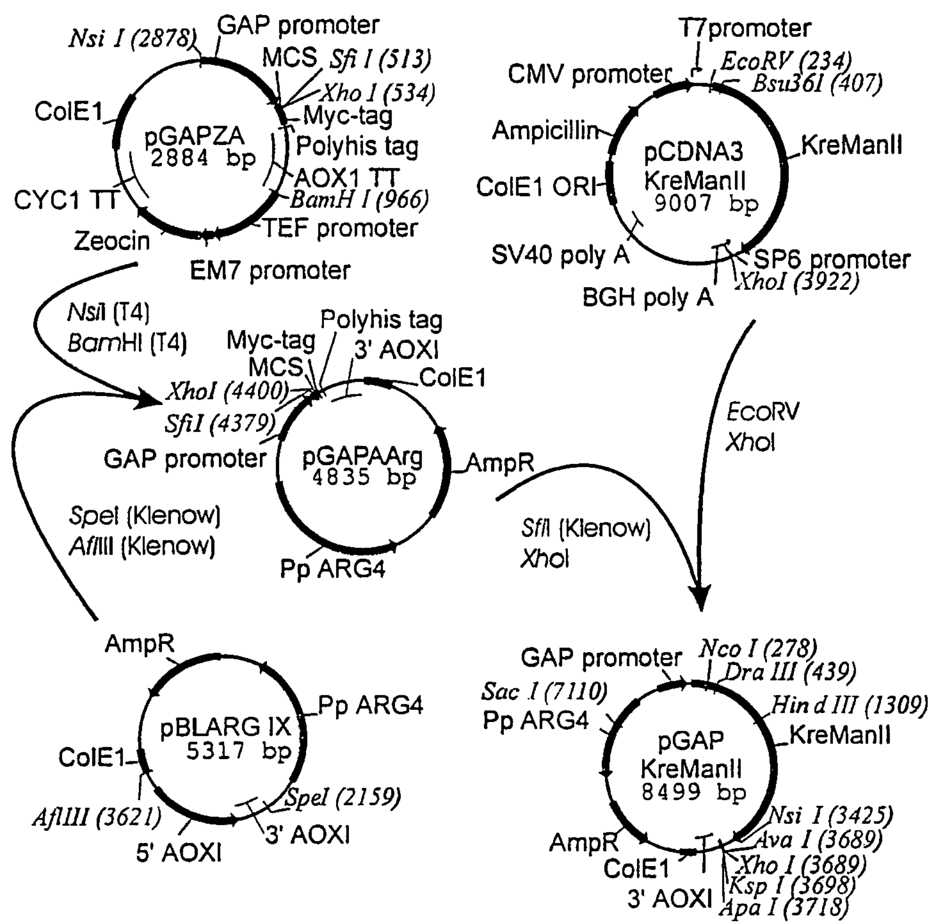

The mannosidase cDNA fragment was purified by PCR. The primers used were the sense primer: 5'CGCGGATCCATGGCCAAAAAGTTCACAAAGCAATTTC3' (SEQ ID NO: 32) and antisense primer: 5'GTGTCCCATTCATTAGATTC3' (SEQ ID NO: 33). The PCR fragment was then digested by BamH I and PflM I and inserted into vector. pcDNA3manII(2) opened with same enzymes. The product was named pcDNA3manII(3). pcDNA3manII(2) was made by digesting pcDNA3manII with Msc I and Stu I, followed by self ligation. A plasmid YEp352Kre2BglII was made through inserting a Bgl II linker into T4 DNA Polymerase blunted plasmid YEp352Kre2, which had been digested by Sac I. YEp352Kre2BglII was cut by Pvu I and blunted by T4 DNA Polymerase to generate the coding sequence for the N-terminal part of Kre2 and subsequently digested by Bgl II. The coding fragment of the N-terminal part of Kre2 was purified and ligated to the vector of pcDNA3manII(3) digested by Msc I and Bam HI. The resulting plasmid was named pcDNA3KreManII. The plasmid carrying a GAP promoter (pGAPZA) was cut by Nsi I and BamH I, made blunt by T4 DNA Polymerase. The fragment containing the GAP promoter was then inserted into the vector pBLARG IX, which carried the selection marker ARG4, opened by Spe I and Afl II digestion, blunted by Klenow enzyme. The intermediate plasmid was named pGAPAArg. pGAPAArg was further digested by Sfi I, blunted by Klenow, followed by Xho I digestion. The resulting vector was then ligated with the insert made from plasmid pcDNA3KreManII digested by EcoR V and Xho I. The final plasmid was named pGAPKreManII. The cloning strategy is depicted in FIGS. 30A and 30B.

7.2 Yeast Transformation and Genomic Integration

MannosidaseHDEL (ManHDEL) was introduced (transformation with pGAPZMFManHDEL) to strain YGC-4. Genomic characterization of the transformed cells was done by PCR using a Gap primer (SEQ ID NO: 10) and a 3'AOX primer (SEQ ID NOs: 9). A band of 2010 bp indicated the presence of the construct in *Pichia pastoris* transformants. N-glycans derived from secreted and cell wall glycoproteins were analyzed by means of DSA FACE. Similar to the results obtained in strain GS115, glycans were trimmed and the presence of $Man_5GlcNAc_2$ was observed. Cell wall glycoproteins (mannoproteins) were prepared in a miniaturized way as described by Peat et al. (*J. Chem. Soc.* 29, 1961).

From the resulting YGC-4 ManHDEL clones, Clone 1 (M1) was transformed with the plasmid pPIC6KrecoGnTI. Genomic DNA was prepared and analyzed by PCR for integration of the construct into the genome using 5'AOX and 3'AOX primers (SEQ ID NOs: 11 and 9). Analysis of mannoproteins revealed the presence of $GlcNAcMan_5GlcNAc_2$ comparable to the situation in the GS115 strain.

Clone 4 (YGC-4 M1 GnTI4) was transformed with plasmid pGAPKreManII by electroporation after linerisation of the plasmid in the 3' AOX I region by a digestion with Pvu II. Transformants having the ARG4 gene were selected on medium containing no arginin. DNA was prepared and analysed for the presence of the construct by PCR using primer SEQ ID NO: 33 and SEQ ID NO: 10. An amplified fragment of 617 bp was seen indicating the presence of the construct.

Example 8

Mannosidase-HDEL Expression and OCH1 Inactivation 8.1 Vector Construction

The following experiments were performed to generate a plasmid that would carry both a mannosidase-HDEL expression unit and an inactivated OCH1 fragment. A point mutation in the very 5' part of the OCH1 CDS was introduced, changing the codon for amino acid 12 to a stop codon, using QuickChange® kit from Stratagene, so that mRNA produced by a potential cryptic promoter activity would translate into an inactive protein. The template used was pUC18PpOCH1. The presence of the stop codon was confirmed by sequencing.

Cloning in pPICZB to pick up the AOX1 transcription terminator was done by ligating the blunted HindIII fragment of the mutated pUC18PpOCH1 variant in the blunted, XhoI/EcoRI opened pPICZB. The resulting plasmid was called pPICZB5'PpOCH1Mut. The Bst BI site in the GAP promoter of pGAPZMFManHDEL was removed to allow linearization of the final vectors in the 5'PpOCH1 sequence for integration. Hereto, pGAPZMFManHDEL was digested with Bst BI and blunted with T4 polymerase and dXTPs. Subsequently, the linearized and blunted plasmid was purified and digested with BamHI. The vector and the released fragment (containing the ManHDEL open reading frame and the 3'AOXI transcription terminator were separated by agarose gel electrophoresis and the DNA fragments were eluted from the gel. Fragment and vector were religated in a 10:1 ratio using T4 DNA ligase, overnight at 16° C.

Figure 33:
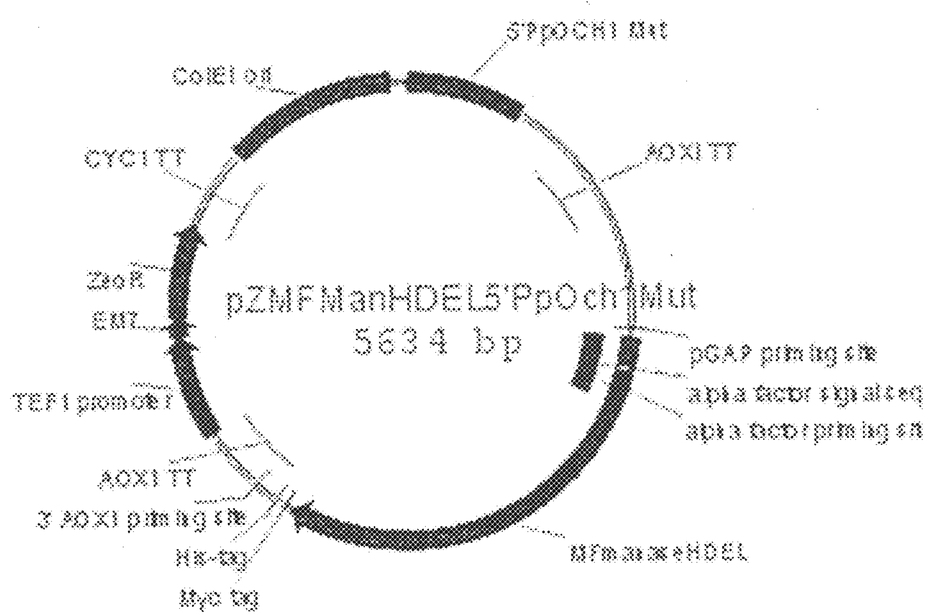
FIG. 33 depicts the expression vector pZMFManHDEL5'PpOCH1Mut (SEQ ID NO: 46)

The mutated 5'PpOCH1-3'AOX1 fragment was released by PstI/BamHI digestion, blunted and ligated in pGAPZMF-ManHDEL-Bst BI that had been opened with BglII and blunted. The resulting plasmid was called pZMFManHDEL5'PpOCH1Mut (SEQ ID NO:46). The map of this plasmid is shown on FIG. 33.

We claim:

1. A method of reducing glycosylation on proteins produced from methylotrophic yeast, comprising providing a methylotrophic yeast strain, which strain is transformed with a nucleic acid coding for a protein which comprises a GlcNAc-transferase I (GnT1) or an enzymatically active fragment thereof wherein said GnT1 is a human, rat or rabbit GnT1, and which strain is also transformed with a nucleic acid coding for a protein which comprises an α-1,2-mannosidase or an enzymatically active fragment thereof, wherein said α-1,2-mannosidase is *T. reesei* α-1,2-mannosidase, and wherein said α-1,2-mannosidase and said enzymatically active fragment are engineered to contain an ER localization signal and convert $Man_8GlcNAc_2$ to $Man_5GlcNAc_2$; and producing glycoproteins from said methylotrophic yeast strain.

2. The method of claim 1, wherein said methylotrophic yeast is *Pichia pastoris*.

3. The method of claim 1, wherein said GnT1 is human GnT1.

4. The method of claim 1, wherein said protein which comprises said GnT1 or said enzymatically active fragment thereof is engineered to contain a Golgi localization signal.

5. The method of claim 4, wherein said Golgi localization signal comprises the signal sequence of *S. cerevisiae* Kre2 protein.

6. The method of claim 1, wherein said enzymatically active fragment of GnT1 is encoded by a nucleic acid comprising the nucleotide sequence as set forth in SEQ ID NO: 36.

7. The method of claim 1, wherein the nucleotide sequence coding for said protein which comprises said GnT1 or said enzymatically active fragment thereof is operably linked to a promoter sequence functional in said strain, and wherein said promoter is the promoter of a gene selected from the group consisting of AOXI, AOXII, GAP, YPT1, and FLD.

8. The method of claim 1, wherein said ER localization signal comprises the peptide HDEL (SEQ ID NO: 1).

9. The method of claim 1, wherein the nucleotide sequence coding for said protein which comprises said α-1,2-mannosidase or said enzymatically active fragment thereof is operably linked to a promoter sequence functional in said strain, and wherein said promoter is the promoter of a gene selected from the group consisting of AOXI, AOXII, GAP, YPT1, and FLD.

10. The method of claim 1, wherein the nucleotide sequence coding for said protein which comprises said α-1,2-mannosidase or said enzymatically active fragment thereof is set forth in SEQ ID NO: 14.

11. The method of claim 1, wherein the endogenous OCH1 gene of said strain has been disrupted.

12. The method of claim 1, wherein said strain is also transformed with a nucleic acid coding for a mannosidase II or an enzymatically active fragment thereof.

13. The method of claim 3, wherein the methylotrophic yeast strain is a *Pichia* strain.

14. The method of claim 13, wherein said *Pichia* is *Pichia pastoris*.

15. The method of claim 13, wherein the endogenous OCH1 gene of said strain has been disrupted.

16. The method of claim 15, wherein the protein which comprises said GnT1 or said enzymatically active fragment thereof is engineered to contain a Golgi localization signal, and the protein which comprises said α-1,2-mannosidase or said enzymatically active fragment thereof is engineered to contain an ER localization signal.

* * * * *

SEQUENCE LISTING

<160> NUMBER OF SEQ ID NOS: 46

<210> SEQ ID NO 1
<211> LENGTH: 4
<212> TYPE: PRT
<213> ORGANISM: Artificial Sequence
<220> FEATURE:
<223> OTHER INFORMATION: Primer

<400> SEQUENCE: 1

His Asp Glu Leu
1

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
gactggttcc aattgacaag c 21

<210> SEQ ID NO 3
<211> LENGTH: 44
<212> TYPE: DNA
<213> ORGANISM: Artificial Sequence
<220> FEATURE:
<223> OTHER INFORMATION: Primer

<400> SEQUENCE: 3
agtctagatt acaactcgtc gtgagcaagg tggccgcccc gtcg 44

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
ccattgagga cgcatgccgc gcc 23

<210> SEQ ID NO 5
<211> LENGTH: 85
<212> TYPE: DNA
<213> ORGANISM: Artificial Sequence
<220> FEATURE:
<223> OTHER INFORMATION: Primer

<400> SEQUENCE: 5
gtatctagat tacaactcgt cgtgcagatc ctcttctgag atgagttttt gttcagcaag 60
gtggccgccc cgtcgtgatg atgaa 85

<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6
aactcgagat ggactcttca aaacacaaac gc 32

<210> SEQ ID NO 7

<211> LENGTH: 46
<212> TYPE: DNA
<213> ORGANISM: Artificial Sequence
<220> FEATURE:
<223> OTHER INFORMATION: Primer

<400> SEQUENCE: 7
ttgcggccgc ttacaactcg tcgtgtcgga cagcaggatt acctga 46

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
ccattgagga cgcatgccgc gcc 23

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
gcaaatggca ttctgacatc ct 22

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
gtccctattt caatcaattg aa 22

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
gactggttcc aattgacaag c 21

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
ccgctcgaga tggtcctttt gaaatggctc 30

<210> SEQ ID NO 13
<211> LENGTH: 31
<212> TYPE: DNA
<213> ORGANISM: Artificial Sequence
<220> FEATURE:
<223> OTHER INFORMATION: Primer

<400> SEQUENCE: 13
ccgggcccaa aaataacttc ccaatcttca g 31

<210> SEQ ID NO 14
<211> LENGTH: 1785
<212> TYPE: DNA
<213> ORGANISM: Trichoderma reesei

<400> SEQUENCE: 14
atgagatttc cttcaatttt tactgctgtt ttattcgcag catcctccgc attagctgct 60
ccagtcaaca ctacaacaga agatgaaacg gcacaaattc cggctgaagc tgtcatcggt 120
tactcagatt tagaagggga tttcgatgtt gctgttttgc cattttccaa cagcacaaat 180
aacgggttat tgtttataaa tactactatt gccagcattg ctgctaaaga agaaggggta 240
tctctcgaga aaagagaggc tgaagctgaa ttcgccacaa aacgtggatc tcccaaccct 300
acgagggcgg cagcagtcaa ggccgcattc cagacgtcgt ggaacgctta ccaccatttt 360
gcctttcccc atgacgacct ccacccggtc agcaacagct ttgatgatga gagaaacggc 420
tggggctcgt cggcaatcga tggcttggac acggctatcc tcatggggga tgccgacatt 480
gtgaacacga tccttcagta tgtaccgcag atcaacttca ccacgactgc ggttgccaac 540
caaggatcct ccgtgttcga gaccaacatt cggtacctcg gtggcctgct ttctgcctat 600
gacctgttgc gaggtccttt cagctccttg gcgacaaacc agaccctggt aaacagcctt 660
ctgaggcagg ctcaaacact ggccaacggc ctcaaggttg cgttcaccac tcccagcggt 720
gtcccggacc ctaccgtctt cttcaaccct actgtccgga gaagtggtgc atctagcaac 780
aacgtcgctg aaattggaag cctggtgctc gagtggacac ggttgagcga cctgacggga 840
aacccgcagt atgcccagct tgcgcagaag ggcgagtcgt atctcctgaa tccaaaggga 900
agcccggagg catggcctgg cctgattgga acgtttgtca gcacgagcaa cggtaccttt 960
caggatagca gcggcagctg gtccggcctc atggacagct tctacgagta cctgatcaag 1020
atgtacctgt acgacccggt tgcgtttgca cactacaagg atcgctgggt ccttggtgcc 1080
gactcgacca ttgggcatct cggctctcac ccgtcgacgc gcaaggactt gacctttttg 1140
tcttcgtaca acggacagtc tacgtcgcca aactcaggac atttggccag ttttggcggt 1200
ggcaacttca tcttgggagg cattctcctg aacgagcaaa agtacattga ctttggaatc 1260
aagcttgcca gctcgtactt tggcacgtac acccagacgg cttctggaat cggccccgaa 1320
ggcttcgcgt gggtggacag cgtgacgggc gccggcggct cgccgccctc gtcccagtcc 1380
gggttctact cgtcggcagg attctgggtg acggcaccgt attacatcct gcggccggag 1440
acgctggaga gcttgtacta cgcataccgc gtcacgggcg actccaagtg gcaggacctg 1500
gcgtgggaag cgttgagtgc cattgaggac gcatgccgcg ccggcagcgc gtactcgtcc 1560
atcaacgacg tgacgcaggc caacggcggg ggtgcctctg acgatatgga gagcttctgg 1620
tttgccgagg cgctcaagta tgcgtacctg atctttgcgg aggagtcgga tgtgcaggtg 1680
caggccaccg gcgggaacaa atttgtcttt aacacggagg cgcacccctt tagcatccgt 1740
tcatcatcac gacggggcgg ccaccttgct cacgacgagt tgtaa 1785

<210> SEQ ID NO 15
<211> LENGTH: 2016
<212> TYPE: DNA
<213> ORGANISM: Mus musculus

<400> SEQUENCE: 15

```
atgagatttc cttcaatttt tactgctgtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaaggggta     240
tctctcgaga tggactcttc aaaacacaaa cgctttgatc tgggcttaga agatgtgtta     300
attcctcacg tagatgccgg caaaggagct aaaaaccccg gcgtcttcct gatccatgga     360
cccgacgaac acagacacag ggaagaagaa gagcgtctga gaaataagat tagagctgac     420
catgagaaag ccctggaaga agcaaaagaa aaattaagaa agtcaagaga ggaaatccgt     480
gcagaaattc agacagagaa aaacaaagta gcccaagcaa tgaagacaaa agagaccagg     540
gtactgccgc ctgtccctgt cccacaacgt gtaggggtca gtggtgggga tccagaagac     600
atggagatca agaagaaaag agacaaaatt aaagagatga tgaaacatgc ctgggataat     660
tacagaacat acggatgggg acataatgaa ctaaggccta ttgcaaggaa aggccattcc     720
actaacatat tcggaagctc acagatgggt gccaccatag tggatgcttt ggataccctt     780
tatatcatgg ggcttcatga tgaattcatg gatgggcaaa gatggattga agaaaacctt     840
gatttcagtg tgaattcaga agtgtctgtc tttgaagtta acattcgctt tattggaggg     900
ctcctcgctg catattacct gtcaggagag gaaatattca agactaaagc agtgcagttg     960
gctgagaaac tccttcctgc ctttaacaca cctactggga ttccctgggc aatggtgaac    1020
ctgaaaagtg gagtaggtcg aaactggggc tgggcgtctg caggcagcag catcctggct    1080
gagttcggca ccctgcacat ggagtttgtg cacctcagct acttgaccgg tgacttgact    1140
tactataata aggtcatgca cattcggaaa ctactgcaga aatggaacg cccaaatggt     1200
ctttatccaa attatttaaa cccaagaaca gggcgctggg gtcagtatca cacatcagtt    1260
ggtggtctgg gagatagttt ttatgaatac ttactgaaag catggctgac gtcagataaa    1320
acagaccacg aggcaagaag gatgtatgac gatgctgttg aggctataga aaaacatctt    1380
attaagaagt cccgaggagg tctggttttt attggagaat ggaagaatgg acacttggaa    1440
aggaagatgg ggcacttggc ctgctttgct gggggaatgc ttgcccttgg agcagatggt    1500
tccagaaagg ataaagctgg ccactactta gaactagggg cagaaattgc acgaacatgt    1560
catgagtcat atgacagaac tgcattgaaa ctaggtccgg agtcattcaa gtttgatggt    1620
gcagtggaag ccgtggctgt gcggcaggct gaaaagtatt acatccttcg tccagaagta    1680
attgaaacct attggtatct atggcgattt acccacgacc caagatacag gcagtggggc    1740
tgggaagcag cactggctat tgagaagtcg tgccgggtca gcggtgggtt ttctggtgtc    1800
aaggatgtat acgccccgac ccctgtgcat gacgacgtgc agcagagctt ttctcttgct    1860
gaaacattaa aatacttgta cctgctgttc tctggcgatg accttctacc tttagaccac    1920
tgggtgttta acacagaggc gcaccctctg ccggtgttgc gcttagccaa cagcactctt    1980
tcaggtaatc ctgctgtccg acacgacgag ttgtaa                              2016
```

<210> SEQ ID NO 16
<211> LENGTH: 6757
<212> TYPE: DNA
<213> ORGANISM: Artificial Sequence
<220> FEATURE:
<223> OTHER INFORMATION: plasmid pAOX2ZAGLSII

<400> SEQUENCE: 16

```
catggccaag ttgaccagtg ccgttccggt gctcaccgcg cgcgacgtcg ccggagcggt      60
```

-continued

```
cgagttctgg accgaccggc tcgggttctc ccgggacttc gtggaggacg acttcgccgg    120
tgtggtccgg gacgacgtga ccctgttcat cagcgcggtc caggaccagg tggtgccgga    180
caacaccctg gcctgggtgt gggtgcgcgg cctggacgag ctgtacgccg agtggtcgga    240
ggtcgtgtcc acgaacttcc gggacgcctc cgggccggcc atgaccgaga tcggcgagca    300
gccgtggggg cgggagttcg ccctgcgcga cccggccggc aactgcgtgc acttcgtggc    360
cgaggagcag gactgacacg tccgacggcg gcccacgggt cccaggcctc ggagatccgt    420
ccccctttc ctttgtcgat atcatgtaat tagttatgtc acgcttacat tcacgccctc    480
cccccacatc cgctctaacc gaaaaggaag gagttagaca acctgaagtc taggtcccta    540
tttattttt tatagttatg ttagtattaa gaacgttatt tatatttcaa atttttcttt    600
tttttctgta cagacgcgtg tacgcatgta acattatact gaaaaccttg cttgagaagg    660
ttttgggacg ctcgaaggct ttaatttgca agctggagac caacatgtga gcaaaaggcc    720
agcaaaaggc caggaaccgt aaaaaggccg cgttgctggc gtttttccat aggctccgcc    780
cccctgacga gcatcacaaa aatcgacgct caagtcagag gtggcgaaac ccgacaggac    840
tataaagata ccaggcgttt ccccctggaa gctccctcgt gcgctctcct gttccgaccc    900
tgccgcttac cggatacctg tccgcctttc tcccttcggg aagcgtggcg ctttctcaat    960
gctcacgctg taggtatctc agttcggtgt aggtcgttcg ctccaagctg ggctgtgtgc   1020
acgaaccccc cgttcagccc gaccgctgcg ccttatccgg taactatcgt cttgagtcca   1080
acccggtaag acacgactta tcgccactgg cagcagccac tggtaacagg attagcagag   1140
cgaggtatgt aggcggtgct acagagttct tgaagtggtg gcctaactac ggctacacta   1200
gaaggacagt atttggtatc tgcgctctgc tgaagccagt taccttcgga aaaagagttg   1260
gtagctcttg atccggcaaa caaaccaccg ctggtagcgg tggttttttt gtttgcaagc   1320
agcagattac gcgcagaaaa aaaggatctc aagaagatcc tttgatcttt tctacggggt   1380
ctgacgctca gtggaacgaa aactcacgtt aagggatttt ggtcatgaga tcagatcttt   1440
ttttcagacc atatgaccgg tccatcttct acggggggat tatctatgct ttgacctcta   1500
tcttgattct tttatgattc aaatcacttt tacgttattt attacttact ggttatttac   1560
ttagcgcctt ttctgaaaaa catttactaa aaatcataca tcggcactct caaacacgac   1620
agattgtgat caagaagcag agacaatcac cactaaggtt gcacatttga gccagtaggc   1680
tcctaataga ggttcgatac ttattttgat aatacgacat attgtcttac ctctgaatgt   1740
gtcaatactc tctcgttctt cgtctcgtca gctaaaaata taacacttcg agtaagatac   1800
gcccaattga aggctacgag ataccagact atcactagta gaactttgac atctgctaaa   1860
gcagatcaaa tatccattta tccagaatca attaccttcc tttagcttgt cgaaggcatg   1920
aaaaagctac atgaaaatcc ccatccttga agttttgtca gcttaaagga ctccatttcc   1980
taaaatttca agcagtcctc tcaactaaat ttttttccat tcctctgcac ccagccctct   2040
tcatcaaccg tccagccttc tcaaaagtcc aatgtaagta gcctgcaaat tcaggttaca   2100
acccctcaat tttccatcca agggcgatcc ttacaaagtt aatatcgaac agcagagact   2160
aagcgagtca tcatcaccac ccaacgatgg tgaaaaactt taagcataga ttgatggagg   2220
gtgtatggca cttggcggct gcattagagt ttgaaactat ggggtaatac atcacatccg   2280
gaactgatcc gactccgaga tcatatgcaa agcacgtgat gtaccccgta aactgctcgg   2340
attatcgttg caattcatcg tcttaaacag tacaagaaac tttattcatg ggtcattgga   2400
```

-continued

```
ctctgatgag gggcacattt ccccaatgat tttttgggaa agaaagccgt aagaggacag   2460
ttaagcgaaa gagacaagac aacgaacagc aaaagtgaca gctgtcagct acctagtgga   2520
cagttgggag tttccaattg gttggttttg aatttttacc catgttgagt tgtccttgct   2580
tctccttgca aacaatgcaa gttgataaga catcaccttc caagataggc tatttttgtc   2640
gcataaattt ttgtctcgga gtgaaaaccc cttttatgtg aacagattac agaagcgtcc   2700
tacccttcac cggttgagat ggggagaaaa ttaagcgatg aggagacgat tattggtata   2760
aaagaagcaa ccaaaatccc ttattgtcct tttctgatca gcatcaaaga atattgtctt   2820
aaaacgggct tttaactaca ttgttcttac acattgcaaa cctcttcctt ctatttcgga   2880
tcaactgtat tgactacatt gatctttttt aacgaagttt acgacttact aaatccccac   2940
aaacaaatca actgagaaaa gaattcacgt ggcccagccg gccgtctcgg atcggtacct   3000
cgagatggtc cttttgaaat ggctcgtatg ccaattggtc ttctttaccg ctttttcgca   3060
tgcgtttacc gactatctat taaagaagtg tgcgcaatct gggttttgcc atagaaacag   3120
ggtttatgca gaaaatattg ccaaatctca tcactgctat tacaaagtgg acgccgagtc   3180
tattgcacac gatcctttag agaatgtgct tcatgctacc ataattaaaa ctataccaag   3240
attggagggc gatgatatag ccgttcagtt cccattctct ctctcttttt tacaggatca   3300
ctcagtaagg ttcactataa atgagaaaga gagaatgcca accaacagca gcggtttgtt   3360
gatctcttca caacggttca atgagacctg gaagtacgca ttcgacaaga aatttcaaga   3420
ggaggcgaac aggaccagta ttccacaatt ccacttcctt aagcaaaaac aaactgtgaa   3480
ctcattctgg tcgaaaatat cttcattttt gtcactttca aactccactg cagacacatt   3540
tcatcttcga aacggtgatg tatccgtaga aatctttgct gaacctttc aattgaaagt    3600
ttactggcaa aatgcgctga aacttattgt aaacgagcaa aatttcctga acattgaaca   3660
tcatagaact aagcaggaaa acttcgcaca cgtgctgcca gaagaaacaa ctttcaacat   3720
gtttaaggac aatttcttgt attcaaagca tgactctatg cctttggggc ctgaatcggt   3780
tgcgctagat ttctctttca tgggttctac taatgtctac ggtataccgg aacatgcgac   3840
gtcgctaagg ctgatggaca cttcaggtgg aaaggaaccc tacaggcttt tcaacgttga   3900
tgtctttgag tacaacatcg gtaccagcca accaatgtac ggttcgatcc cattcatgtt   3960
ttcatcttcg tccacatcta tcttttgggt caatgcagct gacacttggg tagacataaa   4020
gtatgacacc agtaaaaata aaacgatgac tcattggatc tccgaaaatg gtgtcataga   4080
tgtagtcatg tccctggggc cagatattcc aactatcatt gacaaattta ccgatttgac   4140
tggtagaccc tttttaccgc ccatttcctc tatagggtac catcaatgta gatggaatta   4200
taatgatgag atggacgttc tcacagtgga ctctcagatg gatgctcata tgattcctta   4260
cgattttatt tggttggact tggagtatac gaacgacaaa aaatatttta cttggaagca   4320
gcactccttt cccaatccaa aaaggctgtt atccaaatta aaaaagttgg gtagaaatct   4380
tgtcgtacta atcgatcctc atttaaagaa agattatgaa atcagtgaca gggtaattaa   4440
tgaaaatgta gcagtcaagg atcacaatgg aaatgactat gtaggtcatt gctggccagg   4500
taattctata tggattgata ccataagcaa atatggccaa aagatttgga agtccttttt   4560
cgaacggttt atggatctgc cggctgattt aactaattta ttcatttgga atgatatgaa   4620
cgagccttcg attttcgatg gcccagagac cacagctcca aaagatttga ttcacgacaa   4680
ttacattgag gaaagatccg tccataacat atatggtcta tcagtgcatg aagctactta   4740
cgacgcaata aaatcgattt attcaccatc cgataagcgt cctttccttc taacaagggc   4800
```

-continued

```
ttttttgcc ggctctcaac gtactgctgc cacatggact ggtgacaatg tggccaattg   4860
ggattactta aagatttcca ttcctatggt tctgtcaaac aacattgctg gtatgccatt   4920
tataggagcc gacatagctg gctttgctga ggatcctaca cctgaattga ttgcacgttg   4980
gtaccaagcg ggcttatggt acccattttt tagagcacac gcccatatag acaccaagag   5040
aagagaacca tacttattca atgaaccttt gaagtcgata gtacgtgata ttatccaatt   5100
gagatatttc ctgctaccta ccttatacac catgtttcat aaatcaagtg tcactggatt   5160
tccgataatg aatccaatgt ttattgaaca ccctgaattt gctgaattgt atcatatcga   5220
taaccaattt tactggagta attcaggtct attagtcaaa cctgtcacgg agcctggtca   5280
atcagaaacg gaaatggttt tcccacccgg tatattctat gaattcgcat ctttacactc   5340
ttttataaac aatggtactg atttgataga aaagaatatt tctgcaccat tggataaaat   5400
tccattattt attgaaggcg gtcacattat cactatgaaa gataagtata gaagatcttc   5460
aatgttaatg aaaaacgatc catatgtaat agttatagcc cctgataccg agggacgagc   5520
cgttggagat ctttatgttg atgatggaga aacttttggc taccaaagag gtgagtacgt   5580
agaaactcag ttcattttcg aaaacaatac cttaaaaaat gttcgaagtc atattcccga   5640
gaatttgaca ggcattcacc acaatacttt gaggaatacc aatattgaaa aaatcattat   5700
cgcaaagaat aatttacaac acaacataac gttgaaagac agtattaaag tcaaaaaaaa   5760
tggcgaagaa agttcattgc cgactagatc gtcatatgag aatgataata agatcaccat   5820
tcttaaccta tcgcttgaca taactgaaga ttgggaagtt atttttgggc ccgaacaaaa   5880
actcatctca gaagaggatc tgaatagcgc cgtcgaccat catcatcatc atcattgagt   5940
tttagcctta gacatgactg ttcctcagtt caagttgggc acttacgaga agaccggtct   6000
tgctagattc taatcaagag gatgtcagaa tgccatttgc ctgagagatg caggcttcat   6060
ttttgatact tttttatttg taacctatat agtataggat ttttttgtc attttgtttc   6120
ttctcgtacg agcttgctcc tgatcagcct atctcgcagc tgatgaatat cttgtggtag   6180
gggtttggga aaatcattcg agtttgatgt ttttcttggt atttcccact cctcttcaga   6240
gtacagaaga ttaagtgaga ccttcgtttg tgcggatccc ccacacacca tagcttcaaa   6300
atgtttctac tcctttttta ctcttccaga ttttctcgga ctccgcgcat cgccgtacca   6360
cttcaaaaca cccaagcaca gcatactaaa ttttccctct ttcttcctct agggtgtcgt   6420
taattacccg tactaaaggt ttggaaaaga aaaaagagac cgcctcgttt ctttttcttc   6480
gtcgaaaaag gcaataaaaa tttttatcac gtttcttttt cttgaaattt ttttttttag   6540
tttttttctc tttcagtgac ctccattgat atttaagtta ataaacggtc ttcaatttct   6600
caagtttcag tttcattttt cttgttctat tacaactttt tttacttctt gttcattaga   6660
aagaaagcat agcaatctaa tctaagggcg gtgttgacaa ttaatcatcg gcatagtata   6720
tcggcatagt ataatacgac aaggtgagga actaaac                            6757
```

```
<210> SEQ ID NO 17
<211> LENGTH: 8272
<212> TYPE: DNA
<213> ORGANISM: Artificial Sequence
<220> FEATURE:
<223> OTHER INFORMATION: plasmid pAOX2ADE1glsII

<400> SEQUENCE: 17
```

```
tcgaccggct gcattaatga atcggccaac gcgcggggag aggcggtttg cgtattgggc     60
```

-continued

```
gctcttccgc ttcctcgctc actgactcgc tgcgctcggt cgttcggctg cggcgagcgg    120

tatcagctca ctcaaaggcg gtaatacggt tatccacaga atcaggggat aacgcaggaa    180

agaacatgtg agcaaaaggc cagcaaaagg ccaggaaccg taaaaaggcc gcgttgctgg    240

cgtttttcca taggctccgc ccccctgacg agcatcacaa aaatcgacgc tcaagtcaga    300

ggtggcgaaa cccgacagga ctataaagat accaggcgtt tccccctgga agctccctcg    360

tgcgctctcc tgttccgacc ctgccgctta ccggatacct gtccgccttt ctcccttcgg    420

gaagcgtggc gctttctcat agctcacgct gtaggtatct cagttcggtg taggtcgttc    480

gctccaagct gggctgtgtg cacgaacccc ccgttcagcc cgaccgctgc gccttatccg    540

gtaactatcg tcttgagtcc aacccggtaa gacacgactt atcgccactg gcagcagcca    600

ctggtaacag gattagcaga gcgaggtatg taggcggtgc tacagagttc ttgaagtggt    660

ggcctaacta cggctacact agaaggacag tatttggtat ctgcgctctg ctgaagccag    720

ttaccttcgg aaaaagagtt ggtagctctt gatccggcaa acaaaccacc gctggtagcg    780

gtggtttttt tgtttgcaag cagcagatta cgcgcagaaa aaaaggatct caagaagatc    840

ctttgatctt ttctacgggg tctgacgctc agtggaacga aaactcacgt taagggattt    900

tggtcatgag attatcaaaa aggatcttca cctagatcct tttaaattaa aaatgaagtt    960

ttaaatcaat ctaaagtata tatgagtaaa cttggtctga cagttaccaa tgcttaatca   1020

gtgaggcacc tatctcagcg atctgtctat ttcgttcatc catagttgcc tgactccccg   1080

tcgtgtagat aactacgata cgggagggct taccatctgg ccccagtgct gcaatgatac   1140

cgcgagaccc acgctcaccg gctccagatt tatcagcaat aaaccagcca gccggaaggg   1200

ccgagcgcag aagtggtcct gcaactttat ccgcctccat ccagtctatt aattgttgcc   1260

gggaagctag agtaagtagt tcgccagtta atagtttgcg caacgttgtt gccattgcta   1320

caggcatcgt ggtgtcacgc tcgtcgtttg gtatggcttc attcagctcc ggttcccaac   1380

gatcaaggcg agttacatga tcccccatgt tgtgcaaaaa agcggttagc tccttcggtc   1440

ctccgatcgt tgtcagaagt aagttggccg cagtgttatc actcatggtt atggcagcac   1500

tgcataattc tcttactgtc atgccatccg taagatgctt ttctgtgact ggtgagtact   1560

caaccaagtc attctgagaa tagtgtatgc ggcgaccgag ttgctcttgc ccggcgtcaa   1620

tacgggataa taccgcgcca catagcagaa ctttaaaagt gctcatcatt ggaaaacgtt   1680

cttcggggcg aaaactctca aggatcttac cgctgttgag atccagttcg atgtaaccca   1740

ctcgtgcacc caactgatct tcagcatctt ttactttcac cagcgtttct gggtgagcaa   1800

aaacaggaag gcaaaatgcc gcaaaaaagg gaataagggc gacacggaaa tgttgaatac   1860

tcatactctt cctttttcaa tagctccaag gcaacaaatt gactactcag accgacattc   1920

attcgttatt gattttaaat caacgataaa cggaatggtt acttgaatga tttcacttta   1980

tgatcattgt ttactaatta cctaaatagg attttatatg gaattggaag aataagggaa   2040

atttcagatg tctgaaaaag gcgaggaggg tactaatcat tcaagcccat ttcttgccag   2100

taattgcttc ataagcttca atatactttt ctttactctt gatagcaatt tctgcatcca   2160

tggctacgcc ctctttgcca ttcaatccgt tggccgtcaa ccaatctctg agaaactgct   2220

tatcgtaact ctcttgcgat ttacccactt ggtaagtctt ttgattccaa aatctagaag   2280

aatctggagt taaaacttca tctactagta ccaattcatt gttttcgtcc agtccaaatt   2340

cgaatttcgt atcagcaata atgatcccct tcaaaagggc gaagtttttt gcagcagaat   2400

acaactcgac cgccttgaca gcgaccttct cacaaatgtc tttacctaca atctcagcag   2460
```

-continued

```
cttgttcaat agagatgttt tcatcgtgtt caccctgttc agctttcgtt gaaggtgtga   2520
aaatcggagt tggaaaggcg tcgctctctt gaaggttctc gttttcaacc ttgactccat   2580
ggacagtttt tgagttcttg tactctttcc atgcacttcc agtgatgtaa cctctgacaa   2640
tggcttccaa aggtatcagt ctgtgctttt ttactatcaa ggatcgtccc tctaattgag   2700
atttgtattt ttcttcagac agttttgatg gtagtaaagc aaagacttcc ttgtcattag   2760
aagcaaccaa atgattcttt atgtagggtg ccaaaaaatc aaaccagaaa actgagagct   2820
gagtcaaaat ctttccctta tcaggaatac cgtttgtcat aatcacatcg taagcggaga   2880
tacggtcagt tgcgacgaac agcaagttgt tctcatcgac tgcataaatg tctctaacct   2940
ttcctttggc gattaaaggt aggattccgt ccagatcagt gttcacaatg gacatacttg   3000
gaaggataca gcaaagtgtg ttggaagcga tgacacatgg aaaggaattt ttcgagtttc   3060
ctagagtagt atattggggc ggtgaaagtt cagatgttta atgcttaata ctcttatact   3120
cttcaaagcg cccaagtgtt tctgccaacc tgactttttt ctgaataatg aatcgttcaa   3180
gtggagtatt taaaccatga ttaagttacg tgatttggca ctggataagg tcgaaaaata   3240
tccgtattca taaacgatta ttggtaaaag ttacaaaata ccactaatta cggagaagct   3300
tagtaacagt tatcatctct tggtcgatta acgcttacaa tttccattcg ccattcaggc   3360
tgcgcaactg ttgggaaggg cgatcggtgc gggcctcttc gctattacgc cagggcctcg   3420
aggcacaaac gaacgtctca cttaatcttc tgtactctga agaggagtgg gaaataccaa   3480
gaaaaacatc aaactcgaat gattttccca aacccctacc acaagatatt catcagctgc   3540
gagataggct gatcaggagc aagctcgtac gagaagaaac aaaatgacaa aaaaaatcct   3600
atactatata ggttacaaat aaaaaagtat caaaaatgaa gcctgcatct ctcaggcaaa   3660
tggcattctg acatcctctt gattagaatc tagcaagacc ggtcttctcg taagtgccca   3720
acttgaactg aggaacagtc atgtctaagg ctaaaactca atgatgatga tgatgatggt   3780
cgacggcgct attcagatcc tcttctgaga tgagtttttg ttcgggccca aaaataactt   3840
cccaatcttc agttatgtca agcgataggt taagaatggt gatcttatta tcattctcat   3900
atgacgatct agtcggcaat gaactttctt cgccattttt tttgacttta atactgtctt   3960
tcaacgttat gttgtgttgt aaattattct ttgcgataat gatttttttca atattggtat   4020
tcctcaaagt attgtggtga atgcctgtca aattctcggg aatatgactt cgaacatttt   4080
ttaaggtatt gttttcgaaa atgaactgag tttctacgta ctcacctctt tggtagccaa   4140
aagtttctcc atcatcaaca taaagatctc caacggctcg tccctcggta tcaggggcta   4200
taactattac atatggatcg tttttcatta acattgaaga tcttctatac ttatctttca   4260
tagtgataat gtgaccgcct tcaataaata atggaatttt atccaatggt gcagaaatat   4320
tcttttctat caaatcagta ccattgttta taaaagagtg taaagatgcg aattcataga   4380
atataccggg tgggaaaacc atttccgttt ctgattgacc aggctccgtg acaggtttga   4440
ctaatagacc tgaattactc cagtaaaatt ggttatcgat atgatacaat tcagcaaatt   4500
cagggtgttc aataaacatt ggattcatta tcggaaatcc agtgacactt gatttatgaa   4560
acatggtgta taaggtaggt agcaggaaat atctcaattg gataatatca cgtactatcg   4620
acttcaaagg ttcattgaat aagtatggtt ctcttctctt ggtgtctata tgggcgtgtg   4680
ctctaaaaaa tgggtaccat aagcccgctt ggtaccaacg tgcaatcaat tcaggtgtag   4740
gatcctcagc aaagccagct atgtcggctc ctataaatgg cataccagca atgttgtttg   4800
```

```
acagaaccat aggaatggaa atctttaagt aatcccaatt ggccacattg tcaccagtcc   4860
atgtggcagc agtacgttga gagccggcaa aaaaagccct tgttagaagg aaaggacgct   4920
tatcggatgg tgaataaatc gattttattg cgtcgtaagt agcttcatgc actgatagac   4980
catatatgtt atggacggat ctttcctcaa tgtaattgtc gtgaatcaaa tcttttggag   5040
ctgtggtctc tgggccatcg aaaatcgaag gctcgttcat atcattccaa atgaataaat   5100
tagttaaatc agccggcaga tccataaacc gttcgaaaaa ggacttccaa atcttttggc   5160
catatttgct tatggtatca atccatatag aattacctgg ccagcaatga cctacatagt   5220
catttccatt gtgatccttg actgctacat tttcattaat taccctgtca ctgatttcat   5280
aatctttctt taaatgagga tcgattagta cgacaagatt tctacccaac tttttttaatt  5340
tggataacag ccttttttgga ttgggaaagg agtgctgctt ccaagtaaaa tattttttgt  5400
cgttcgtata ctccaagtcc aaccaaataa aatcgtaagg aatcatatga gcatccatct   5460
gagagtccac tgtgagaacg tccatctcat cattataatt ccatctacat tgatggtacc   5520
ctatagagga aatgggcggt aaaaagggtc taccagtcaa atcggtaaat ttgtcaatga   5580
tagttggaat atctggcccc agggacatga ctacatctat gacaccattt tcggagatcc   5640
aatgagtcat cgttttattt ttactggtgt catactttat gtctacccaa gtgtcagctg   5700
cattgaccca aaagatagat gtggacgaag atgaaaacat gaatgggatc gaaccgtaca   5760
ttggttggct ggtaccgatg ttgtactcaa agacatcaac gttgaaaagc ctgtagggtt   5820
cctttccacc tgaagtgtcc atcagcctta gcgacgtcgc atgttccggt ataccgtaga   5880
cattagtaga acccatgaaa gagaaatcta gcgcaaccga ttcaggcccc aaaggcatag   5940
agtcatgctt tgaatacaag aaattgtcct taaacatgtt gaaagttgtt tcttctggca   6000
gcacgtgtgc gaagttttcc tgcttagttc tatgatgttc aatgttcagg aaattttgct   6060
cgtttacaat aagtttcagc gcattttgcc agtaaacttt caattgaaaa ggttcagcaa   6120
agatttctac ggatacatca ccgtttcgaa gatgaaatgt gtctgcagtg gagtttgaaa   6180
gtgacaaaaa tgaagatatt ttcgaccaga atgagttcac agtttgtttt tgcttaagga   6240
agtggaattg tggaatactg gtcctgttcg cctcctcttg aaatttcttg tcgaatgcgt   6300
acttccaggt ctcattgaac cgttgtgaag agatcaacaa accgctgctg ttggttggca   6360
ttctctcttt ctcatttata gtgaacctta ctgagtgatc ctgtaaaaaa gagagagaga   6420
atgggaactg aacggctata tcatcgccct ccaatcttgg tatagtttta attatggtag   6480
catgaagcac attctctaaa ggatcgtgtg caatagactc ggcgtccact ttgtaatagc   6540
agtgatgaga tttggcaata ttttctgcat aaaccctgtt tctatggcaa aacccagatt   6600
gcgcacactt ctttaataga tagtcggtaa acgcatgcga aaaagcggta aagaagacca   6660
attggcatac gagccatttc aaaaggacca tctcgaggta ccgatccgag acggccggct   6720
gggccacgtg aattcttttc tcagttgatt tgtttgtggg gatttagtaa gtcgtaaact   6780
tcgttaaaaa agatcaatgt agtcaataca gttgatccga aatagaagga agaggtttgc   6840
aatgtgtaag aacaatgtag ttaaaagccc gttttaagac aatattcttt gatgctgatc   6900
agaaaaggac aataagggat tttggttgct tcttttatac caataatcgt ctcctcatcg   6960
cttaattttc tccccatctc aaccggtgaa gggtaggacg cttctgtaat ctgttcacat   7020
aaaaggggtt ttcactccga gacaaaaatt tatgcgacaa aaatagccta tcttggaagg   7080
tgatgtctta tcaacttgca ttgtttgcaa ggagaagcaa ggacaactca acatgggtaa   7140
aaattcaaaa ccaaccaatt ggaaactccc aactgtccac taggtagctg acagctgtca   7200
```

```
cttttgctgt tcgttgtctt gtctctttcg cttaactgtc ctcttacggc tttctttccc   7260

aaaaaatcat tggggaaatg tgcccctcat cagagtccaa tgacccatga ataaagtttc   7320

ttgtactgtt taagacgatg aattgcaacg ataatccgag cagtttacgg ggtacatcac   7380

gtgctttgca tatgatctcg gagtcggatc agttccggat gtgatgtatt accccatagt   7440

ttcaaactct aatgcagccg ccaagtgcca tacaccctcc atcaatctat gcttaaagtt   7500

tttcaccatc gttgggtggt gatgatgact cgcttagtct ctgctgttcg atattaactt   7560

tgtaaggatc gcccttggat ggaaaattga ggggttgtaa cctgaatttg caggctactt   7620

acattggact tttgagaagg ctggacggtt gatgaagagg gctgggtgca gaggaatgga   7680

aaaaaattta gttgagagga ctgcttgaaa ttttaggaaa tggagtcctt taagctgaca   7740

aaacttcaag gatggggatt ttcatgtagc tttttcatgc cttcgacaag ctaaaggaag   7800

gtaattgatt ctggataaat ggatatttga tctgctttag cagatgtcaa agttctacta   7860

gtgatagtct ggtatctcgt agccttcaat tgggcgtatc ttactcgaag tgttatattt   7920

ttagctgacg agacgaagaa cgagagagta ttgacacatt cagaggtaag acaatatgtc   7980

gtattatcaa aataagtatc gaacctctat taggagccta ctggctcaaa tgtgcaacct   8040

tagtggtgat tgtctctgct tcttgatcac aatctgtcgt gtttgagagt gccgatgtat   8100

gatttttagt aaatgttttt cagaaaaggc gctaagtaaa taaccagtaa gtaataaata   8160

acgtaaaagt gatttgaatc ataaaagaat caagatagag gtcaaagcat agataatccc   8220

cccgtagaag atggaccggt catatggtct gaaaaaaaga tctgatctca tg           8272
```

```
<210> SEQ ID NO 18
<211> LENGTH: 5727
<212> TYPE: DNA
<213> ORGANISM: Artificial Sequence
<220> FEATURE:
<223> OTHER INFORMATION: plasmid pGAPZAGLSII

<400> SEQUENCE: 18

tcgagatggt ccttttgaaa tggctcgtat gccaattggt cttctttacc gctttttcgc     60

atgcgtttac cgactatcta ttaaagaagt gtgcgcaatc tgggttttgc catagaaaca    120

gggtttatgc agaaaatatt gccaaatctc atcactgcta ttacaaagtg gacgccgagt    180

ctattgcaca cgatccttta gagaatgtgc ttcatgctac cataattaaa actataccaa    240

gattggaggg cgatgatata gccgttcagt tcccattctc tctctctttt ttacaggatc    300

actcagtaag gttcactata aatgagaaag agagaatgcc aaccaacagc agcggtttgt    360

tgatctcttc acaacggttc aatgagacct ggaagtacgc attcgacaag aaatttcaag    420

aggaggcgaa caggaccagt attccacaat tccacttcct taagcaaaaa caaactgtga    480

actcattctg gtcgaaaata tcttcatttt tgtcactttc aaactccact gcagacacat    540

ttcatcttcg aaacggtgat gtatccgtag aaatctttgc tgaacctttt caattgaaag    600

tttactggca aaatgcgctg aaacttattg taaacgagca aaatttcctg aacattgaac    660

atcatagaac taagcaggaa aacttcgcac acgtgctgcc agaagaaaca actttcaaca    720

tgtttaagga caatttcttg tattcaaagc atgactctat gcctttgggg cctgaatcgg    780

ttgcgctaga tttctctttc atgggttcta ctaatgtcta cggtataccg gaacatgcga    840

cgtcgctaag gctgatggac acttcaggtg gaaaggaacc ctacaggctt ttcaacgttg    900

atgtctttga gtacaacatc ggtaccagcc aaccaatgta cggttcgatc ccattcatgt    960
```

```
tttcatcttc gtccacatct atcttttggg tcaatgcagc tgacacttgg gtagacataa   1020
agtatgacac cagtaaaaat aaaacgatga ctcattggat ctccgaaaat ggtgtcatag   1080
atgtagtcat gtccctgggg ccagatattc caactatcat tgacaaattt accgatttga   1140
ctggtagacc ctttttaccg cccatttcct ctatagggta ccatcaatgt agatggaatt   1200
ataatgatga gatggacgtt ctcacagtgg actctcagat ggatgctcat atgattcctt   1260
acgattttat ttggttggac ttggagtata cgaacgacaa aaaatatttt acttggaagc   1320
agcactcctt tcccaatcca aaaaggctgt tatccaaatt aaaaaagttg ggtagaaatc   1380
ttgtcgtact aatcgatcct catttaaaga aagattatga aatcagtgac agggtaatta   1440
atgaaaatgt agcagtcaag gatcacaatg gaaatgacta tgtaggtcat tgctggccag   1500
gtaattctat atggattgat accataagca aatatggcca aaagatttgg aagtcctttt   1560
tcgaacggtt tatggatctg ccggctgatt taactaattt attcatttgg aatgatatga   1620
acgagccttc gattttcgat ggcccagaga ccacagctcc aaaagatttg attcacgaca   1680
attacattga ggaaagatcc gtccataaca tatatggtct atcagtgcat gaagctactt   1740
acgacgcaat aaaatcgatt tattcaccat ccgataagcg tcctttcctt ctaacaaggg   1800
ctttttttgc cggctctcaa cgtactgctg ccacatggac tggtgacaat gtggccaatt   1860
gggattactt aaagatttcc attcctatgg ttctgtcaaa caacattgct ggtatgccat   1920
ttataggagc cgacatagct ggctttgctg aggatcctac acctgaattg attgcacgtt   1980
ggtaccaagc gggcttatgg tacccatttt ttagagcaca cgcccatata gacaccaaga   2040
gaagagaacc atacttattc aatgaacctt tgaagtcgat agtacgtgat attatccaat   2100
tgagatattt cctgctacct accttataca ccatgtttca taaatcaagt gtcactggat   2160
ttccgataat gaatccaatg tttattgaac accctgaatt tgctgaattg tatcatatcg   2220
ataaccaatt ttactggagt aattcaggtc tattagtcaa acctgtcacg gagcctggtc   2280
aatcagaaac ggaaatggtt ttcccacccg gtatattcta tgaattcgca tctttacact   2340
cttttataaa caatggtact gatttgatag aaaagaatat ttctgcacca ttggataaaa   2400
ttccattatt tattgaaggc ggtcacatta tcactatgaa agataagtat agaagatctt   2460
caatgttaat gaaaaacgat ccatatgtaa tagttatagc ccctgatacc gagggacgag   2520
ccgttggaga tctttatgtt gatgatggag aaacttttgg ctaccaaaga ggtgagtacg   2580
tagaaactca gttcattttc gaaaacaata ccttaaaaaa tgttcgaagt catattcccg   2640
agaatttgac aggcattcac cacaatactt tgaggaatac caatattgaa aaaatcatta   2700
tcgcaaagaa taatttacaa cacaacataa cgttgaaaga cagtattaaa gtcaaaaaaa   2760
atggcgaaga aagttcattg ccgactagat cgtcatatga gaatgataat aagatcacca   2820
ttcttaacct atcgcttgac ataactgaag attgggaagt tatttttggg cccgaacaaa   2880
aactcatctc agaagaggat ctgaatagcg ccgtcgacca tcatcatcat catcattgag   2940
ttttagcctt agacatgact gttcctcagt tcaagttggg cacttacgag aagaccggtc   3000
ttgctagatt ctaatcaaga ggatgtcaga atgccatttg cctgagagat gcaggcttca   3060
tttttgatac ttttttattt gtaacctata tagtatagga ttttttttgt cattttgttt   3120
cttctcgtac gagcttgctc ctgatcagcc tatctcgcag ctgatgaata tcttgtggta   3180
ggggtttggg aaaatcattc gagtttgatg tttttcttgg tatttcccac tcctcttcag   3240
agtacagaag attaagtgag accttcgttt gtgcggatcc cccacacacc atagcttcaa   3300
aatgtttcta ctcctttttt actcttccag attttctcgg actccgcgca tcgccgtacc   3360
```

-continued

```
acttcaaaac acccaagcac agcatactaa attttccctc tttcttcctc tagggtgtcg   3420
ttaattaccc gtactaaagg tttggaaaag aaaaaagaga ccgcctcgtt tctttttctt   3480
cgtcgaaaaa ggcaataaaa atttttatca cgtttctttt tcttgaaatt ttttttttta   3540
gtttttttct ctttcagtga cctccattga tatttaagtt aataaacggt cttcaatttc   3600
tcaagtttca gtttcatttt tcttgttcta ttacaacttt ttttacttct tgttcattag   3660
aaagaaagca tagcaatcta atctaagggc ggtgttgaca attaatcatc ggcatagtat   3720
atcggcatag tataatacga caaggtgagg aactaaacca tggccaagtt gaccagtgcc   3780
gttccggtgc tcaccgcgcg cgacgtcgcc ggagcggtcg agttctggac cgaccggctc   3840
gggttctccc gggacttcgt ggaggacgac ttcgccggtg tggtccggga cgacgtgacc   3900
ctgttcatca gcgcggtcca ggaccaggtg gtgccggaca acaccctggc ctgggtgtgg   3960
gtgcgcggcc tggacgagct gtacgccgag tggtcggagg tcgtgtccac gaacttccgg   4020
gacgcctccg ggccggccat gaccgagatc ggcgagcagc cgtgggggcg ggagttcgcc   4080
ctgcgcgacc cggccggcaa ctgcgtgcac ttcgtggccg aggagcagga ctgacacgtc   4140
cgacggcggc ccacgggtcc caggcctcgg agatccgtcc ccctttttcct ttgtcgatat   4200
catgtaatta gttatgtcac gcttacattc acgccctccc cccacatccg ctctaaccga   4260
aaaggaagga gttagacaac ctgaagtcta ggtccctatt tattttttta tagttatgtt   4320
agtattaaga acgttattta tatttcaaat ttttcttttt tttctgtaca gacgcgtgta   4380
cgcatgtaac attatactga aaaccttgct tgagaaggtt ttgggacgct cgaaggcttt   4440
aatttgcaag ctggagacca acatgtgagc aaaaggccag caaaaggcca ggaaccgtaa   4500
aaaggccgcg ttgctggcgt ttttccatag gctccgcccc cctgacgagc atcacaaaaa   4560
tcgacgctca agtcagaggt ggcgaaaccc gacaggacta taaagatacc aggcgtttcc   4620
ccctggaagc tccctcgtgc gctctcctgt tccgaccctg ccgcttaccg gatacctgtc   4680
cgcctttctc ccttcgggaa gcgtggcgct ttctcaatgc tcacgctgta ggtatctcag   4740
ttcggtgtag gtcgttcgct ccaagctggg ctgtgtgcac gaaccccccg ttcagcccga   4800
ccgctgcgcc ttatccggta actatcgtct tgagtccaac ccggtaagac acgacttatc   4860
gccactggca gcagccactg gtaacaggat tagcagagcg aggtatgtag gcggtgctac   4920
agagttcttg aagtggtggc ctaactacgg ctacactaga aggacagtat ttggtatctg   4980
cgctctgctg aagccagtta ccttcggaaa aagagttggt agctcttgat ccggcaaaca   5040
aaccaccgct ggtagcggtg gtttttttgt ttgcaagcag cagattacgc gcagaaaaaa   5100
aggatctcaa gaagatcctt tgatcttttc tacggggtct gacgctcagt ggaacgaaaa   5160
ctcacgttaa gggattttgg tcatgcatga gatcagatct tttttgtaga aatgtcttgg   5220
tgtcctcgtc caatcaggta gccatctctg aaatatctgg ctccgttgca actccgaacg   5280
acctgctggc aacgtaaaat tctccggggt aaaacttaaa tgtggagtaa tggaaccaga   5340
aacgtctctt cccttctctc tccttccacc gcccgttacc gtccctagga aattttactc   5400
tgctggagag cttcttctac ggcccccttg cagcaatgct cttcccagca ttacgttgcg   5460
ggtaaaacgg aggtcgtgta cccgacctag cagcccaggg atggaaaagt cccggccgtc   5520
gctggcaata atagcgggcg gacgcatgtc atgagattat tggaaaccac cagaatcgaa   5580
tataaaaggc gaacaccttt cccaattttg gtttctcctg acccaaagac tttaaattta   5640
atttatttgt ccctatttca atcaattgaa caactatttc gaaacgagga attcacgtgg   5700
```

```
cccagccggc cgtctcggat cggtacc                                        5727


<210> SEQ ID NO 19
<211> LENGTH: 7236
<212> TYPE: DNA
<213> ORGANISM: Artificial Sequence
<220> FEATURE:
<223> OTHER INFORMATION: plasmid pGAPADE1glsII

<400> SEQUENCE: 19

tcgaccggct gcattaatga atcggccaac gcgcggggag aggcggtttg cgtattgggc      60

gctcttccgc ttcctcgctc actgactcgc tgcgctcggt cgttcggctg cggcgagcgg     120

tatcagctca ctcaaaggcg gtaatacggt tatccacaga atcaggggat aacgcaggaa     180

agaacatgtg agcaaaaggc cagcaaaagg ccaggaaccg taaaaaggcc gcgttgctgg     240

cgtttttcca taggctccgc ccccctgacg agcatcacaa aaatcgacgc tcaagtcaga     300

ggtggcgaaa cccgacagga ctataaagat accaggcgtt tccccctgga agctccctcg     360

tgcgctctcc tgttccgacc ctgccgctta ccggatacct gtccgccttt ctcccttcgg     420

gaagcgtggc gctttctcat agctcacgct gtaggtatct cagttcggtg taggtcgttc     480

gctccaagct gggctgtgtg cacgaacccc ccgttcagcc cgaccgctgc gccttatccg     540

gtaactatcg tcttgagtcc aacccggtaa gacacgactt atcgccactg gcagcagcca     600

ctggtaacag gattagcaga gcgaggtatg taggcggtgc tacagagttc ttgaagtggt     660

ggcctaacta cggctacact agaaggacag tatttggtat ctgcgctctg ctgaagccag     720

ttaccttcgg aaaaagagtt ggtagctctt gatccggcaa acaaaccacc gctggtagcg     780

gtggtttttt tgtttgcaag cagcagatta cgcgcagaaa aaaaggatct caagaagatc     840

ctttgatctt ttctacgggg tctgacgctc agtggaacga aaactcacgt taagggattt     900

tggtcatgag attatcaaaa aggatcttca cctagatcct tttaaattaa aaatgaagtt     960

ttaaatcaat ctaaagtata tatgagtaaa cttggtctga cagttaccaa tgcttaatca    1020

gtgaggcacc tatctcagcg atctgtctat ttcgttcatc catagttgcc tgactccccg    1080

tcgtgtagat aactacgata cgggagggct taccatctgg ccccagtgct gcaatgatac    1140

cgcgagaccc acgctcaccg gctccagatt tatcagcaat aaaccagcca gccggaaggg    1200

ccgagcgcag aagtggtcct gcaactttat ccgcctccat ccagtctatt aattgttgcc    1260

gggaagctag agtaagtagt tcgccagtta atagtttgcg caacgttgtt gccattgcta    1320

caggcatcgt ggtgtcacgc tcgtcgtttg gtatggcttc attcagctcc ggttcccaac    1380

gatcaaggcg agttacatga tcccccatgt tgtgcaaaaa agcggttagc tccttcggtc    1440

ctccgatcgt tgtcagaagt aagttggccg cagtgttatc actcatggtt atggcagcac    1500

tgcataattc tcttactgtc atgccatccg taagatgctt ttctgtgact ggtgagtact    1560

caaccaagtc attctgagaa tagtgtatgc ggcgaccgag ttgctcttgc ccggcgtcaa    1620

tacgggataa taccgcgcca catagcagaa ctttaaaagt gctcatcatt ggaaaacgtt    1680

cttcggggcg aaaactctca aggatcttac cgctgttgag atccagttcg atgtaaccca    1740

ctcgtgcacc caactgatct tcagcatctt ttactttcac cagcgtttct gggtgagcaa    1800

aaacaggaag gcaaaatgcc gcaaaaaagg gaataagggc gacacggaaa tgttgaatac    1860

tcatactctt cctttttcaa tagctccaag gcaacaaatt gactactcag accgacattc    1920

attcgttatt gattttaaat caacgataaa cggaatggtt acttgaatga tttcacttta    1980

tgatcattgt ttactaatta cctaaatagg attttatatg gaattggaag aataagggaa    2040
```

```
atttcagatg tctgaaaaag gcgaggaggg tactaatcat tcaagcccat ttcttgccag   2100
taattgcttc ataagcttca atatactttt ctttactctt gatagcaatt tctgcatcca   2160
tggctacgcc ctctttgcca ttcaatccgt tggccgtcaa ccaatctctg agaaactgct   2220
tatcgtaact ctcttgcgat ttacccactt ggtaagtctt ttgattccaa aatctagaag   2280
aatctggagt taaaacttca tctactagta ccaattcatt gttttcgtcc agtccaaatt   2340
cgaatttcgt atcagcaata atgatcccct tcaaaagggc gaagtttttt gcagcagaat   2400
acaactcgac cgccttgaca gcgaccttct cacaaatgtc tttacctaca atctcagcag   2460
cttgttcaat agagatgttt tcatcgtgtt caccctgttc agctttcgtt gaaggtgtga   2520
aaatcggagt tggaaaggcg tcgctctctt gaaggttctc gttttcaacc ttgactccat   2580
ggacagtttt tgagttcttg tactctttcc atgcacttcc agtgatgtaa cctctgacaa   2640
tggcttccaa aggtatcagt ctgtgctttt ttactatcaa ggatcgtccc tctaattgag   2700
atttgtattt ttcttcagac agttttgatg gtagtaaagc aaagacttcc ttgtcattag   2760
aagcaaccaa atgattcttt atgtagggtg ccaaaaaatc aaaccagaaa actgagagct   2820
gagtcaaaat ctttccctta tcaggaatac cgtttgtcat aatcacatcg taagcggaga   2880
tacggtcagt tgcgacgaac agcaagttgt tctcatcgac tgcataaatg tctctaacct   2940
ttcctttggc gattaaaggt aggattccgt ccagatcagt gttcacaatg gacatacttg   3000
gaaggataca gcaaagtgtg ttggaagcga tgacacatgg aaaggaattt ttcgagtttc   3060
ctagagtagt atattggggc ggtgaaagtt cagatgttta atgcttaata ctcttatact   3120
cttcaaagcg cccaagtgtt tctgccaacc tgactttttt ctgaataatg aatcgttcaa   3180
gtggagtatt taaaccatga ttaagttacg tgatttggca ctggataagg tcgaaaaata   3240
tccgtattca taaacgatta ttggtaaaag ttacaaaata ccactaatta cggagaagct   3300
tagtaacagt tatcatctct tggtcgatta acgcttacaa tttccattcg ccattcaggc   3360
tgcgcaactg ttgggaaggg cgatcggtgc gggcctcttc gctattacgc cagggcctcg   3420
aggcacaaac gaacgtctca cttaatcttc tgtactctga agaggagtgg gaaataccaa   3480
gaaaaacatc aaactcgaat gattttccca aacccctacc acaagatatt catcagctgc   3540
gagataggct gatcaggagc aagctcgtac gagaagaaac aaaatgacaa aaaaaatcct   3600
atactatata ggttacaaat aaaaaagtat caaaaatgaa gcctgcatct ctcaggcaaa   3660
tggcattctg acatcctctt gattagaatc tagcaagacc ggtcttctcg taagtgccca   3720
acttgaactg aggaacagtc atgtctaagg ctaaaactca atgatgatga tgatgatggt   3780
cgacggcgct attcagatcc tcttctgaga tgagtttttg ttcgggccca aaaataactt   3840
cccaatcttc agttatgtca agcgataggt taagaatggt gatcttatta tcattctcat   3900
atgacgatct agtcggcaat gaactttctt cgccattttt tttgacttta atactgtctt   3960
tcaacgttat gttgtgttgt aaattattct ttgcgataat gatttttttca atattggtat   4020
tcctcaaagt attgtggtga atgcctgtca aattctcggg aatatgactt cgaacatttt   4080
ttaaggtatt gttttcgaaa atgaactgag tttctacgta ctcacctctt tggtagccaa   4140
aagtttctcc atcatcaaca taaagatctc caacggctcg tccctcggta tcaggggcta   4200
taactattac atatggatcg tttttcatta acattgaaga tcttctatac ttatctttca   4260
tagtgataat gtgaccgcct tcaataaata atggaatttt atccaatggt gcagaaatat   4320
tcttttctat caaatcagta ccattgttta taaaagagtg taaagatgcg aattcataga   4380
```

-continued

```
atataccggg tgggaaaacc atttccgttt ctgattgacc aggctccgtg acaggtttga   4440
ctaatagacc tgaattactc cagtaaaatt ggttatcgat atgatacaat tcagcaaatt   4500
cagggtgttc aataaacatt ggattcatta tcggaaatcc agtgacactt gatttatgaa   4560
acatggtgta taaggtaggt agcaggaaat atctcaattg gataatatca cgtactatcg   4620
acttcaaagg ttcattgaat aagtatggtt ctcttctctt ggtgtctata tgggcgtgtg   4680
ctctaaaaaa tgggtaccat aagcccgctt ggtaccaacg tgcaatcaat tcaggtgtag   4740
gatcctcagc aaagccagct atgtcggctc ctataaatgg cataccagca atgttgtttg   4800
acagaaccat aggaatggaa atctttaagt aatcccaatt ggccacattg tcaccagtcc   4860
atgtggcagc agtacgttga gagccggcaa aaaaagccct tgttagaagg aaaggacgct   4920
tatcggatgg tgaataaatc gattttattg cgtcgtaagt agcttcatgc actgatagac   4980
catatatgtt atggacggat ctttcctcaa tgtaattgtc gtgaatcaaa tcttttggag   5040
ctgtggtctc tgggccatcg aaaatcgaag gctcgttcat atcattccaa atgaataaat   5100
tagttaaatc agccggcaga tccataaacc gttcgaaaaa ggacttccaa atcttttggc   5160
catatttgct tatggtatca atccatatag aattacctgg ccagcaatga cctacatagt   5220
catttccatt gtgatccttg actgctacat tttcattaat taccctgtca ctgatttcat   5280
aatctttctt taaatgagga tcgattagta cgacaagatt tctacccaac tttttttaatt   5340
tggataacag ccttttttgga ttgggaaagg agtgctgctt ccaagtaaaa tattttttgt   5400
cgttcgtata ctccaagtcc aaccaaataa aatcgtaagg aatcatatga gcatccatct   5460
gagagtccac tgtgagaacg tccatctcat cattataatt ccatctacat tgatggtacc   5520
ctatagagga aatgggcggt aaaaagggtc taccagtcaa atcggtaaat ttgtcaatga   5580
tagttggaat atctggcccc agggacatga ctacatctat gacaccattt tcggagatcc   5640
aatgagtcat cgttttattt ttactggtgt catactttat gtctacccaa gtgtcagctg   5700
cattgaccca aaagatagat gtggacgaag atgaaaacat gaatgggatc gaaccgtaca   5760
ttggttggct ggtaccgatg ttgtactcaa agacatcaac gttgaaaagc ctgtagggtt   5820
cctttccacc tgaagtgtcc atcagcctta gcgacgtcgc atgttccggt ataccgtaga   5880
cattagtaga acccatgaaa gagaaatcta gcgcaaccga ttcaggcccc aaaggcatag   5940
agtcatgctt tgaatacaag aaattgtcct taaacatgtt gaaagttgtt tcttctggca   6000
gcacgtgtgc gaagttttcc tgcttagttc tatgatgttc aatgttcagg aaattttgct   6060
cgtttacaat aagtttcagc gcattttgcc agtaaacttt caattgaaaa ggttcagcaa   6120
agatttctac ggatacatca ccgtttcgaa gatgaaatgt gtctgcagtg gagtttgaaa   6180
gtgacaaaaa tgaagatatt ttcgaccaga atgagttcac agtttgtttt tgcttaagga   6240
agtggaattg tggaatactg gtcctgttcg cctcctcttg aaatttcttg tcgaatgcgt   6300
acttccaggt ctcattgaac cgttgtgaag agatcaacaa accgctgctg ttggttggca   6360
ttctctcttt ctcatttata gtgaacctta ctgagtgatc ctgtaaaaaa gagagagaga   6420
atgggaactg aacggctata tcatcgccct ccaatcttgg tatagtttta attatggtag   6480
catgaagcac attctctaaa ggatcgtgtg caatagactc ggcgtccact ttgtaatagc   6540
agtgatgaga tttggcaata ttttctgcat aaaccctgtt tctatggcaa aacccagatt   6600
gcgcacactt ctttaataga tagtcggtaa acgcatgcga aaaagcggta aagaagacca   6660
attggcatac gagccatttc aaaaggacca tctcgaggta ccgatccgag acggccggct   6720
gggccacgtg aattcctcgt ttcgaaatag ttgttcaatt gattgaaata gggacaaata   6780
```

```
aattaaattt aaagtctttg ggtcaggaga aaccaaaatt gggaaaggtg ttcgcctttt   6840

atattcgatt ctggtggttt ccaataatct catgacatgc gtccgcccgc tattattgcc   6900

agcgacggcc gggacttttc catccctggg ctgctaggtc gggtacacga cctccgtttt   6960

acccgcaacg taatgctggg aagagcattg ctgcaagggg gccgtagaag aagctctcca   7020

gcagagtaaa atttcctagg gacggtaacg ggcggtggaa ggagagagaa gggaagagac   7080

gtttctggtt ccattactcc acatttaagt tttaccccgg agaattttac gttgccagca   7140

ggtcgttcgg agttgcaacg gagccagata tttcagagat ggctacctga ttggacgagg   7200

acaccaagac atttctacaa aaaagatctg atctca                             7236
```

```
<210> SEQ ID NO 20
<211> LENGTH: 6173
<212> TYPE: DNA
<213> ORGANISM: Artificial Sequence
<220> FEATURE:
<223> OTHER INFORMATION: plasimd pPICZAGLSII

<400> SEQUENCE: 20

cgaacaaaaa ctcatctcag aagaggatct gaatagcgcc gtcgaccatc atcatcatca     60

tcattgagtt tgtagcctta gacatgactg ttcctcagtt caagttgggc acttacgaga    120

agaccggtct tgctagattc taatcaagag gatgtcagaa tgccatttgc ctgagagatg    180

caggcttcat ttttgatact ttttttatttg taacctatat agtataggat ttttttgtc    240

attttgtttc ttctcgtacg agcttgctcc tgatcagcct atctcgcagc tgatgaatat    300

cttgtggtag gggtttggga aaatcattcg agtttgatgt tttcttggt atttcccact    360

cctcttcaga gtacagaaga ttaagtgaga ccttcgtttg tgcggatccc ccacacacca    420

tagcttcaaa atgtttctac tccttttttta ctcttccaga ttttctcgga ctccgcgcat    480

cgccgtacca cttcaaaaca cccaagcaca gcatactaaa ttttccctct ttcttcctct    540

agggtgtcgt taattacccg tactaaaggt ttggaaaaga aaaaagagac cgcctcgttt    600

ctttttcttc gtcgaaaaag gcaataaaaa tttttatcac gtttcttttt cttgaaattt    660

tttttttttag ttttttttctc tttcagtgac ctccattgat atttaagtta ataaacggtc    720

ttcaatttct caagtttcag tttcattttt cttgttctat tacaactttt tttacttctt    780

gttcattaga aagaaagcat agcaatctaa tctaaggggc ggtgttgaca attaatcatc    840

ggcatagtat atcggcatag tataatacga caaggtgagg aactaaacca tggccaagtt    900

gaccagtgcc gttccggtgc tcaccgcgcg cgacgtcgcc ggagcggtcg agttctggac    960

cgaccggctc gggttctccc gggacttcgt ggaggacgac ttcgccggtg tggtccggga   1020

cgacgtgacc ctgttcatca gcgcggtcca ggaccaggtg gtgccggaca acaccctggc   1080

ctgggtgtgg gtgcgcggcc tggacgagct gtacgccgag tggtcggagg tcgtgtccac   1140

gaacttccgg gacgcctccg ggccggccat gaccgagatc ggcgagcagc cgtgggggcg   1200

ggagttcgcc ctgcgcgacc cggccggcaa ctgcgtgcac ttcgtggccg aggagcagga   1260

ctgacacgtc cgacggcggc ccacgggtcc caggcctcgg agatccgtcc ccctttttcct   1320

ttgtcgatat catgtaatta gttatgtcac gcttacattc acgccctccc cccacatccg   1380

ctctaaccga aaggaaggga gttagacaac ctgaagtcta ggtccctatt tatttttttta   1440

tagttatgtt agtattaaga acgttattta tatttcaaat ttttcttttt tttctgtaca   1500

gacgcgtgta cgcatgtaac attatactga aaaccttgct tgagaaggtt ttgggacgct   1560
```

-continued

```
cgaaggcttt aatttgcaag ctggagacca acatgtgagc aaaaggccag caaaaggcca   1620
ggaaccgtaa aaaggccgcg ttgctggcgt ttttccatag gctccgcccc cctgacgagc   1680
atcacaaaaa tcgacgctca agtcagaggt ggcgaaaccc gacaggacta taaagatacc   1740
aggcgtttcc ccctggaagc tccctcgtgc gctctcctgt tccgaccctg ccgcttaccg   1800
gatacctgtc cgcctttctc ccttcgggaa gcgtggcgct ttctcaatgc tcacgctgta   1860
ggtatctcag ttcggtgtag gtcgttcgct ccaagctggg ctgtgtgcac gaaccccccg   1920
ttcagcccga ccgctgcgcc ttatccggta actatcgtct tgagtccaac ccggtaagac   1980
acgacttatc gccactggca gcagccactg gtaacaggat tagcagagcg aggtatgtag   2040
gcggtgctac agagttcttg aagtggtggc ctaactacgg ctacactaga aggacagtat   2100
ttggtatctg cgctctgctg aagccagtta ccttcggaaa aagagttggt agctcttgat   2160
ccggcaaaca aaccaccgct ggtagcggtg gtttttttgt ttgcaagcag cagattacgc   2220
gcagaaaaaa aggatctcaa gaagatcctt tgatcttttc tacggggtct gacgctcagt   2280
ggaacgaaaa ctcacgttaa gggattttgg tcatgagatc agatctaaca tccaaagacg   2340
aaaggttgaa tgaaaccttt ttgccatccg acatccacag gtccattctc acacataagt   2400
gccaaacgca acaggagggg atacactagc agcagaccgt tgcaaacgca ggacctccac   2460
tcctcttctc ctcaacaccc acttttgcca tcgaaaaacc agcccagtta ttgggcttga   2520
ttggagctcg ctcattccaa ttccttctat taggctacta acaccatgac tttattagcc   2580
tgtctatcct ggcccccctg gcgaggttca tgtttgttta tttccgaatg caacaagctc   2640
cgcattacac ccgaacatca ctccagatga gggctttctg agtgtggggt caaatagttt   2700
catgttcccc aaatggccca aaactgacag tttaaacgct gtcttggaac ctaatatgac   2760
aaaagcgtga tctcatccaa gatgaactaa gtttggttcg ttgaaatgct aacggccagt   2820
tggtcaaaaa gaaacttcca aaagtcggca taccgtttgt cttgtttggt attgattgac   2880
gaatgctcaa aaataatctc attaatgctt agcgcagtct ctctatcgct tctgaacccc   2940
ggtgcacctg tgccgaaacg caaatgggga aacacccgct tttggatga ttatgcattg    3000
tctccacatt gtatgcttcc aagattctgg tgggaatact gctgatagcc taacgttcat   3060
gatcaaaatt taactgttct aacccctact tgacagcaat atataaacag aaggaagctg   3120
ccctgtctta aacctttttt tttatcatca ttattagctt actttcataa ttgcgactgg   3180
ttccaattga caagcttttg attttaacga cttttaacga caacttgaga agatcaaaaa   3240
acaactaatt attcgaaacg aggaattcac gtggcccagc cggccgtctc ggatcggtac   3300
ctcgagatgg tccttttgaa atggctcgta tgccaattgg tcttctttac cgctttttcg   3360
catgcgttta ccgactatct attaaagaag tgtgcgcaat ctgggttttg ccatagaaac   3420
agggtttatg cagaaaatat tgccaaatct catcactgct attacaaagt ggacgccgag   3480
tctattgcac acgatccttt agagaatgtg cttcatgcta ccataattaa aactatacca   3540
agattggagg gcgatgatat agccgttcag ttcccattct ctctctcttt tttacaggat   3600
cactcagtaa ggttcactat aaatgagaaa gagagaatgc caaccaacag cagcggtttg   3660
ttgatctctt cacaacggtt caatgagacc tggaagtacg cattcgacaa gaaatttcaa   3720
gaggaggcga acaggaccag tattccacaa ttccacttcc ttaagcaaaa acaaactgtg   3780
aactcattct ggtcgaaaat atcttcattt ttgtcacttt caaactccac tgcagacaca   3840
tttcatcttc gaaacggtga tgtatccgta gaaatctttg ctgaaccttt tcaattgaaa   3900
gtttactggc aaaatgcgct gaaacttatt gtaaacgagc aaaatttcct gaacattgaa   3960
```

```
catcatagaa ctaagcagga aaacttcgca cacgtgctgc cagaagaaac aactttcaac   4020

atgtttaagg acaatttctt gtattcaaag catgactcta tgcctttggg gcctgaatcg   4080

gttgcgctag atttctcttt catgggttct actaatgtct acggtatacc ggaacatgcg   4140

acgtcgctaa ggctgatgga cacttcaggt ggaaaggaac cctacaggct tttcaacgtt   4200

gatgtctttg agtacaacat cggtaccagc caaccaatgt acggttcgat cccattcatg   4260

ttttcatctt cgtccacatc tatcttttgg gtcaatgcag ctgacacttg ggtagacata   4320

aagtatgaca ccagtaaaaa taaaacgatg actcattgga tctccgaaaa tggtgtcata   4380

gatgtagtca tgtccctggg gccagatatt ccaactatca ttgacaaatt taccgatttg   4440

actggtagac cctttttacc gcccatttcc tctatagggt accatcaatg tagatggaat   4500

tataatgatg agatggacgt tctcacagtg gactctcaga tggatgctca tatgattcct   4560

tacgatttta tttggttgga cttggagtat acgaacgaca aaaaatattt tacttggaag   4620

cagcactcct ttcccaatcc aaaaaggctg ttatccaaat taaaaaagtt gggtagaaat   4680

cttgtcgtac taatcgatcc tcatttaaag aaagattatg aaatcagtga cagggtaatt   4740

aatgaaaatg tagcagtcaa ggatcacaat ggaaatgact atgtaggtca ttgctggcca   4800

ggtaattcta tatggattga taccataagc aaatatggcc aaaagatttg gaagtccttt   4860

ttcgaacggt ttatggatct gccggctgat ttaactaatt tattcatttg gaatgatatg   4920

aacgagcctt cgattttcga tggcccagag accacagctc caaaagattt gattcacgac   4980

aattacattg aggaaagatc cgtccataac atatatggtc tatcagtgca tgaagctact   5040

tacgacgcaa taaaatcgat ttattcacca tccgataagc gtcctttcct tctaacaagg   5100

gctttttttg ccggctctca acgtactgct gccacatgga ctggtgacaa tgtggccaat   5160

tgggattact taaagatttc cattcctatg gttctgtcaa acaacattgc tggtatgcca   5220

tttataggag ccgacatagc tggctttgct gaggatccta cacctgaatt gattgcacgt   5280

tggtaccaag cgggcttatg gtacccattt tttagagcac acgcccatat agacaccaag   5340

agaagagaac catacttatt caatgaacct ttgaagtcga tagtacgtga tattatccaa   5400

ttgagatatt tcctgctacc taccttatac accatgtttc ataaatcaag tgtcactgga   5460

tttccgataa tgaatccaat gtttattgaa caccctgaat ttgctgaatt gtatcatatc   5520

gataaccaat tttactggag taattcaggt ctattagtca aacctgtcac ggagcctggt   5580

caatcagaaa cggaaatggt tttcccaccc ggtatattct atgaattcgc atctttacac   5640

tcttttataa acaatggtac tgatttgata gaaaagaata tttctgcacc attggataaa   5700

attccattat ttattgaagg cggtcacatt atcactatga aagataagta tagaagatct   5760

tcaatgttaa tgaaaaacga tccatatgta atagttatag cccctgatac cgagggacga   5820

gccgttggag atctttatgt tgatgatgga gaaacttttg gctaccaaag aggtgagtac   5880

gtagaaactc agttcatttt cgaaaacaat accttaaaaa atgttcgaag tcatattccc   5940

gagaatttga caggcattca ccacaatact ttgaggaata ccaatattga aaaaatcatt   6000

atcgcaaaga ataatttaca acacaacata acgttgaaag acagtattaa agtcaaaaaa   6060

aatggcgaag aaagttcatt gccgactaga tcgtcatatg agaatgataa taagatcacc   6120

attcttaacc tatcgcttga cataactgaa gattgggaag ttatttttgg gcc          6173
```

<210> SEQ ID NO 21
<211> LENGTH: 7639
<212> TYPE: DNA

```
<213> ORGANISM: Artificial Sequence
<220> FEATURE:
<223> OTHER INFORMATION: plasmid pPICADE1glsII

<400> SEQUENCE: 21

aaattcctcg tttcgaataa ttagttgttt tttgatcttc tcaagttgtc gttaaaagtc     60

gttaaaatca aaagcttgtc aattggaacc agtcgcaatt atgaaagtaa gctaataatg    120

atgataaaaa aaaaggttta agacagggca gcttccttct gtttatatat tgctgtcaag    180

taggggttag aacagttaaa ttttgatcat gaacgttagg ctatcagcag tattcccacc    240

agaatcttgg aagcatacaa tgtggagaca atgcataatc atccaaaaag cgggtgtttc    300

cccatttgcg tttcggcaca ggtgcaccgg ggttcagaag cgatagagag actgcgctaa    360

gcattaatga gattattttt gagcattcgt caatcaatac caaacaagac aaacggtatg    420

ccgacttttg gaagtttctt tttgaccaac tggccgttag catttcaacg aaccaaactt    480

agttcatctt ggatgagatc acgcttttgt catattaggt tccaagacag cgtttaaact    540

gtcagttttg ggccatttgg ggaacatgaa actatttgac cccacactca gaaagccctc    600

atctggagtg atgttcgggt gtaatgcgga gcttgttgca ttcggaaata aacaaacatg    660

aacctcgcca ggggggccag gatagacagg ctaataaagt catggtgtta gtagcctaat    720

agaaggaatt ggaatgagcg agctccaatc aagcccaata actgggctgg tttttcgatg    780

gcaaaagtgg gtgttgagga gaagaggagt ggaggtcctg cgtttgcaac ggtctgctgc    840

tagtgtatcc cctcctgttg cgtttggcac ttatgtgtga gaatggacct gtggatgtcg    900

gatggcaaaa aggtttcatt caacctttcg tctttggatg ttgtcgaccg gctgcattaa    960

tgaatcggcc aacgcgcggg gagaggcggt ttgcgtattg ggcgctcttc cgcttcctcg   1020

ctcactgact cgctgcgctc ggtcgttcgg ctgcggcgag cggtatcagc tcactcaaag   1080

gcggtaatac ggttatccac agaatcaggg gataacgcag gaaagaacat gtgagcaaaa   1140

ggccagcaaa aggccaggaa ccgtaaaaag gccgcgttgc tggcgttttt ccataggctc   1200

cgcccccctg acgagcatca caaaaatcga cgctcaagtc agaggtggcg aaacccgaca   1260

ggactataaa gataccaggc gtttccccct ggaagctccc tcgtgcgctc tcctgttccg   1320

accctgccgc ttaccggata cctgtccgcc tttctccctt cgggaagcgt ggcgctttct   1380

catagctcac gctgtaggta tctcagttcg gtgtaggtcg ttcgctccaa gctgggctgt   1440

gtgcacgaac cccccgttca gcccgaccgc tgcgccttat ccggtaacta tcgtcttgag   1500

tccaacccgg taagacacga cttatcgcca ctggcagcag ccactggtaa caggattagc   1560

agagcgaggt atgtaggcgg tgctacagag ttcttgaagt ggtggcctaa ctacggctac   1620

actagaagga cagtatttgg tatctgcgct ctgctgaagc cagttacctt cggaaaaaga   1680

gttggtagct cttgatccgg caaacaaacc accgctggta gcggtggttt ttttgtttgc   1740

aagcagcaga ttacgcgcag aaaaaaagga tctcaagaag atcctttgat cttttctacg   1800

gggtctgacg ctcagtggaa cgaaaactca cgttaaggga ttttggtcat gagattatca   1860

aaaaggatct tcacctagat ccttttaaat taaaaatgaa gttttaaatc aatctaaagt   1920

atatatgagt aaacttggtc tgacagttac caatgcttaa tcagtgaggc acctatctca   1980

gcgatctgtc tatttcgttc atccatagtt gcctgactcc ccgtcgtgta gataactacg   2040

atacgggagg gcttaccatc tggccccagt gctgcaatga taccgcgaga cccacgctca   2100

ccggctccag atttatcagc aataaaccag ccagccggaa gggccgagcg cagaagtggt   2160

cctgcaactt tatccgcctc catccagtct attaattgtt gccgggaagc tagagtaagt   2220
```

```
agttcgccag ttaatagttt gcgcaacgtt gttgccattg ctacaggcat cgtggtgtca   2280
cgctcgtcgt ttggtatggc ttcattcagc tccggttccc aacgatcaag gcgagttaca   2340
tgatccccca tgttgtgcaa aaaagcggtt agctccttcg gtcctccgat cgttgtcaga   2400
agtaagttgg ccgcagtgtt atcactcatg gttatggcag cactgcataa ttctcttact   2460
gtcatgccat ccgtaagatg cttttctgtg actggtgagt actcaaccaa gtcattctga   2520
gaatagtgta tgcggcgacc gagttgctct tgcccggcgt caatacggga taataccgcg   2580
ccacatagca gaactttaaa agtgctcatc attggaaaac gttcttcggg gcgaaaactc   2640
tcaaggatct taccgctgtt gagatccagt tcgatgtaac ccactcgtgc acccaactga   2700
tcttcagcat cttttacttt caccagcgtt tctgggtgag caaaaacagg aaggcaaaat   2760
gccgcaaaaa agggaataag ggcgacacgg aaatgttgaa tactcatact cttccttttt   2820
caatagctcc aaggcaacaa attgactact cagaccgaca ttcattcgtt attgatttta   2880
aatcaacgat aaacggaatg gttacttgaa tgatttcact ttatgatcat tgtttactaa   2940
ttacctaaat aggattttat atggaattgg aagaataagg gaaatttcag atgtctgaaa   3000
aaggcgagga gggtactaat cattcaagcc catttcttgc cagtaattgc ttcataagct   3060
tcaatatact ttctttactt cttgatagca atttctgcat ccatggctac gccctctttg   3120
ccattcaatc cgttggccgt caaccaatct ctgagaaact gcttatcgta actctcttgc   3180
gatttaccca cttggtaagt cttttgattc caaaatctag aagaatctgg agttaaaact   3240
tcatctacta gtaccaattc attgttttcg tccagtccaa attcgaattt cgtatcagca   3300
ataatgatcc ccttcaaaag ggcgaagttt tttgcagcag aatacaactc gaccgccttg   3360
acagcgacct tctcacaaat gtctttacct acaatctcag cagcttgttc aatagagatg   3420
ttttcatcgt gttcaccctg ttcagctttc gttgaaggtg tgaaaatcgg agttggaaag   3480
gcgtcgctct cttgaaggtt ctcgttttca accttgactc catggacagt tttgagttc    3540
ttgtactctt tccatgcact tccagtgatg taacctctga caatggcttc caaaggtatc   3600
agtctgtgct tttttactat caaggatcgt ccctctaatt gagatttgta tttttcttca   3660
gacagttttg atggtagtaa agcaaagact tccttgtcat tagaagcaac caaatgattc   3720
tttatgtagg gtgccaaaaa atcaaaccag aaaactgaga gctgagtcaa aatctttccc   3780
ttatcaggaa taccgtttgt cataatcaca tcgtaagcgg agatacggtc agttgcgacg   3840
aacagcaagt tgttctcatc gactgcataa atgtctctaa cctttccttt ggcgattaaa   3900
ggtaggattc cgtccagatc agtgttcaca atggacatac ttggaaggat acagcaaagt   3960
gtgttggaag cgatgacaca tggaaaggaa tttttcgagt ttcctagagt agtatattgg   4020
ggcggtgaaa gttcagatgt ttaatgctta atactcttat actcttcaaa gcgcccaagt   4080
gtttctgcca acctgacttt tttctgaata atgaatcgtt caagtggagt atttaaacca   4140
tgattaagtt acgtgatttg gcactggata aggtcgaaaa atatccgtat tcataaacga   4200
ttattggtaa aagttacaaa ataccactaa ttacggagaa gcttagtaac agttatcatc   4260
tcttggtcga ttaacgctta caatttccat tcgccattca ggctgcgcaa ctgttgggaa   4320
gggcgatcgg tgcgggcctc ttcgctatta cgccagggcc tcgaggcaca aacgaacgtc   4380
tcacttaatc ttctgtactc tgaagaggag tgggaaatac caagaaaaac atcaaactcg   4440
aatgattttc ccaaacccct accacaagat attcatcagc tgcgagatag gctgatcagg   4500
agcaagctcg tacgagaaga aacaaaatga caaaaaaaat cctatactat ataggttaca   4560
```

```
aataaaaaag tatcaaaaat gaagcctgca tctctcaggc aaatggcatt ctgacatcct   4620
cttgattaga atctagcaag accggtcttc tcgtaagtgc ccaacttgaa ctgaggaaca   4680
gtcatgtcta aggctacaaa ctcaatgatg atgatgatga tggtcgacgg cgctattcag   4740
atcctcttct gagatgagtt tttgttcggg cccaaaaata acttcccaat cttcagttat   4800
gtcaagcgat aggttaagaa tggtgatctt attatcattc tcatatgacg atctagtcgg   4860
caatgaactt tcttcgccat ttttttgac tttaatactg tctttcaacg ttatgttgtg   4920
ttgtaaatta ttctttgcga taatgatttt ttcaatattg gtattcctca aagtattgtg   4980
gtgaatgcct gtcaaattct cgggaatatg acttcgaaca ttttttaagg tattgttttc   5040
gaaaatgaac tgagtttcta cgtactcacc tctttggtag ccaaaagttt ctccatcatc   5100
aacataaaga tctccaacgg ctcgtccctc ggtatcaggg gctataacta ttacatatgg   5160
atcgtttttc attaacattg aagatcttct atacttatct ttcatagtga taatgtgacc   5220
gccttcaata aataatggaa ttttatccaa tggtgcagaa atattctttt ctatcaaatc   5280
agtaccattg tttataaaag agtgtaaaga tgcgaattca tagaatatac cgggtgggaa   5340
aaccatttcc gtttctgatt gaccaggctc cgtgacaggt ttgactaata gacctgaatt   5400
actccagtaa aattggttat cgatatgata caattcagca aattcagggt gttcaataaa   5460
cattggattc attatcggaa atccagtgac acttgattta tgaaacatgg tgtataaggt   5520
aggtagcagg aaatatctca attggataat atcacgtact atcgacttca aaggttcatt   5580
gaataagtat ggttctcttc tcttggtgtc tatatgggcg tgtgctctaa aaaatgggta   5640
ccataagccc gcttggtacc aacgtgcaat caattcaggt gtaggatcct cagcaaagcc   5700
agctatgtcg gctcctataa atggcatacc agcaatgttg tttgacagaa ccataggaat   5760
ggaaatcttt aagtaatccc aattggccac attgtcacca gtccatgtgg cagcagtacg   5820
ttgagagccg gcaaaaaaag cccttgttag aaggaaagga cgcttatcgg atggtgaata   5880
aatcgatttt attgcgtcgt aagtagcttc atgcactgat agaccatata tgttatggac   5940
ggatctttcc tcaatgtaat tgtcgtgaat caaatctttt ggagctgtgg tctctgggcc   6000
atcgaaaatc gaaggctcgt tcatatcatt ccaaatgaat aaattagtta aatcagccgg   6060
cagatccata aaccgttcga aaaaggactt ccaaatcttt tggccatatt tgcttatggt   6120
atcaatccat atagaattac ctggccagca atgacctaca tagtcatttc cattgtgatc   6180
cttgactgct acattttcat taattaccct gtcactgatt tcataatctt tctttaaatg   6240
aggatcgatt agtacgacaa gatttctacc caactttttt aatttggata acagcctttt   6300
tggattggga aaggagtgct gcttccaagt aaaatatttt ttgtcgttcg tatactccaa   6360
gtccaaccaa ataaaatcgt aaggaatcat atgagcatcc atctgagagt ccactgtgag   6420
aacgtccatc tcatcattat aattccatct acattgatgg taccctatag aggaaatggg   6480
cggtaaaaag ggtctaccag tcaaatcggt aaatttgtca atgatagttg gaatatctgg   6540
ccccagggac atgactacat ctatgacacc attttcggag atccaatgag tcatcgtttt   6600
atttttactg gtgtcatact ttatgtctac ccaagtgtca gctgcattga cccaaaagat   6660
agatgtggac gaagatgaaa acatgaatgg gatcgaaccg tacattggtt ggctggtacc   6720
gatgttgtac tcaaagacat caacgttgaa aagcctgtag ggttcctttc cacctgaagt   6780
gtccatcagc cttagcgacg tcgcatgttc cggtataccg tagacattag tagaacccat   6840
gaaagagaaa tctagcgcaa ccgattcagg ccccaaaggc atagagtcat gctttgaata   6900
caagaaattg tccttaaaca tgttgaaagt tgtttcttct ggcagcacgt gtgcgaagtt   6960
```

```
ttcctgctta gttctatgat gttcaatgtt caggaaattt tgctcgttta caataagttt   7020
cagcgcattt tgccagtaaa ctttcaattg aaaaggttca gcaaagattt ctacggatac   7080
atcaccgttt cgaagatgaa atgtgtctgc agtggagttt gaaagtgaca aaaatgaaga   7140
tattttcgac cagaatgagt tcacagtttg tttttgctta aggaagtgga attgtggaat   7200
actggtcctg ttcgcctcct cttgaaattt cttgtcgaat gcgtacttcc aggtctcatt   7260
gaaccgttgt gaagagatca acaaaccgct gctgttggtt ggcattctct ctttctcatt   7320
tatagtgaac cttactgagt gatcctgtaa aaaagagaga gagaatggga actgaacggc   7380
tatatcatcg ccctccaatc ttggtatagt tttaattatg gtagcatgaa gcacattctc   7440
taaaggatcg tgtgcaatag actcggcgtc cactttgtaa tagcagtgat gagatttggc   7500
aatattttct gcataaaccc tgtttctatg gcaaaaccca gattgcgcac acttctttaa   7560
tagatagtcg gtaaacgcat gcgaaaaagc ggtaaagaag accaattggc atacgagcca   7620
tttcaaaagg accatctcg                                                7639
```

<210> SEQ ID NO 22
<211> LENGTH: 5742
<212> TYPE: DNA
<213> ORGANISM: Artificial Sequence
<220> FEATURE:
<223> OTHER INFORMATION: plasmid pYPT1ZAGLSII

<400> SEQUENCE: 22

```
cgaacaaaaa ctcatctcag aagaggatct gaatagcgcc gtcgaccatc atcatcatca     60
tcattgagtt tgtagcctta gacatgactg ttcctcagtt caagttgggc acttacgaga    120
agaccggtct tgctagattc taatcaagag gatgtcagaa tgccatttgc ctgagagatg    180
caggcttcat ttttgatact tttttatttg taacctatat agtataggat tttttttgtc    240
attttgtttc ttctcgtacg agcttgctcc tgatcagcct atctcgcagc tgatgaatat    300
cttgtggtag gggtttggga aaatcattcg agtttgatgt tttcttggt atttcccact    360
cctcttcaga gtacagaaga ttaagtgaga ccttcgtttg tgcggatccc ccacacacca    420
tagcttcaaa atgtttctac tccttttta ctcttccaga ttttctcgga ctccgcgcat    480
cgccgtacca cttcaaaaca cccaagcaca gcatactaaa ttttccctct ttcttcctct    540
agggtgtcgt taattacccg tactaaaggt ttggaaaaga aaaaagagac cgcctcgttt    600
ctttttcttc gtcgaaaaag gcaataaaaa tttttatcac gtttcttttt cttgaaattt    660
ttttttttag tttttttctc tttcagtgac ctccattgat atttaagtta ataaacggtc    720
ttcaatttct caagtttcag tttcattttt cttgttctat tacaactttt tttacttctt    780
gttcattaga aagaaagcat agcaatctaa tctaaggggc ggtgttgaca attaatcatc    840
ggcatagtat atcggcatag tataatacga caaggtgagg aactaaacca tggccaagtt    900
gaccagtgcc gttccggtgc tcaccgcgcg cgacgtcgcc ggagcggtcg agttctggac    960
cgaccggctc gggttctccc gggacttcgt ggaggacgac ttcgccggtg tggtccggga   1020
cgacgtgacc ctgttcatca gcgcggtcca ggaccaggtg gtgccggaca acaccctggc   1080
ctgggtgtgg gtgcgcggcc tggacgagct gtacgccgag tggtcggagg tcgtgtccac   1140
gaacttccgg gacgcctccg ggccggccat gaccgagatc ggcgagcagc cgtgggggcg   1200
ggagttcgcc ctgcgcgacc cggccggcaa ctgcgtgcac ttcgtggccg aggagcagga   1260
ctgacacgtc cgacggcggc ccacgggtcc caggcctcgg agatccgtcc cccttttcct   1320
```

-continued

```
ttgtcgatat catgtaatta gttatgtcac gcttacattc acgccctccc cccacatccg   1380

ctctaaccga aaaggaagga gttagacaac ctgaagtcta ggtccctatt tattttttta   1440

tagttatgtt agtattaaga acgttattta tatttcaaat ttttcttttt tttctgtaca   1500

gacgcgtgta cgcatgtaac attatactga aaaccttgct tgagaaggtt ttgggacgct   1560

cgaaggcttt aatttgcaag ctggagacca acatgtgagc aaaaggccag caaaaggcca   1620

ggaaccgtaa aaaggccgcg ttgctggcgt ttttccatag gctccgcccc cctgacgagc   1680

atcacaaaaa tcgacgctca agtcagaggt ggcgaaaccc gacaggacta taaagatacc   1740

aggcgtttcc ccctggaagc tccctcgtgc gctctcctgt tccgaccctg ccgcttaccg   1800

gatacctgtc cgcctttctc ccttcgggaa gcgtggcgct ttctcaatgc tcacgctgta   1860

ggtatctcag ttcggtgtag gtcgttcgct ccaagctggg ctgtgtgcac gaaccccccg   1920

ttcagcccga ccgctgcgcc ttatccggta actatcgtct tgagtccaac ccggtaagac   1980

acgacttatc gccactggca gcagccactg gtaacaggat tagcagagcg aggtatgtag   2040

gcggtgctac agagttcttg aagtggtggc ctaactacgg ctacactaga aggacagtat   2100

ttggtatctg cgctctgctg aagccagtta ccttcggaaa aagagttggt agctcttgat   2160

ccggcaaaca aaccaccgct ggtagcggtg gtttttttgt ttgcaagcag cagattacgc   2220

gcagaaaaaa aggatctcaa gaagatcctt tgatcttttc tacggggtct gacgctcagt   2280

ggaacgaaaa ctcacgttaa gggattttgg tcatgagatc agatctatga tgagtcacaa   2340

tctgcttcca cagacgagta caaggacagg caaaaggaat tggaagaagt tgctaaccca   2400

ataatgagca agttctatgg agctgctggt ggagctcctg gtggagctcc tggtggcttc   2460

cctggaggtt tccctggcgg agctggcgca gctggcggtg ccccaggtgg tgctgcccca   2520

ggcggagaca gcggaccaac cgtggaagaa gtcgattaag caattcaacg gataaattct   2580

ggttaatata tataacgtga ataggaaatt aaggaaattt tggatctaat aatgtgctgt   2640

atgccgacat cgggcatcgt agattgtata gtatcgctga cactataata agccagccaa   2700

aacccctaaa ccagttgccc tccactaatt agtgtactac ccaatcttgc ctcttcgggt   2760

gtcttttata aggacagatt cacaagctct tgttgcccaa tacacacata cacacagaga   2820

taatagcagt cgaattcacg tggcccagcc ggccgtctcg gatcggtacc tcgagatggt   2880

ccttttgaaa tggctcgtat gccaattggt cttctttacc gctttttcgc atgcgtttac   2940

cgactatcta ttaaagaagt gtgcgcaatc tgggttttgc catagaaaca gggtttatgc   3000

agaaaatatt gccaaatctc atcactgcta ttacaaagtg gacgccgagt ctattgcaca   3060

cgatccttta gagaatgtgc ttcatgctac cataattaaa actataccaa gattggaggg   3120

cgatgatata gccgttcagt tcccattctc tctctctttt ttacaggatc actcagtaag   3180

gttcactata aatgagaaag agagaatgcc aaccaacagc agcggtttgt tgatctcttc   3240

acaacggttc aatgagacct ggaagtacgc attcgacaag aaatttcaag aggaggcgaa   3300

caggaccagt attccacaat tccacttcct taagcaaaaa caaactgtga actcattctg   3360

gtcgaaaata tcttcatttt tgtcactttc aaactccact gcagacacat ttcatcttcg   3420

aaacggtgat gtatccgtag aaatctttgc tgaacctttt caattgaaag tttactggca   3480

aaatgcgctg aaacttattg taaacgagca aaatttcctg aacattgaac atcatagaac   3540

taagcaggaa aacttcgcac acgtgctgcc agaagaaaca actttcaaca tgtttaagga   3600

caatttcttg tattcaaagc atgactctat gcctttgggg cctgaatcgg ttgcgctaga   3660

tttctctttc atgggttcta ctaatgtcta cggtataccg gaacatgcga cgtcgctaag   3720
```

```
gctgatggac acttcaggtg gaaaggaacc ctacaggctt ttcaacgttg atgtctttga   3780
gtacaacatc ggtaccagcc aaccaatgta cggttcgatc ccattcatgt tttcatcttc   3840
gtccacatct atcttttggg tcaatgcagc tgacacttgg gtagacataa agtatgacac   3900
cagtaaaaat aaaacgatga ctcattggat ctccgaaaat ggtgtcatag atgtagtcat   3960
gtccctgggg ccagatattc caactatcat tgacaaattt accgatttga ctggtagacc   4020
ctttttaccg cccatttcct ctatagggta ccatcaatgt agatggaatt ataatgatga   4080
gatggacgtt ctcacagtgg actctcagat ggatgctcat atgattcctt acgattttat   4140
ttggttggac ttggagtata cgaacgacaa aaaatatttt acttggaagc agcactcctt   4200
tcccaatcca aaaaggctgt tatccaaatt aaaaaagttg ggtagaaatc ttgtcgtact   4260
aatcgatcct catttaaaga aagattatga aatcagtgac agggtaatta atgaaaatgt   4320
agcagtcaag gatcacaatg gaaatgacta tgtaggtcat tgctggccag gtaattctat   4380
atggattgat accataagca aatatggcca aaagatttgg aagtcctttt tcgaacggtt   4440
tatggatctg ccggctgatt taactaattt attcatttgg aatgatatga acgagccttc   4500
gattttcgat ggcccagaga ccacagctcc aaaagatttg attcacgaca attacattga   4560
ggaaagatcc gtccataaca tatatggtct atcagtgcat gaagctactt acgacgcaat   4620
aaaatcgatt tattcaccat ccgataagcg tcctttcctt ctaacaaggg cttttttttgc   4680
cggctctcaa cgtactgctg ccacatggac tggtgacaat gtggccaatt gggattactt   4740
aaagatttcc attcctatgg ttctgtcaaa caacattgct ggtatgccat ttataggagc   4800
cgacatagct ggctttgctg aggatcctac acctgaattg attgcacgtt ggtaccaagc   4860
gggcttatgg tacccatttt ttagagcaca cgcccatata gacaccaaga gaagagaacc   4920
atacttattc aatgaacctt tgaagtcgat agtacgtgat attatccaat tgagatattt   4980
cctgctacct accttataca ccatgtttca taaatcaagt gtcactggat ttccgataat   5040
gaatccaatg tttattgaac accctgaatt tgctgaattg tatcatatcg ataaccaatt   5100
ttactggagt aattcaggtc tattagtcaa acctgtcacg gagcctggtc aatcagaaac   5160
ggaaatggtt ttcccacccg gtatattcta tgaattcgca tctttacact cttttataaa   5220
caatggtact gatttgatag aaaagaatat ttctgcacca ttggataaaa ttccattatt   5280
tattgaaggc ggtcacatta tcactatgaa agataagtat agaagatctt caatgttaat   5340
gaaaaacgat ccatatgtaa tagttatagc cctgataccc gagggacgag ccgttggaga   5400
tctttatgtt gatgatggag aaacttttgg ctaccaaaga ggtgagtacg tagaaactca   5460
gttcattttc gaaaacaata ccttaaaaaa tgttcgaagt catattcccg agaatttgac   5520
aggcattcac cacaatactt tgaggaatac caatattgaa aaaatcatta tcgcaaagaa   5580
taatttacaa cacaacataa cgttgaaaga cagtattaaa gtcaaaaaaa atggcgaaga   5640
aagttcattg ccgactagat cgtcatatga gaatgataat aagatcacca ttcttaacct   5700
atcgcttgac ataactgaag attgggaagt tatttttggg cc                      5742
```

```
<210> SEQ ID NO 23
<211> LENGTH: 7256
<212> TYPE: DNA
<213> ORGANISM: Artificial Sequence
<220> FEATURE:
<223> OTHER INFORMATION: plasmid pYPT1ADE1glsII

<400> SEQUENCE: 23
```

-continued

```
gtcgaccggc tgcattaatg aatcggccaa cgcgcgggga gaggcggttt gcgtattggg     60
cgctcttccg cttcctcgct cactgactcg ctgcgctcgg tcgttcggct gcggcgagcg    120
gtatcagctc actcaaaggc ggtaatacgg ttatccacag aatcagggga taacgcagga    180
aagaacatgt gagcaaaagg ccagcaaaag gccaggaacc gtaaaaaggc cgcgttgctg    240
gcgtttttcc ataggctccg cccccctgac gagcatcaca aaaatcgacg ctcaagtcag    300
aggtggcgaa acccgacagg actataaaga taccaggcgt ttccccctgg aagctccctc    360
gtgcgctctc ctgttccgac cctgccgctt accggatacc tgtccgcctt tctcccttcg    420
ggaagcgtgg cgctttctca tagctcacgc tgtaggtatc tcagttcggt gtaggtcgtt    480
cgctccaagc tgggctgtgt gcacgaaccc cccgttcagc ccgaccgctg cgccttatcc    540
ggtaactatc gtcttgagtc caacccggta agacacgact tatcgccact ggcagcagcc    600
actggtaaca ggattagcag agcgaggtat gtaggcggtg ctacagagtt cttgaagtgg    660
tggcctaact acggctacac tagaaggaca gtatttggta tctgcgctct gctgaagcca    720
gttaccttcg gaaaaagagt tggtagctct tgatccggca aacaaaccac cgctggtagc    780
ggtggttttt ttgtttgcaa gcagcagatt acgcgcagaa aaaaaggatc tcaagaagat    840
cctttgatct tttctacggg gtctgacgct cagtggaacg aaaactcacg ttaagggatt    900
ttggtcatga gattatcaaa aaggatcttc acctagatcc ttttaaatta aaaatgaagt    960
tttaaatcaa tctaaagtat atatgagtaa acttggtctg acagttacca atgcttaatc   1020
agtgaggcac ctatctcagc gatctgtcta tttcgttcat ccatagttgc ctgactcccc   1080
gtcgtgtaga taactacgat acgggagggc ttaccatctg gccccagtgc tgcaatgata   1140
ccgcgagacc cacgctcacc ggctccagat ttatcagcaa taaaccagcc agccggaagg   1200
gccgagcgca gaagtggtcc tgcaacttta tccgcctcca tccagtctat taattgttgc   1260
cgggaagcta gagtaagtag ttcgccagtt aatagtttgc gcaacgttgt tgccattgct   1320
acaggcatcg tggtgtcacg ctcgtcgttt ggtatggctt cattcagctc cggttcccaa   1380
cgatcaaggc gagttacatg atcccccatg ttgtgcaaaa aagcggttag ctccttcggt   1440
cctccgatcg ttgtcagaag taagttggcc gcagtgttat cactcatggt tatggcagca   1500
ctgcataatt ctcttactgt catgccatcc gtaagatgct tttctgtgac tggtgagtac   1560
tcaaccaagt cattctgaga atagtgtatg cggcgaccga gttgctcttg cccggcgtca   1620
atacgggata ataccgcgcc acatagcaga actttaaaag tgctcatcat tggaaaacgt   1680
tcttcggggc gaaaactctc aaggatctta ccgctgttga gatccagttc gatgtaaccc   1740
actcgtgcac ccaactgatc ttcagcatct tttactttca ccagcgtttc tgggtgagca   1800
aaaacaggaa ggcaaaatgc cgcaaaaaag ggaataaggg cgacacggaa atgttgaata   1860
ctcatactct tcctttttca atagctccaa ggcaacaaat tgactactca gaccgacatt   1920
cattcgttat tgattttaaa tcaacgataa acggaatggt tacttgaatg atttcacttt   1980
atgatcattg tttactaatt acctaaatag gattttatat ggaattggaa gaataaggga   2040
aatttcagat gtctgaaaaa ggcgaggagg gtactaatca ttcaagccca tttcttgcca   2100
gtaattgctt cataagcttc aatatacttt tctttactct tgatagcaat ttctgcatcc   2160
atggctacgc cctctttgcc attcaatccg ttggccgtca accaatctct gagaaactgc   2220
ttatcgtaac tctcttgcga tttacccact tggtaagtct tttgattcca aaatctagaa   2280
gaatctggag ttaaaacttc atctactagt accaattcat tgttttcgtc cagtccaaat   2340
tcgaatttcg tatcagcaat aatgatcccc ttcaaaaggg cgaagttttt tgcagcagaa   2400
```

```
tacaactcga ccgccttgac agcgaccttc tcacaaatgt ctttacctac aatctcagca   2460
gcttgttcaa tagagatgtt ttcatcgtgt tcaccctgtt cagctttcgt tgaaggtgtg   2520
aaaatcggag ttggaaaggc gtcgctctct tgaaggttct cgttttcaac cttgactcca   2580
tggacagttt ttgagttctt gtactctttc catgcacttc cagtgatgta acctctgaca   2640
atggcttcca aaggtatcag tctgtgcttt tttactatca aggatcgtcc ctctaattga   2700
gatttgtatt tttcttcaga cagttttgat ggtagtaaag caaagacttc cttgtcatta   2760
gaagcaacca aatgattctt tatgtagggt gccaaaaaat caaaccagaa aactgagagc   2820
tgagtcaaaa tctttccctt atcaggaata ccgtttgtca taatcacatc gtaagcggag   2880
atacggtcag ttgcgacgaa cagcaagttg ttctcatcga ctgcataaat gtctctaacc   2940
tttcctttgg cgattaaagg taggattccg tccagatcag tgttcacaat ggacatactt   3000
ggaaggatac agcaaagtgt gttggaagcg atgacacatg gaaaggaatt tttcgagttt   3060
cctagagtag tatattgggg cggtgaaagt tcagatgttt aatgcttaat actcttatac   3120
tcttcaaagc gcccaagtgt ttctgccaac ctgacttttt tctgaataat gaatcgttca   3180
agtggagtat ttaaaccatg attaagttac gtgatttggc actggataag gtcgaaaaat   3240
atccgtattc ataaacgatt attggtaaaa gttacaaaat accactaatt acggagaagc   3300
ttagtaacag ttatcatctc ttggtcgatt aacgcttaca atttccattc gccattcagg   3360
ctgcgcaact gttgggaagg gcgatcggtg cgggcctctt cgctattacg ccagggcctc   3420
gaggcacaaa cgaacgtctc acttaatctt ctgtactctg aagaggagtg ggaaatacca   3480
agaaaaacat caaactcgaa tgattttccc aaacccctac cacaagatat tcatcagctg   3540
cgagataggc tgatcaggag caagctcgta cgagaagaaa caaaatgaca aaaaaaatcc   3600
tatactatat aggttacaaa taaaaaagta tcaaaaatga agcctgcatc tctcaggcaa   3660
atggcattct gacatcctct tgattagaat ctagcaagac cggtcttctc gtaagtgccc   3720
aacttgaact gaggaacagt catgtctaag gctacaaact caatgatgat gatgatgatg   3780
gtcgacggcg ctattcagat cctcttctga gatgagtttt tgttcgggcc caaaaataac   3840
ttcccaatct tcagttatgt caagcgatag gttaagaatg gtgatcttat tatcattctc   3900
atatgacgat ctagtcggca atgaactttc ttcgccattt tttttgactt taatactgtc   3960
tttcaacgtt atgttgtgtt gtaaattatt ctttgcgata atgatttttt caatattggt   4020
attcctcaaa gtattgtggt gaatgcctgt caaattctcg ggaatatgac ttcgaacatt   4080
ttttaaggta ttgttttcga aaatgaactg agtttctacg tactcacctc tttggtagcc   4140
aaaagtttct ccatcatcaa cataaagatc tccaacggct cgtccctcgg tatcaggggc   4200
tataactatt acatatggat cgtttttcat taacattgaa gatcttctat acttatcttt   4260
catagtgata atgtgaccgc cttcaataaa taatggaatt ttatccaatg gtgcagaaat   4320
attcttttct atcaaatcag taccattgtt tataaaagag tgtaaagatg cgaattcata   4380
gaatataccg ggtgggaaaa ccatttccgt ttctgattga ccaggctccg tgacaggttt   4440
gactaataga cctgaattac tccagtaaaa ttggttatcg atatgataca attcagcaaa   4500
ttcagggtgt tcaataaaca ttggattcat tatcggaaat ccagtgacac ttgatttatg   4560
aaacatggtg tataaggtag gtagcaggaa atatctcaat tggataatat cacgtactat   4620
cgacttcaaa ggttcattga ataagtatgg ttctcttctc ttggtgtcta tatgggcgtg   4680
tgctctaaaa aatgggtacc ataagcccgc ttggtaccaa cgtgcaatca attcaggtgt   4740
```

```
aggatcctca gcaaagccag ctatgtcggc tcctataaat ggcataccag caatgttgtt   4800
tgacagaacc ataggaatgg aaatctttaa gtaatcccaa ttggccacat tgtcaccagt   4860
ccatgtggca gcagtacgtt gagagccggc aaaaaaagcc cttgttagaa ggaaaggacg   4920
cttatcggat ggtgaataaa tcgattttat tgcgtcgtaa gtagcttcat gcactgatag   4980
accatatatg ttatggacgg atctttcctc aatgtaattg tcgtgaatca aatcttttgg   5040
agctgtggtc tctgggccat cgaaaatcga aggctcgttc atatcattcc aaatgaataa   5100
attagttaaa tcagccggca gatccataaa ccgttcgaaa aaggacttcc aaatcttttg   5160
gccatatttg cttatggtat caatccatat agaattacct ggccagcaat gacctacata   5220
gtcatttcca ttgtgatcct tgactgctac attttcatta attaccctgt cactgatttc   5280
ataatctttc tttaaatgag gatcgattag tacgacaaga tttctaccca actttttttaa   5340
tttggataac agcctttttg gattgggaaa ggagtgctgc ttccaagtaa aatatttttt   5400
gtcgttcgta tactccaagt ccaaccaaat aaaatcgtaa ggaatcatat gagcatccat   5460
ctgagagtcc actgtgagaa cgtccatctc atcattataa ttccatctac attgatggta   5520
ccctatagag gaaatgggcg gtaaaaaggg tctaccagtc aaatcggtaa atttgtcaat   5580
gatagttgga atatctggcc ccagggacat gactacatct atgacaccat tttcggagat   5640
ccaatgagtc atcgttttat ttttactggt gtcatacttt atgtctaccc aagtgtcagc   5700
tgcattgacc caaaagatag atgtggacga agatgaaaac atgaatggga tcgaaccgta   5760
cattggttgg ctggtaccga tgttgtactc aaagacatca acgttgaaaa gcctgtaggg   5820
ttcctttcca cctgaagtgt ccatcagcct tagcgacgtc gcatgttccg gtataccgta   5880
gacattagta gaacccatga aagagaaatc tagcgcaacc gattcaggcc ccaaaggcat   5940
agagtcatgc tttgaataca agaaattgtc cttaaacatg ttgaaagttg tttcttctgg   6000
cagcacgtgt gcgaagtttt cctgcttagt tctatgatgt tcaatgttca ggaaattttg   6060
ctcgtttaca ataagtttca gcgcattttg ccagtaaact ttcaattgaa aaggttcagc   6120
aaagatttct acggatacat caccgtttcg aagatgaaat gtgtctgcag tggagtttga   6180
aagtgacaaa aatgaagata ttttcgacca gaatgagttc acagtttgtt tttgcttaag   6240
gaagtggaat tgtggaatac tggtcctgtt cgcctcctct tgaaatttct tgtcgaatgc   6300
gtacttccag gtctcattga accgttgtga agagatcaac aaaccgctgc tgttggttgg   6360
cattctctct ttctcattta tagtgaacct tactgagtga tcctgtaaaa aagagagaga   6420
gaatgggaac tgaacggcta tatcatcgcc ctccaatctt ggtatagttt taattatggt   6480
agcatgaagc acattctcta aaggatcgtg tgcaatagac tcggcgtcca ctttgtaata   6540
gcagtgatga gatttggcaa tattttctgc ataaaccctg tttctatggc aaaacccaga   6600
ttgcgcacac ttctttaata gatagtcggt aaacgcatgc gaaaaagcgg taaagaagac   6660
caattggcat acgagccatt tcaaaaggac catctcgagg taccgatccg agacggccgg   6720
ctgggccacg tgaattcgac tgctattatc tctgtgtgta tgtgtgtatt gggcaacaag   6780
agcttgtgaa tctgtcctta taaaagacac ccgaagaggc aagattgggt agtacactaa   6840
ttagtggagg gcaactggtt taggggtttt ggctggctta ttatagtgtc agcgatacta   6900
tacaatctac gatgcccgat gtcggcatac agcacattat tagatccaaa atttccttaa   6960
tttcctattc acgttatata tattaaccag aatttatccg ttgaattgct taatcgactt   7020
cttccacggt tggtccgctg tctccgcctg gggcagcacc acctggggca ccgccagctg   7080
cgccagctcc gccagggaaa cctccaggga agccaccagg agctccacca ggagctccac   7140
```

cagcagctcc atagaacttg ctcattattg ggttagcaac ttcttccaat tccttttgcc 7200
tgtccttgta ctcgtctgtg gaagcagatt gtgactcatc atagatctga tctcat 7256

<210> SEQ ID NO 24
<211> LENGTH: 5721
<212> TYPE: DNA
<213> ORGANISM: Artificial Sequence
<220> FEATURE:
<223> OTHER INFORMATION: plasmid pGAPZAglsIIHDEL

<400> SEQUENCE: 24
tcgagatggt ccttttgaaa tggctcgtat gccaattggt cttctttacc gctttttcgc 60
atgcgtttac cgactatcta ttaaagaagt gtgcgcaatc tgggttttgc catagaaaca 120
gggtttatgc agaaaatatt gccaaatctc atcactgcta ttacaaagtg gacgccgagt 180
ctattgcaca cgatccttta gagaatgtgc ttcatgctac cataattaaa actataccaa 240
gattggaggg cgatgatata gccgttcagt tcccattctc tctctctttt ttacaggatc 300
actcagtaag gttcactata aatgagaaag agagaatgcc aaccaacagc agcggtttgt 360
tgatctcttc acaacggttc aatgagacct ggaagtacgc attcgacaag aaatttcaag 420
aggaggcgaa caggaccagt attccacaat tccacttcct taagcaaaaa caaactgtga 480
actcattctg gtcgaaaata tcttcatttt tgtcactttc aaactccact gcagacacat 540
ttcatcttcg aaacggtgat gtatccgtag aaatctttgc tgaacctttt caattgaaag 600
tttactggca aaatgcgctg aaacttattg taaacgagca aaatttcctg aacattgaac 660
atcatagaac taagcaggaa aacttcgcac acgtgctgcc agaagaaaca actttcaaca 720
tgtttaagga caatttcttg tattcaaagc atgactctat gcctttgggg cctgaatcgg 780
ttgcgctaga tttctctttc atgggttcta ctaatgtcta cggtataccg gaacatgcga 840
cgtcgctaag gctgatggac acttcaggtg gaaaggaacc ctacaggctt ttcaacgttg 900
atgtctttga gtacaacatc ggtaccagcc aaccaatgta cggttcgatc ccattcatgt 960
tttcatcttc gtccacatct atcttttggg tcaatgcagc tgacacttgg gtagacataa 1020
agtatgacac cagtaaaaat aaaacgatga ctcattggat ctccgaaaat ggtgtcatag 1080
atgtagtcat gtccctgggg ccagatattc caactatcat tgacaaattt accgatttga 1140
ctggtagacc ctttttaccg cccatttcct ctatagggta ccatcaatgt agatggaatt 1200
ataatgatga gatggacgtt ctcacagtgg actctcagat ggatgctcat atgattcctt 1260
acgattttat ttggttggac ttggagtata cgaacgacaa aaaatatttt acttggaagc 1320
agcactcctt tcccaatcca aaaaggctgt tatccaaatt aaaaaagttg ggtagaaatc 1380
ttgtcgtact aatcgatcct catttaaaga aagattatga aatcagtgac agggtaatta 1440
atgaaaatgt agcagtcaag gatcacaatg gaaatgacta tgtaggtcat tgctggccag 1500
gtaattctat atggattgat accataagca aatatggcca aaagatttgg aagtcctttt 1560
tcgaacggtt tatggatctg ccggctgatt taactaattt attcatttgg aatgatatga 1620
acgagccttc gattttcgat ggcccagaga ccacagctcc aaaagatttg attcacgaca 1680
attacattga ggaaagatcc gtccataaca tatatggtct atcagtgcat gaagctactt 1740
acgacgcaat aaaatcgatt tattcaccat ccgataagcg tcctttcctt ctaacaaggg 1800
ctttttttgc cggctctcaa cgtactgctg ccacatggac tggtgacaat gtggccaatt 1860
gggattactt aaagatttcc attcctatgg ttctgtcaaa caacattgct ggtatgccat 1920

```
ttataggagc cgacatagct ggctttgctg aggatcctac acctgaattg attgcacgtt   1980
ggtaccaagc gggcttatgg tacccatttt ttagagcaca cgcccatata gacaccaaga   2040
gaagagaacc atacttattc aatgaacctt tgaagtcgat agtacgtgat attatccaat   2100
tgagatattt cctgctacct accttataca ccatgtttca taaatcaagt gtcactggat   2160
ttccgataat gaatccaatg tttattgaac accctgaatt tgctgaattg tatcatatcg   2220
ataaccaatt ttactggagt aattcaggtc tattagtcaa acctgtcacg gagcctggtc   2280
aatcagaaac ggaaatggtt ttcccacccg gtatattcta tgaattcgca tctttacact   2340
cttttataaa caatggtact gatttgatag aaaagaatat ttctgcacca ttggataaaa   2400
ttccattatt tattgaaggc ggtcacatta tcactatgaa agataagtat agaagatctt   2460
caatgttaat gaaaaacgat ccatatgtaa tagttatagc ccctgatacc gagggacgag   2520
ccgttggaga tctttatgtt gatgatggag aaacttttgg ctaccaaaga ggtgagtacg   2580
tagaaactca gttcattttc gaaaacaata ccttaaaaaa tgttcgaagt catattcccg   2640
agaatttgac aggcattcac cacaatactt tgaggaatac caatattgaa aaaatcatta   2700
tcgcaaagaa taatttacaa cacaacataa cgttgaaaga cagtattaaa gtcaaaaaaa   2760
atggcgaaga aagttcattg ccgactagat cgtcatatga gaatgataat aagatcacca   2820
ttcttaacct atcgcttgac ataactgaag attgggaagt tatttttggg cccgaacaaa   2880
aactcatctc agaagaggat ctgaatagcg ccgtcgacca cgacgaactg tgagttttag   2940
ccttagacat gactgttcct cagttcaagt tgggcactta cgagaagacc ggtcttgcta   3000
gattctaatc aagaggatgt cagaatgcca tttgcctgag agatgcaggc ttcatttttg   3060
atactttttt atttgtaacc tatatagtat aggatttttt ttgtcatttt gtttcttctc   3120
gtacgagctt gctcctgatc agcctatctc gcagctgatg aatatcttgt ggtaggggtt   3180
tgggaaaatc attcgagttt gatgtttttc ttggtatttc ccactcctct tcagagtaca   3240
gaagattaag tgagaccttc gtttgtgcgg atcccccaca caccatagct tcaaaatgtt   3300
tctactcctt ttttactctt ccagattttc tcggactccg cgcatcgccg taccacttca   3360
aaacacccaa gcacagcata ctaaattttc cctctttctt cctctagggt gtcgttaatt   3420
acccgtacta aaggtttgga aaagaaaaaa gagaccgcct cgtttctttt tcttcgtcga   3480
aaaaggcaat aaaaattttt atcacgtttc tttttcttga aatttttttt tttagttttt   3540
ttctctttca gtgacctcca ttgatattta agttaataaa cggtcttcaa tttctcaagt   3600
ttcagtttca tttttcttgt tctattacaa ctttttttac ttcttgttca ttagaaagaa   3660
agcatagcaa tctaatctaa gggcggtgtt gacaattaat catcggcata gtatatcggc   3720
atagtataat acgacaaggt gaggaactaa accatggcca agttgaccag tgccgttccg   3780
gtgctcaccg cgcgcgacgt cgccggagcg gtcgagttct ggaccgaccg gctcgggttc   3840
tcccgggact tcgtggagga cgacttcgcc ggtgtggtcc gggacgacgt gaccctgttc   3900
atcagcgcgg tccaggacca ggtggtgccg gacaacaccc tggcctgggt gtgggtgcgc   3960
ggcctggacg agctgtacgc cgagtggtcg gaggtcgtgt ccacgaactt ccgggacgcc   4020
tccgggccgg ccatgaccga gatcggcgag cagccgtggg ggcgggagtt cgccctgcgc   4080
gacccggccg gcaactgcgt gcacttcgtg gccgaggagc aggactgaca cgtccgacgg   4140
cggcccacgg gtcccaggcc tcggagatcc gtcccccttt tcctttgtcg atatcatgta   4200
attagttatg tcacgcttac attcacgccc tccccccaca tccgctctaa ccgaaaagga   4260
aggagttaga caacctgaag tctaggtccc tatttatttt tttatagtta tgttagtatt   4320
```

```
aagaacgtta tttatatttc aaatttttct ttttttctg tacagacgcg tgtacgcatg   4380

taacattata ctgaaaacct tgcttgagaa ggttttggga cgctcgaagg ctttaatttg   4440

caagctggag accaacatgt gagcaaaagg ccagcaaaag gccaggaacc gtaaaaaggc   4500

cgcgttgctg gcgtttttcc ataggctccg cccccctgac gagcatcaca aaaatcgacg   4560

ctcaagtcag aggtggcgaa acccgacagg actataaaga taccaggcgt ttccccctgg   4620

aagctccctc gtgcgctctc ctgttccgac cctgccgctt accggatacc tgtccgcctt   4680

tctcccttcg ggaagcgtgg cgctttctca atgctcacgc tgtaggtatc tcagttcggt   4740

gtaggtcgtt cgctccaagc tgggctgtgt gcacgaaccc cccgttcagc ccgaccgctg   4800

cgccttatcc ggtaactatc gtcttgagtc caacccggta agacacgact tatcgccact   4860

ggcagcagcc actggtaaca ggattagcag agcgaggtat gtaggcggtg ctacagagtt   4920

cttgaagtgg tggcctaact acggctacac tagaaggaca gtatttggta tctgcgctct   4980

gctgaagcca gttaccttcg gaaaaagagt tggtagctct tgatccggca aacaaaccac   5040

cgctggtagc ggtggttttt ttgtttgcaa gcagcagatt acgcgcagaa aaaaaggatc   5100

tcaagaagat cctttgatct tttctacggg gtctgacgct cagtggaacg aaaactcacg   5160

ttaagggatt ttggtcatgc atgagatcag atctttttg tagaaatgtc ttggtgtcct   5220

cgtccaatca ggtagccatc tctgaaatat ctggctccgt tgcaactccg aacgacctgc   5280

tggcaacgta aaattctccg ggtaaaact taaatgtgga gtaatggaac cagaaacgtc   5340

tcttcccttc tctctccttc caccgcccgt taccgtccct aggaaatttt actctgctgg   5400

agagcttctt ctacggcccc cttgcagcaa tgctcttccc agcattacgt tgcgggtaaa   5460

acggaggtcg tgtacccgac ctagcagccc agggatggaa aagtcccggc cgtcgctggc   5520

aataatagcg ggcggacgca tgtcatgaga ttattggaaa ccaccagaat cgaatataaa   5580

aggcgaacac ctttcccaat tttggtttct cctgacccaa agactttaaa tttaatttat   5640

ttgtccctat ttcaatcaat tgaacaacta tttcgaaacg aggaattcac gtggcccagc   5700

cggccgtctc ggatcggtac c                                              5721
```

```
<210> SEQ ID NO 25
<211> LENGTH: 7230
<212> TYPE: DNA
<213> ORGANISM: Artificial Sequence
<220> FEATURE:
<223> OTHER INFORMATION: plasmid pGAPADE1glsIIHDEL

<400> SEQUENCE: 25

cgtactcacc tctttggtag ccaaaagttt ctccatcatc aacataaaga tctccaacgg     60

ctcgtccctc ggtatcaggg gctataacta ttacatatgg atcgtttttc attaacattg    120

aagatcttct atacttatct ttcatagtga taatgtgacc gccttcaata aataatggaa    180

ttttatccaa tggtgcagaa atattctttt ctatcaaatc agtaccattg tttataaaag    240

agtgtaaaga tgcgaattca tagaatatac cgggtgggaa aaccatttcc gtttctgatt    300

gaccaggctc cgtgacaggt ttgactaata gacctgaatt actccagtaa aattggttat    360

cgatatgata caattcagca aattcagggt gttcaataaa cattggattc attatcggaa    420

atccagtgac acttgattta tgaaacatgg tgtataaggt aggtagcagg aaatatctca    480

attggataat atcacgtact atcgacttca aaggttcatt gaataagtat ggttctcttc    540

tcttggtgtc tatatgggcg tgtgctctaa aaaatgggta ccataagccc gcttggtacc    600
```

-continued

```
aacgtgcaat caattcaggt gtaggatcct cagcaaagcc agctatgtcg gctcctataa    660
atggcatacc agcaatgttg tttgacagaa ccataggaat ggaaatcttt aagtaatccc    720
aattggccac attgtcacca gtccatgtgg cagcagtacg ttgagagccg gcaaaaaaag    780
cccttgttag aaggaaagga cgcttatcgg atggtgaata aatcgatttt attgcgtcgt    840
aagtagcttc atgcactgat agaccatata tgttatggac ggatctttcc tcaatgtaat    900
tgtcgtgaat caaatctttt ggagctgtgg tctctgggcc atcgaaaatc gaaggctcgt    960
tcatatcatt ccaaatgaat aaattagtta aatcagccgg cagatccata aaccgttcga   1020
aaaaggactt ccaaatcttt tggccatatt tgcttatggt atcaatccat atagaattac   1080
ctggccagca atgacctaca tagtcatttc cattgtgatc cttgactgct acattttcat   1140
taattaccct gtcactgatt tcataatctt tctttaaatg aggatcgatt agtacgacaa   1200
gatttctacc caactttttt aatttggata acagcctttt tggattggga aaggagtgct   1260
gcttccaagt aaaatatttt ttgtcgttcg tatactccaa gtccaaccaa ataaaatcgt   1320
aaggaatcat atgagcatcc atctgagagt ccactgtgag aacgtccatc tcatcattat   1380
aattccatct acattgatgg taccctatag aggaaatggg cggtaaaaag ggtctaccag   1440
tcaaatcggt aaatttgtca atgatagttg gaatatctgg ccccagggac atgactacat   1500
ctatgacacc attttcggag atccaatgag tcatcgtttt atttttactg gtgtcatact   1560
ttatgtctac ccaagtgtca gctgcattga cccaaaagat agatgtggac gaagatgaaa   1620
acatgaatgg gatcgaaccg tacattggtt ggctggtacc gatgttgtac tcaaagacat   1680
caacgttgaa aagcctgtag ggttcctttc cacctgaagt gtccatcagc cttagcgacg   1740
tcgcatgttc cggtataccg tagacattag tagaacccat gaaagagaaa tctagcgcaa   1800
ccgattcagg ccccaaaggc atagagtcat gctttgaata caagaaattg tccttaaaca   1860
tgttgaaagt tgtttcttct ggcagcacgt gtgcgaagtt ttcctgctta gttctatgat   1920
gttcaatgtt caggaaattt tgctcgttta caataagttt cagcgcattt tgccagtaaa   1980
ctttcaattg aaaaggttca gcaaagattt ctacggatac atcaccgttt cgaagatgaa   2040
atgtgtctgc agtggagttt gaaagtgaca aaaatgaaga tattttcgac cagaatgagt   2100
tcacagtttg tttttgctta aggaagtgga attgtggaat actggtcctg ttcgcctcct   2160
cttgaaattt cttgtcgaat gcgtacttcc aggtctcatt gaaccgttgt gaagagatca   2220
acaaaccgct gctgttggtt ggcattctct ctttctcatt tatagtgaac cttactgagt   2280
gatcctgtaa aaaagagaga gagaatggga actgaacggc tatatcatcg ccctccaatc   2340
ttggtatagt tttaattatg gtagcatgaa gcacattctc taaaggatcg tgtgcaatag   2400
actcggcgtc cactttgtaa tagcagtgat gagatttggc aatattttct gcataaaccc   2460
tgtttctatg gcaaaaccca gattgcgcac acttctttaa tagatagtcg gtaaacgcat   2520
gcgaaaaagc ggtaaagaag accaattggc atacgagcca tttcaaaagg accatctcga   2580
ggtaccgatc cgagacggcc ggctgggcca cgtgaattcc tcgtttcgaa atagttgttc   2640
aattgattga aatagggaca aataaattaa atttaaagtc tttgggtcag gagaaaccaa   2700
aattgggaaa ggtgttcgcc ttttatattc gattctggtg gtttccaata atctcatgac   2760
atgcgtccgc ccgctattat tgccagcgac ggccgggact tttccatccc tgggctgcta   2820
ggtcgggtac acgacctccg ttttacccgc aacgtaatgc tgggaagagc attgctgcaa   2880
gggggccgta gaagaagctc tccagcagag taaaatttcc tagggacggt aacgggcggt   2940
ggaaggagag agaagggaag agacgtttct ggttccatta ctccacattt aagttttacc   3000
```

```
ccggagaatt ttacgttgcc agcaggtcgt tcggagttgc aacggagcca gatatttcag   3060
agatggctac ctgattggac gaggacacca agacatttct acaaaaaaga tctgatctca   3120
tcgaccggct gcattaatga atcggccaac gcgcggggag aggcggtttg cgtattgggc   3180
gctcttccgc ttcctcgctc actgactcgc tgcgctcggt cgttcggctg cggcgagcgg   3240
tatcagctca ctcaaaggcg gtaatacggt tatccacaga atcaggggat aacgcaggaa   3300
agaacatgtg agcaaaaggc cagcaaaagg ccaggaaccg taaaaaggcc gcgttgctgg   3360
cgtttttcca taggctccgc ccccctgacg agcatcacaa aaatcgacgc tcaagtcaga   3420
ggtggcgaaa cccgacagga ctataaagat accaggcgtt tccccctgga agctccctcg   3480
tgcgctctcc tgttccgacc ctgccgctta ccggatacct gtccgccttt ctcccttcgg   3540
gaagcgtggc gctttctcat agctcacgct gtaggtatct cagttcggtg taggtcgttc   3600
gctccaagct gggctgtgtg cacgaacccc ccgttcagcc cgaccgctgc gccttatccg   3660
gtaactatcg tcttgagtcc aacccggtaa gacacgactt atcgccactg gcagcagcca   3720
ctggtaacag gattagcaga gcgaggtatg taggcggtgc tacagagttc ttgaagtggt   3780
ggcctaacta cggctacact agaaggacag tatttggtat ctgcgctctg ctgaagccag   3840
ttaccttcgg aaaaagagtt ggtagctctt gatccggcaa acaaaccacc gctggtagcg   3900
gtggtttttt tgtttgcaag cagcagatta cgcgcagaaa aaaaggatct caagaagatc   3960
ctttgatctt ttctacgggg tctgacgctc agtggaacga aaactcacgt taagggattt   4020
tggtcatgag attatcaaaa aggatcttca cctagatcct tttaaattaa aaatgaagtt   4080
ttaaatcaat ctaaagtata tatgagtaaa cttggtctga cagttaccaa tgcttaatca   4140
gtgaggcacc tatctcagcg atctgtctat ttcgttcatc catagttgcc tgactccccg   4200
tcgtgtagat aactacgata cgggagggct taccatctgg ccccagtgct gcaatgatac   4260
cgcgagaccc acgctcaccg gctccagatt tatcagcaat aaaccagcca gccggaaggg   4320
ccgagcgcag aagtggtcct gcaactttat ccgcctccat ccagtctatt aattgttgcc   4380
gggaagctag agtaagtagt tcgccagtta atagtttgcg caacgttgtt gccattgcta   4440
caggcatcgt ggtgtcacgc tcgtcgtttg gtatggcttc attcagctcc ggttcccaac   4500
gatcaaggcg agttacatga tcccccatgt tgtgcaaaaa agcggttagc tccttcggtc   4560
ctccgatcgt tgtcagaagt aagttggccg cagtgttatc actcatggtt atggcagcac   4620
tgcataattc tcttactgtc atgccatccg taagatgctt ttctgtgact ggtgagtact   4680
caaccaagtc attctgagaa tagtgtatgc ggcgaccgag ttgctcttgc ccggcgtcaa   4740
tacgggataa taccgcgcca catagcagaa ctttaaaagt gctcatcatt ggaaaacgtt   4800
cttcggggcg aaaactctca aggatcttac cgctgttgag atccagttcg atgtaaccca   4860
ctcgtgcacc caactgatct tcagcatctt ttactttcac cagcgtttct gggtgagcaa   4920
aaacaggaag gcaaaatgcc gcaaaaaagg gaataagggc gacacggaaa tgttgaatac   4980
tcatactctt cctttttcaa tagctccaag gcaacaaatt gactactcag accgacattc   5040
attcgttatt gattttaaat caacgataaa cggaatggtt acttgaatga tttcacttta   5100
tgatcattgt ttactaatta cctaaatagg attttatatg gaattggaag aataagggaa   5160
atttcagatg tctgaaaaag gcgaggaggg tactaatcat tcaagcccat ttcttgccag   5220
taattgcttc ataagcttca atatactttt ctttactctt gatagcaatt tctgcatcca   5280
tggctacgcc ctctttgcca ttcaatccgt tggccgtcaa ccaatctctg agaaactgct   5340
```

```
tatcgtaact ctcttgcgat ttacccactt ggtaagtctt ttgattccaa aatctagaag   5400

aatctggagt taaaacttca tctactagta ccaattcatt gttttcgtcc agtccaaatt   5460

cgaatttcgt atcagcaata atgatcccct tcaaaagggc gaagtttttt gcagcagaat   5520

acaactcgac cgccttgaca gcgaccttct cacaaatgtc tttacctaca atctcagcag   5580

cttgttcaat agagatgttt tcatcgtgtt caccctgttc agctttcgtt gaaggtgtga   5640

aaatcggagt tggaaaggcg tcgctctctt gaaggttctc gttttcaacc ttgactccat   5700

ggacagtttt tgagttcttg tactctttcc atgcacttcc agtgatgtaa cctctgacaa   5760

tggcttccaa aggtatcagt ctgtgctttt ttactatcaa ggatcgtccc tctaattgag   5820

atttgtattt ttcttcagac agttttgatg gtagtaaagc aaagacttcc ttgtcattag   5880

aagcaaccaa atgattcttt atgtagggtg ccaaaaaatc aaaccagaaa actgagagct   5940

gagtcaaaat ctttccctta tcaggaatac cgtttgtcat aatcacatcg taagcggaga   6000

tacggtcagt tgcgacgaac agcaagttgt tctcatcgac tgcataaatg tctctaacct   6060

ttcctttggc gattaaaggt aggattccgt ccagatcagt gttcacaatg gacatacttg   6120

gaaggataca gcaaagtgtg ttggaagcga tgacacatgg aaaggaattt ttcgagtttc   6180

ctagagtagt atattggggc ggtgaaagtt cagatgttta atgcttaata ctcttatact   6240

cttcaaagcg cccaagtgtt tctgccaacc tgactttttt ctgaataatg aatcgttcaa   6300

gtggagtatt taaaccatga ttaagttacg tgatttggca ctggataagg tcgaaaaata   6360

tccgtattca taaacgatta ttggtaaaag ttacaaaata ccactaatta cggagaagct   6420

tagtaacagt tatcatctct tggtcgatta acgcttacaa tttccattcg ccattcaggc   6480

tgcgcaactg ttgggaaggg cgatcggtgc gggcctcttc gctattacgc cagggcctcg   6540

aggcacaaac gaacgtctca cttaatcttc tgtactctga agaggagtgg gaaataccaa   6600

gaaaaacatc aaactcgaat gattttccca aacccctacc acaagatatt catcagctgc   6660

gagataggct gatcaggagc aagctcgtac gagaagaaac aaaatgacaa aaaaaatcct   6720

atactatata ggttacaaat aaaaaagtat caaaaatgaa gcctgcatct ctcaggcaaa   6780

tggcattctg acatcctctt gattagaatc tagcaagacc ggtcttctcg taagtgccca   6840

acttgaactg aggaacagtc atgtctaagg ctaaaactca cagttcgtcg tggtcgacgg   6900

cgctattcag atcctcttct gagatgagtt tttgttcggg cccaaaaata acttcccaat   6960

cttcagttat gtcaagcgat aggttaagaa tggtgatctt attatcattc tcatatgacg   7020

atctagtcgg caatgaactt tcttcgccat ttttttgac tttaatactg tctttcaacg   7080

ttatgttgtg ttgtaaatta ttctttgcga taatgatttt ttcaatattg gtattcctca   7140

aagtattgtg gtgaatgcct gtcaaattct cgggaatatg acttcgaaca ttttttaagg   7200

tattgttttc gaaaatgaac tgagtttcta                                    7230
```

<210> SEQ ID NO 26
<211> LENGTH: 32
<212> TYPE: DNA
<213> ORGANISM: Artificial Sequence
<220> FEATURE:
<223> OTHER INFORMATION: Primer

<400> SEQUENCE: 26

```
gacgagatct ttttttcaga ccatatgacc gg                                    32
```

<210> SEQ ID NO 27
<211> LENGTH: 31

<212> TYPE: DNA
<213> ORGANISM: Artificial Sequence
<220> FEATURE:
<223> OTHER INFORMATION: Primer

<400> SEQUENCE: 27
gcggaattct tttctcagtt gatttgtttg t 31

<210> SEQ ID NO 28
<211> LENGTH: 45
<212> TYPE: DNA
<213> ORGANISM: Artificial Sequence
<220> FEATURE:
<223> OTHER INFORMATION: Primer

<400> SEQUENCE: 28
gcgggtcgac cacgacgaac tgtgagtttt agccttagac atgac 45

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
caggagcaaa gctcgtacga g 21

<210> SEQ ID NO 30
<211> LENGTH: 2208
<212> TYPE: DNA
<213> ORGANISM: Saccharomyces cerevisiae

<400> SEQUENCE: 30
atggccctct ttctcagtaa gagactgttg agatttaccg tcattgcagg tgcggttatt 60
gttctcctcc taacattgaa ttccaacagt agaactcagc aatatattcc gagttccatc 120
tccgctgcat ttgattttac ctcaggatct atatcccctg aacaacaagt catctctgag 180
gaaaatgatg ctaaaaaatt agagcaaagt gctctgaatt cagaggcaag cgaagactcc 240
gaagccatgg atgaagaatc caaggctctg aaagctgccg ctgaaaaggc agatgccccg 300
atcgacacta aaacaaccat ggattatatc actccatctt ttgctaacaa agctggtaag 360
ccaaaagctt gttacgtcac tttggtgaga aacaaggagt tgaaaggttt gctaagctcc 420
attaaatatg tggaaaacaa aattaacaag aaattcccat atccttgggt tttcctaaac 480
gatgaacctt ttactgaaga attcaaggaa gcagtcacca aagctgtttc ttccgaagtt 540
aagtttggta ttttgcccaa ggaacattgg tcatatcctg aatggattaa tcaaaccaag 600
gctgctgaaa ttcgtgcaga tgctgccacc aaatacatat acggtggctc cgaatcttat 660
agacacatgt gtcgttacca atctgggttt ttctggagac atgaattatt agaagagtac 720
gattggtact ggcgtgtgga accagacatc aagttatact gtgatattaa ttacgacgtt 780
tttaagtgga tgcaagaaaa cgaaaaagtt tacggcttta ccgtttctat tcatgaatat 840
gaagtgacga tcccaacact atggcaaacg tccatggatt tcatcaaaaa gaaccccgaa 900
tacttagatg aaaacaacct gatgagtttt ctttcgaacg ataatggtaa aacatacaat 960
ctgtgccatt tctggtcaaa ctttgaaatt gcaaacttga atttgtggag gtcaccagcc 1020
tacagagagt attttgacac tttggatcat caaggtggat ttttctacga aagatggggc 1080
gatgctcccg ttcattctat tgctgctgct ttgtttttgc caaaggataa aatccattat 1140

```
ttttcagaca ttggttacca tcatccacct tatgataact gcccattgga caaggaggtc   1200
tataacagta acaactgtga atgtgaccaa ggtaatgatt tcactttcca aggttactct   1260
tgtggtaagg aatattatga tgctcaaggg ttggtaaagc caaaaaactg gaaaaaattc   1320
cgtgagtaga aatcttggaa catactgttt ctttgttttg actttatact ttctatttat   1380
attttatttt tataactggt taagtacaca taggactgcg tatcaaacat ataagtgagg   1440
caatccacat ttttttaaa gattcgaata tttttattct cattagcgta ttccgagaat   1500
agttcgaaaa aatataaggt atatcaagag tttttacaag tgagaggaaa gaggaataag   1560
ctataagcaa caaaagcgta aaaaaattag ctgaagacat agaactatgg atgttctcaa   1620
agaggtgttg tcactagacc aagataaatt tgaccagctg aaggaaacga gccgagataa   1680
aacaaatgaa acggatgatc cttttgaaaa ctatttgaag gattgtaaat ttaaagcgcc   1740
ttcaaacaaa gatcagtcac catttgctaa acttaaatca ttacaggaaa ctcattctaa   1800
caatgaagcg gctattaata taattattcc tcaattgatt gattacttaa ccgaattcac   1860
taataggtta tcaaattaca cacaagattt agacttcatt aaaaaaaagt ccaatgaatt   1920
acagtcattg ctcgaataca actccactaa actggcacat atctctccta tggttaatga   1980
tttgatgatt cctcctgaac tcattgatga catcattaaa gggaagatca atgaaagctg   2040
gcaggataat ataacattca tagcagataa agaagaaatt tataacaagt ataggtccaa   2100
taatctcgat caagacaaca aggacgcaga aaattcagca atgctagcac caaaggattt   2160
tgataagtta tgtcaactcc tggacatcct aaaaaatgtt attctaga               2208
```

<210> SEQ ID NO 31
<211> LENGTH: 3599
<212> TYPE: DNA
<213> ORGANISM: homosapiens

<400> SEQUENCE: 31

```
aaaatgaagt taagccgcca gttcaccgtg ttcggcagtg cgatcttctg tgtggtgatt     60
ttctcgctct acctgatgct ggaccggggt cacttagact accccaggaa cccgcgccgc    120
gagggctcct tccctcaggg ccagctctca atgttgcaag aaaaaataga ccatttggag    180
cgtttgctag ctgagaataa tgagatcatc tcaaatatta gagactcagt catcaatttg    240
agtgagtctg tggaggatgg tccgaaaagt tcacaaagca atttcagcca aggtgctggc    300
tcacatcttc tgccctcaca attatccctc tcagttgaca ctgcagactg tctgtttgct    360
tcacaaagtg gaagtcacaa ttcagatgtg cagatgttgg atgtttacag tctaatttct    420
tttgacaatc cagatggtgg agtttggaag caaggatttg acattactta tgaatctaat    480
gaatgggaca ctgaacccct tcaagtcttt gtggtgcctc attcccataa cgacccaggt    540
tggttgaaga ctttcaatga ctactttaga gacaagactc agtatatttt taataacatg    600
gtcctaaagc tgaaagaaga ctcacggagg aagtttattt ggtctgagat ctcttacctt    660
tcaaagtggt gggatattat agatattcag aagaaggatg ctgttaaaag tttaatagaa    720
aatggtcagc ttgaaattgt gacaggtggc tgggttatgc ctgatgaagc tactccacat    780
tattttgcct taattgatca actaattgaa ggacatcagt ggctggaaaa taatatagga    840
gtgaaacctc ggtccggctg ggctattgat ccctttggac actcaccaac aatggcttat    900
cttctaaacc gtgctggact ttctcacatg cttatccaga gagttcatta tgcagttaaa    960
aaacactttg cactgcataa aacattggag tttttttgga gacagaattg ggatctggga   1020
tctgtcacag atattttatg ccacatgatg cccttctaca gctatgacat ccctcacact   1080
```

```
tgtggacctg atcctaaaat atgctgccag tttgatttta aacgtcttcc tggaggcaga   1140
tttggttgtc cctggggagt ccccccagaa acaatacatc ctggaaatgt ccaaagcagg   1200
gctcggatgc tactagatca gtaccgaaag aagtcaaagc tttttcgaac caaagttctc   1260
ctggctccac taggagatga tttccgctac tgtgaataca cggaatggga tttacagttt   1320
aagaattatc agcagctttt tgattatatg aattctcagt ccaagtttaa agttaagata   1380
cagtttggaa ctttatcaga ttttttgat gcgctggata aagcagatga aactcagaga   1440
gacaagggcc aatcgatgtt ccctgtttta agtggagatt ttttcactta tgccgatcga   1500
gatgatcatt actggagtgg ctattttaca tccagaccct tttacaaacg aatggacaga   1560
atcatggaat ctcatttaag ggctgctgaa attctttact atttcgccct gagacaagct   1620
cacaaataca agataaataa atttctctca tcatcacttt acacggcact gacagaagcc   1680
agaaggaatt tgggactgtt tcaacatcat gatgctatca caggaactgc aaaagactgg   1740
gtggttgtgg attatggtac cagacttttt cattcgttaa tggttttgga gaagataatt   1800
ggaaattctg catttcttct tattgggaag gacaaactca catacgactc ttactctcct   1860
gataccttcc tggagatgga tttgaaacaa aaatcacaag attctctgcc acaaaaaaat   1920
ataataaggc tgagtgcgga gccaaggtac cttgtggtct ataatccttt agaacaagac   1980
cgaatctcgt tggtctcagt ctatgtgagt tccccgacag tgcaagtgtt ctctgcttca   2040
ggaaaacctg tggaagttca agtcagcgca gtttgggata cagcaaatac tatttcagaa   2100
acagcctatg agatctcttt tcgagcacat ataccgccat tgggactgaa agtgtataag   2160
attttggaat cagcaagttc aaattcacat ttagctgatt atgtcttgta taagaataaa   2220
gtagaagata gcggaatttt caccataaag aatatgataa atactgaaga aggtataaca   2280
ctagagaact cctttgtttt acttcggttt gatcaaactg gacttatgaa gcaaatgatg   2340
actaaagaag atggtaaaca ccatgaagta aatgtgcaat tttcatggta tggaaccaca   2400
attaaaagag acaaaagtgg tgcctacctc ttcttacctg atggtaatgc caagccttat   2460
gtttacacaa caccgccctt tgtcagagtg acacatggaa ggatttattc ggaagtgact   2520
tgcttttttg accatgttac tcatagagtc cgactatacc acatacaggg aatagaagga   2580
cagtctgtgg aagtttccaa tattgtggac atccgaaaag tatataaccg tgagattgca   2640
atgaaaattt cttctgatat aaaaagccaa aatagatttt atactgacct aaatgggtac   2700
cagattcaac ctagaatgac actgagcaaa ttgcctcttc aagcaaatgt ctatcccatg   2760
accacaatgg cctatatcca ggatgccaaa catcgtttga cactgctctc tgctcagtca   2820
ttaggggttt cgagtttgaa tagtggtcag attgaagtta tcatggatcg aagactcatg   2880
caagatgata atcgtggcct tgagcaaggt atccaggata acaagattac agctaatcta   2940
tttcgaatac tactagaaaa aagaagtgct gttaatacgg aagaagaaaa gaagtcggtc   3000
agttatcctt ctctccttag ccacataact tcttctctca tgaatcatcc agtcattcca   3060
atggcaaata agttctcctc acctaccctt gagctgcaag gtgaattctc tccattacag   3120
tcatctttgc cttgtgacat tcatctggtt aatttgagaa caatacagtc aaaggtgggc   3180
aatgggcact ccaatgaggc agccttgatc ctccacagaa aagggtttga ttgtcggttc   3240
tctagcaaag gcacagggct gttttgttct actactcagg gaaagatatt ggtacagaaa   3300
cttttaaaca agtttattgt cgaaagtctc acaccttcat cactatcctt gatgcattca   3360
cctcccggca ctcagaatat aagtgagatc aacttgagtc caatggaaat cagcacattc   3420
```

```
cgaatccagt tgaggtgaac ctgactttca catttggatt gagaatcatt ggcttttata   3480

cctttcttgg tttgacgtgc aataaagaag cacattattt tagcttctgg ctactgtgag   3540

aacatgaatt ctgtgattct gtgggttttt tctttttttc ttttaccagt acagtaaga    3599


<210> SEQ ID NO 32
<211> LENGTH: 37
<212> TYPE: DNA
<213> ORGANISM: Artificial Sequence
<220> FEATURE:
<223> OTHER INFORMATION: Primer

<400> SEQUENCE: 32

cgcggatcca tggccaaaaa gttcacaaag caatttc                               37


<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33

gtgtcccatt cattagattc                                                  20


<210> SEQ ID NO 34
<211> LENGTH: 1338
<212> TYPE: DNA
<213> ORGANISM: homosapiens

<400> SEQUENCE: 34

atgctgaaga agcagtctgc agggcttgtg ctgtggggcg ctatcctctt tgtggcctgg     60

aatgccctgc tgctcctctt cttctggacg cgcccagcac ctggcaggcc accctcagtc    120

agcgctctcg atggcgaccc cgccagcctc acccgggaag tgattcgcct ggcccaagac    180

gccgaggtgg agctggagcg gcagcgtggg ctgctgcagc agatcgggga tgccctgtcg    240

agccagcggg ggagggtgcc caccgcggcc cctcccgccc agccgcgtgt gcctgtgacc    300

cccgcgccgg cggtgattcc catcctggtc atcgcctgtg accgcagcac tgttcggcgc    360

tgcctggaca agctgctgca ttatcggccc tcggctgagc tcttccccat catcgttagc    420

caggactgcg ggcacgagga gacggcccag gccatcgcct cctacggcag cgcggtcacg    480

cacatccggc agcccgacct gagcagcatt gcggtgccgc cggaccaccg caagttccag    540

ggctactaca agatcgcgcg ccactaccgc tgggcgctgg gccaggtctt ccggcagttt    600

cgcttccccg cggccgtggt ggtggaggat gacctggagg tggccccgga cttcttcgag    660

tactttcggg ccacctatcc gctgctgaag gccgacccct ccctgtggtg cgtctcggcc    720

tggaatgaca acggcaagga gcagatggtg gacgccagca ggcctgagct gctctaccgc    780

accgactttt tccctggcct gggctggctg ctgttggccg agctctgggc tgagctggag    840

cccaagtggc caaaggcctt ctgggacgac tggatgcggc ggccggagca gcggcagggg    900

cgggcctgca tacgccctga gatctcaaga acgatgacct ttggccgcaa gggtgtgagc    960

cacgggcagt tctttgacca gcacctcaag tttatcaagc tgaaccagca gtttgtgcac   1020

ttcacccagc tggacctgtc ttacctgcag cgggaggcct atgaccgaga tttcctcgcc   1080

cgcgtctacg gtgctcccca gctgcaggtg gagaaagtga ggaccaatga ccggaaggag   1140

ctgggggagg tgcgggtgca gtatacgggc agggacagct tcaaggcttt cgccaaggct   1200

ctgggtgtca tggatgacct taagtcgggg gttccgagag ctggctaccg ggtattgtc   1260
```

accttccagt tccggggccg ccgtgtccac ctggcgcccc caccgacgtg ggagggctat 1320
gatcctagct ggaattag 1338

<210> SEQ ID NO 35
<211> LENGTH: 100
<212> TYPE: PRT
<213> ORGANISM: Saccharomyces cerevisiae

<400> SEQUENCE: 35

Met Ala Leu Phe Leu Ser Lys Arg Leu Leu Arg Phe Thr Val Ile Ala
1 5 10 15

Gly Ala Val Ile Val Leu Leu Leu Thr Leu Asn Ser Asn Ser Arg Thr
20 25 30

Gln Gln Tyr Ile Pro Ser Ser Ile Ser Ala Ala Phe Asp Phe Thr Ser
35 40 45

Gly Ser Ile Ser Pro Glu Gln Gln Val Ile Ser Glu Glu Asn Asp Ala
50 55 60

Lys Lys Leu Glu Gln Ser Ala Leu Asn Ser Glu Ala Ser Glu Asp Ser
65 70 75 80

Glu Ala Met Asp Glu Glu Ser Lys Ala Leu Lys Ala Ala Ala Glu Lys
85 90 95

Ala Asp Ala Pro
100

<210> SEQ ID NO 36
<211> LENGTH: 4677
<212> TYPE: DNA
<213> ORGANISM: Artificial Sequence
<220> FEATURE:
<223> OTHER INFORMATION: plasmid pPIC6AKrecoGnTI

<400> SEQUENCE: 36
gaaatttttt tttttagttt ttttctcttt cagtgacctc cattgatatt taagttaata 60
aacggtcttc aatttctcaa gtttcagttt catttttctt gttctattac aacttttttt 120
acttcttgtt cattagaaag aaagcatagc aatctaatct aaggggcggt gttgacaatt 180
aatcatcggc atagtatatc ggcatagtat aatacgacaa ggtgaggaac taaaccatgg 240
ccaagccttt gtctcaagaa gaatccaccc tcattgaaag agcaacggct acaatcaaca 300
gcatccccat ctctgaagac tacagcgtcg ccagcgcagc tctctctagc gacggccgca 360
tcttcactgg tgtcaatgta tatcatttta ctgggggacc ttgtgcagaa ctcgtggtgc 420
tgggcactgc tgctgctgcg gcagctggca acctgacttg tatcgtcgcg atcggaaatg 480
agaacagggg catcttgagc ccctgcggac ggtgccgaca ggtgcttctc gatctgcatc 540
ctgggatcaa agccatagtg aaggacagtg atggacagcc gacggcagtt gggattcgtg 600
aattgctgcc ctctggttat gtgtgggagg gctaagcact tcgtggccga ggagcaggac 660
tgacacgtcc gacggcggcc cacgggtccc aggcctcgga gatccgtccc ccttttcctt 720
tgtcgatatc atgtaattag ttatgtcacg cttacattca cgccctcccc ccacatccgc 780
tctaaccgaa aaggaaggag ttagacaacc tgaagtctag gtccctattt attttttat 840 agttatgtta gtattaagaa cgttatttat atttcaaatt tttctttttt ttctgtacag 900
acgcgtgtac gcatgtaaca ttatactgaa aaccttgctt gagaaggttt tgggacgctc 960
gaaggcttta atttgcaagc tggagaccaa catgtgagca aaaggccagc aaaaggccag 1020
gaaccgtaaa aaggccgcgt tgctggcgtt tttccatagg ctccgccccc ctgacgagca 1080

```
tcacaaaaat cgacgctcaa gtcagaggtg gcgaaacccg acaggactat aaagatacca   1140
ggcgtttccc cctggaagct ccctcgtgcg ctctcctgtt ccgaccctgc cgcttaccgg   1200
atacctgtcc gcctttctcc cttcgggaag cgtggcgctt tctcaatgct cacgctgtag   1260
gtatctcagt tcggtgtagg tcgttcgctc caagctgggc tgtgtgcacg aaccccccgt   1320
tcagcccgac cgctgcgcct tatccggtaa ctatcgtctt gagtccaacc cggtaagaca   1380
cgacttatcg ccactggcag cagccactgg taacaggatt agcagagcga ggtatgtagg   1440
cggtgctaca gagttcttga agtggtggcc taactacggc tacactagaa ggacagtatt   1500
tggtatctgc gctctgctga agccagttac cttcggaaaa agagttggta gctcttgatc   1560
cggcaaacaa accaccgctg gtagcggtgg tttttttgtt tgcaagcagc agattacgcg   1620
cagaaaaaaa ggatctcaag aagatccttt gatcttttct acggggtctg acgctcagtg   1680
gaacgaaaac tcacgttaag ggattttggt catgagatca gatctaacat ccaaagacga   1740
aaggttgaat gaaacctttt tgccatccga catccacagg tccattctca cacataagtg   1800
ccaaacgcaa caggagggga tacactagca gcagaccgtt gcaaacgcag gacctccact   1860
cctcttctcc tcaacaccca cttttgccat cgaaaaacca gcccagttat tgggcttgat   1920
tggagctcgc tcattccaat tccttctatt aggctactaa caccatgact ttattagcct   1980
gtctatcctg gcccccctgg cgaggttcat gtttgtttat ttccgaatgc aacaagctcc   2040
gcattacacc cgaacatcac tccagatgag ggctttctga gtgtggggtc aaatagtttc   2100
atgttcccca aatggcccaa aactgacagt ttaaacgctg tcttggaacc taatatgaca   2160
aaagcgtgat ctcatccaag atgaactaag tttggttcgt tgaaatgcta acggccagtt   2220
ggtcaaaaag aaacttccaa aagtcggcat accgtttgtc ttgtttggta ttgattgacg   2280
aatgctcaaa aataatctca ttaatgctta gcgcagtctc tctatcgctt ctgaaccccg   2340
gtgcacctgt gccgaaacgc aaatggggaa acacccgctt tttggatgat tatgcattgt   2400
ctccacattg tatgcttcca agattctggt gggaatactg ctgatagcct aacgttcatg   2460
atcaaaattt aactgttcta acccctactt gacagcaata tataaacaga aggaagctgc   2520
cctgtcttaa accttttttt ttatcatcat tattagctta ctttcataat tgcgactggt   2580
tccaattgac aagcttttga ttttaacgac ttttaacgac aacttgagaa gatcaaaaaa   2640
caactaatta ttcgaaacga ggaattatcc atattcgcaa gcagttccac tcgaaagcat   2700
ggccctcttt ctcagtaaga gactgttgag atttaccgtc attgcaggtg cggttattgt   2760
tctcctccta acattgaatt ccaacagtag aactcagcaa tatattccga gttccatctc   2820
cgctgcattt gattttacct caggatctat atcccctgaa caacaagtca tctctgagga   2880
aaatgatgct aaaaaattag agcaaagtgc tctgaattca gaggcaagcg aagactccga   2940
agccatggat gaagaatcca aggctctgaa agctgccgct gaaaaggcag atgccccgcc   3000
ggcggtgatt cccatcctgg tcatcgcctg tgaccgcagc actgttcggc gctgcctgga   3060
caagctgctg cattatcggc cctcggctga gctcttcccc atcatcgtta gccaggactg   3120
cgggcacgag gagacggccc aggccatcgc ctcctacggc agcgcggtca cgcacatccg   3180
gcagcccgac ctgagcagca ttgcggtgcc gccggaccac cgcaagttcc agggctacta   3240
caagatcgcg cgccactacc gctgggcgct gggccaggtc ttccggcagt ttcgcttccc   3300
cgcggccgtg gtggtggagg atgacctgga ggtggccccg gacttcttcg agtactttcg   3360
ggccacctat ccgctgctga aggccgaccc ctccctgtgg tgcgtctcgg cctggaatga   3420
```

```
caacggcaag gagcagatgg tggacgccag caggcctgag ctgctctacc gcaccgactt   3480

tttccctggc ctgggctggc tgctgttggc cgagctctgg gctgagctgg agcccaagtg   3540

gccaaaggcc ttctgggacg actggatgcg gcggccggag cagcggcagg ggcgggcctg   3600

catacgccct gagatctcaa gaacgatgac ctttggccgc aagggtgtga gccacgggca   3660

gttctttgac cagcacctca agtttatcaa gctgaaccag cagtttgtgc acttcaccca   3720

gctggacctg tcttacctgc agcgggaggc ctatgaccga gatttcctcg cccgcgtcta   3780

cggtgctccc cagctgcagg tggagaaagt gaggaccaat gaccggaagg agctgggga    3840

ggtgcgggtg cagtatacgg gcagggacag cttcaaggct ttcgccaagg ctctgggtgt   3900

catggatgac cttaagtcgg gggttccgag agctggctac cggggtattg tcaccttcca   3960

gttccggggc cgccgtgtcc acctggcgcc cccaccgacg tgggagggct atgatcctag   4020

ctggaattag cacctgtcga ctggagacct gcaggcatgc aagcttcgac catcatcatc   4080

atcatcattg agtttgtagc cttagacatg actgttcctc agttcaagtt gggcacttac   4140

gagaagaccg gtcttgctag attctaatca agaggatgtc agaatgccat ttgcctgaga   4200

gatgcaggct tcatttttga tacttttta tttgtaacct atatagtata ggattttttt    4260

tgtcattttg tttcttctcg tacgagcttg ctcctgatca gcctatctcg cagctgatga   4320

atatcttgtg gtaggggttt gggaaaatca ttcgagtttg atgtttttct tggtatttcc   4380

cactcctctt cagagtacag aagattaagt gagaccttcg tttgtgcgga tcccccacac   4440

accatagctt caaaatgttt ctactccttt tttactcttc cagattttct cggactccgc   4500

gcatcgccgt accacttcaa aacacccaag cacagcatac taaattttcc ctctttcttc   4560

ctctagggtg tcgttaatta cccgtactaa aggtttggaa aagaaaaaag agaccgcctc   4620

gtttcttttt cttcgtcgaa aaaggcaata aaaattttta tcacgtttct ttttctt      4677
```

<210> SEQ ID NO 37
<211> LENGTH: 8499
<212> TYPE: DNA
<213> ORGANISM: Artificial Sequence
<220> FEATURE:
<223> OTHER INFORMATION: sequence of plasmid pGAPKreManII

<400> SEQUENCE: 37

```
atccatattc gcaagcagtt ccactcgaaa gcatggccct ctttctcagt aagagactgt     60

tgagatttac cgtcattgca ggtgcggtta ttgttctcct cctaacattg aattccaaca    120

gtagaactca gcaatatatt ccgagttcca tctccgctgc atttgatttt acctcaggat    180

ctatatcccc tgaacaacaa gtcatctctg aggaaaatga tgctaaaaaa ttagagcaaa    240

gtgctctgaa ttcagaggca agcgaagact ccgaagccat ggatgaagaa tccaaggctc    300

tgaaagctgc cgctgaaaag gcagatgccc cgccaaaaag ttcacaaagc aatttcagcc    360

aaggtgctgg ctcacatctt ctgccctcac aattatccct ctcagttgac actgcagact    420

gtctgtttgc ttcacaaagt ggaagtcaca attcagatgt gcagatgttg gatgtttaca    480

gtctaatttc ttttgacaat ccagatggtg gagtttggaa gcaaggattt gacattactt    540

atgaatctaa tgaatgggac actgaacccc ttcaagtctt tgtggtgcct cattcccata    600

acgacccagg ttggttgaag actttcaatg actactttag agacaagact cagtatattt    660

ttaataacat ggtcctaaag ctgaaagaag actcacggag gaagtttatt tggtctgaga    720

tctcttacct ttcaaagtgg tgggatatta tagatattca gaagaaggat gctgttaaaa    780

gtttaataga aaatggtcag cttgaaattg tgacaggtgg ctgggttatg cctgatgaag    840
```

```
ctactccaca ttattttgcc ttaattgatc aactaattga aggacatcag tggctggaaa     900
ataatatagg agtgaaacct cggtccggct gggctattga tccctttgga cactcaccaa     960
caatggctta tcttctaaac cgtgctggac tttctcacat gcttatccag agagttcatt    1020
atgcagttaa aaaacacttt gcactgcata aaacattgga gtttttttgg agacagaatt    1080
gggatctggg atctgtcaca gatattttat gccacatgat gcccttctac agctatgaca    1140
tccctcacac ttgtggacct gatcctaaaa tatgctgcca gtttgatttt aaacgtcttc    1200
ctggaggcag atttggttgt ccctggggag tcccccaga aacaatacat cctggaaatg    1260
tccaaagcag ggctcggatg ctactagatc agtaccgaaa gaagtcaaag ctttttcgta    1320
ccaaagttct cctggctcca ctaggagatg atttccgcta ctgtgaatac acggaatggg    1380
atttacagtt taagaattat cagcagcttt ttgattatat gaattctcag tccaagttta    1440
aagttaagat acagtttgga actttatcag attttttga tgcgctggat aaagcagatg     1500
aaactcagag agacaagggc cagtcgatgt tccctgtttt aagtggagat tttttcactt    1560
atgccgatcg agatgatcat tactggagtg gctattttac atccagaccc ttttacaaac    1620
gaatggacag aatcatggaa tctcatttaa gggctgctga aattctttac tatttcgccc    1680
tgagacaagc tcacaaatac aagataaata aatttctctc atcatcactt tacacggcac    1740
tgacagaagc cagaaggaat ttgggactgt ttcaacatca tgatgctatc acaggaactg    1800
caaaagactg ggtggttgtg gattatggta ccagactttt tcattcgtta atggttttgg    1860
agaagataat tggaaattct gcatttcttc ttattttgaa ggacaaactc acatacgact    1920
cttactctcc tgataccttc ctggagatgg atttgaaaca aaaatcacaa gattctctgc    1980
cacaaaaaaa tataataagg ctgagtgcgg agccaaggta ccttgtggtc tataatcctt    2040
tagaacaaga ccgaatctcg ttggtctcag tctatgtgag ttccccgaca gtgcaagtgt    2100
tctctgcttc aggaaaacct gtggaagttc aagtcagcgc agtttgggat acagcaaata    2160
ctatttcaga aacagcctat gagatctctt ttcgagcaca tataccgcca ttgggactga    2220
aagtgtataa gattttggaa tcagcaagtt caaattcaca tttagctgat tatgtcttgt    2280
ataagaataa agtagaagat agcggaattt tcaccataaa gaatatgata aatactgaag    2340
aaggtataac actagagaac tcctttgttt tacttcggtt tgatcaaact ggacttatga    2400
agcaaatgat gactaaagaa gatggtaaac accatgaagt aaatgtgcaa ttttcatggt    2460
atggaaccac aattaaaaga gacaaaagtg gtgcctacct cttcttacct gatggtaatg    2520
ccaagcctta tgtttacaca acaccgccct ttgtcagagt gacacatgga aggatttatt    2580
cggaagtgac ttgctttttt gaccatgtta ctcatagagt ccgactatac cacatacagg    2640
gaatagaagg acagtctgtg gaagtttcca atattgtgga catccgaaaa gtatataacc    2700
gtgagattgc aatgaaaatt tcttctgata taaaaagcca aaatagattt tatactgacc    2760
taaatgggta ccagattcaa cctagaatga cactgagcaa attgcctctt caagcaaatg    2820
tctatcccat gaccacaatg gcctatatcc aggatgccaa acatcgtttg acactgctct    2880
ctgctcagtc tttaggggtt tcgagtttga atagtggtca gattgaagtt atcatggatc    2940
gaagactcat gcaagatgat aatcgtggcc ttgagcaagg tatccaggat aacaagatta    3000
cagctaatct atttcgaata ctactagaaa aaagaagtgc tgttaatacg gaagaagaaa    3060
agaagtcggt cagttatcct tctctcctta gccacataac ttcttctctc atgaatcatc    3120
cagtcattcc aatggcaaat aagttctcac ctacccttga gctgcaaggt gaattctctc    3180
```

```
cattacagtc atctttgcct tgtgacattc atctggttaa tttgagaaca atacagtcaa   3240
aggtgggcaa tgggcactcc aatgaggcag ccttgatcct ccacagaaaa gggtttgatt   3300
gtcggttctc tagcaaaggc acagggctgt tttgttctac tactcaggga aagatattgg   3360
tacagaaact tttaaacaag tttattgtcg aaagtctcac accttcatca ctatccttga   3420
tgcattcacc tcccggcact cagaatataa gtgagatcaa cttgagtcca atggaaatca   3480
gcacattccg aatccagttg aggtgaacct gactttcaca tttggattga gaatcattgg   3540
cttttatacc tttcttggtt tgacgtgcaa taaagaagca cattatttta gcttctggct   3600
actgtgagaa catgaattct gtgattctgt gggttttttc tttttctttt taccagtaca   3660
gtaagaaaaa aaaaaaaaaa aaaaaaactc gagccgcggc ggccgccagc ttgggcccga   3720
acaaaaactc atctcagaag aggatctgaa tagcgccgtc gaccatcatc atcatcatca   3780
ttgagtttta gccttagaca tgactgttcc tcagttcaag ttgggcactt acgagaagac   3840
cggtcttgct agattctaat caagaggatg tcagaatgcc atttgcctga gagatgcagg   3900
cttcattttt gatacttttt tatttgtaac ctatatagta taggattttt tttgtcattt   3960
tgtttcttct cgtacgagct tgctcctgat cagcctatct cgcagctgat gaatatcttg   4020
tggtaggggt ttgggaaaat cattcgagtt tgatgttttt cttggtattt cccactcctc   4080
ttcagagtac agaagattaa gtgagacctt cgtttgtgcg gatccatgtg agcaaaaggc   4140
cagcaaaagg ccaggaaccg taaaaaggcc gcgttgctgg cgtttttcca taggctccgc   4200
ccccctgacg agcatcacaa aaatcgacgc tcaagtcaga ggtggcgaaa cccgacagga   4260
ctataaagat accaggcgtt tccccctgga agctccctcg tgcgctctcc tgttccgacc   4320
ctgccgctta ccggatacct gtccgccttt ctcccttcgg gaagcgtggc gctttctcat   4380
agctcacgct gtaggtatct cagttcggtg taggtcgttc gctccaagct gggctgtgtg   4440
cacgaacccc ccgttcagcc cgaccgctgc gccttatccg gtaactatcg tcttgagtcc   4500
aacccggtaa gacacgactt atcgccactg gcagcagcca ctggtaacag gattagcaga   4560
gcgaggtatg taggcggtgc tacagagttc ttgaagtggt ggcctaacta cggctacact   4620
agaaggacag tatttggtat ctgcgctctg ctgaagccag ttaccttcgg aaaaagagtt   4680
ggtagctctt gatccggcaa acaaaccacc gctggtagcg gtggtttttt tgtttgcaag   4740
cagcagatta cgcgcagaaa aaaggatctc aagaagatcc tttgatcttt tctacggggt   4800
tctgacgctc agtggaacga aaactcacgt taagggattt tggtcatgag attatcaaaa   4860
aggatcttca cctagatcct tttaaattaa aaatgaagtt ttaaatcaat ctaaagtata   4920
tatgagtaaa cttggtctga cagttaccaa tgcttaatca gtgaggcacc tatctcagcg   4980
atctgtctat ttcgttcatc catagttgcc tgactccccg tcgtgtagat aactacgata   5040
cgggagggct taccatctgg ccccagtgct gcaatgatac cgcgagaccc acgctcaccg   5100
gctccagatt tatcagcaat aaaccagcca gccggaaggg ccgagcgcag aagtggtcct   5160
gcaactttat ccgcctccat ccagtctatt aattgttgcc gggaagctag agtaagtagt   5220
tcgccagtta atagtttgcg caacgttgtt gccattgcta caggcatcgt ggtgtcacgc   5280
tcgtcgtttg gtatggcttc attcagctcc ggttcccaac gatcaaggcg agttacatga   5340
tcccccatgt tgtgcaaaaa agcggttagc tccttcggtc ctccgatcgt tgtcagaagt   5400
aagttggccg cagtgttatc actcatggtt atggcagcac tgcataattc tcttactgtc   5460
atgccatccg taagatgctt ttctgtgact ggtgagtact caaccaagtc attctgagaa   5520
tagtgtatgc ggcgaccgag ttgctcttgc ccggcgtcaa tacgggataa taccgcgcca   5580
```

```
catagcagaa ctttaaaagt gctcatcatt ggaaaacgtt cttcggggcg aaaactctca   5640
aggatcttac cgctgttgag atccagttcg atgtaaccca ctcgtgcacc caactgatct   5700
tcagcatctt ttactttcac cagcgtttct gggtgagcaa aaacaggaag gcaaaatgcc   5760
gcaaaaaagg gaataagggc gacacggaaa tgttgaatac tcatactctt cctttttcaa   5820
tgcttctagt ggtaggaatt aattctgtac cggtttacag aaggacgact cttgatgcgc   5880
caaccacagt gacaatagac atagaggaaa tgacaaaagg attatgcgag gatgctgctg   5940
gagacgattc aaagtttagt ttagaaaggt cctccattta tgctgataga atactagata   6000
cccgtgaact ttgtctcagg agatccgcat cagacgaagg atgttccgac ctgcaaataa   6060
tcgaagaaga gaccccctagg ccgtacgaca gtcagttagt agatatttat accattctgc   6120
gagaaggtcc cccagtatag ataagagagt ttcaattgta tgtactataa cagtttattg   6180
tatcattaac aaactcagta taaaaccttc aagactctag cttttcattc agtgcatcca   6240
attgctttaa aacagcagtc ttagaagttc ctccggtggc agttcttttt tcaacactgg   6300
cttcaaagtc aaacgttgaa gccacatcag cctcaaaacg ggagtcaatg gatttcaatt   6360
gttcgaggga caactgatca ataccagaaa ggttcaactc ctcggcttgt ctgacacatt   6420
caccagaaat gtggtgagtt tctctgaatg gaactcccct tctaactaaa tagtcggcaa   6480
gatctgtagc cagcatatcc atagttagag cattcttcat tcgttcggca tcaatgttca   6540
aggtagaaac tacaccggat gctatcaaaa tcgagtgctc tacagtgatt agagtatcaa   6600
ataaaggctc cttatcctct tgcatatctt tgttataggt tgacggaatg gacttaatag   6660
acatgaggaa accagccaag gccccaaaac atctaccaga tttacccctc aataactcca   6720
aagagtctgg gttttttttt tgaggcatca gagaagatcc agtagaataa gcatctgcca   6780
acttgataaa tccaaactct ccagtggagt aaatgatcaa atcttctgag aatcgagaaa   6840
tatgattcat aaacaacgaa gaccagaaca tggtttcgac tacaaaatct ctgtctgaaa   6900
cagcggccaa agaattacca ataacagaat caaaccctaa tctctcagca atgtattcac   6960
gatcaattcc ataaggatga ccagccaaag ctccagctcc caatggggat ttgttcaacc   7020
ttttaacgat ttgattcagt ctctcataat cttcagtgaa ataggtagca tacatgctca   7080
accagtgaga ccatctgatt ggttgagctc tttgcaagtg agtataaccg ggcatcaaga   7140
cgtctatttc ctgttcagct ctcttgatga ttacttgaat gaactgcttc agatagtcag   7200
ccaactgagt tagattgtct ctgacataca accgcatatc agtggcaact tgatcatttc   7260
tagaccttcc ggtatgaacc ttaccagaga ttccacgacc aatcaactca cccaagcgac   7320
gttcattagc agtgtgaata tcctcatccc ctggcttctc aacaaacttc ccttctgccc   7380
actctgcttc aatcaatttg agaccacgat gaatctcact tagttcgtct ttagttagca   7440
aattaatttt ctccaggccc tcagtgtaaa cttttgttcc ttctaaatcc accttgtaca   7500
ttttcttgtc gtaaggtaag gaagcgttat acaaatccat caaggggtca gtagccccag   7560
taaacctgcc accccacagt ttaagtcttt cttcttgatt cgacatagat agctggtaat   7620
aagtttagaa caaaaggaaa gagaaggtag aatataggtg aaagaattgc caaaagaggc   7680
agcgcggtaa aaagaaaaat gaatcatcga aattagtcta gattctcgta tttctgttgg   7740
ttattgtatt atctaatcag ggtaaaacac ctaaggctta catctcccag tgaaacgtgg   7800
gtataatgaa cagtctttca cagtgaatct gtcgcacaac catgctaaga tacgttccgt   7860
tcctagaccg taaccaccgt gagggcagat taacgcttac aatttccatt cgccattcag   7920
```

```
gctgcgcaac tgttgggaag ggcgatcggt gcgggcctct tcgctattac gccagggcac   7980

tagtgagatc agatcttttt tgtagaaatg tcttggtgtc ctcgtccaat caggtagcca   8040

tctctgaaat atctggctcc gttgcaactc cgaacgacct gctggcaacg taaaattctc   8100

cggggtaaaa cttaaatgtg gagtaatgga accagaaacg tctcttccct tctctctcct   8160

tccaccgccc gttaccgtcc ctaggaaatt ttactctgct ggagagcttc ttctacggcc   8220

cccttgcagc aatgctcttc ccagcattac gttgcgggta aaacggaggt cgtgtacccg   8280

acctagcagc ccagggatgg aaaagtcccg gccgtcgctg gcaataatag cgggcggacg   8340

catgtcatga gattattgga aaccaccaga atcgaatata aaaggcgaac acctttccca   8400

attttggttt ctcctgaccc aaagacttta aatttaattt atttgtccct atttcaatca   8460

attgaacaac tatttcgaaa cgaggaattc acgtggccc                          8499


<210> SEQ ID NO 38
<211> LENGTH: 441
<212> TYPE: PRT
<213> ORGANISM: Saccharomyces cerevisiae

<400> SEQUENCE: 38

Met Ala Leu Phe Leu Ser Lys Arg Leu Leu Arg Phe Thr Val Ile Ala
1               5                   10                  15

Gly Ala Val Ile Val Leu Leu Leu Thr Leu Asn Ser Asn Ser Arg Thr
            20                  25                  30

Gln Gln Tyr Ile Pro Ser Ser Ile Ala Ala Phe Asp Phe Thr Ser Gly
        35                  40                  45

Ser Ile Ser Pro Glu Gln Gln Val Ile Ser Glu Glu Asn Asp Ala Lys
    50                  55                  60

Lys Leu Glu Gln Ser Ala Leu Asn Ser Glu Ala Ser Glu Asp Ser Glu
65                  70                  75                  80

Ala Met Asp Glu Glu Ser Lys Ala Leu Lys Ala Ala Ala Glu Lys Ala
                85                  90                  95

Asp Ala Pro Ile Asp Thr Lys Thr Thr Met Asp Tyr Ile Thr Pro Ser
            100                 105                 110

Phe Ala Asn Lys Ala Gly Lys Pro Lys Ala Cys Tyr Val Thr Leu Val
        115                 120                 125

Arg Asn Lys Glu Leu Lys Gly Leu Leu Ser Ser Ile Lys Tyr Val Glu
    130                 135                 140

Asn Lys Ile Asn Lys Lys Phe Pro Tyr Pro Trp Val Phe Leu Asn Asp
145                 150                 155                 160

Glu Pro Phe Thr Glu Glu Phe Lys Glu Ala Val Thr Lys Ala Val Ser
                165                 170                 175

Ser Glu Val Lys Phe Gly Ile Leu Pro Lys Glu His Trp Ser Tyr Pro
            180                 185                 190

Glu Trp Ile Asn Gln Thr Lys Ala Ala Glu Ile Arg Ala Asp Ala Ala
        195                 200                 205

Thr Lys Tyr Ile Tyr Gly Gly Ser Glu Ser Tyr Arg His Met Cys Arg
    210                 215                 220

Tyr Gln Ser Gly Phe Phe Trp Arg His Glu Leu Leu Glu Glu Tyr Asp
225                 230                 235                 240

Trp Tyr Trp Arg Val Glu Pro Asp Ile Lys Leu Tyr Cys Asp Ile Asn
                245                 250                 255

Tyr Asp Val Phe Lys Trp Met Gln Glu Asn Glu Lys Val Tyr Gly Phe
            260                 265                 270
```

```
Thr Val Ser Ile His Glu Tyr Glu Val Thr Ile Pro Thr Leu Trp Gln
        275                 280                 285

Thr Ser Met Asp Phe Ile Lys Lys Asn Pro Glu Tyr Leu Asp Glu Asn
    290                 295                 300

Asn Leu Met Ser Phe Leu Ser Asn Asp Asn Gly Lys Thr Tyr Asn Leu
305                 310                 315                 320

Cys His Phe Trp Ser Asn Phe Glu Ile Ala Asn Leu Asn Leu Trp Arg
                325                 330                 335

Ser Pro Ala Tyr Arg Glu Tyr Phe Asp Thr Leu Asp His Gln Gly Gly
            340                 345                 350

Phe Phe Tyr Glu Arg Trp Gly Asp Ala Pro Val His Ser Ile Ala Ala
        355                 360                 365

Ala Leu Phe Leu Pro Lys Asp Lys Ile His Tyr Phe Ser Asp Ile Gly
    370                 375                 380

Tyr His His Pro Pro Tyr Asp Asn Cys Pro Leu Asp Lys Glu Val Tyr
385                 390                 395                 400

Asn Ser Asn Asn Cys Glu Cys Asp Gln Gly Asn Asp Phe Thr Phe Gln
                405                 410                 415

Gly Tyr Ser Cys Gly Lys Glu Tyr Tyr Asp Ala Gln Gly Leu Val Lys
            420                 425                 430

Pro Lys Asn Trp Lys Lys Phe Arg Glu
        435                 440


<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39

aaggagttag acaacctgaa gtcta                                            25


<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40

aaggagtaga aacattttga agcta                                            25


<210> SEQ ID NO 41
<211> LENGTH: 24
<212> TYPE: DNA
<213> ORGANISM: Artificial Sequence
<220> FEATURE:
<223> OTHER INFORMATION: Primer

<400> SEQUENCE: 41

ccatggcgaa ggcagatggc agtt                                             24


<210> SEQ ID NO 42
<211> LENGTH: 26
<212> TYPE: DNA
<213> ORGANISM: Artificial Sequence
<220> FEATURE:
<223> OTHER INFORMATION: Primer

<400> SEQUENCE: 42
```

agatctttag tccttccaac ttcctt 26

<210> SEQ ID NO 43
<211> LENGTH: 30
<212> TYPE: DNA
<213> ORGANISM: Artificial Sequence
<220> FEATURE:
<223> OTHER INFORMATION: Primer

<400> SEQUENCE: 43
atctaagcta tattcgccgt ttctgtcatt 30

<210> SEQ ID NO 44
<211> LENGTH: 30
<212> TYPE: DNA
<213> ORGANISM: Artificial Sequence
<220> FEATURE:
<223> OTHER INFORMATION: Primer

<400> SEQUENCE: 44
cgattatgga tgttagatct gatctcatga 30

<210> SEQ ID NO 45
<211> LENGTH: 2875
<212> TYPE: DNA
<213> ORGANISM: Artificial Sequence
<220> FEATURE:
<223> OTHER INFORMATION: plasmid pZ5'PpOCH1Trunc

<400> SEQUENCE: 45
tcatgagatc agatctaaca tccataatcg atctaagcta tattcgccgt ttctgtcatt 60
tgcgttttgt acggaccctc acaacaatta tcatctccaa aaatagacta tgatccattg 120
acgctccgat cacttgattt gaagactttg gaagctcctt cacagttgag tccaggcacc 180
gtagaagata atcttcgaag acaattggag tttcattttc cttaccgcag ttacgaacct 240
tttccccaac atatttggca aacgtggaaa gtttctccct ctgatagttc ctttccgaaa 300
aacttcaaag acttaggtga aagttggctg caaaggtccc caaattatga tcattttgtg 360
atacccgatg atgcagcatg ggaacttatt caccatgaat acgaacgtgt accagaagtc 420
ttggaagctt ttgattttaa cgacttttaa cgacaacttg agaagatcaa aaaacaacta 480
attattcgcg aaacgaggaa ttcacgtggc ccagccggcc gtctcggatc ggtacctcga 540
gccgcggcgg ccgccagctt tctagagaac aaaaactcat ctcagaagag gatctgaata 600
gcgccgtcga ccatcatcat catcatcatt gagtttgtag ccttagacat gactgttcct 660
cagttcaagt tgggcactta cgagaagacc ggtcttgcta gattctaatc aagaggatgt 720
cagaatgcca tttgcctgag agatgcaggc ttcatttttg atactttttt atttgtaacc 780
tatatagtat aggatttttt ttgtcatttt gtttcttctc gtacgagctt gctcctgatc 840
agcctatctc gcagctgatg aatatcttgt ggtaggggtt tgggaaaatc attcgagttt 900
gatgtttttc ttggtatttc ccactcctct tcagagtaca gaagattaag tgagaccttc 960
gtttgtgcgg atcccccaca caccatagct tcaaaatgtt tctactcctt ttttactctt 1020
ccagattttc tcggactccg cgcatcgccg taccacttca aaacacccaa gcacagcata 1080
ctaaatttcc cctctttctt cctctagggt gtcgttaatt acccgtacta aaggtttgga 1140
aaagaaaaaa gagaccgcct cgtttctttt tcttcgtcga aaaaggcaat aaaaattttt 1200
atcacgtttc tttttcttga aatttttttt tttagttttt ttctctttca gtgacctcca 1260
ttgatattta agttaataaa cggtcttcaa tttctcaagt ttcagtttca tttttcttgt 1320

```
tctattacaa cttttttttac ttcttgttca ttagaaagaa agcatagcaa tctaatctaa   1380
ggggcggtgt tgacaattaa tcatcggcat agtatatcgg catagtataa tacgacaagg   1440
tgaggaacta aaccatggcc aagttgacca gtgccgttcc ggtgctcacc gcgcgcgacg   1500
tcgccggagc ggtcgagttc tggaccgacc ggctcgggtt ctcccgggac ttcgtggagg   1560
acgacttcgc cggtgtggtc cgggacgacg tgaccctgtt catcagcgcg gtccaggacc   1620
aggtggtgcc ggacaacacc ctggcctggg tgtgggtgcg cggcctggac gagctgtacg   1680
ccgagtggtc ggaggtcgtg tccacgaact tccgggacgc ctccgggccg gccatgaccg   1740
agatcggcga gcagccgtgg gggcgggagt tcgccctgcg cgacccggcc ggcaactgcg   1800
tgcacttcgt ggccgaggag caggactgac acgtccgacg gcggcccacg ggtcccaggc   1860
ctcggagatc cgtccccctt ttcctttgtc gatatcatgt aattagttat gtcacgctta   1920
cattcacgcc ctccccccac atccgctcta accgaaaagg aaggagttag acaacctgaa   1980
gtctaggtcc ctatttattt ttttatagtt atgttagtat taagaacgtt atttatattt   2040
caaatttttc ttttttttct gtacagacgc gtgtacgcat gtaacattat actgaaaacc   2100
ttgcttgaga aggttttggg acgctcgaag gctttaattt gcaagctgga gaccaacatg   2160
tgagcaaaag gccagcaaaa ggccaggaac cgtaaaaagg ccgcgttgct ggcgtttttc   2220
cataggctcc gcccccctga cgagcatcac aaaaatcgac gctcaagtca gaggtggcga   2280
aacccgacag gactataaag ataccaggcg tttccccctg gaagctccct cgtgcgctct   2340
cctgttccga ccctgccgct taccggatac ctgtccgcct ttctcccttc gggaagcgtg   2400
gcgctttctc aatgctcacg ctgtaggtat ctcagttcgg tgtaggtcgt tcgctccaag   2460
ctgggctgtg tgcacgaacc ccccgttcag cccgaccgct gcgccttatc cggtaactat   2520
cgtcttgagt ccaacccggt aagacacgac ttatcgccac tggcagcagc cactggtaac   2580
aggattagca gagcgaggta tgtaggcggt gctacagagt tcttgaagtg gtggcctaac   2640
tacggctaca ctagaaggac agtatttggt atctgcgctc tgctgaagcc agttaccttc   2700
ggaaaaagag ttggtagctc ttgatccggc aaacaaacca ccgctggtag cggtggtttt   2760
tttgtttgca agcagcagat tacgcgcaga aaaaaaggat ctcaagaaga tcctttgatc   2820
ttttctacgg ggtctgacgc tcagtggaac gaaaactcac gttaagggat tttgg        2875
```

<210> SEQ ID NO 46
<211> LENGTH: 5634
<212> TYPE: DNA
<213> ORGANISM: Artificial Sequence
<220> FEATURE:
<223> OTHER INFORMATION: plasmid pZMFManHDEL5'PpOCH1Mut

<400> SEQUENCE: 46

```
ggtcgactct agaatggcga aggcacatgg cagtttgctc tagtataatc ctcacaatcc     60
acccagaagg tattacttct acatggctat attcgccgtt tctgtcattt gcgttttgta    120
cggaccctca caacaattat catctccaaa aatagactat gatccattga cgctccgatc    180
acttgatttg aagactttgg aagctccttc acagttgagt ccaggcaccg tagaagataa    240
tcttcgaaga caattggagt ttcattttcc ttaccgcagt tacgaacctt ttccccaaca    300
tatttggcaa acgtggaaag tttctccctc tgatagttcc tttccgaaaa acttcaaaga    360
cttaggtgaa agttggctgc aaaggtcccc aaattatgat cattttgtga tacccgatga    420
tgcagcatgg gaacttattc accatgaata cgaacgtgta ccagaagtct tggaagcttt    480
```

-continued

```
tgattttaac gacttttaac gacaacttga gaagatcaaa aaacaactaa ttattcgcga    540
aacgaggaat tcacgtggcc cagccggccg tctcggatcg gtacctcgag ccgcggcggc    600
cgccagcttt ctagagaaca aaaactcatc tcagaagagg atctgaatag cgccgtcgac    660
catcatcatc atcatcattg agtttgtagc cttagacatg actgttcctc agttcaagtt    720
gggcacttac gagaagaccg gtcttgctag attctaatca agaggatgtc agaatgccat    780
ttgcctgaga gatgcaggct tcatttttga tactttttta tttgtaacct atatagtata    840
ggattttttt tgtcattttg tttcttctcg tacgagcttg ctcctgatca gcctatctcg    900
cagctgatga atatcttgtg gtaggggttt gggaaaatca ttcgagtttg atgtttttct    960
tggtatttcc cactcctctt cagagtacag aagattaagt gagaccttcg tttgtgcgga   1020
tcctttttg tagaaatgtc ttggtgtcct cgtccaatca ggtagccatc tctgaaatat   1080
ctggctccgt tgcaactccg aacgacctgc tggcaacgta aaattctccg ggtaaaact   1140
taaatgtgga gtaatggaac cagaaacgtc tcttcccttc tctctccttc caccgcccgt   1200
taccgtccct aggaaatttt actctgctgg agagcttctt ctacggcccc cttgcagcaa   1260
tgctcttccc agcattacgt tgcgggtaaa acggaggtcg tgtacccgac ctagcagccc   1320
agggatggaa aagtcccggc cgtcgctggc aataatagcg ggcggacgca tgtcatgaga   1380
ttattggaaa ccaccagaat cgaatataaa aggcgaacac ctttcccaat tttggtttct   1440
cctgacccaa agactttaaa tttaatttat ttgtccctat ttcaatcaat tgaacaacta   1500
tttcgcgaaa cgatgagatt tccttcaatt tttactgctg ttttattcgc agcatcctcc   1560
gcattagctg ctccagtcaa cactacaaca gaagatgaaa cggcacaaat tccggctgaa   1620
gctgtcatcg gttactcaga tttagaaggg gatttcgatg ttgctgtttt gccattttcc   1680
aacagcacaa ataacgggtt attgtttata aatactacta ttgccagcat tgctgctaaa   1740
gaagaagggg tatctctcga gaaaagagag gctgaagctg aattcgccac aaaacgtgga   1800
tctcccaacc ctacgagggc ggcagcagtc aaggccgcat tccagacgtc gtggaacgct   1860
taccaccatt ttgcctttcc ccatgacgac ctccacccgg tcagcaacag ctttgatgat   1920
gagagaaacg gctggggctc gtcggcaatc gatggcttgg acacggctat cctcatgggg   1980
gatgccgaca ttgtgaacac gatccttcag tatgtaccgc agatcaactt caccacgact   2040
gcggttgcca accaaggatc ctccgtgttc gagaccaaca ttcggtacct cggtggcctg   2100
ctttctgcct atgacctgtt gcgaggtcct ttcagctcct tggcgacaaa ccagaccctg   2160
gtaaacagcc ttctgaggca ggctcaaaca ctggccaacg gcctcaaggt tgcgttcacc   2220
actcccagcg gtgtcccgga ccctaccgtc ttcttcaacc ctactgtccg gagaagtggt   2280
gcatctagca acaacgtcgc tgaaattgga agcctggtgc tcgagtggac acggttgagc   2340
gacctgacgg gaaacccgca gtatgcccag cttgcgcaga agggcgagtc gtatctcctg   2400
aatccaaagg gaagcccgga ggcatggcct ggcctgattg gaacgtttgt cagcacgagc   2460
aacggtacct ttcaggatag cagcggcagc tggtccggcc tcatggacag cttctacgag   2520
tacctgatca agatgtacct gtacgacccg gttgcgtttg cacactacaa ggatcgctgg   2580
gtccttggtg ccgactcgac cattgggcat ctcggctctc acccgtcgac gcgcaaggac   2640
ttgacctttt tgtcttcgta caacggacag tctacgtcgc caaactcagg acatttggcc   2700
agttttggcg gtggcaactt catcttggga ggcattctcc tgaacgagca aaagtacatt   2760
gactttggaa tcaagcttgc cagctcgtac tttggcacgt acacccagac ggcttctgga   2820
atcggccccg aaggcttcgc gtgggtggac agcgtgacgg gcgccggcgg ctcgccgccc   2880
```

```
tcgtcccagt ccgggttcta ctcgtcggca ggattctggg tgacggcacc gtattacatc   2940
ctgcggccgg agacgctgga gagcttgtac tacgcatacc gcgtcacggg cgactccaag   3000
tggcaggacc tggcgtggga agcgttgagt gccattgagg acgcatgccg cgccggcagc   3060
gcgtactcgt ccatcaacga cgtgacgcag gccaacggcg ggggtgcctc tgacgatatg   3120
gagagcttct ggtttgccga ggcgctcaag tatgcgtacc tgatctttgc ggaggagtcg   3180
gatgtgcagg tgcaggccac cggcgggaac aaatttgtct ttaacacgga ggcgcacccc   3240
tttagcatcc gttcatcatc acgacggggc ggccaccttg ctcacgacga gttgtaatct   3300
agggcggccg ccagctttct agaacaaaaa ctcatctcag aagaggatct gaatagcgcc   3360
gtcgaccatc atcatcatca tcattgagtt ttagccttag acatgactgt tcctcagttc   3420
aagttgggca cttacgagaa gaccggtctt gctagattct aatcaagagg atgtcagaat   3480
gccatttgcc tgagagatgc aggcttcatt tttgatactt ttttatttgt aacctatata   3540
gtataggatt ttttttgtca ttttgtttct tctcgtacga gcttgctcct gatcagccta   3600
tctcgcagct gatgaatatc ttgtggtagg ggtttgggaa aatcattcga gtttgatgtt   3660
tttcttggta tttcccactc ctcttcagag tacagaagat taagtgagac cttcgtttgt   3720
gcggatcccc cacacaccat agcttcaaaa tgtttctact ccttttttac tcttccagat   3780
tttctcggac tccgcgcatc gccgtaccac ttcaaaacac ccaagcacag catactaaat   3840
tttccctctt tcttcctcta gggtgtcgtt aattacccgt actaaaggtt tggaaaagaa   3900
aaaagagacc gcctcgtttc tttttcttcg tcgaaaaagg caataaaaat ttttatcacg   3960
tttctttttc ttgaaatttt tttttttagt ttttttctct ttcagtgacc tccattgata   4020
tttaagttaa taaacggtct tcaatttctc aagtttcagt ttcatttttc ttgttctatt   4080
acaacttttt ttacttcttg ttcattagaa agaaagcata gcaatctaat ctaagggcgg   4140
tgttgacaat taatcatcgg catagtatat cggcatagta taatacgaca aggtgaggaa   4200
ctaaaccatg gccaagttga ccagtgccgt tccggtgctc accgcgcgcg acgtcgccgg   4260
agcggtcgag ttctggaccg accggctcgg gttctcccgg gacttcgtgg aggacgactt   4320
cgccggtgtg gtccgggacg acgtgaccct gttcatcagc gcggtccagg accaggtggt   4380
gccggacaac accctggcct gggtgtgggt gcgcggcctg gacgagctgt acgccgagtg   4440
gtcggaggtc gtgtccacga acttccggga cgcctccggg ccggccatga ccgagatcgg   4500
cgagcagccg tgggggcggg agttcgccct gcgcgacccg gccggcaact gcgtgcactt   4560
cgtggccgag gagcaggact gacacgtccg acggcggccc acgggtccca ggcctcggag   4620
atccgtcccc cttttccttt gtcgatatca tgtaattagt tatgtcacgc ttacattcac   4680
gccctccccc cacatccgct ctaaccgaaa aggaaggagt tagacaacct gaagtctagg   4740
tccctattta tttttttata gttatgttag tattaagaac gttatttata tttcaaattt   4800
ttcttttttt tctgtacaga cgcgtgtacg catgtaacat tatactgaaa accttgcttg   4860
agaaggtttt gggacgctcg aaggctttaa tttgcaagct ggagaccaac atgtgagcaa   4920
aaggccagca aaaggccagg aaccgtaaaa aggccgcgtt gctggcgttt ttccataggc   4980
tccgcccccc tgacgagcat cacaaaaatc gacgctcaag tcagaggtgg cgaaacccga   5040
caggactata aagataccag gcgtttcccc ctggaagctc cctcgtgcgc tctcctgttc   5100
cgaccctgcc gcttaccgga tacctgtccg cctttctccc ttcgggaagc gtggcgcttt   5160
ctcaatgctc acgctgtagg tatctcagtt cggtgtaggt cgttcgctcc aagctgggct   5220
```

-continued

```
gtgtgcacga accccccgtt cagcccgacc gctgcgcctt atccggtaac tatcgtcttg   5280

agtccaaccc ggtaagacac gacttatcgc cactggcagc agccactggt aacaggatta   5340

gcagagcgag gtatgtaggc ggtgctacag agttcttgaa gtggtggcct aactacggct   5400

acactagaag gacagtattt ggtatctgcg ctctgctgaa gccagttacc ttcggaaaaa   5460

gagttggtag ctcttgatcc ggcaaacaaa ccaccgctgg tagcggtggt ttttttgttt   5520

gcaagcagca gattacgcgc agaaaaaaag gatctcaaga agatcctttg atcttttcta   5580

cggggtctga cgctcagtgg aacgaaaact cacgttaagg gattttggtc atgc         5634
```